US006759431B2

(12) United States Patent
Hunter et al.

(10) Patent No.: US 6,759,431 B2
(45) Date of Patent: Jul. 6, 2004

(54) COMPOSITIONS AND METHODS FOR TREATING OR PREVENTING DISEASES OF BODY PASSAGEWAYS

(75) Inventors: William L. Hunter, Vancouver (CA); Lindsay S. Machan, Vancouver (CA)

(73) Assignees: Angiotech Pharmaceuticals, Inc., Vancouver (CA); The University of British Columbia, Vancouver (CA)

( * ) Notice: Subject to any disclaimer, the term of this patent is extended or adjusted under 35 U.S.C. 154(b) by 0 days.

(21) Appl. No.: 09/933,652

(22) Filed: Aug. 20, 2001

(65) Prior Publication Data

US 2002/0052404 A1 May 2, 2002

Related U.S. Application Data

(63) Continuation of application No. 08/653,207, filed on May 24, 1996, now abandoned.

(51) Int. Cl.[7] ........................... A61P 35/00; A61K 9/16; A61K 31/337
(52) U.S. Cl. ..................... 514/449; 424/501; 424/426; 424/403
(58) Field of Search ............................... 514/449, 824; 424/501, 426, 423

(56) References Cited

U.S. PATENT DOCUMENTS

| | | | |
|---|---|---|---|
| 3,312,753 A | 4/1967 | Bailey et al. | 260/823 |
| 3,797,485 A | 3/1974 | Urquhart | 128/213 |
| 4,357,312 A | 11/1982 | Hsieh et al. | 424/15 |
| 4,526,938 A | 7/1985 | Churchill et al. | 525/415 |
| 4,531,936 A | 7/1985 | Gordon | 604/49 |
| 4,591,496 A | 5/1986 | Cohen et al. | 424/15 |
| 4,663,308 A | 5/1987 | Saffran et al. | 514/3 |

(List continued on next page.)

FOREIGN PATENT DOCUMENTS

| | | |
|---|---|---|
| CA | 2113683 | 7/1995 |
| EP | 516 749 B1 | 12/1992 |
| EP | 531 938 B1 | 3/1993 |
| EP | 547 530 A1 | 6/1993 |
| EP | 584 001 A1 | 7/1993 |
| EP | 623 354 A1 | 11/1994 |
| EP | 627 226 A1 | 12/1994 |
| EP | 639 380 A1 | 2/1995 |
| EP | 645 145 A2 | 3/1995 |
| EP | 689 807 A2 | 1/1996 |
| EP | 704 222 A1 | 4/1996 |
| EP | 716 836 A1 | 6/1996 |
| EP | 717 041 A1 | 6/1996 |
| WO | WO 90/13332 | 11/1990 |
| WO | WO 91/07154 | 5/1991 |
| WO | WO 92/15282 | 9/1992 |
| WO | WO 94/02595 | 2/1993 |
| WO | WO 93/18751 | 9/1993 |
| WO | WO 93/19739 | 10/1993 |
| WO | WO 93/24476 | 12/1993 |

(List continued on next page.)

OTHER PUBLICATIONS

Gebelein et al., "The Release Of 5–Fluorouracil From Polycaprolactone Matrices," *Polym. Sci. Technol.* 38(Appl. Bioact. Polym. Mater.):151–163, 1988.

(List continued on next page.)

*Primary Examiner*—Edward J. Webman
(74) *Attorney, Agent, or Firm*—Seed Intellectual Property Law Group, PLLC

(57) ABSTRACT

The present invention provides methods for treating or preventing diseases associated with body passageways, comprising the step of delivering to an external portion of the body passageway a therapeutic agent. Representative examples of therapeutic agents include anti-angiogenic factors, anti-proliferative agents, anti-inflammatory agents, and antibiotics.

31 Claims, 95 Drawing Sheets

U.S. PATENT DOCUMENTS

| | | | |
|---|---|---|---|
| 4,745,160 A | 5/1988 | Churchill et al. | 525/415 |
| 4,768,523 A | 9/1988 | Cahalan et al. | 128/785 |
| 4,808,402 A | 2/1989 | Leibovich et al. | 424/423 |
| 4,814,470 A | 3/1989 | Colin et al. | 514/449 |
| 4,863,735 A | 9/1989 | Kohn et al. | 424/422 |
| 4,882,168 A | 11/1989 | Casey et al. | 424/468 |
| 4,906,474 A | 3/1990 | Langer et al. | 424/428 |
| 4,942,184 A | 7/1990 | Haugwitz et al. | 514/449 |
| 4,947,840 A | 8/1990 | Yannas et al. | 128/156 |
| 4,987,071 A | 1/1991 | Cech et al. | 435/91 |
| 4,989,601 A | 2/1991 | Marchosky et al. | 128/399 |
| 5,002,572 A | 3/1991 | Picha | 623/11 |
| 5,019,096 A | 5/1991 | Fox, Jr. et al. | 623/1 |
| 5,032,572 A | 7/1991 | Saffran et al. | 514/3 |
| 5,049,132 A | 9/1991 | Shaffer et al. | 604/101 |
| 5,053,048 A | 10/1991 | Pinchuk | 623/1 |
| 5,057,606 A | 10/1991 | Garbe | 536/54 |
| 5,059,166 A | 10/1991 | Fischell et al. | 600/3 |
| 5,089,606 A | 2/1992 | Cole et al. | 536/54 |
| 5,100,668 A | 3/1992 | Edelman et al. | 424/422 |
| 5,126,141 A | 6/1992 | Henry | 424/423 |
| 5,145,684 A | 9/1992 | Liversidge et al. | 424/489 |
| 5,157,049 A | 10/1992 | Haugwitz et al. | 514/449 |
| 5,171,217 A | 12/1992 | March et al. | 604/53 |
| 5,171,262 A | 12/1992 | MacGregor | 623/1 |
| 5,179,174 A | 1/1993 | Elton | 525/409 |
| 5,213,580 A | 5/1993 | Slepian et al. | 623/1 |
| 5,225,347 A | 7/1993 | Goldberg et al. | 435/320.1 |
| 5,254,678 A | 10/1993 | Haseloff et al. | 536/23.2 |
| 5,258,042 A | 11/1993 | Mehta | 623/66 |
| 5,262,409 A | 11/1993 | Margolis et al. | 514/183 |
| 5,278,324 A | 1/1994 | Kingston et al. | 549/510 |
| 5,284,868 A | 2/1994 | Dell et al. | 514/454 |
| 5,286,254 A | 2/1994 | Shapland et al. | 604/21 |
| 5,288,502 A | 2/1994 | McGinity et al. | 424/484 |
| 5,288,503 A | 2/1994 | Wood et al. | 424/497 |
| 5,290,585 A | 3/1994 | Elton | 427/2 |
| 5,301,664 A | 4/1994 | Sievers et al. | 128/200.23 |
| 5,302,397 A | 4/1994 | Amsden et al. | 424/473 |
| 5,304,121 A | 4/1994 | Sahatjian | 604/53 |
| 5,304,377 A | 4/1994 | Yamada et al. | 424/426 |
| 5,314,444 A | 5/1994 | Gianturco | 606/195 |
| 5,314,688 A | 5/1994 | Kauffman et al. | 424/423 |
| 5,318,780 A | 6/1994 | Viegas et al. | 424/427 |
| 5,324,519 A | 6/1994 | Dunn et al. | 424/426 |
| 5,328,471 A | 7/1994 | Slepian | 604/101 |
| 5,330,768 A | 7/1994 | Park et al. | 424/501 |
| 5,340,849 A | 8/1994 | Dunn et al. | 523/113 |
| 5,342,348 A | 8/1994 | Kaplan | 604/891.1 |
| 5,362,831 A | 11/1994 | Mongelli et al. | 526/304 |
| 5,383,928 A | 1/1995 | Scott et al. | 623/1 |
| 5,391,164 A | 2/1995 | Giampapa | 604/891.1 |
| 5,399,363 A | 3/1995 | Liversidge et al. | 424/490 |
| 5,399,666 A | 3/1995 | Ford | 528/354 |
| 5,405,919 A | 4/1995 | Keefer et al. | 525/377 |
| 5,407,683 A | 4/1995 | Shively | 424/439 |
| 5,410,016 A | 4/1995 | Hubbell et al. | 528/354 |
| 5,415,869 A | 5/1995 | Straubinger et al. | 424/450 |
| 5,419,760 A | 5/1995 | Narciso, Jr. | 604/8 |
| 5,421,826 A | 6/1995 | Crocker et al. | 604/53 |
| 5,424,073 A | 6/1995 | Rahman et al. | 424/450 |
| 5,434,241 A | 7/1995 | Kim et al. | 528/354 |
| 5,438,072 A | 8/1995 | Bobee et al. | 514/449 |
| 5,439,446 A | 8/1995 | Barry | 604/96 |
| 5,439,686 A | 8/1995 | Desai et al. | 424/451 |
| 5,441,947 A | 8/1995 | Dodge et al. | 514/179 |
| 5,443,508 A | 8/1995 | Giampapa | 623/11 |
| 5,446,070 A | 8/1995 | Mantelle | 514/772.6 |
| 5,447,724 A | 9/1995 | Helmus et al. | 424/426 |
| 5,449,513 A | 9/1995 | Yokoyama et al. | 424/78.08 |
| 5,455,027 A | 10/1995 | Zalipsky et al. | 424/78.17 |
| 5,455,039 A | 10/1995 | Edelman et al. | 424/422 |
| 5,455,046 A | 10/1995 | Baichwal | 424/457 |
| 5,457,113 A | 10/1995 | Cullinan et al. | 514/319 |
| 5,461,140 A | 10/1995 | Heller et al. | 528/425 |
| 5,462,523 A | 10/1995 | Samson et al. | 604/30 |
| 5,462,751 A | 10/1995 | Kossovsky et al. | 424/494 |
| 5,462,937 A | 10/1995 | Cullinan et al. | 514/212 |
| 5,464,450 A | 11/1995 | Buscemi et al. | 623/6 |
| 5,464,650 A | 11/1995 | Berg et al. | 427/2.3 |
| 5,464,932 A | 11/1995 | Allcock et al. | 528/399 |
| 5,466,262 A | 11/1995 | Saffran | 623/16 |
| 5,470,307 A | 11/1995 | Lindall | 604/20 |
| 5,473,055 A | 12/1995 | Mongelli et al. | 530/329 |
| 5,476,909 A | 12/1995 | Kim et al. | 525/408 |
| 5,494,683 A | 2/1996 | Liversidge et al. | 424/490 |
| 5,496,581 A | 3/1996 | Yianni et al. | 427/2.12 |
| 5,496,846 A | 3/1996 | Wilson et al. | 514/449 |
| 5,502,158 A | 3/1996 | Sinclair et al. | 528/354 |
| 5,512,055 A | 4/1996 | Domb et al. | 604/265 |
| 5,512,297 A | 4/1996 | Baichwal | 424/451 |
| 5,514,092 A | 5/1996 | Forman et al. | 604/101 |
| 5,516,522 A | 5/1996 | Peyman et al. | 424/426 |
| 5,519,042 A | 5/1996 | Morris et al. | 514/378 |
| 5,523,092 A | 6/1996 | Hanson et al. | 424/423 |
| 5,525,356 A | 6/1996 | Jevne et al. | 424/484 |
| 5,527,532 A | 6/1996 | Edelman et al. | 424/422 |
| 5,531,716 A | 7/1996 | Luzio et al. | 604/265 |
| 5,531,735 A | 7/1996 | Thompson | 604/891.1 |
| 5,532,388 A | 7/1996 | Bouchard et al. | 549/510 |
| 5,534,287 A | 7/1996 | Lukic | 427/2.25 |
| 5,534,449 A | 7/1996 | Dennison et al. | 437/34 |
| 5,536,794 A | 7/1996 | Yezrielev et al. | 525/443 |
| 5,538,504 A | 7/1996 | Linden et al. | 604/53 |
| 5,540,912 A | 7/1996 | Roorda et al. | 424/422 |
| 5,540,928 A | 7/1996 | Edelman et al. | 424/422 |
| 5,543,218 A | 8/1996 | Bennett et al. | 428/375 |
| 5,545,208 A | 8/1996 | Wolff et al. | 623/1 |
| 5,545,569 A | 8/1996 | Grainger et al. | 436/518 |
| 5,548,035 A | 8/1996 | Kim et al. | 525/408 |
| 5,554,147 A | 9/1996 | Batich et al. | 604/890.1 |
| 5,554,182 A | 9/1996 | Dinh et al. | 623/1 |
| 5,554,387 A | 9/1996 | Baichwal | 424/488 |
| 5,556,635 A | 9/1996 | Istin et al. | 424/448 |
| 5,556,877 A | 9/1996 | Bouchard et al. | 514/449 |
| 5,556,878 A | 9/1996 | Kelly et al. | 514/449 |
| 5,558,642 A | 9/1996 | Schweich, Jr. et al. | 604/96 |
| 5,560,933 A | 10/1996 | Soon-Shiong et al. | 424/489 |
| 5,562,922 A | 10/1996 | Lambert | 424/486 |
| 5,565,432 A | 10/1996 | Novak et al. | 514/25 |
| 5,565,523 A | 10/1996 | Chen et al. | 525/176 |
| 5,567,435 A | 10/1996 | Hubbell et al. | 424/426 |
| 5,569,197 A | 10/1996 | Helmus et al. | 604/96 |
| 5,569,720 A | 10/1996 | Mongelli et al. | 525/329.4 |
| 5,573,781 A | 11/1996 | Brown et al. | 424/484 |
| 5,573,934 A | 11/1996 | Hubbell et al. | 435/177 |
| 5,575,815 A | 11/1996 | Slepian et al. | 623/1 |
| 5,576,072 A | 11/1996 | Hostettler et al. | 427/532 |
| 5,578,661 A | 11/1996 | Fox et al. | 624/27 |
| 5,580,575 A | 12/1996 | Unger et al. | 424/450 |
| 5,580,899 A | 12/1996 | Mayhew et al. | 514/449 |
| 5,582,591 A | 12/1996 | Cheikh | 604/51 |
| 5,585,348 A | 12/1996 | Crain et al. | 514/12 |
| 5,588,962 A | 12/1996 | Nicholas et al. | 604/52 |
| 5,593,683 A | 1/1997 | Viegas et al. | 424/427 |
| 5,595,974 A | 1/1997 | Tomaru | 514/21 |
| 5,597,798 A | 1/1997 | Howell et al. | 514/12 |
| 5,599,307 A | 2/1997 | Bacher et al. | 604/101 |
| 5,599,335 A | 2/1997 | Goldman et al. | 604/368 |
| 5,599,553 A | 2/1997 | Chung | 424/435 |
| 5,599,820 A | 2/1997 | Ojima et al. | 514/320 |

| | | | |
|---|---|---|---|
| 5,599,844 A | 2/1997 | Grainger et al. | 514/651 |
| 5,602,112 A | 2/1997 | Rubinfeld | 514/58 |
| 5,605,702 A | 2/1997 | Teillaud et al. | 424/448 |
| 5,607,418 A | 3/1997 | Arzbaecher | 604/891.1 |
| 5,607,686 A | 3/1997 | Totakura et al. | 424/426 |
| 5,609,574 A | 3/1997 | Kaplan et al. | 604/53 |
| 5,609,629 A | 3/1997 | Fearnot et al. | 623/1 |
| 5,614,506 A | 3/1997 | Falk et al. | 514/54 |
| 5,614,549 A | 3/1997 | Greenwald et al. | 514/449 |
| 5,616,608 A | 4/1997 | Kinsella et al. | 514/449 |
| 5,653,760 A | 8/1997 | Saffran | 623/11 |
| 5,660,225 A | 8/1997 | Saffran | 623/16 |
| 5,766,584 A | 6/1998 | Edelman et al. | 424/93.7 |
| 5,886,026 A | 3/1999 | Hunter et al. | 514/449 |
| 5,994,341 A | 11/1999 | Hunter et al. | 514/210 |
| 6,091,980 A | 7/2000 | Squire et al. | 600/381 |
| 6,179,858 B1 | 1/2001 | Squire et al. | 606/198 |
| 6,231,585 B1 | 5/2001 | Takahashi et al. | 606/191 |
| 6,326,017 B1 | 12/2001 | Mayberg | 424/422 |

FOREIGN PATENT DOCUMENTS

| | | |
|---|---|---|
| WO | WO 94/00156 | 1/1994 |
| WO | WO 94/14415 | 7/1994 |
| WO | WO 94/20089 | 9/1994 |
| WO | WO 94/21308 | 9/1994 |
| WO | WO 94/21309 | 9/1994 |
| WO | WO 94/25020 | 11/1994 |
| WO | WO 94/26254 | 11/1994 |
| WO | WO 94/26728 | 11/1994 |
| WO | WO 95/03036 | 2/1995 |
| WO | WO 95/03795 | 2/1995 |
| WO | WO 95/20582 | 8/1995 |
| WO | WO 96/03984 | 2/1996 |
| WO | WO 96/25176 | 8/1996 |

OTHER PUBLICATIONS

Golomb et al., *Encyclopedic handbook of biomaterials and bioengineering, Part B: Applications*, vol. 1 and 2, Wise et al. (eds.), Marcel Dekker, Inc., New York, NY, USA; Basel, Switzerland 1995, Chapter 37, "Perivascular Polymeric Controlled–Release Therapy," pp. 1043–1055.

Gonschior et al., "A new catheter for prolonged local drug application," *Coronary Artery Disease* 6:329–334, 1995.

Langer and Peppas, "Present and future applications of biomaterials in controlled drug delivery systems," *Biomaterials* 2:201–214, 1981.

Li and Feng, "Biodegradable polymeric matrix for long–acting and zero–order release drug delivery systems," *Makromol. Chem. Macromol. Symp.* 33:253–264, 1990.

Li et al., "Synthesis, characterization, and hydrolytic degredation of PLA/Peo?PLA triblock copolymers with long poly ($_L$–lactic acid) blocks," *Macromolecules* 29:57–62, 1996.

Lovich and Edelman, "Mechanisms of Transmural Heparin Transport in the Rat Abdominal Aorta After Local Vascular Delivery," *Circulation Research* 77(6):1143–1150, 1995.

Lyatskaya and Birshtein, "Triblock copolymers: the role of interfacial tension coefficients at two interfaces," *Polymer* 36(5):975–980, 1995.

March et al., "Biodegradable Microspheres Containing a Colchicine Analogue Inhibit DNA Synthesis in Vascular Smooth Muscle Cells," *Circulation* 89(5):1929–1933, 1994.

Martini et al., "The bioadhesive properties of a triblock copolymer of ε–caprolactone and ethylene oxide," *International Journal of Pharmaceutics* 113:223–229, 1995.

Martini et al., "The Release of 5–Fluorouracil from a Swellable Matrix of a Triblock Copolymer of ε–Caprolactone and Ethylene Oxide," *Pharmaceutical Research* 12(11): 1786–1790, 1995.

Matsuda et al., "Photoinduced prevention of tissue adhesion," *ASAIO Journal* 38:M154–M157, 1992.

Milas et al., "Kinetics of mitotic arrest and apoptosis in murine mammary and ovarian tumors treated with taxol," *Cancer Chemother. Pharmacol.* 35:297–303, 1995.

Miyamoto et al., "Polylactic Acid–Polyethylene Glycol Block Copolymer," *Clinical Orthopaedics and Related Research* 294:333–343, 1993.

Muller et al., "Intramural Methotrexate Therapy for the Prevention of Neointimal Thickening After Balloon Angioplasty," *JACC* 20(2):460–466, 1996.

Nakafuku and Sakoda, "Melting and crystallion of poly ($_L$–lactic acid) and poly (ethylene oxide) binary mixture," *Polymer Journal* 25(9):909–917, 1993.

Nakayama and Matsuda, "Preparation and characteristics of photocrosslinkable hydrophillic polymer having cinnamate moiety," *Journal of Polymer Science: Part A: Polymer Chemistry* 30:2451–2457, 1992.

Nakayama and Matsuda, "Surface fixation of poly (ethylene glycol) via photodimerization of Cinnamate group," *Journal of Polymer Science: Part A: Polymer Chemistry* 31:3299–3305, 1993.

Nasser et al., "Microparticle depositon in periarterial microvasculature and intramural dissections after porous balloon delivery into atherosclerotic vessels: Quantitation and localization by confocal scanning laser microscopy," *American Heart Journal* 131(5):892–898, 1996.

Nojima et al., "Crystallization of Block Copolymers II. Morphological study of poly (ethylene glycol)–poly (ε–caprolactone) block copolymers," *Polymer Journal* 24(11):1271–1280, 1992.

Nojima et al., "Morphology formed in binary blends of poly (ε–caprolactone) and ε–caprolactone–butadiene diblock copolymer," *Polymer* 36(14):2853–2856, 1995.

Nomura et al., "Prediction of the Coding Sequences of Unidentified Human Genes. II. The Coding Sequences of 40 New Genes (KIAA0041–KIAA0080) Deduced by Analysis of cDNA Clones from Human Cell Line KG–1," *DNA Research* 1:223–229, 1994.

Okada et al., "Localized Release of Perivascular Heparin Inhibits Intimal Proliferation after Endothelial Injury without Systemic Anticoagulation," *Neurosurgery* 25(6):892–898, 1989.

Okana, "Molecular Design of Stimuli–Responsive Hydrogels for Temporal Controlled Drug Delivery," *Proceed. Intern. Symp. Control. Rel. Bioact. Mater* 22:111–112, 1995.

Okana et al., "Temperature–responsive poly (N–isopropylacrylamide) as a modulator for alteration of hydrophilic/hydrophobic surface properties to control activation/inactivation of platelets," *Journal of Controlled Release* 36:125–133, 1995.

Oliver et al., "Suppression of Collagen–Induced Arthritis Using and Angiogenesis Inhibitor, AGM–1470, and a Microtubule Stabilizer, Taxol," *Cellular Immunology* 157:291–299, 1994.

Osada and Ross–Murphy, "Intelligent Gels," *Scientific American* (May):82–97, 1993.

Oudhuis et al., "A comparison beween the morphology of semicrystalline polymer blends of poly(ε–caprolactone)/poly(vinyl methylether) and poly(ε–caprolactone)/(styrene–acrylonitrile)," *Polymer* 36(18):3936–3942, 1994.

Paavola et al., "Controlled release of lidocaine from injectable gels and efficacy in rat sciatic nerve block," *Pharmaceutical Research* 12(12):1997–2002, 1995.

Palasis and Gehrke, "Permeability of responsive poly (N–isopropylacrylamide) gel to solutes," *Journal of Controlled Release* 18:1–12, 1992.

Park et al., "Poly ($_L$–lactic acid)/pluornic blends: characterization of phase seperation behavior, degradation, and morphology and use as protein–releasing matrices," *Macromolecules* 25:116–122, 1992.

Peng et al., "Role of polymers in improving the results of stenting in coronary arteries," *Biomaterials* 17:685–694, 1996.

Peppas and Sahlin, "Hydrogels as mucoadhesive and bioadhesive materials: a review," *Biomaterials* 17:1553–1561, 1996.

Perego et al., "Preparation of a new nerve guide from a poly(L–lactide–co–6–caprolactone)," *Biomaterials* 15(3):189–193, 1994.

Pitt, "Poly–ε–Caprolactone and Its Copolymers," in *Biodegradable Polymers as Drug Delivery Systems*, (Eds. Langen, R., and Chasin, M), Marcel Dekker, New York, NY, pp 71–120, 1990.

Pitt and Gu, "Modification of the rates of chain cleavage of poly(ε–caprolactone) and related plyseters in the solid state," *Journal of Controlled Release* 4:283–292, 1987.

Pitt et al., "Aliphatic polyesters II. The degradation of poly (DL–lactide), poly (ε–caprolactone), and their copolymers in vivo," *Biomaterials* 2:215–220, 1981.

Pitt et al., "Biodegradable Drug Delivery Systems Based On Aliphatic Polyesters: Application To Contraceptives and Narcotic Antagonists," in Richard W. Baker (ed.), *Controlled Release Of Bioactive Materials* [Symp. Int. Meet. Controlled Release Soc.], Academic Press, Inc., New York, NY, 1980, pp. 19–43.

Pitt et al., "Blends of PVA and PGLA: control of the permeability and degradability of hydrogels by blending," *Journal of Controlled Release* 19:189–200, 1992.

Pitt et al., "Sustained Drug Delivery Systems II: Factors Affecting Release Rates from Poly(ε–caprolactone) and Related Biodegradable Polyesters," *Journal of Pharmaceutical Sciences* 68(2):1534–1538, 1979.

Pitt et al., "Sustained Drug Delivery Systems. I. The Permeability of Poly (ε–Caprolactone), Poly (DL–Lactic Acid), and Their Copolymers," *Journal of Biomedical Materials Research* 13:497–507, 1979.

Pitt et al., "The Enzymatic Surface Erosion of Aliphatic Polyesters," *Journal of Controlled Release* 1:3–14, 1984.

Ranucci and Ferruti, "High swelling gels for sensing applications," *Macromol. Symp.* 109: 89–103, 1996.

Rashkov et al., "Synthesis, characterization, and hydrolytic degradation of PLA/PEO/PLA triblock copolymers with short poly ($_L$–lactic acid) chains," *Macromolecules* 29:50–56, 1996.

Rim and Runt, "Melting Behavior of Crystalline/Compatible Polymer Blends: Poly(ε–caprolactone)/Poly(styrene–co–acrylonitrile)," *Macromolecules* 16(5):763–768, 1983.

Rowinsky and Donehower, "Paclitaxel (Taxol)," *The New England Journal of Medicine* 332(15):1004–1014, 1995.

Rowinsky and Donehower, "Taxol: Twenty Years Later, the Story Unfolds," *Journal of the National Cancer Institute* 83(24):1778–1781, 1991.

Rowinsky et al., "Clinical Toxicities Encountered With Paclitaxel (Taxol®)," *Seminars in Oncology* 20(4 Suppl. 3):1–15, 1993.

Rowinsky et al., "Taxol: A Novel Investigation Antimicrotubule Agent," *J. Natl. Cancer Inst.* 82(15):1247–1259, 1990.

Rowinsky et al., "Taxol: The First of the Taxanes, an Important New Class of Antitumor Agents," *Seminars in Oncology* 19(6):646–662, 1992.

Sauro et al., "The Anti–Tumor Agent, Taxol, Attenuates Contractile Activity In Rat Aortic Smooth Muscle," *Life Sciences* 56(7):157–161, 1995.

Sawhney and Hubbell, "Rapidly degraded terpolymers of dl–lactide, glycolide, and ε–caprolactone with increased hydrophilicity by copolymerization with polyethers," *Journal of Biomedical Materials Research* 24:1397–1411, 1990.

Shah et al., "A biodegradable injectable implant for delivering micro and macromolecules using poly(lactic–co–glycolic) acid (PLGA) copolymers," *Journal of Controlled Release* 27: 139–147, 1993.

Sharma and Straubinger, "Novel Taxol Formulations: Preparation and Characterization of Taxol–Containing Liposomes," *Pharmaceutical Research* 11(6):889–896, 1994.

Sharma et al., "Antitumor Effect of Taxol–containing Liposomes in a Taxol–resistant Murine Tumor Model," *Cancer Research* 53:5877–5881, 1993.

Sharma et al., "Antitumor Efficacy of Taxane Liposomes on a Human Ovarian Tumor Xenograft in Nude Athymic Mice," *Journal of Pharmaceutical Sciences* 84(12):1400–1404, 1995.

Sharma et al., "Novel Taxol® Formulation: Polyvinylpyrrolidone Nanoparticle–Encapsulated Taxol® for Drug Delivery in Cancer Therapy," *Oncology Research* 8(7/8):281–286, 1996.

Sharma et al., "Pharmaceutical and Physical Properties of Paclitaxel (Taxol) Complexes with Cyclodextrins," *Journal of Pharmaceutical Sciences* 84(10):1223–1230, 1995.

Shen–Guo and Bo, "Polycaprolactone–poly(ethylene glycol) block copolymer, I: Synthesis and Degradability in vitro," *Polymers for Advanced Technologies* 4:363–366, 1993.

Shen–Guo et al., "Polycaprolactone–poly (ethylene glycol) block copolymer, II. Relationship among composition, crystallinity and degradability," *Acta Polymeric Sinica* 5:560–565, 1995 (+ English Abstract on p. 565).

Shi et al., "Transcatheter Delivery of c–myc Antisense Oligomers Reduces Neointimal Formation in a Porcine Model of Coronary Artery Balloon Injury," *Circulation* 90(2):944–951, 1994.

Shively et al., "Physico–chemical characterization of polymeric injectable implant delivery system," *Journal of Controlled Release* 33:237–243, 1995.

Smetana Jr. et al., "Influence of intraperitoneal injection of three types of hydrogel beads on expression of carbohydrate–binding sites in spleen macrophages," *Biomaterials* 17(24):2335–2341, 1996.

Sollott et al., "Taxol Inhibits Neointimal Smooth Muscle Cell Accumulation after Angioplasty in the Rat," *J. Clin. Invest.* 95:1869–1876, 1995.

Spencer and Faulds, "Paclitex. A Review of its Pharmacodynamic and Pharmacokinetic Properties and Therapeutic Potential in the Treatment of Cancer," *Drugs* 48(5):795–847, 1994.

Tarr et al., "A New Parenteral Emulsion for the Administration of Taxol," *Pharmaceutical Research* 4(2):162–165, 1987.

Thomas et al., "Local intracoronary heparin delivery with a microporous balloon catheter," *Am. Heart J.* 132(5):969–972, 1996.

Trigo et al., "Anticancer drug, ara–C, release from pHEMA hydrogels," *Biomaterials* 15(14): 1181–1186, 1994.

Tsitsilianis et al., "Amphiphilic heteroarm star copolymers of polystyrene and poly (ethylene oxide)," *Polymer* 36(19):3745–3752, 1995.

Tung, "Rheological behavior of poloxamer 407 aqueous solutions during sol–gel and dehydration processes," *International Journal of Pharmaceutics* 107:85–90, 1994.

Ulbrich et al., "Synthesis of novel hydrolytically degradable hydrogels for controlled drug release," *Journal of Controlled Release* 34:155–165, 1995.

Van den Mooter et al., "The Relation Between Sweeling Properties and Enzymatic Degradation of Azo Polymers Designed for Colon–Specific Drug Delivery," *Pharm. Res.* 11(12):1737–1741, 1994.

Violante and Lanzafame, "Cremaphor–free Paclitaxel Formulation," *Proceedings of the American Association for Cancer Research Annual Meeting vol. 36*: Abstract No. 1841, 1995.

Wada et al., "in Vitro Evaluation of Sustained Drug Release from Biodegradable Elastomer," *Pharmaceutical Research* 8(10):1291–1295, 1991.

Walter et al., "Interstitial Taxol Delivered from a Biodegradable Polymer Implant against Experimental Malignant Glioma," *Cancer Research* 54:2207–2212, 1994.

Wang et al., "Preparation and Characterization of Poly(lactic–co–glycolic acid) Microspheres for Targeted Delivery of a Novel Anticancer Agent, Taxol," *Chem. Pharm. Bull* 44(10): 1935–1940, 1996.

Wilensky et al., "Direct intraarterial wall injection of microparticles via a catheter: A potential drug delivery strategy following angioplasty," *Am. Heart J.* 122(vol. 4)(Part 1):1136–1140, 1991.

Wilensky et al., "Regional and arterial localization of radioactive microparticles after local delivery by unsupported or supported porous balloon catheters," *American Heart Journal* 129(5):852–859, 1995

Winternitz et al., "Development of a Polymeric Surgical Paste Formulation for Taxol," *Pharmaceutical Research* 13(3):368–375, 1996.

Wolinsky et al., "Use of a Perforated Balloon Catheter to Deliver Concentrated Heparin Into the Wall of the Normal Canine Artery," *JACC* 15(2):475–481, 1990.

Woodward et al., "The intracellular degradation of poly($\epsilon$–caprolactone)," *Journal of Biomedical Materials Research* 19:437–444, 1985.

Yang et al., "Structures of oxyethylene/oxybutylene diblock copolymers in their solid and liquid states," *Macromolecules* 28:6029–6041, 1995.

Yasurmori et al., "Placement of covered self–expanding metallic stents in the common bile duct: A feasibility study," *Journal of Vascular and Interventional Radiology Nov.–Dec.*:773–778, 1993.

Ye and Chien, "Dual–controlled drug delivery across biodegradable copolymer. II. Delivery kinetics of levonorgestrel and estradiol from (matrix/matrix) laminate drug delivery system," *Journal of Controlled Release* 41:259–269, 1996.

Yoshida et al., "Positive thermosensitive pulsatile drug release using negative thermosensitive hydrogels," *Journal of Controlled Release* 32:97–102, 1994.

Youxin and Kissel, "Synthesis and properties of biodegradable ABA triblock copolymers consisting of poly ($_L$–lactic acid) or poly ($_L$–lactic–co–glycolic acid) A–blocks attached to central poly (oxyethylene) B–blocks," *Journal of Controlled Release* 27:247–257, 1993.

Youxin et al., "In–vitro degradation and bovine serum albumin release of the ABA triblock copolymers consisting of poly (L(+)lactic acid), or poly(L(+)lactic acid–co–glycolic acid) A–blocks attached to central polyoxyethylene B–blocks," *Journal of Controlled Release* 32:121–138, 1994.

Yu and Grainger, "Novel thermo–sensitive amphiphilic gels: poly N–isopropylacrylamide–co–sodium acrylate–co–n–N–alkylacrylamide network synthesis and physicochemical characterization," at *Sixth International Symposium on Recent Advances in Drug Delivery Systems*, Salt Lake City, Utah, USA, Feb. 21–24, 1993, pp. 820–821.

Yu and Grainger, "Thermo–sensitive swelling behavior in crosslinked N–isopropylacrylamide networks: cationic, anionic and ampholytic hydrogels," *Polym. Prepr.* 34(1):829–830, 1993.

Zhou and Smid, "Physical hydrogels of associative star polymers," *Polym. Prepr. (Am. Chem. Soc., Div. Polym. Chem)* 34(1): 822–823, 1993.

Zhu et al., "Preparation, characterization, and properties of polylactide (PLA)–poly (ethylene glycol) (PEG) copolymers: a potential drug carrier," *Journal of Applied Polymer Science* 39:1–9, 1990.

Zhu et al., "Super microcapsules (SMC). I. Preparation and characterization of star polythylene oxide (PEO)–polyactide (PLA) copolymers," *Journal of Polymer Science: Part A: Polymer Chemistry* 27:2151–2159, 1989.

Harada et al., "Basic Fibroblast Growth Factor Improves Myocardial Function in Chronically Ischemic Porcine Hearts," *J. Clin. Invest.* 94: 623–630, 1994.

Riessen and Isner, "Prospects for Site–Specific Delivery of Pharmacologic and Molecular Therapies," *JACC* 23(5): 1234–1244, 1994.

Villa et al., "Local Delivery of Dexamethasone for Prevention of Neointimal Proliferation in a Rat Model of Balloon Angioplasty," *J. Clin. Invest.* 93:1243–1249, 1994.

Adams et al., "Taxol: A History of Pharmaceutical Development and Current Pharmaceutical Concerns," *Monogr. Natl. Cancer Inst.* 15: 141–147, 1993.

Ajani et al., "Activity of Taxol in Patients With Squamous Cell Carcinoma and Adenocarcinoma of th Esophagus," *J. Natl. Cancer Inst.* 86: 1086–1091, 1994.

Ali et al., "Mechanisms of polymer degradation in implantable devices," *Biomaterials* 14(9): 648–656, 1993.

Alkan–Onyuksel et al., "A Mixed Micellar Formulation Suitable for the Parenteral Administration of Taxol," *Pharmaceutical Research* 11(2): 206–212, 1994.

Anonymous, "Taxol," *The Lancet* 339: 1447–1448, 1992.

Anseth et al., "Mechanical properties of hydrogels and their experimental determination," *Biomaterials* 17: 1647–1657, 1996.

Bae et al., ""On–Off" thermocontrol of solute transport. I. Temperature dependence of swelling of N–isopropylacrylamide networks modified with hydrophobic components in water," *Pharmaceutical Research* 8(4): 531–537, 1991.

Bartoli et al., "In vitro and in vivo antitumoral activity of free, and encapsulated taxol," *J. Microencapsulation* 7(2): 191–197, 1990.

Belcheva et al., "Crosslinked poly (ethylene oxide) for drug release systems," *Macromol. Symp. 103*: 193–211, 1996.

Berrabah et al., "GC–MS determination of phenobarbitone entrapped in poly–ε–caprolactone nanocapsules," *Journal of Pharmaceutical & Biomedical Analysis* 12(3): 373–378, 1994.

Bissett and Kaye, "Taxol and Taxotere–Current Status and Future Prospects," *Eur. J. Cancer* 29A(9): 1228–1231, 1993.

Blanco–Fuente et al., "Tanned leather: a good model for determining hydrogels bioadhesion," *International Journal of Pharmaceutics 138*: 103–112, 1996.

Brahn et al., "Regression Of Collagen–Induced Arthritis With Taxol, A Microtubule Stabilizer," *Arthritis & Rheumatism* 37(6): 839–845, 1994.

Brem and Langer, "Polymer–Based Drug Delivery to the Brain," *Science and Medicine* Jul./Aug.: 52–61, 1996.

Bromberg, "Crosslinked poly (ethylene glycol) networks as reservoirs for protein delivery," *Journal of Applied Polymer Science 59*: 459–466, 1996.

Brown et al., in *Comprehensive Polymer Science: The Synthesis, characterization, reactions and applications of polymers.* vol 2–Polymer Properties, Allen et al (eds.)., Pergamon Press, Oxford, 1989, pp. 155–198.

Bruin et al., "Biodegradable lysine diisocyanate–based poly(glycolide–co–ε–caprolactone)–urethane network in artificial skin," *Biomaterials 11*: 291–295, 1990.

Burt et al., "Controlled delivery of taxol from microspheres composed of a blend of ethylene–vinyl acetate copolymer and poly (d,l–lactic acid)," *Cancer Letters 88*: 73–79, 1995.

Calvo et al., "Study of the mechanisms of interaction of poly(ε–caprolactone) nanocapsules with the cornea by confocal laser scanning microscopy," *International Journal of Pharmaceutics 103*: 283–291, 1994.

Cascone et al., "Collagen and hyaluronic acid based polymeric blends as drug delivery systems for the release of physiological concentrations of growth hormone," *Journal of Materials Science Materials in Medicine 5*: 770–774, 1994.

Cerrai et al., "Block copolymers of L–lactide and poly (ethylene glycol) for biomedical applications," *Journal of Materials Science: Materials in Medicine 5*: 308–313, 1994.

Chen et al., "Novel hydrogels of a temperature–sensitive pluronic® grafted to a bioadhesive polyacrylic acid backbone for vaginal drug delivery," *Proceed. Intern. Symp. Control. Rel. Bioact. Mate.* 22: 167–168, 1995.

Coffin and McGinity, "17. Physical and Chemical Stability of Aqueous Colloidal Dispersions of Poly (DL–Lactide and Poly (ε–Prolactone)," *Drug Targeting Delivery 1*: 197–214, 1992.

Cohn and Younes, "Compositional and structural analysis of PELA bioderadable block copolymers degrading under in vitro conditions," *Biomaterials 10*: 466–474, 1989.

Cornejo–Bravo et al., "Kinetics of drug release from hydrophobic polybasic gels: effect of buffer acidity," *Journal of Controlled Release 33*: 223–229, 1995.

Cserháti, "Interaction of some anticancer drugs with carboxymethyl–β–cyclodextrin," *International Journal of Pharmaceuticals 124*: 205–211, 1995.

De Scheerder et al., "Biocompatibility of polymer–coated oversized metallic stents implanted in normal porcine coronary arteries," *Athersclerosis 114*: 105–114, 1995.

Dinarvand and D'Emanuele, "The use of thermoresponsive hydrogels for on–off release of molecules," *Journal of Controlled Release 36*: 221–227, 1995.

Dolan et al., "Biodistribution of $O^6$–benzyguanine and its effectiveness against human brain tumor xenografts when given in polythylene glycol or cremophor–EL," *Cancer Chemother Pharmacol 35*: 121–126, 1994.

Dong and Hoffman, "A novel approach for preparation of pH–sensitive hydrogels for enteric drug delivery," *Journal of Controlled Release 15*: 141–152, 1991.

Dong et al., "Controlled release of amylase from a thermal and pH–sensitive, macroporous hydrogels," *Journal of Controlled Release 19*: 171–178, 1992.

Dordunoo et al., "Release of taxol from poly(ε–caprolactone) pastes: effect of water–soluble additives," *Journal of Controlled Release 44*: 87–94, 1997.

Dordunoo et al., "Taxol encapsulation in poly(ε–caprolactone) microspheres," *Cancer Chemother Pharmacol 36*: 279–282, 1995.

Dunn et al., "Polystyrene–Poly (Ethylene Glycol) (PS–PEG2000) Particles as Model Systems for Site Specific Drug Delivery. 2. The Effect of PEG Surface Density on the in Vitro Cell Interaction and in Vivo Biodistribution," *Pharmaceutical Research* 11(7): 1016–1022, 1994.

Embelton and Tighe, "Polymers for Biodegradable medical devices. X. Microencapsulation studies: control of poly–hydroxybutyrate–hydroxyvalerate microcapsules porosity via polycaprolactone blending," *J. Microencapsulation* 10(3): 341–352, 1993.

Engelberg and Kohn, "Physico–mechanical properties of degradable polymers used in medical applications: a comparative study," *Biomaterials 12*: 292–304, 1991.

Ettinger, "Overview of Paclitaxel (TAXOL®) in Advanced Lung Cancer," *Seminars in Oncology* 20(4 Suppl. 3): 46–49, Aug. 1993.

Fernández–Ortiz et al., "A New Approach for Local Intravascular Drug Delivery (Iontophoretic Balloon)," *Circulation* 89(4): 1518–1522, 1994.

French et al., "Physicochemical aspects of controlled release of substituted benzoic and napthoic acids from Carbopol® gels," *Journal of Controlled Release 37*: 281–289, 1995.

Fukuzaki et al., "A New Biodegradable Pasty–Type Copolymer of $_L$–Lactic Acid and δ–Valerolactive With Relatively Low Molecular Weight for Application in Drug Delivery Systems," *Journal of Controlled Release 10*: 293–303, 1989.

Fukuzaki et al., "In vivo characteristics of low moleclar weight copolymers composed of $_L$–Lactic acid and various DL–hydroxy acids as biodegradable carriers for drug delivery systems," *Biomaterials 11*: 441–446, 1990.

Gao et al., "Controlled Release of a Contraceptive Steroid from Biodegradable and Injectable Gel Formulations: In Vitro Evaluation," *Pharmaceutical Research* 12(6): 857–863, 1995.

Golomb et al., "Controlled delivery of a tryphostin inhibits hyperplasia in a rat cartoid artery injury model," *Atherosclerosis 125*: 171–182, 1996.

Gonschior et al., "Comparison of local intravascular drug–delivery catheter systems," *Am Heart J* 130(6): 1174–1181, 1995.

Grijpma et al., "Star–shaped polylactide–containing block copolymers," *Makromol. Chem. Rapid Commun.* 14: 155–161, 1993.

Grosvenor and Staniforth, "The effect of Molecular weight on the rheological and tensile properties of Poly($\epsilon$–caprolactone)," *International Journal of Pharmaceutics* 135: 103–109, 1996.

Gu et al., "Biodegradable block copolymer matrices for long–acting contraceptives with constant release," *Journal of Controlled Release* 22: 3–14, 1992.

Gutowska et al., "Heparin release from the thermosensitive hydrogels," *Journal of Controlled Release* 22: 95–104, 1992.

Harland and Peppas, "Hydrophilic/hydrophobic, block and graft copolymeric hydrogels: synthesis, characterization, and solute partition and penetration" *Journal of Controlled Release* 26: 157–174, 1993.

Harsh and Gehrke, "Controlling the swelling characteristics of temperature–sensitive cellulose ether hydrogels," *Journal of Controlled Release* 17: 175–186, 1991.

Hekmat, E., "Fatal Myocardial Infarction Potentially Induced By Paclitaxel," *Ann Pharmacother* 30: 1110–1112, 1996.

Heller et al., "The Sustained Release of Galardin and Taxol from Gelatin Chondroitin Sulfate Coacervate Films," *Mat. Res. Soc. Symp. Proc.* 394: 55–60, 1995.

Hoffman, "Applications of Thermally Reversible Polymers and Hydrogels in Therapeutics and Diagnostics," at *Third International Symposium on Recent Advances in Drug Delivery Systems*, Salt Lake City, UT, Feb. 24–27, 1987, pp. 297–305.

Hoffman, "Thermally Reversible Hydrogels Containing Biologically Active Species," *Polymers in Medicine III* , C. Miglaires et al. (eds.), Elsevier Science Publishers B. V., Amsterdam, pp. 161–167, 1988.

Hoffman et al., "Characterization pore Sizes and Water "Structure" in Stimuli–Responsive Hydrogels," *Polym. Prepr. (Am. Chem. Soc., Div. Polym. Chem.)* 34(1): 828, 1993.

Holland et al., "Polymers for Biodegradable Medical Devices. 1. The Potential of Polyesters as Controlled Macromolecular Release Systems," *Journal of Controlled Release* 4: 155–180, 1986.

Hong et al., "The Effect of Porous Infusion Balloon–Delivered Angiopeptin on Myointimal Hyperplasia After Balloon Injury in the Rabbit," *Circulation* 88(2): 638–648, 1993.

Hu and Liu, "Effect of soft segment on degradation kinetics in polyethylene glycol/poly ($_L$–lactide) block copolymers," *Polymer Bulletin* 30: 669–676, 1993.

Hu and Liu, "Effects of soft segments and hydrolysis on the crystallization behavior of degradable poly (oxyethylene)/poly ($_L$–lactide) block copolymers," *Macromol. Chem. Phys.* 195: 1213–1223, 1994.

Huehns et al., "Adventia as a target for intravascular local drug delivery," *Am Heart J* 75: 537–538, 1996.

Iwamiya et al ., "Repeated arterial infusion chemotherapy for inoperable hepatocellular carcinoma using an implantable drug delivery system." *Cancer Chemother Pharmacol.* 33(Suppl.): S134–S138, 1994.

Izuka et al., "Molecular weight dependence of viscoelasticity of polycaprolactone critical gels," *Macromolecules* 25(9): 2422–2428, 1992.

Jampel et al., "Glaucoma Filtration Surgery in Nonhuman Primates Using Taxol and Etoposide in Polyanhydride Carriers," *Investigative Ophthalmology & Visual Science* 34(11): 3076–3083, 1993.

Janarthanan et al., "Intramolecular Interactions in Poly(styrene–co–acrylonitrile)/Poly($\epsilon$–caprolactone) Blends," *Journal of Polymer Science:Part B:Polymer Physics* 31: 1013–1017, 1993.

Jedlinski et al., "Polymerization of lactones, 17 synthesis of ethylene glycol–$_L$–lactide block copolymers," *Makromol. Chem.* 194(6): 1681–1689, 1993.

Jianzhong et al., "Polycaprolactone–poly (ethylene glycol) block copolymer, III. Drug release behavior," *Chinese Journal of Polymer Science* 13(2): 154–161, 1995.

Jin et al., "Lipobeads: a hydrogel anchored lipid vesicle system," *FEBS Letters* 397: 70–74, 1996.

Johnston et al., "Sustained Delivery of Interleukin–2 from a poloxamer 407 Gel Matrix Following Intraperitoneal Injection in Mice," *Pharmaceutical Research* 9(3): 425–433, 1992.

Jones et al., "Phase II Study of Paclitaxel Therapy for Unrespectable Biliary Tree Carcinomas," *Journal of Clinical Oncology* 14(8): 2306–2310, 1996.

Katono et al., "Thermo–responsive swelling and drug release switching of interpenetrating polymer networks composed of poly (acrylamide–co–butyl methacrylate) and poly (acrylic acid)," *Journal of Controlled Release* 16: 215–228, 1991.

Kazanskii et al., Ionizable hydrogels of new type based on poly (ethylene glycol) phosphates, *Polymer Gels and Networks* 4: 335–349, 1996.

Kelsen et al., "A Phase II Trial of Paclitaxel (Taxol) in Advanced Esophageal Cancer: Preliminary Report," *Seminars in Oncology* 21(5): 44–48, 1994.

Kennedy et al., "Prevention of experimental postoperative peritoneal adhesions by N,O–carboxymethyl chitosan," *Surgery* 120(5): 866–870, 1996.

Kim et al., "Hydrogels: swelling, drug loading, and release," *Pharmaceutical Reasearch* 9(3): 283–290, 1992.

Kimura et al., "Preparation of block copoly (ester–ether) comprising poly ($_L$–lactide) and poly (oxypropylene) and degradation of its fibre in vitro and in vivo," *Polymer* 30(7): 1342–1349, 1989.

Koenig and Huang, "Biodegradable blends and composites of polycaprolactone and starch derivatives," *Polymer* 36(9): 1877–1882, 1995.

Kohler and Goldspiel, "Paclitaxel (Taxol)," *Pharmacotherapy* 14(1): 3–34, 1994.

Kono et al., "Temperature–sensitive liposomes: liposomes bearing poly (N–isopropylacrylamide)," *Journal of Controlled Release* 30: 69–75, 1994.

Krüger et al., "Elastic properties of thin ultraoriented poly ($\epsilon$–caprolactone) films grown on PTFE substrates as revealed by brillouin spectroscopy," *Journal of Polymer Science: Part B: Polymer Physics* 30: 1173–1176, 1992.

Kumar and Himmelstein, "Modification of in Situ Gelling Behavior of Carbopol Solutions by Hydroxypropyl Methylcellulose," *Journal of Pharmaceutical Sciences* 84(3): 344–348, 1995.

EFFECT OF TREATMENT ON THE WEIGHT OF TUMOURS AND MICE WEIGHTS.

| MOUSE NUMBER | MOUSE WEIGHT (g) | | TUMOUR WEIGHT (g) | |
| --- | --- | --- | --- | --- |
| | CONTROL | TREATED | CONTROL | TREATED |
| 1 | 19.4 | 19.0 | 1.76 | 1.14 |
| 2 | 20.4 | 18.6 | 1.85 | 1.98 |
| 3 | 20.6 | 19.5 | 2.4 | 0.65 |
| 4 | 19.8 | 18.5 | 2.31 | 0.20 |
| 5 | 20.0 | 18.9 | 3.2 | 0.35 |
| 6 | – | 19.1 | – | 1.51 |
| 7 | – | 19.9 | – | 0.61 |
| 8 | – | 19.3 | – | 0.40 |
| MEAN | 20.4 | 19.1 | 2.3 | 0.85 |
| STD. DEV. | 0.47 | 0.46 | 0.57 | 0.62 |

*Fig. 20*

MELTING TEMPERATURE, ENTHALPY, MOLECULAR WEIGHT ($M_n$), POLYDISPERSITY ($M_w/M_n$), AND INTRINSIC VISCOSITY ($[\eta]$) OF PDLLA-PEG-PDLLA

| PDLLA-PEG-PDLLA PEG CONTENT | MELTING TEMP.[a], °C | $\Delta H^a$, J/g | $M_n^b$, $\times 10^{-4}$ | $M_w/M_n^b$ | $[\eta]^c$, dl/g |
|---|---|---|---|---|---|
| 100% | 61.8 | 184.8 | 0.8[d] | -- | -- |
| 70% | 50.2 | 72.2 | 2.1 | 1.21 | 0.27 |
| 40% | 46.3 | 42.8 | 4.5 | 3.5 | 0.29 |
| 30% | NONE | NONE | 5.9 | 2.95 | 1.0 |
| 20% | NONE | NONE | 5.1 | 2.96 | 1.45 |
| 10% | NONE | NONE | 11 | 2.38 | 1.5 |
| TAXOL | 212 | 59.3 | -- | -- | -- |
| 20% taxol loaded COPOLYMER (30%PEG) | 212.1 | 5.6 | -- | -- | -- | a: MEASURED BY DSC.
b: MEASURED BY GPC, RELATIVE TO POLYSTYRENE STANDARD.
c: IN $CHCl_3$ AT 25°C
d: DATA SUPPLIED BY MANUFACTURER

*Fig. 21*

MASS LOSS AND POLYMER COMPOSITION CHANGE OF PDLLA-PEG-PDLLA CYLINDERS (LOADED WITH 20% TAXOL) DURING THE RELEASE INTO PBS ALBUMIN BUFFER AT 37 °C

| SAMPLE[a] | TIME, DAY | DRY WT. LOSS, % | 1.65/5.1[b] | 3.6/5.1[b] |
|---|---|---|---|---|
| 20% PEG-1mm | 0 | 0 | 3.51 | 1.65 |
| 20% PEG-1mm | 32 | 7.9 | - | - |
| 20% PEG-1mm | 69 | 19.2 | 3.63 | 0.68 |
| 30% PEG-1mm | 0 | 0 | 3.39 | 3.91 |
| 30% PEG-1mm | 32 | 28.9 | - | - |
| 30% PEG-1mm | 69 | 45.5 | 4.3 | 0.56 |
| 30% PEG-0.65mm | 0 | 0 | 3.39 | 3.91 |
| 30% PEG-0.65mm | 32 | 26.7 | - | - |
| 30% PEG-0.65mm | 69 | 57.5 | 5.8 | 0.21 | a: PDLLA-PEG-PDLLA copolymer cylinders showing PEG content and diameter of cylinder.
b: measured by $^1$H-NMR in CDCl$_3$; 1.65/5.1 represents the ratio of peak areas at 1.65ppm (due to -CHCH$_3$*- in PDLLA) and 5.1 ppm (due to -CH*CH$_3$- in PDLLA); 3.6/5.1 represents the ratio of peak areas at 3.6ppm (due to -CH$_2$*CH$_2$*- in PEG) and 5.1ppm.

*Fig. 26*

Efficacy of taxol loaded surgical paste formulations applied locally to subcutaneous tumor in mice.

| | non-treated | PCL | | 80:20 PDLLA:PCL blend | | 90:10 PDLLA:PCL blend | | PDLLA-PEG-PDLLA[a] | |
|---|---|---|---|---|---|---|---|---|---|
| | | control | 20% taxol | control | 20% taxol | control | 20% taxol | control | 20% taxol |
| n[b] | 5 | 5 | 4 | 5 | 5 | 12 | 15 | 10 | 13 |
| death[c] | 0 | 0 | 1 | 0 | 0 | 0 | 0 | 0 | 0 |
| weight[d], g | 1.71 | 1.64 | 1.55 | 1.63 | 1.22 | 1.51 | 0.87 | 1.46 | 0.88 |
| std[e] | 0.61 | 0.68 | 0.49 | 0.75 | 0.49 | 0.84 | 0.57 | 0.71 | 0.42 |
| regression[f] | -- | -- | 5.7% | -- | 25.2% | -- | 54.0% | -- | 39.9% |
| p[g] | -- | -- | 0.818 | -- | 0.331 | -- | 0.0269 | -- | 0.0231 | a: with 30% PEG
b: the number of mice
c: the number of deaths of mice during the experiment
d: the average weight of the tumor
e: standard deviation of the tumor weights
f: percentage of tumor weight reduction
g: the significance level obtained using a two tail t-test

Fig. 29

MOLECULAR WEIGHTS, CMCs AND MAXIMUM TAXOL LOADINGS OF THE DIBLOCK COPOLYMERS

| POLYMERS | MOLECULAR WEIGHT | | CMC AT 25°C, % | | MAX. TAXOL LOADING, % |
| --- | --- | --- | --- | --- | --- |
| | CALCULATED | GPC | INTENSITY | ANISOTROPY | |
| PDLLA-MePEG | | | | | |
| 2000-50/50 | 4000 | 5632 | 0.016 | 0.012 | 15 |
| 2000-40/60 | 3333 | 5339 | 0.03 | 0.016 | 10 |
| 5000-30/70 | 7142 | 14948 | 0.03 | 0.018 | 5 |
| 5000-20/80 | 6250 | 13745 | -- | -- | 3 |
| PCL-MePEG | | | | | |
| 2000-40/60 | 4000 | 6125 | -- | -- | 30 |
| 5000-30/70 | 7142 | 17703 | -- | -- | 10 |
| PDLLACL-MePEG | | | | | |
| 2000-20/20/60 | 4000 | 5575 | 0.05 | 0.07 | 30 |
| 5000-15/15/70 | 7142 | 15498 | 0.05 | 0.07 | 10 |

*Fig. 43*

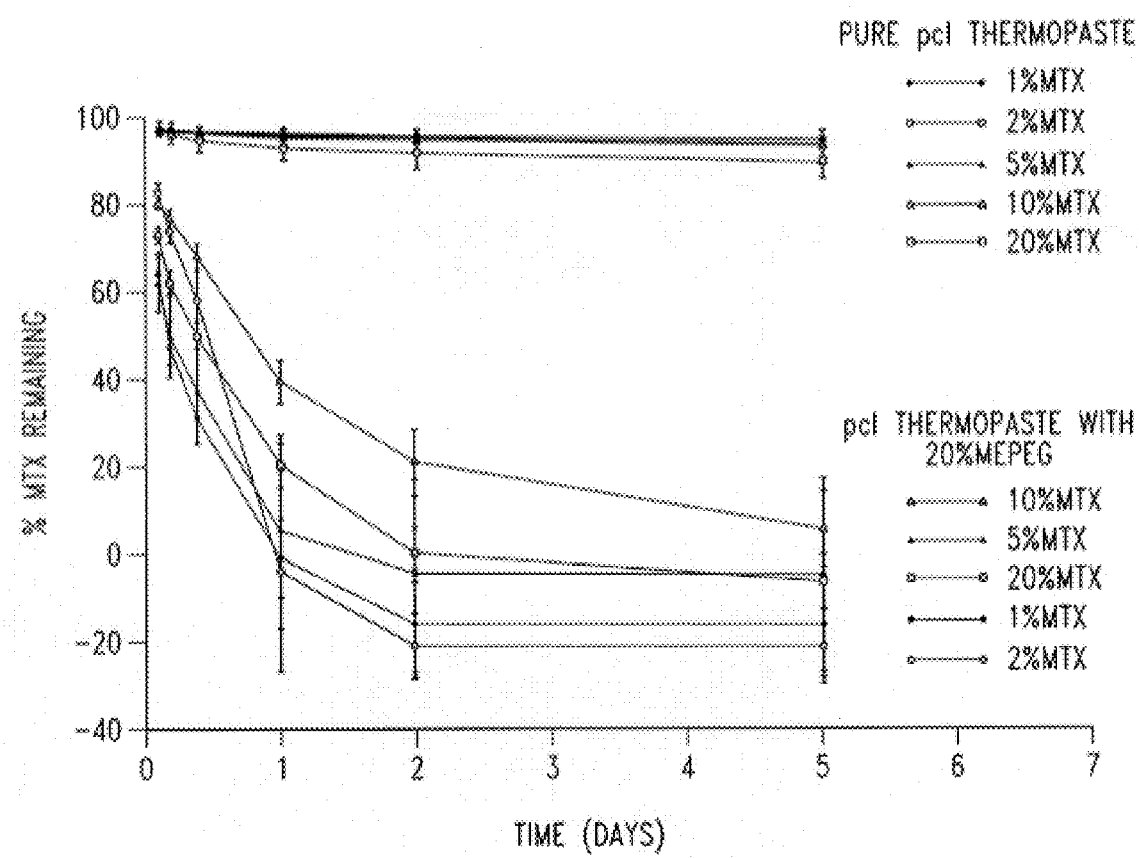
*Fig. 61C*
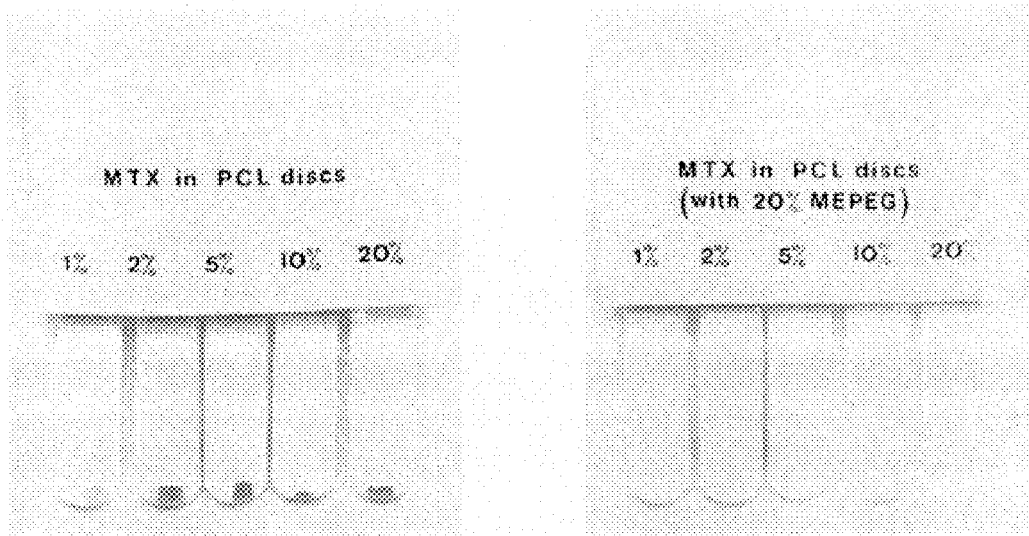
*Fig. 61D*     *Fig. 61E*

1. Effect of BMOV loaded paste on the weights of MDAY-D2 tumours grown in mice.

|  | Tumor Weights (g) | | | |
| --- | --- | --- | --- | --- |
|  | Control | 25% BMOV | 30% BMOV | 35% BMOV |
|  | 1.68 | 1.05 | -- | -- |
|  | 1.01 | 0.48 | -- | -- |
|  | 0.96 | 0.20 | -- | -- |
|  | 0.91 | 0.14 | -- | -- |
|  | 1.23 | 0.80 | -- | -- |
| mean | 1.16 | 0.53 | -- | -- |
| st dev | 0.32 | 0.39 | -- | -- |
|  | 1.15 | -- | 0.02 | 0.36 |
|  | 1.12 | -- | 0.17 | 0.50 |
|  | 1.04 | -- | 0.13 | 0.15 |
|  | 2.05 | -- | 1.40 | 0.69 |
|  | 1.02 | -- | 0.37 | 0.16 |
|  | 2.25 | -- | 0.20 | 0.00 |
| mean | 1.57 | -- | 0.38 | 0.31 |
| st dev | 0.53 | -- | 0.51 | 0.25 |

*Fig. 71*

2. Effect of BMOV loaded PCL:MePEG paste on the weights of RIF-1 tumours grown in mice.

|  |  | Tumor Weights (g) | | |
| --- | --- | --- | --- | --- |
| Animal | Treatment | Day 4 | Day 5 | Day 6 |
| 1 | control | 0.162 | 0.226 | -- |
| 2 | control | 0.131 | 0.146 | 0.114 |
| 3 | control | 0.133 | 0.173 | 0.233 |
| 4 | control | 0.000 | 0.024 | 0.027 |
| 5 | control | 0.122 | 0.148 | 0.161 |
| 6 | control | 0.173 | 0.078 | 0.164 |
| 7-12 | 5% BMOV | 0.000 | 0.000 | 0.000 |

*Fig. 72*

COMPOSITIONS AND METHODS FOR TREATING OR PREVENTING DISEASES OF BODY PASSAGEWAYS

CROSS-REFERENCE TO RELATED APPLICATION

This application is a continuation of U.S. patent application Ser. No. 08/653,207, filed May 24, 1996, now abandoned, which application is incorporated herein by reference in its entirety.

TECHNICAL FIELD

The present invention relates generally to compositions and methods for treating or preventing diseases of body passageways, and more specifically, to compositions comprising therapeutic agents which may be delivered to the external walls of body passageways.

BACKGROUND OF THE INVENTION

There are many passageways within the body which allow the flow of essential materials. These include, for example, arteries and veins, the esophagus, stomach, small and large intestine, biliary tract, ureter, bladder, urethra, nasal passageways, trachea and other airways, and the male and female reproductive tract. Injury, various surgical procedures, or disease can result in the narrowing, weakening and/or obstruction of such body passageways, resulting in serious complications and/or even death.

For example, many types of tumors (both benign and malignant) can result in damage to the wall of a body passageway or obstruction of the lumen, thereby slowing or preventing the flow of materials through the passageway. In 1996 alone, it has been estimated that over 11,200 deaths will occur due to esophageal cancer, over 51,000 deaths due to large and small intestine cancer and nearly 17,000 deaths due to rectal cancer in the United States. Obstruction in body passageways that are affected by cancer are not only in and of themselves life-threatening, they also limit the quality of a patient's life.

The primary treatment for the majority of tumors which cause neoplastic obstruction is surgical removal and/or chemotherapy, radiation therapy or laser therapy. Unfortunately, by the time a tumor causes an obstruction in a body passageway it is frequently inoperable and generally will not responded to traditional therapies. One approach to this problem has been the insertion of endoluminal stents. Briefly, stents are devices placed into the lumen of a body passageway to physically hold open a passageway that has been blocked by a tumor or other tissues/substances. Representative examples of commonly deployed stents include the Wallstent, Stecker stent, Gianturco stent and Palmaz stent (see e.g., U.S. Pat. Nos. 5,102,417, 5,195,984, 5,176, 626, 5,147,370, 5,141,516, 4,776,337). A significant drawback however to the use of stents in neoplastic obstruction is that the tumor is often able to grow into the lumen through the interstices of the stent. In addition, the presence of a stent in the lumen can induce the ingrowth of reactive or inflammatory tissue (e.g., blood vessels, fibroblasts and white blood cells) onto the surface of the stent. If this ingrowth (composed of tumor cells and/or inflammatory cells) reaches the inner surface of the stent and compromises the lumen, the result is re-blockage of the body passageway which the stent was inserted to correct.

Other diseases, which although not neoplastic nevertheless involve proliferation, can likewise obstruct body passageways. For example, narrowing of the prostatic urethra due to benign prostatic hyperplasia is a serious problem affecting 60% of all men over the age of 60 years of age and 100% of all men over the age of 80 years of age. Present pharmacological treatments, such as 5-alphareductase inhibitors (e.g., Finasteride), or alpha-adrenergic blockers (e.g., Terazozan) are generally only effective in a limited population of patients.

Moreover, of the surgical procedures that can be performed (e.g., trans-urethral resection of the prostate (TURPs); open prostatectomy, or endo-urologic procedures such as laser prostatectomy, use of microwaves, hypothermia, cryosurgery or stenting), numerous complications such as bleeding, infection, incontinence, impotence, and recurrent disease, typically result.

In addition to neoplastic or proliferative diseases, other diseases such vascular disease can result in the narrowing, weakening and/or obstruction of body passageways. According to 1993 estimates (source-U.S. Heart and Stroke Foundation homepage), over 60 million Americans have one or more forms of cardiovascular disease. These diseases claimed 954,138 lives in the same year (41% of all deaths in the United States).

Balloon angioplasty (with or without stenting) is one of the most widely used treatments for vascular disease; other options such as laser angioplasty are also available. While this is the treatment of choice in many cases of severe narrowing of the vasculature, about one-third of patients undergoing balloon angioplasty (source Heart and Stoke Foundation homepage) have renewed narrowing of the treated arteries (restenosis) within 6 months of the initial procedure; often serious enough to necessitate further interventions.

Such vascular diseases (including for example, restenosis) are due at least in part to intimal thickening secondary to vascular smooth muscle cell (VSMC) migration, VSMC proliferation, and extra-cellular matrix deposition. Briefly, vascular endothelium acts as a nonthrombogenic surface over which blood can flow smoothly and as a barrier which separates the blood components from the tissues comprising the vessel wall. Endothelial cells also release heparin sulphate, prostacyclin, EDRF and other factors that inhibit platelet and white cell adhesion,VSMC contraction, VSMC migration and VSMC proliferation. Any loss or damage to the endothelium, such as occurs during balloon angioplasty, atherectomy, or stent insertion, can result in platelet adhesion, platelet aggregation and thrombus formation. Activated platelets can release substances that produce vasoconstriction (serotonin and thromboxane) and/or promote VSMC migration and proliferation (PDGF, epidermal growth factor, TGF-β, and heparinase). Tissue factors released by the arteries stimulates clot formation resulting in a fibrin matrix into which smooth muscle cells can migrate and proliferate.

This cascade of events leads to the transformation of vascular smooth muscle cells from a contractile to a secretory phenotype. Angioplasty induced cell lysis and matrix destruction results in local release of basic fibroblast growth factor (bFGF) which in turn stimulates VSMC proliferation directly and indirectly through the induction of PDGF production. In addition to PDGF and bFGF, VSMC proliferation is also stimulated by platelet released EGF and insulin growth factor −1.

Vascular smooth muscle cells are also induced to migrate into the media and intima of the vessel. This is enabled by release and activation of matrix metalloproteases which degrade a pathway for the VSMC through the extra-cellular matrix and internal elastic lamina of the vessel wall. After migration and proliferation the vascular smooth muscle cells then deposit an extra-cellular matrix consisting of gylcosaminoglycans, elastin and collagen which comprises the largest part of intimal thickening. A significant portion of the restenosis process may be due to remodeling of the vascular wall leading to changes in the overall size of the artery; at least some of which is secondary to proliferation within the adventitia (in addition to the media). The net result of these processes is a recurrence of the narrowing of the vascular wall which is often severe enough to require a repeat intervention.

In summary, virtually any forceful manipulation within the lumen of a blood vessel will damage or denude its endothelial lining. Thus, treatment options for vascular diseases themselves and for restenosis following therapeutic interventions continue to be major problems with respect to longterm outcomes for such conditions.

In addition to neoplastic obstructions and vascular disease, there are also a number of acute and chronic inflammatory diseases which result in obstructions of body passages. These include, for example, vasculitis, gastrointestinal tract diseases (e.g. Crohn's disease, ulcerative colitis) and respiratory tract diseases (e.g. asthma, chronic obstructive pulmonary disease).

Each of these diseases can be treated, to varying degrees of success, with medications such as anti-inflammatories or immunosuppressants. Current regimens however are often ineffective at slowing the progression of disease, and can result in systemic toxicity and undesirable side effects. Surgcal procedures can also be utilized instead of or in addition to medication regimens. Such surgical procedures however have a high rate of local recurrence to due to scar formation, and can under certain conditions (e.g., through the use of balloon catheters), result in benign reactive overgrowth.

Other diseases that can also obstruct body passageways include infectious diseases. Briefly, there are a number of acute and chronic infectious processes that can result in the obstruction of body passageways including for example, urethritis, prostatitis and other diseases of the male reproductive tract, various diseases of the female reproductive tract, cystitis and urethritis (diseases of the urinary tract), chronic bronchitis, tuberculosis and other mycobacteria infections and other respiratory problems and certain cardiovascular diseases.

Such diseases are presently treated either by a variety of different therapeutic regimens and/or by surgical procedures. As above however, such therapeutic regimens have the difficulty of associated systemic toxicity that can result in undesired side effects. In addition, as discussed above surgical procedures can result in local recurrence due to scar formation, and in certain procedures (e.g., insertion of commercially available stents), may result in benign reactive overgrowth.

The existing treatments for the above diseases and conditions for the most part share the same limitations. The use of therapeutic agents have not resulted in the reversal of these conditions and whenever an intervention is used to treat the conditions, there is a risk to the patient as a result of the body's response to the intervention. The present invention provides compositions and methods suitable for treating the conditions and diseases which are generally discussed above. These compositions and methods address the problems associated with the existing procedures, offer significant advantages when compared to existing procedures, and in addition, provide other, related advantages.

SUMMARY OF THE INVENTION

Briefly stated, the present invention provides methods for treating or preventing diseases associated with body passageways, comprising the step of delivering to an external portion of the body passageway a therapeutic agent. Within a related aspect, methods for treating or preventing diseases associated with body passageways are provided comprising the step of delivering to smooth muscle cells of said body passageway, via the adventia, a therapeutic agent. By delivering the therapeutic compound locally to the site of disease, systemic and unwanted side effects can be avoided and total dosages can potentially be reduced. Delivery quadrantically or circumferentially around diseased passageway also avoids many of the disadvantages of endoluminal manipulation, including damage to the epithelial lining of the tissue. For example damage to the endothelium can result in thrombosis, changes to laminar flow patterns, and/or a foreign body reaction to an endoluminal device, any of which can initiate the restenosis cascade. In the case of prostatic disease, avoiding instrumentation of the urethra can reduce the likelihood of strictures and preserve continence and potency.

A wide variety of therapeutic agents may be utilized within the scope of the present invention, including for example anti-angiogenic agents, anti-proliferative agents, anti-inflammatory agents, and antibiotics.

Within certain embodiments of the invention, the therapeutic agents may further comprise a carrier (either polymeric or non-polymeric), such as, for example, poly (ethylene-vinyl acetate) (40% crosslinked), copolymers of lactic acid and glycolic acid, poly (caprolactone), poly (lactic acid), copolymers of poly (lactic acid) and poly (caprolactone), gelatin, hyaluronic acid, collagen matrices, and albumen.

The therapeutic agents may be utilized to treat or prevent a wide variety of diseases, including for example, vascular diseases, neoplastic obstructions, inflammatory diseases and infectious diseases. Representative body passageways which may be treated include, for example, arteries, the esophagus, the stomach, the duodenum, the small intestine, the large intestine, biliary tracts, the ureter, the bladder, the urethra, lacrimal ducts, the trachea, bronchi, bronchioles, nasal airways, eustachian tubes, the external auditory canal, uterus and fallopian tubes.

Within one particularly preferred embodiment of the invention, the therapeutic agent is delivered to an artery by direct injection via an outer wall of the artery into the adventia.

These and other aspects of the present invention will become evident upon reference to the following detailed description and attached drawings. In addition, various references are set forth below which describe in more detail certain procedures, devices or compositions, and are therefore incorporated by reference in their entirety.

BRIEF DESCRIPTION OF THE DRAWINGS

FIG. 20 is a table which shows the effect of peri-tumoral injection of paclitaxel-gelatin-PCL paste into mice with established tumors.

FIG. 21 is a table which shows the melting temperature, enthalpy, molecular weight, polydispersity and intrinsic viscosity of PDLLA-PEG-PDLLA compositions.

FIG. 26 is a table which shows the mass loss and polymer composition change of PDLLA-PEG-PDLLA cylinders (loaded with 20% paclitaxel) during the release into PBS albumin buffer at 37° C.

FIG. 29 is a table which shows the efficacy of paclitaxel loaded surgicalpaste formulations applied locally tosubcutaneous tumor in mice.

FIG. 43 is a table which shows the molecular weights, CMCs and maximum paclitaxel loadings of selected diblock copolymers.

FIG. 51B is an underside view of the CAM shown in 51A. Briefly, this view demonstrates the radial appearance of the blood vessels which enter the tumor like the spokes of a wheel. Note that the blood vessel density is greater in the vicinity of the tumor than it is in the surrounding normal CAM tissue. FIG. 51D is taken from the underside of the CAM shown in 51C, and demonstrates the disruption of blood flow into the tumor when compared to control tumor tissue. Note that the blood vessel density is reduced in the vicinity of the tumor and is sparser than that of the normal surrounding CAM tissue.

FIG. 71 is a table which shows the effect of BMOV loaded paste on the weights of MDAY-D2 tumors grown in mice. Briefly, PCL paste (150 mg) containing either 25%, 30%, or 35% BMOV was injected subcutaneously into mice bearing MDAY-2 tumors. Tumor weights were determined after 10 days treatment. This table shows the results from 2 separate experiments using (top table) 25% BMOV and (bottom table) 30% or 35% BMOV. Control data describes mice treated with PCL containing no BMOV.

FIG. 72 is a table which sets forth the effects of BMOV loaded PCL:MePEG paste on the weights of RIF-1 tumors grown in mice. Briefly, RIF-1 tumors were grown in mice for 5 days at which time 90% of the tumor was surgically removed and the resection site treated with 150 mg of PCL:MePEG (80:20, w:w) paste containing either no BMOV (control) or 5% BMOV. Tumor regrowth was determined on days 4, 5 and 6 following this treatment.

FIG. 73A shows the effect of increased loading of BEMOV in PCL thermopaste (150 mg pellet) on the time course of BEMOV released into 15 mL PBS/ALB. FIG. 73B also shows the effect of increase loading of BEMOV in PCL thermopaste (150 mg pellet) on the time course of BEMOV released into 15 mL PBS/ALB. Drug release is expressed as the % of BEMOV remaining in the pellet.

FIG. 74A shows the effect of increased loading of V5 in PCL thermopaste (150 mg pellet) on the time course of V5 released into 15 mL PBS/ALB. FIG. 74B also shows the effect of increase loading of V5 in PCL thermopaste (150 mg pellet) on the time course of V5 released into 15 mL PBS/ALB. Drug release is expressed as the % of V5 remaining in the pellet.

FIG. 75A shows the effect of increased loading of PRC-V in PCL thermopaste (150 mg pellet) on the time course of PRC-V released into 15 mL PBS/ALB. FIG. 75B also shows the effect of increase loading of PRC-V in PCL thermopaste (150 mg pellet) on the time course of PRC-V released into 15 mL PBS/ALB. Drug release is expressed as the % of PRC-V remaining in the pellet.

DETAILED DESCRIPTION OF THE INVENTION

Figure 1:
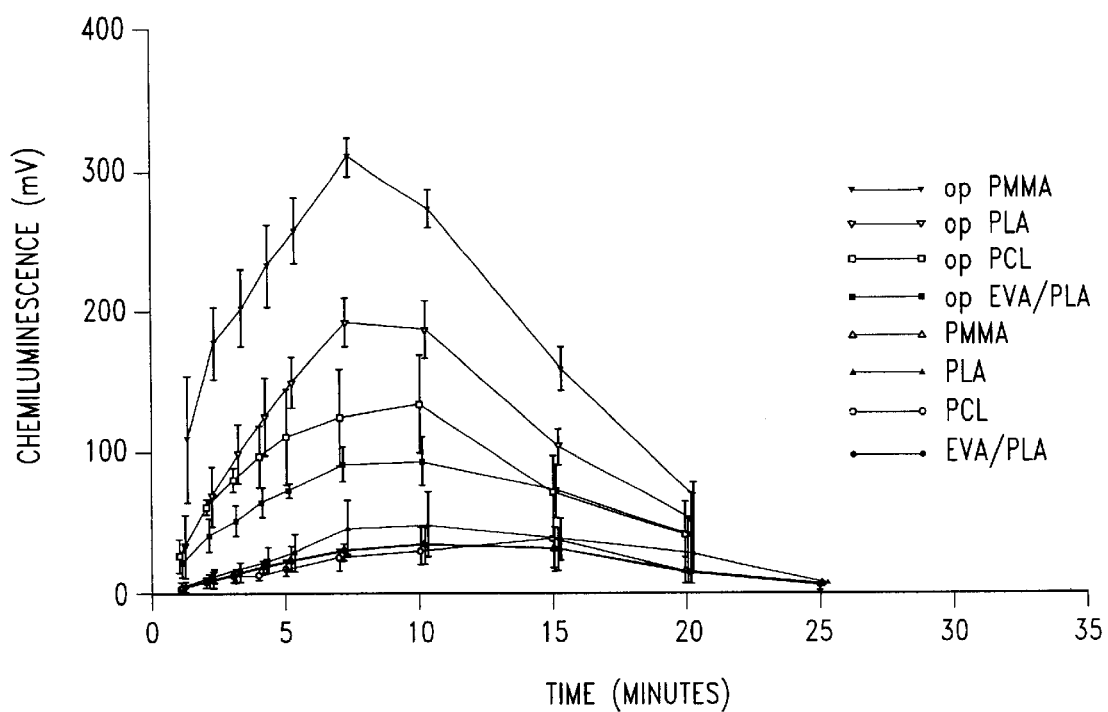
FIG. 1 is a graph which shows the effect of plasma opsonization of polymeric microspheres on the chemiluminescence response of neutrophils (20 mg/ml microspheres in 0.5 ml of cells (conc. $5 \times 10^6$ cells/ml) to PCL microspheres.
Figure 2:
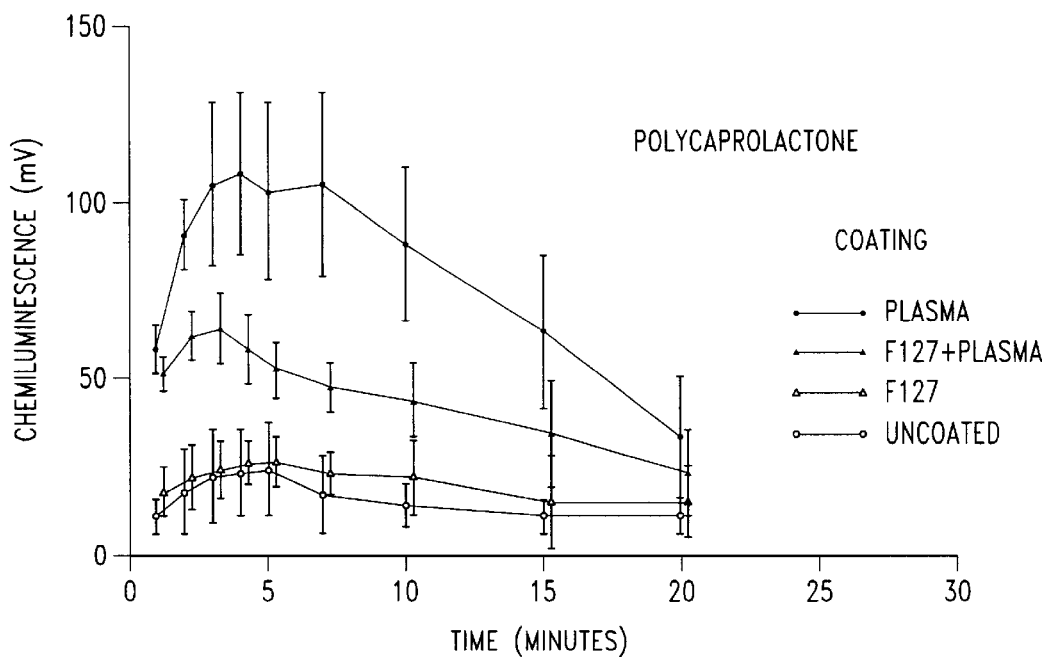
FIG. 2 is a graph which shows the effect of precoating plasma +/-2% pluronic F127 on the chemiluminescence response of neutrophils ($5 \times 10^6$ cells/ml) to PCL microspheres
Figure 3:
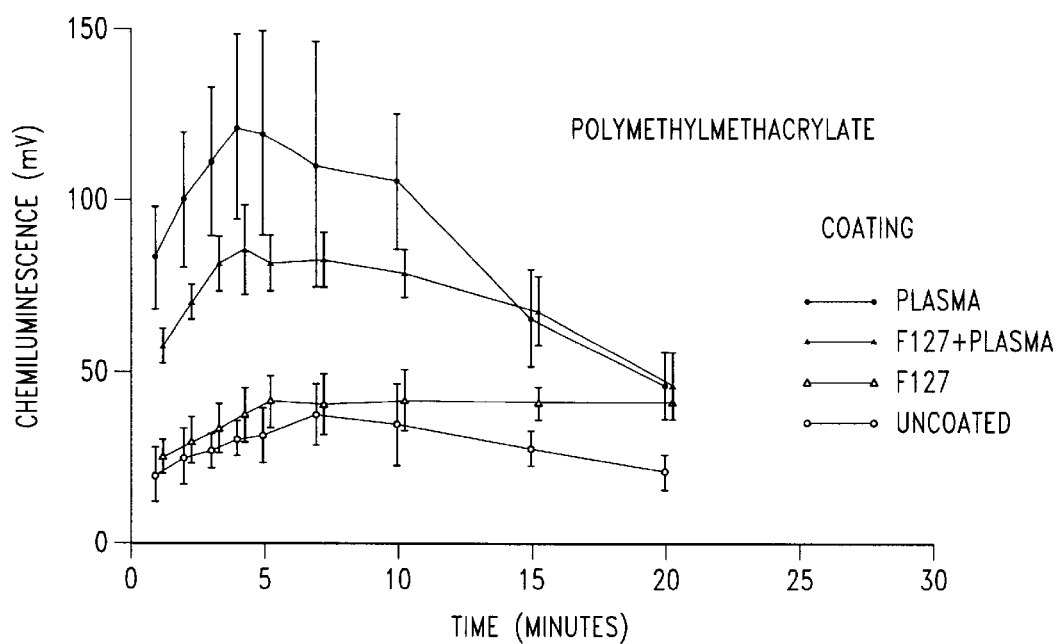
FIG. 3 is a graph which shows the effect of precoating plasma +/−2% pluronic F127 on the chemiluminescence response of neutrophils (5×10⁶ cells/ml) to PMMA microspheres
Figure 4:
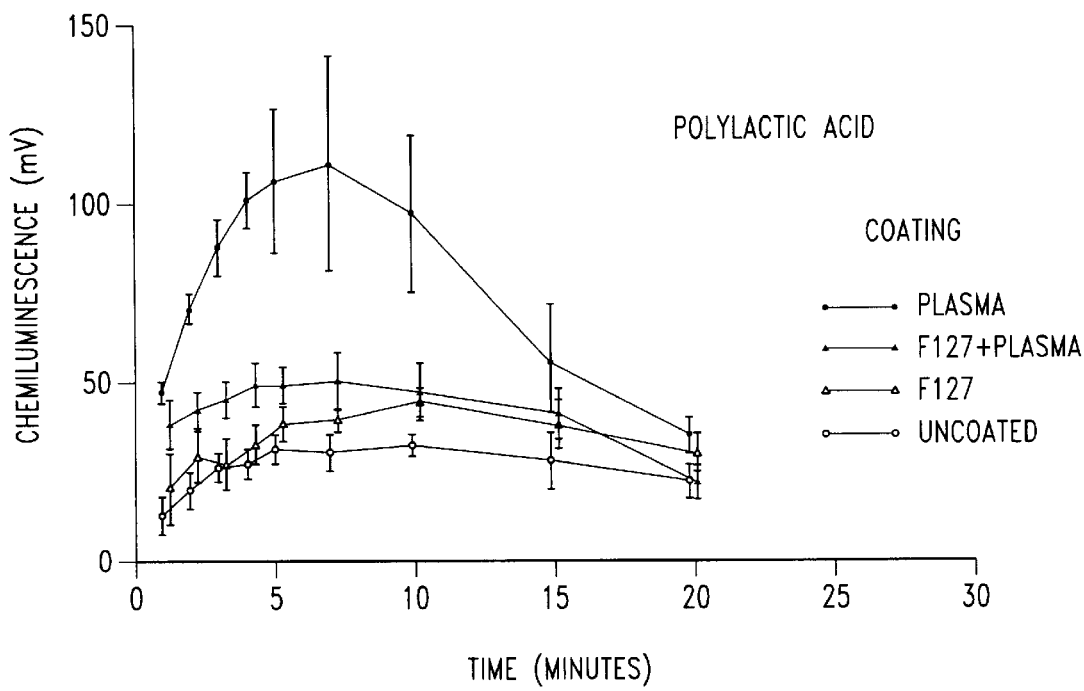
FIG. 4 is a graph which shows the effect of precoating plasma +/−2% pluronic F127 on the chemiluminescence response of neutrophils (5×10⁶ cells/ml) to PLA microspheres
Figure 5:
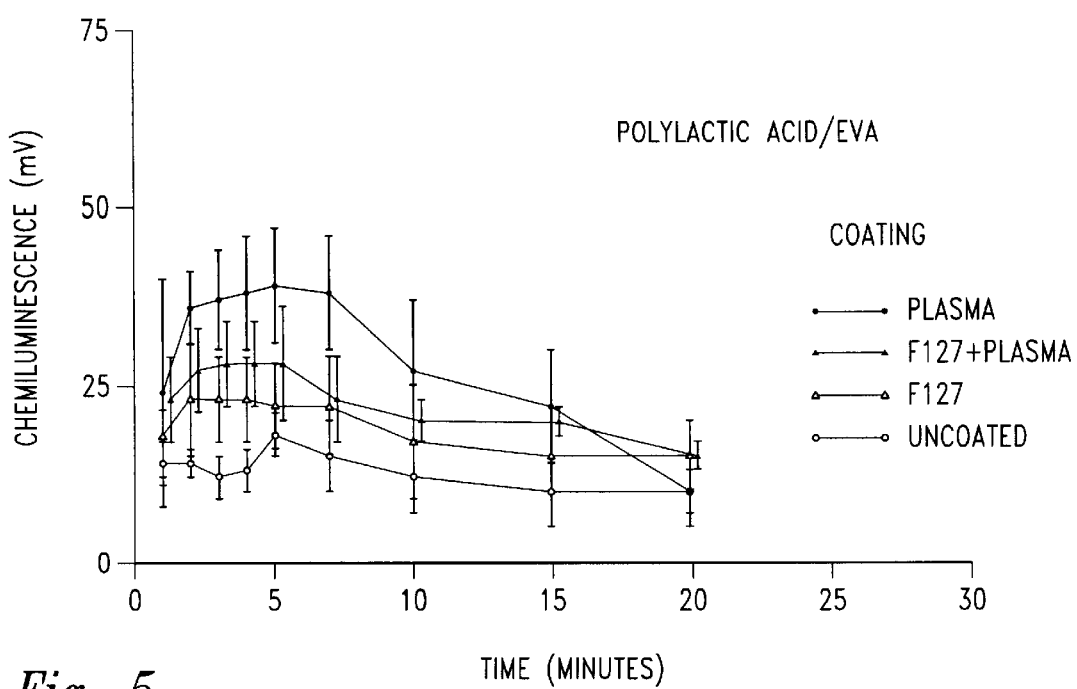
FIG. 5 is a graph which shows the effect of precoating plasma +/−2% pluronic F127 on the chemiluminescence response of neutrophils (5×10⁶ cells/ml) to EVA:PLA microspheres
Figure 6:
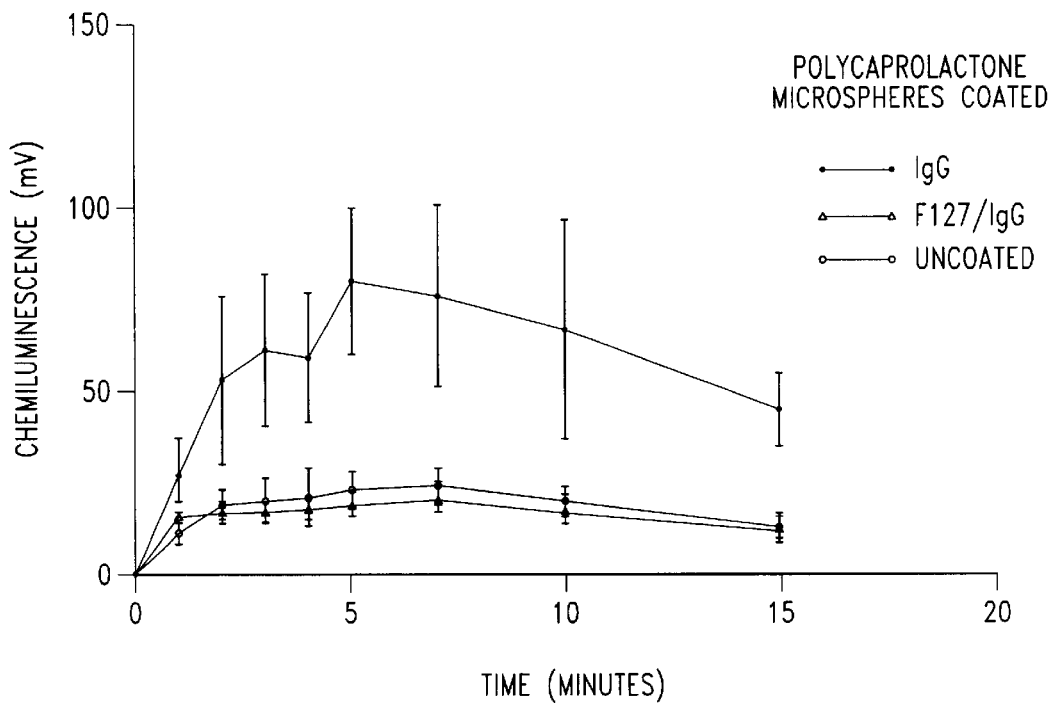
FIG. 6 is a graph which shows the effect of precoating IgG (2 mg/ml), or 2% pluronic F127 then IgG (2 mg/ml) on the chemiluminescence response of neutrophils to PCL microspheres.
Figure 7:
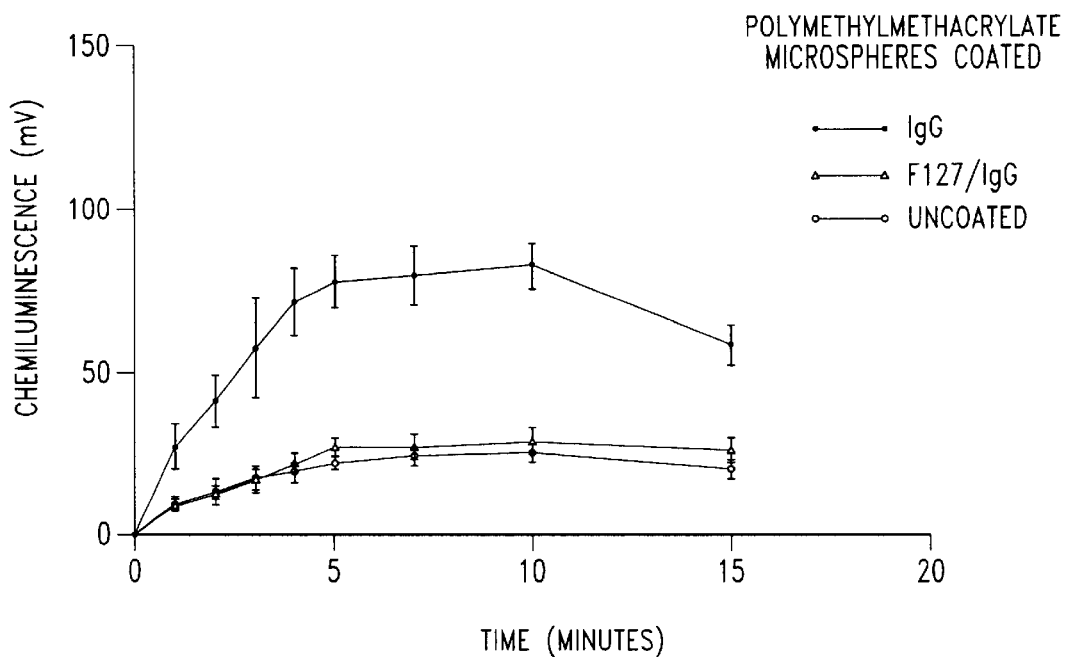
FIG. 7 is a graph which shows the effect of precoating IgG (2 mg/ml), or 2% pluronic F127 then IgG (2 mg/ml) on the chemiluminescence response of neutrophils to PMMA microspheres.
Figure 8:
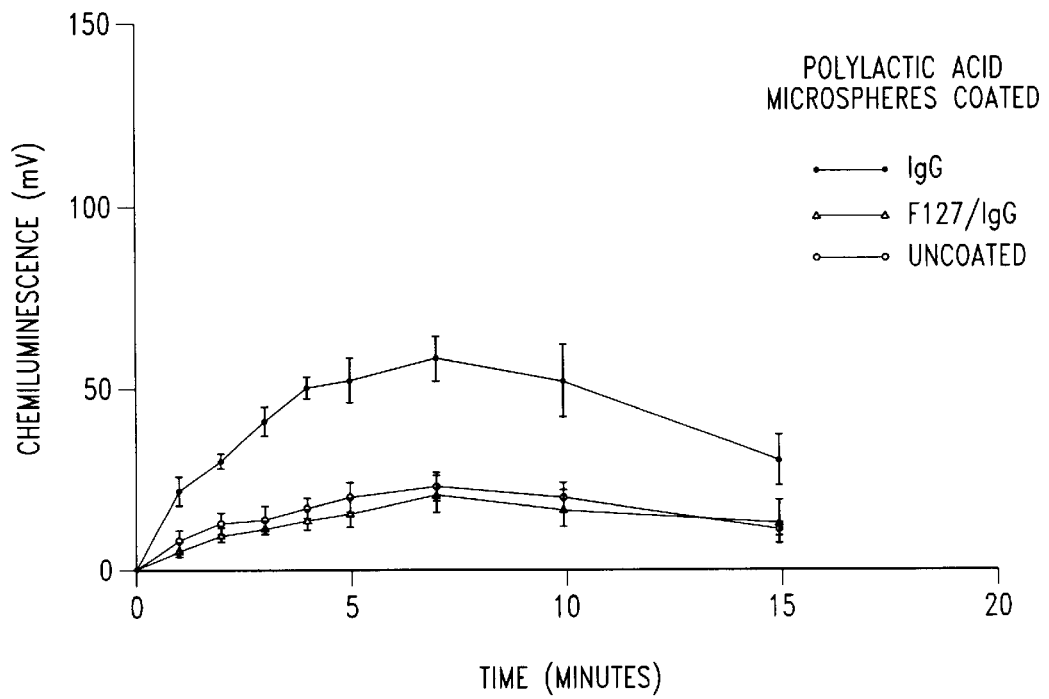
FIG. 8 is a graph which shows the effect of precoating IgG (2 mg/ml), or 2% pluronic F127 then IgG (2 mg/ml) on the chemiluminescence response of neutrophils to PVA microspheres.
Figure 9:
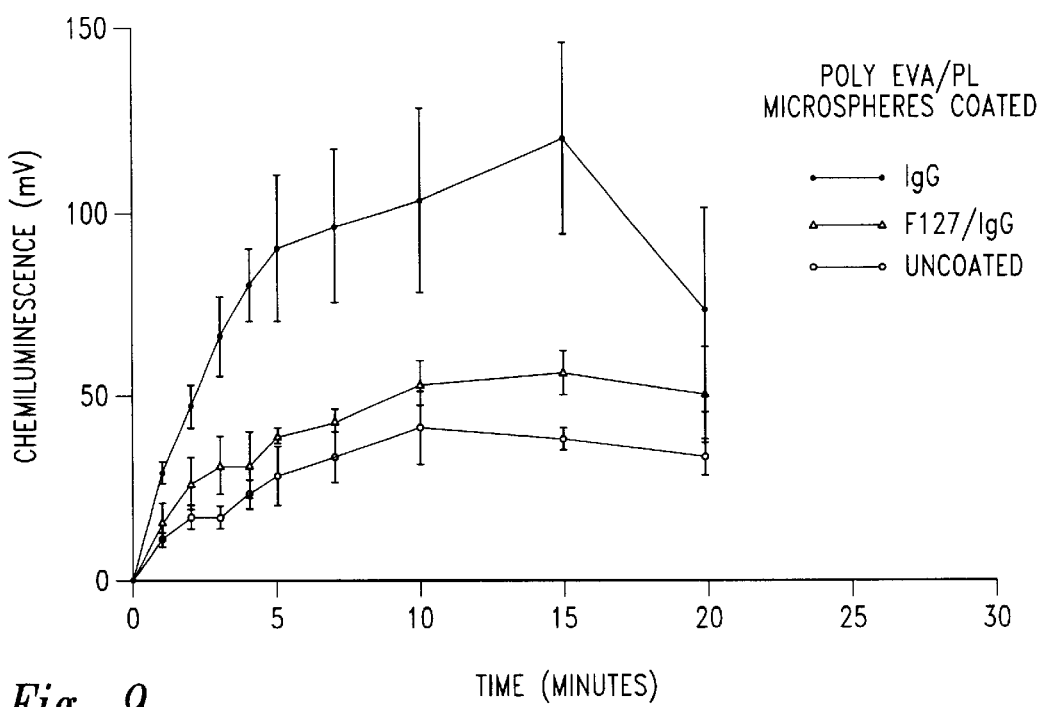
FIG. 9 is a graph which shows the effect of precoating IgG (2 mg/ml), or 2% pluronic F127 then IgG (2 mg/ml) on the chemiluminescence response of neutrophils to EVA:PLA microspheres.

Prior to setting forth the invention, it may be helpful to an understanding thereof to set forth definitions of certain terms that will be used hereinafter.

"Body passageway" as used herein refers to any of number of passageways, tubes, pipes, tracts, canals, sinuses or conduits which have an inner lumen and allow the flow of materials within the body. Representative examples of body passageways include arteries and veins, lacrimal ducts, the trachea, bronchi, bronchiole, nasal passages (including the sinuses) and other airways, eustachian tubes, the external auditory canal, oral cavities, the esophagus, the stomach, the duodenum, the small intestine, the large intestine, biliary tracts, the ureter, the bladder, the urethra, the fallopian tubes, uterus, vagina and other passageways of the female reproductive tract, the vasdeferens and other passageways of the male reproductive tract, and the ventricular system (cerebrospinal fluid) of the brain and the spinal cord.

"Therapeutic agent" as used herein refers to those agents which can mitigate, treat, cure, or prevent a given disease or condition. Representative examples of therapeutic agents are discussed in more detail below, and include, for example, anti-angiogenic agents, anti-proliferative agents, anti-inflammatory agents, and antibiotics.

As noted above, the present invention provides methods for treating or preventing diseases associated with body passageways, comprising the step of delivering to an external portion of the body passageway (i.e., a non-luminal surface), a composition comprising a therapeutic agent, and within preferred embodiments, a compositions comprising a therapeutic agent and a polymeric carrier. Briefly, delivery of a therapeutic agent to an external portion of a body passageway (e.g., quadrantically or circumferentially) avoids many of the disadvantages of traditional approaches which involve endoluminal manipulation. In addition, delivery of a therapeutic agent as described herein allows the administration of greater quantities of the therapeutic agent with less constraint upon the volume to be delivered.

As discussed in more detail below, a wide variety of therapeutic agents may be delivered to external portions of body passageways, either with or without a carrier (e.g., polymeric), in order to treat or prevent a disease associated with the body passageway. Each of these aspects is discussed in more detail below.

Therapeutic Agents

As noted above, the present invention provides methods and compositions which utilize a wide variety of therapeutic agents. Within one aspect of the invention, the therapeutic agent is an anti-angiogenic factor. Briefly, within the context of the present invention anti-angiogenic factors should be understood to include any protein, peptide, chemical, or other molecule which acts to inhibit vascular growth. A variety of methods may be readily utilized to determine the anti-angiogenic activity of a given factor, including for example, chick chorioallantoic membrane ("CAM") assays. Briefly, a portion of the shell from a freshly fertilized chicken egg is removed, and a methyl cellulose disk containing a sample of the anti-angiogenic factor to be tested is placed on the membrane. After several days (e.g., 48 hours), inhibition of vascular growth by the sample to be tested may be readily determined by visualization of the chick chorioallantoic membrane in the region surrounding the methyl cellulose disk. Inhibition of vascular growth may also be determined quantitatively, for example, by determining the number and size of blood vessels surrounding the methyl cellulose disk, as compared to a control methyl cellulose disk. Although anti-angiogenic factors as described herein are considered to inhibit the formation of new blood vessels if they do so in merely a statistically significant manner, as compared to a control, within preferred aspects such anti-angiogenic factors completely inhibits the formation of new blood vessels, as well as reduce the size and number of previously existing vessels.

In addition to the CAM assay described above, a variety of other assays may also be utilized to determine the efficacy of anti-angiogenic factors in vivo, including for example, mouse models which have been developed for this purpose (see Roberston et al., *Cancer. Res.* 51:1339–1344, 1991).

A wide variety of anti-angiogenic factors may be readily utilized within the context of the present invention. Representative examples include Anti-Invasive Factor, retinoic acid and derivatives thereof, Suramin, Tissue Inhibitor of Metalloproteinase-1, Tissue Inhibitor of Metalloproteinase-2, Plasminogen Activator Inhibitor-1, Plasminogen Activator Inhibitor-2, compounds which disrupt microtubule function, and various forms of the lighter "d group" transition metals. These and other anti-angiogenic factors will be discussed in more detail below.

Briefly, Anti-Invasive Factor, or "AIF" which is prepared from extracts of cartilage, contains constituents which are responsible for inhibiting the growth of new blood vessels. These constituents comprise a family of 7 low molecular weight proteins (<50,000 daltons) (Kuettner and Pauli, "Inhibition of neovascularization by a cartilage factor" in *Development of the Vascular System*, Pitman Books (CIBA Foundation Symposium 100), pp. 163–173, 1983), including a variety of proteins which have inhibitory effects against a variety of proteases (Eisentein et al, *Am. J. Pathol.* 81:337–346, 1975; Langer et al., *Science* 193:70–72, 1976; and Horton et al., *Science* 199:1342–1345, 1978). AIF suitable for use within the present invention may be readily prepared utilizing techniques known in the art (e.g., Eisentein et al, supra; Kuettner and Pauli, supra; and Langer et al., supra). Purified constituents of AIF such as Cartilage-Derived Inhibitor ("CDI") (see Moses et al., *Science* 248:1408–1410, 1990) may also be readily prepared and utilized within the context of the present invention.

Retinoic acids alter the metabolism of extracellular matrix components, resulting in the inhibition of angiogenesis. Addition of proline analogs, angiostatic steroids, or heparin may be utilized in order to synergistically increase the anti-angiogenic effect of transretinoic acid. Retinoic acid, as well as derivatives thereof which may also be utilized in the context of the present invention, may be readily obtained from commercial sources, including for example, Sigma Chemical Co. (# R2625).

Suramin is a polysulfonated naphthylurea compound that is typically used as a trypanocidal agent. Briefly, Suramin blocks the specific cell surface binding of various growth factors such as platelet derived growth factor ("PDGF"), epidermal growth factor ("EGF"), transforming growth factor ("TGF-$\beta$"), insulin-like growth factor ("IGF-1"), and fibroblast growth factor ("$\beta$FGF"). Suramin may be prepared in accordance with known techniques, or readily obtained from a variety of commercial sources, including for example Mobay Chemical Co., New York. (see Gagliardi et al., *Cancer Res.* 52:5073–5075, 1992; and Coffey, Jr., et al., *J. of Cell. Phys.* 132:143–148, 1987).

Tissue Inhibitor of Metalloproteinases-1 ("TIMP") is secreted by endothelial cells which also secrete MMPases. TIMP is glycosylated and has a molecular weight of 28.5 kDa. TIMP-1 regulates angiogenesis by binding to activated metalloproteinases, thereby suppressing the invasion of blood vessels into the extracellular matrix. Tissue Inhibitor of Metalloproteinases-2 ("TIMP-2") may also be utilized to inhibit angiogenesis. Briefly, TIMP-2 is a 21 kDa nonglycosylated protein which binds to metalloproteinases in both the active and latent, proenzyme forms. Both TIMP-1 and TIMP-2 may be obtained from commercial sources such as Synergen, Boulder, Colo.

Plasminogen Activator Inhibitor-1 (PA) is a 50 kDa glycoprotein which is present in blood platelets, and can also be synthesized by endothelial cells and muscle cells. PAI-1 inhibits t-PA and urokinase plasminogen activator at the basolateral site of the endothelium, and additionally regulates the fibrinolysis process. Plasminogen Activator Inhibitor-2 (PAI-2) is generally found only in the blood under certain circumstances such as in pregnancy, and in the presence of tumors. Briefly, PAI-2 is a 56 kDa protein which is secreted by monocytes and macrophages. It is believed to regulate fibrinolytic activity, and in particular inhibits urokinase plasminogen activator and tissue plasminogen activator, thereby preventing fibrinolysis.

Therapeutic agents of the present invention also include compounds which disrupt microtubule function. Representative examples of such compounds include estramustine (available from Sigma; Wang and Stearns *Cancer Res.*

48:6262–6271, 1988), epothilone, curacin-A, colchicine, methotrexate, and paclitaxel, vinblastine, vincristine, $D_2O$ and 4-tert-butyl-[3-(2-chloroethyl)ureido]benzene ("tBCEU"). Briefly, such compounds can act in several different manners. For example, compounds such as colchicine and vinblastine act by depolymerizing microtubules.

Within one preferred embodiment of the invention, the therapeutic agent is paclitaxel, a compound which disrupts microtubule formation by binding to tubulin to form abnormal mitotic spindles. Briefly, paclitaxel is a highly derivatized diterpenoid (Wani et al., *J. Am. Chem. Soc.* 93:2325, 1971) which has been obtained from the harvested and dried bark of *Taxus brevifolia* (Pacific Yew.) and Taxomyces Andreanae and Endophytic Fungus of the Pacific Yew (Stierle et al., *Science* 60:214–216, 1993). "Paclitaxel" (which should be understood herein to include prodrugs, analogues and derivatives such as, for example, TAXOL®, TAXOTERE®, 10-desacetyl analogues of paclitaxel and 3'N-desbenzoyl-3'N-t-butoxy carbonyl analogues of paclitaxel) may be readily prepared utilizing techniques known to those skilled in the art (see WO 94/07882, WO 94/07881, WO 94/07880, WO 94/07876, WO 93/23555, WO 93/10076, W094/00156, WO 93/24476, EP 590267, WO 94/20089; U.S. Pat. Nos. 5,294,637, 5,283,253, 5,279,949, 5,274,137, 5,202,448, 5,200,534, 5,229,529, 5,254,580, 5,412,092, 5,395,850, 5,380,751, 5,350,866, 4,857,653, 5,272,171, 5,411,984, 5,248,796, 5,248,796, 5,422,364, 5,300,638, 5,294,637, 5,362,831, 5,440,056, 4,814,470, 5,278,324, 5,352,805, 5,411,984, 5,059,699, 4,942,184; *Tetrahedron Letters* 35(52):9709–9712, 1994; *J. Med. Chem.* 35:4230–4237, 1992; *J. Med. Chem.* 34:992–998, 1991; *J. Natural Prod.* 57(10):1404–1410, 1994; *J. Natural Prod.* 57(11):1580–1583, 1994; *J. Am. Chem. Soc.* 110:6558–6560, 1988), or obtained from a variety of commercial sources, including for example, Sigma Chemical Co., St. Louis, Mo. (T7402—from *Taxus brevifolia*).

Representative examples of such paclitaxel derivatives or analogues include 7-deoxy-docetaxol, 7,8-Cyclopropataxanes, N-Substituted 2-Azetidones, 6,7-Epoxy Paclitaxels, 6,7-Modified Paclitaxels, 10-Desacetoxytaxol, 10-Deacetyltaxol (from 10-deacetylbaccatin III), Phosphonooxy and Carbonate Derivatives of Taxol, Taxol 2',7-di (sodium 1,2-benzenedicarboxylate, 10-desacetoxy-11,12-dihydrotaxol-10,12(18)-diene derivatives, 10-desacetoxytaxol, Protaxol (2'-and/or 7-O-ester derivatives), (2'-and/or 7-O-carbonate derivatives), Asymmetric Synthesis of Taxol Side Chain, Fluoro Taxols, 9-deoxotaxane, (13-acetyl-9-deoxobaccatine III, 9-deoxotaxol, 7-deoxy-9-deoxotaxol, 10-desacetoxy-7-deoxy-9-deoxotaxol, Derivatives containing hydrogen or acetyl group and a hydroxy and tert-butoxycarbonylamino, sulfonated 2'-acryloyltaxol and sulfonated 2'-O-acyl acid taxol derivatives, succinyltaxol,2'-γ-aminobutyryltaxol formate, 2'-acetyl taxol, 7-acetyl taxol, 7-glycine carbamate taxol, 2'-OH-7-PEG(5000)carbamate taxol, 2'-benzoyl and 2',7-dibenzoyl taxol derivatives, other prodrugs (2'-acetyltaxol; 2',7-diacetyltaxol; 2'succinyltaxol; 2'-(beta-alanyl)-taxol); 2'gamma-aminobutyryltaxol formate; ethylene glycol derivatives of 2'-succinyltaxol; 2'-glutaryltaxol; 2'-(N,N-dimethylglycyl)taxol; 2'-[2-(N,N-dimethylamino) propionyl]taxol; 2'orthocarboxybenzoyl taxol; 2'aliphatic carboxylic acid derivatives of taxol, Prodrugs {2'(N,N-diethylaminopropionyl)taxol, 2'(N,N-dimethylglycyl)taxol, 7(N,N-dimethylglycyl)taxol, 2',7-di-(N,N-dimethylglycyl) taxol, 7(N,N-diethylaminopropionyl)taxol, 2',7-di(N,N-diethylaminopropionyl)taxol, 2'-(L-glycyl)taxol, 7-(L-glycyl)taxol, 2',7-di(L-glycyl)taxol, 2'-(L-alanyl)taxol, 7-(L-alanyl)taxol, 2',7-di(L-alanyl)taxol, 2'-(L-leucyl)taxol, 7-(L-leucyl)taxol, 2',7-di(L-leucyl)taxol, 2'-(L-isoleucyl) taxol, 7-(L-isoleucyl)taxol, 2',7-di(L-isoleucyl)taxol, 2'-(L-valyl)taxol, 7-(L-valyl)taxol, 2',7-di(L-valyl)taxol, 2'-(L-phenylalanyl)taxol, 7-(L-phenylalanyl)taxol, 2',7-di(L-phenylalanyl)taxol, 2'-(L-prolyl)taxol, 7-(L-prolyl)taxol, 2',7-di(L-prolyl)taxol, 2'-(L-lysyl)taxol, 7-(L-lysyl)taxol, 2',7-di(L-lysyl)taxol, 2'-(L-glutamyl)taxol, 7-(L-glutamyl) taxol, 2',7-di(L-glutamyl)taxol, 2'-(L-arginyl)taxol, 7-(L-arginyl)taxol, 2',7-di(L-arginyl)taxol}, Taxol analogs with modified phenylisoserine side chains, taxotere, (N-debenzoyl-N-tert-(butoxycaronyl)-10-deacetyltaxol, and taxanes (e.g., baccatin III, cephalomannine, 10-deacetylbaccatin III, brevifoliol, yunantaxusin and taxusin)

Other therapeutic agents which may be utilized within the present invention include lighter "d group" transition metals, such as, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate (i.e., $VO_3^-$) and orthovanadate (i.e., $VO_4^{3-}$) complexes such as, for example, ammonium metavanadate (i.e., $NH_4VO_3$), sodium metavanadate (i.e., $NaVO_3$), and sodium orthovanadate (i.e., $Na_3VO_4$). Suitable vanadyl (i.e., $VO^{2+}$) complexes include, for example, vanadyl acetylacetonate and vanadyl sulfate including vanadyl sulfate hydrates such as vanadyl sulfate mono- and trihydrates, Bis[maltolato (oxovanadium)] (IV)] ("BMOV"), Bis[(ethylmaltolato) oxovanadium] (IV) ("BEOV"), and Bis(cysteine, amide N-octyl)oxovanadium (IV) ("naglivan").

Representative examples of tungsten and molybdenum complexes also include oxo complexes. Suitable oxo tungsten complexes include tungstate and tungsten oxide complexes. Suitable tungstate (i.e., $WO_4^{2-}$) complexes include ammonium tungstate (ie., $(NH_4)_2WO_4$), calcium tungstate (i.e., $CaWO_4$), sodium tungstate dihydrate (i.e., $Na_2WO_4.2H_2O$), and tungstic acid (i.e., $H_2WO_4$). Suitable tungsten oxides include tungsten (IV) oxide (i.e., $WO_2$) and tungsten (VI) oxide (i.e., $WO_3$). Suitable oxo molybdenum complexes include molybdate, molybdenum oxide, and molybdenyl complexes. Suitable molybdate (i.e., $MoO_4^{2-}$) complexes include ammonium molybdate (i.e., $(NH_4)_2MoO_4$) and its hydrates, sodium molybdate (i.e., $Na_2MoO_4$) and its hydrates, and potassium molybdate (i.e., $K_2MoO_4$) and its hydrates. Suitable molybdenum oxides include molybdenum (VI) oxide (i.e., $MoO_2$), molybdenum (VI) oxide (i.e., $MoO_3$), and molybdic acid. Suitable molybdenyl (i.e., $MoO_2^{2+}$) complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include Platelet Factor 4 (Sigma Chemical Co., #F1385); Protamine Sulphate (Clupeine) (Sigma Chemical Co., #P4505); Sulphated Chitin Derivatives (prepared from queen crab shells), (Sigma Chemical Co., #C3641; Murata et al., *Cancer Res.* 51:22–26, 1991); Sulphated Polysaccharide Peptidoglycan Complex (SP-PG) (the function of this compound may be enhanced by the presence of steroids such as estrogen, and tamoxifen citrate); Staurosporine (Sigma Chemical Co., #S4400); Modulators of Matrix Metabolism, including for example, proline analogs {[(L-azetidine-2-carboxylic acid (LACA) (Sigma Chemical Co., #A0760)), cishydroxyproline, d,L-3,4-dehydroproline (Sigma Chemical Co., #D0265), Thiaproline (Sigma Chemical Co., #T0631)], α,α-dipyridyl (Sigma Chemical Co., #D7505), β-aminopropionitrile fumarate (Sigma Chemical Co., #A3134)]}; MDL 27032 (4-propyl-5-(4-pyridinyl)-2(3H)-oxazolone; Merion Merrel Dow Research Institute); Methotrexate (Sigma Chemical Co., #A6770; Hirata et al., *Arthritis and Rheumatism* 32:1065–1073, 1989); Mitoxantrone (Polverini and Novak, *Biochem. Biophys. Res. Comm.* 140:901–907); Heparin (Folkman, *Bio. Phar.* 34:905–909, 1985; Sigma Chemical Co., #P8754); Interferons (e.g., Sigma Chemical Co., #13265); 2 Macroglobulin-serum (Sigma Chemical Co., #M7151); ChIMP-3 (Pavloff et al., *J. Bio. Chem.* 267:17321–17326, 1992); Chymostatin (Sigma Chemical Co., #C7268; Tomkinson et al., *Biochem J.* 286:475–480, 1992); β-Cyclodextrin Tetradecasulfate (Sigma Chemical Co., #C4767); Eponemycin; Camptothecin; Fumagillin and derivatives (Sigma Chemical Co., #F6771; Canadian Patent No. 2,024,306; Ingber et al., *Nature* 348:555–557, 1990); Gold Sodium Thiomalate ("GST"; Sigma:G4022; Matsubara and Ziff, *J. Clin. Invest.* 79:1440–1446, 1987); (D-Penicillamine ("CDPT"; Sigma Chemical Co., #P4875 or P5000(HCl)); β-1-anticollagenase-serum; α2-antiplasmin (Sigma Chem. Co.:A0914; Holmes et al., *J. Biol. Chem.* 262(4):1659–1664, 1987); Bisantrene (National Cancer Institute); Lobenzarit disodium (N-(2)-carboxyphenyl-4-chloroanthronilic acid disodium or "CCA"; Takeuchi et al., *AgentsActions* 36:312–316, 1992); Thalidomide; Angostatic steroid; AGM-1470; carboxynaminolmidazole; and metalloproteinase inhibitors such as BB94, estrogen and estrogen analogues, antiestrogens, antioxidants, bioflavonoids (Pycnogenol), ether lipids (s-phosphonate, ET-18-OCH$_3$), tyrosine kinase inhibitors (genisteine, erbstatin, herbamycin A, lavendustine-c, hydroxycinnamates), a chemokines [Human interferon-inducible protein 10 (IP-10)], —C—X—C— Chemokines (Gro-beta), Nitric Oxide, Antifungal Agents (Radicicol), 15-deoxyspergualin, Metal Complexes (Titanocene dichloride—cyclopentadienyl titanium dichloride), Triphenylmethane Derivatives (aurintricarboxylic acid), Linomide, Thalidomide, IL-12, Heparinase, Angiostatin, Antimicrobial Agents (Minocycline), Plasma Proteins (Apolipoprotein E), Anthracyclines (TAN-1 120), Proliferin-Related Protein, FR-111142, Saponin of *Panax ginseng* (Ginsenoside-Rb2), Pentosan polysulfate Compositions of the present invention may also contain a wide variety of other therapeutic agents, including for example: α-adrenergic blocking agents, angiotensin II receptor antagonists and receptor antagonists for histamine, serotonin, endothelin; inhibitors of the sodium/hydrogen antiporter (e.g., amiloride and its derivatives); agents that modulate intracellular $Ca^{2+}$ transport such as L-type (e.g., diltiazem, nifedipine, verapamil) or T-type $Ca^{2+}$ channel blockers (e.g., amiloride), calmodulin antagonists (e.g., H$_7$) and inhibitors of the sodium/calcium antiporter (e.g., amiloride); ap-1 inhibitors (for tyrosine kinases, protein kinase C, myosin light chain kinase, $Ca^{2+}$/calmodulin kinase II, casein kinase II); anti-depressants (e.g., amytriptyline, fluoxetine, LUVOX® and PAXIL®); cytokine and/or growth factors, as well as their respective receptors, (e.g., the interleukins, α, β or γ-IFN, GM-CSF, G-CSF, epidermal growth factor, transforming growth factors alpha and beta, TNF, and antagonists of vascular epithelial growth factor, endothelial growth factor, acidic or basic fibroblast growth factors, and platelet dervived growth factor); inhibitors of the IP$_3$ receptor (e.g., heparin); protease and collagenase inhibitors (e.g., TIMPs, discussed above); nitrovasodilators (e.g., isosorbide dinitrate); anti-mitotic agents (e.g., colchicine, anthracyclines and other antibiotics, folate antagonists and other anti-metabolites, vinca alkaloids, nitrosoureas, DNA alkylating agents, topoisomerase inhibitors, purine antagonists and analogs, pyrimidine antagonists and analogs, alkyl sulfonates); immunosuppressive agents (e.g., adrenocorticosteroids, cyclosporine); sense or antisense oligonucleotides (e.g., DNA, RNA, nucleic acid analogues (e.g., peptide nucleic acids) or any combinations of these); and inhibitors of transcription factor activity (e.g., lighter d group transition metals).

Other therapeutic agents that can be utilized within the present invention include a wide variety of antibiotics, including antibacterial, antimicrobial, antiviral, antiprotozoal and antifungal agents. Representative examples of such agents include systemic antibiotics such as aminoglycosides (e.g., streptomycin, amikacin, gentamicin, netilmicin, tobramycin); 1st, 2nd, and 3rd generation cephalosporins (e.g., cephalothin, cefazolin, cephapirin, cephradine, cephalexin, cefadroxil, cefaclor, cefamandole, cefuroxime, cefuroxime axetil, cefonicid, ceforanide, cefoxitin, cefotaxime, cefotetan, ceftizoxime, cefoperazone, ceftazidime, ceftriaxone, moxalactam, other semisynthetic cephalosporins such as cefixime and cefpodoxime proxetil); penicillins (e.g., penicillin G (benzathine and procaine salts), cloxacillin, dicloxacillin, methicillin, nafcillin, oxacillin, penicillin V, ampicillin, amoxicillin, bacampicillin, cyclacillin, carbenicillin, ticarcillin, mezlocillin, piperacillin, azlocillin, amdinocillin, and penicillins combined with clavulanic acid); quinolones (e.g., cinoxacin, ciprofloxacin, nalidixic acid, norfloxacin, pipemidic acid, perloxacin, fleroxacin, enoxacin, ofloxacin, tosufloxacin, lomefloxacin, stereoisomers of the quinolones); sulfonamides (e.g., sulfacytine, sulfamethizole, sulfamethoxazole, sufisoxazole, sulfasalazine, and trimethoprim plus sulfamethoxazole combinations); tetracyclines (e.g., doxycycline, demeclocycline, methacycline, minocycline, oxytetracycline, tetracycline); macrolides (e.g., erythromycins, other semisythetic macrolides such as azithromycin and clarithromycin); monobactams (new synthetic class) (e.g.,aztreonam, loracarbef); and miscellaneous agents such as actinomycin D, doxorubicin, mitomycin C, novobiocin, plicamycin, rifampin, bleomycin, chloramphenicol, clindamycin, oleandomycin, kanamycin, lincomycin, neomycin, paromomycin, spectinomycin, troleandomycin, amphotericin B, colistin, nystatin, polymyxin B, griseofulvin, aztreonam, cycloserine, clindamycin, colistimethate, imipenem-cilastatin, methenamine, metronidazole, nitrofurantoin, rifabutan, spectinomycin, trimethoprim, bacitracin, vancomycin, other β-lactam antibiotics.

Further therapeutic agents that can be utilized within the present invention include topical antibiotics such as bacitracin, zinc, neomycin, mupirocin, clindamcin; antipathogenic polypeptides such as cecropionins, mangainins; and Antitubercular agents such as sulfadimethoxine, sulfisoxazole, sulfisomidine, ethambutor hydrochloride, isoniazide, calcium paraaminosalicylate.

Other therapeutic agents that can be utilized within the present invention include antibiotics such as iodine, povidone iodine, boric acid, sodium borate, oxydale, potassium permanganate, ethanol, isopropanol, formalin, cresol, dimazole, siccanin, phenyliodoundecynoate, hexachlorophene, resorcin, benzethonin chloride, sodium lauryl sulfate, mercuric chloride, mercurochrome, silver sulfadiazine and other inorganic and organic silver and zinc salts, salts of mono- and divalent cations, chlorhexidine gluconate, alkylpolyaminoethylglycine hydrochloride, benzalkonium chloride, nitrofurazone, nystatin, acesulfamin, clotrimazole, sulfamethizole, sulfacetamide, diolamine, tolnaftate, pyrrolnitrin, undecylenic acid, microazole, variotin, haloprogin, and dimazole, (meclocycline, trichomycin and pentamycin), penicillins. Antifungal agents include flucytosine, fluconazole, griseofulvin, ketoconazole and miconazole. Antiviral and AIDS agents include acyclovir, amantadine, didanosine (formerly ddI), griseofulvin, flucytosine, foscamet, ganciclovir, idoxuridine, miconazole, clotrimazole, pyrimethamine, ribavirin, rimantadine, stavudine (formerly d4T), trifluridine, trisulfapyrimidine, valacyclovir, vidarabine, zalcitabine (formerly ddC) and zidovudine (formerly AZT). Adjunct therapeutic agents for AIDS (e.g., erythropoietin; fluconazole (antifungal); interferon alpha-2a and -2b (Kaposi's sarcoma); atovaquone, pentamidine and trimetrexate (antiprotozoal); megestraol acetate (appetite enhancer); rifabutin (antimycobacterial). Representative examples of antiprotozoal agents include: pentamidine isethionate, quinine, chloroquine, and mefloquine.

Other therapeutic agents that can be utilized within the present invention include anti-proliferative, anti-neoplastic or chemotherapeutic agents. Representative examples of such agents include androgen inhibitors, antiestrogens and hormones such as flutamide, leuprolide, tamoxifen, estradiol, estramustine, megestrol, diethylstilbestrol, testolactone, goserelin, medroxyprogesterone; Cytotoxic agents such as altretamine, bleomycin, busulfan, carboplatin, carmustine(BiCNU), cisplantin, cladribine, dacarbazine, dactinomycin, daunorubicin, doxorubicin, estramustine, etoposide, lomustine, cyclophosphamide, cytarabine, hydroxyurea, idarubicin, interferon alpha-2a and -2b, ifosfamide, mitoxantrone, mitomycin, paclitaxel, streptozocin, teniposide, thiotepa, vinblastine, vincristine, vinorelbine; Antimetabolites and antimitotic agents such as floxuridine, 5-fluorouracil, fluarabine, interferon alpha-2a and -2b, leucovorin, mercaptopurine, methotrexate, mitotane, plicamycin, thioguanine, colchicine, anthracyclines and other antibiotics, folate antagonists and other anti-metabolites, vinca alkaloids, nitrosoureas, DNA alkylating agents, purine antagonists and analogs, pyrimidine antagonists and analogs, alkyl solfonates; enzymes such as asparaginase, pegaspargase; radioactive agents (e.g., Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212 and Bi-212), toxins (e.g., ricin, abrin, diphtheria toxin, cholera toxin, gelonin, pokeweed antiviral protein, tritin, Shigella toxin, and Pseudomonas exotoxin A), adjunct therapeutic agents such as granisetron and ondansetron (antinauseants, antiemetics), dexrazoxane (cardiomyopathy), gallium nitrate (hypercalcemia), GCSF and GMSCF (chemotherapy and BMT), IL-1 alpha, IL-2, IL-3, IL-4, levamisole, pilocarpine (saliva generation in radiation therapy setting), strontium 89 (bone tumors).

Further therapeutic agents that can be utilized within the present invention include Cardiovascular agents; Antihypertensive agents; Adrenergic blockers and stimulators (e.g., doxazosin, guanadrel, guanethidine, pheoxybenzamine, prazosin plus polythiazide, terazosin, methyldopa, clonidine, guanabenz, guanfacine); Alpha-/beta-adrenergic blockers (e.g., Labetalol); angiotensin converting enzyme (ACE) inhibitors (e.g., benazepril, catopril, enalapril, enalaprilat, fosinopril, lisinopril, moexipril, quinapril, ramipril, and combinations with calcium channel blockers and diuretics; ACE-receptor antagonists (e.g., losartan); Beta blockers (e.g., acebutolol, atenolol, betaxolol, bisoprolol, carteolol, esmolol, fimolol, pindolol, propranolol, penbatolol, metoprolol, nadolol, sotalol); Calcium channel blockers (e.g., Amiloride, amlodipine, bepridil, diltiazem, isradipine, nifedipine, verapamil, felodipine, nicardipine, nimodipine); Antiarrythmics, groups I–IV (e.g., bretylium, disopyramide, encainide, flecainide, lidocaine, mexiletine, moricizine, propafenone, procainamide, quinidine, tocainide, esmolol, propranolol, acebutolol, amiodarone, sotalol, verapamil, diltiazem, pindolol, bupranolol hydrochloride, trichlormethiazide, furosemide, prazosin hydrochloride, metoprolol tartrate, carteolol hydrochloride, oxprenolol hydrochloride, and propranolol hydrochloride); and miscellaneous antiarrythmics and cardiotonics (e.g., adenosine, digoxin; metildigoxin, caffeine, dopamine hydrochloride, dobutamine hydrochloride, octopamine hydrochloride, diprophylline, ubidecarenon, digitalis).

Other therapeutic agents that can be utilized within the present invention include diuretics (e.g., acetazolamide, amiloride, triamterene plus hydrochlorothiazide combinations, spironolactone plus hydrochlorothiazide combinations, torsemide, furosemide, ethacrynate, bumetanide, triamterene, methylchorothizide, hydrochlorothiazide, metdazone, chlorthalidone, hydroflumethiazide, metolazone, methyclothiazide, polythiazide, quinithazone, trichlormethiazide, benroflumethiazide, benzthiazide); hypotensive diuretics (e.g., mefruside, penflutizide, bumetamide, hydrothiazide, bentroflumethiazide, reserpine); Inotropic agents (e.g., digoxin, digitoxin, dobutamine, amrinone, milrinone); vasodilators (e.g., papaverine, isosorbide mono- and dinitrates, nitroglycerin, dizoxide, hydralazine, minoxidil, nitroprusside, prazosin, terazosin, 1,2,3-propanetriolmononitrate, 1,2,3-propanetriolnitrate and their ester derivatives, pentaerythritol tetranitrate, hepronicate, molsidomine, nicomol, simfibrate, diltiazem hydrochloride, cinnarizine, dipyridamole, trapidil, trimetazidine hydrochloride, carbocromene, prenylamine lactate, dilazep dihydrochloride); vasopressors (e.g., metaraminol, isoproterenol, phenylephrine, methaxamine); anticoagulant and thrombolytic agents (e.g., tissue plasminogen activator (TPA), urokinase, streptokinase, pro-urokinase, urokinase, heparin, warfarin); Calmodulin antagonists (e.g., $H_7$); inhibitors of the sodium/calcium antiporter (e.g., Amiloride); and inhibitors of the ryanodine receptor (e.g., Ryanodine); inhibitors of the $IP_3$ receptor (e.g., Heparin).

Other therapeutic agents that can be utilized within the present invention include anti-inflammatory agents. Representative examples of such agents include nonsteroidal agents ("NSAIDS") such as salicylates (e.g., salsalate, mesalamine, diflunisal, choline magnesium trisalicylate), diclofenac, diflunisal, etodolac, fenoprofen, flurbiprofen, ibuprofen, indomethacin, mefenamic acid, nabumetone, naproxen, piroxicam, phenylbutazone, ketoprofen, S-ketoprofen, ketorolac tromethamine, sulindac, tolmetin). Other anti-inflammatory drugs include steroidal agents such as beclomethasone, betamethasone, cortisone, dexamethasone, fluocinolone, flunisolide, fluticasone proprionate, fluorinated-corticoids, triamcinolone-diacetate, hydorcortisone, prednisolone, methylprednisolone and prednisone. Immunosuppressive agents (e.g., adenocorticosteroids, cyclosporin); and antihistamines and decongestants (e.g., astemizole(histamine H1-receptor antagonist), azatidine, brompheniramine, clemastine, chlorpheniramine, cromolyn, cyproheptadine, diphenylimidazole, diphenhydramine hydrochloride, hydroxyzine, glycyrrhetic acid, homochlorocyclizine hydrochloride, ketotifen, loratadine, naphazoline, phenindamine, pheniramine, promethazine, terfenadine, trimeprazine, tripelennamine, tranilast, and the decongestants phenylpropanolamine and pseudoephedrine.

Further therapeutic agents that can be utilized within the present invention include central nervous system agents. Representative examples of such agents include antidepressants (e.g., Prozac, Paxil, Luvox, Mannerex and Effexor); CNS stimulants (e.g., pemoline, methamphetamine, dextroamphetamine); hypnotic agents (e.g., pentobarbital, estazolam, ethchlorynol, flurazepam, propofol, secobarbital, temazepam, triazolam, quazepam, zolpidem tartrate); antimanic agents (e.g., lithium); sedatives and anticonvulsant barbiturates (e.g., pentobarbitol, phenobarbital, secobarbital, mephobarbital, butabarbital primidone, amobarbital); non-barbiturate sedatives (e.g., diphehydramine, doxylamine, midazolam, diazepam, promethazine, lorazepam, temazepam); and other miscellaneous hypnotics and sedatives (e.g., methaqualone, glutethimide, flurazepam, bromovalerylurea, flurazepam, hydrochloride, haloxazolam, triazolam, phenobarbital, chloral hydrate, nimetazepam, estazolam).

Other therapeutic agents that can be utilized within the present invention include Alzheimer's agents such as tacrine (reversible cholinesterase inhibitor); Parkinson's disease agents such as amantadine, bromocriptine mesylate, biperiden, benztropine mesylate, carbidopa-levodopa, diphenhydramine, hyoscyamine, levodopa, pergolide mesylate, procyclidine, selegiline HCl, trihexyphenidyl HCl; and other miscellaneous CNS agents such as fluphenazine, flutazolam, phenobarbital, methylphenobarbital, thioridazine, diazepam, benzbromarone, clocapramine hydrochloride, clotiazepam, chlorpromazine, haloperidol, lithium carbonate.

Further therapeutic agents that can be utilized within the present invention include anti-migraine agents (e.g., ergotamine, methylsergide, propranolol, dihydroergotamine, Sertroline and Immitrex); Post-cerebral embolism agents (e.g., nicardipine hydrochloride, cinepazide maleate, pentoxifylline, ifenprodil tartrate); local anesthetics (e.g., lidocaine, benzocaine, ethyl aminobenzoate, procaine hydrochloride, dibucaine, procaine; antiulcer/antireflux agents (e.g., Losec (Omeprazole), aceglutamide aluminum, cetraxate hydrochloride, pirenzepine hydrochloride, cimetidine, famotidine, metoclopramide, ranitidine, L-glutamine, gefamate, and any stereoisomer of these compounds, and the pharmaceutically acceptable salts of these compounds, such compound used singly or in combination of more than one compound, properly chosen); protease inhibitors (e.g., serine protease, metalloendoproteases and aspartyl proteases (such as HIV protease, renin and cathepsin) and thiol protease inhibitors (e.g., benzyloxycarbonyl-leu-norleucinal (calpeptin) and acetyl-leu-leu-norleucinal); phosphodiesterase inhibitors (e.g., isobutyl methylxanthine); Phenothiazines; growth factor receptor antagonists (e.g., platelet-derived growth factor (PDGF), epidermal growth factor, interleukins, transforming growth factors alpha and beta, and acidic or basic fibroblast growth factors); antisense oligonucleotides (e.g., sequences complementary to portions of mRNA encoding DPGF or other growth factors); and protein kinase inhibitors (e.g., For tyrosine kinases, protein kinase C, myosin light chain kinase, $Ca^{2+}$/calmodulin kinase II, casein kinase II);

Other therapeutic agents that can be utilized within the present invention include anti-tissue damage agents. Representative examples of such agents include Superoxide dismutase; Immune Modulators (e.g., lymphokines, monokines, interferon $\alpha$, $\beta$, $\tau$-1b, $\alpha$-n3, $\alpha$-2b, $\alpha$-2b; Growth Regulators (e.g., IL-2, tumor necrosis factor, epithelial growth factor, somatrem, fibronectin, GM-CSF, CSF, platelet derived growth factor, somatotropin, rG-CSF, epidermal growth factor, IGF-1).

Other therapeutic agents that can be utilized within the present invention include monoclonal and polyclonal antibodies (e.g., those active against: venoms, toxins, tumor necrosis factor, bacteria); hormones (e.g., estrogen, progestin, testosterone, human growth hormone, epinephrine, levarterenol, thyroxine, thyroglobulin, oxytocin, vasopressin, ACTH, somatropin, thyrotropin, insulin, parathyrin, calcitonin); vitamins (e.g., vitamins A, B and its subvitamins, C, D, E, F, G, J, K, N, P, PP, T, U and their subspecies); amino acids such as arginine, histidine, proline, lysine, methionine, alanine, phenylalanine, aspartic acid, glutamic acid, glutamine, threonine, tryptophan, glycine, isoleucine, leucine, valine; Prostaglandins (e.g., $E_1$, $E_2$, $F_{2\alpha}$, $I_2$); enzymes such as pepsin, pancreatin, rennin, papain, trypsin, pancrelipase, chymopapain, bromelain, chymotrypsin, streptokinase, urokinase, tissue plasminogen activator, fibrinolysin, desoxyribonuclease, sutilains, collagenase, asparaginase, heparinase; buffers and salts (e.g., NaCl, cations including: $Na^+$, $K^+$, $Ca^{++}$, $Mg^{++}$, $Zn^{++}$, $NH_4^+$ triethanolamine, anions including: phosphate, sulfate, chloride, citrate, ascorbate, acetate, borate, carbonate ions); preservatives (e.g., benzalkonium chloride, Na or K bisulfite, Na or K thiosulfate, parabans); antigout agents (e.g., allopurinol, cochicine, probenicid, sulfinpyrazone); antidepressant agents such as amitriptyline, amoxapine, desipramine, doxepin, imipramine, nortriptyline, protriptyline, trimipramine; contraceptives (e.g., norethindrone combinations, such as with ethinyl estradiol or with mestranol); and antinauseants/antiemetic agents (e.g., dimenhydrinate, hydroxyzine, meclizine, metoclopramide, prochlorperazine, promethazine, scopolamine, thiethylperazine, triethobenzamide).

Other therapeutic agents that can likewise be utilized within the present invention include antiasthmatic agents, antipsychotic agents, bronchodilators, gold compounds, hypoglycemic agents, hypolipedemic agents, anesthetics, vaccines, agents which affect bone metabolism, antidiarrhetics, fertility agents, muscle relaxants, appetite suppressants, hormones such as thyroid hormone, estrogen, progesterone, cortisone and/or growth hormone, other biologically active molecules such as insulin, as well as $T_H1$ (e.g., Interleukins -2, -12, and -15, gamma interferon) or $T_H2$ (e.g., Interleukins -4 and -10) cytokines.

Although the above therapeutic agents have been provided for the purposes of illustration, it should be understood that the present invention is not so limited. For example, although agents are specifically referred to above, the present invention should be understood to include analogues, derivatives and conjugates of such agents. As an illustration, paclitaxel should be understood to refer to not only the common chemically available form of paclitaxel, but analogues (e.g., taxotere, as noted above) and paclitaxel conjugates (e.g., paclitaxel-PEG, paclitaxel-dextran, or paclitaxel-xylos). In addition, as will be evident to one of skill in the art, although the agents set forth above may be noted within the context of one class, many of the agents listed in fact have multiple biological activities. Further, more than one therapeutic agent may be utilized at a time (i.e., in combination), or delivered sequentially.

Polymeric Carriers

As noted above, therapeutic compositions of the present invention may additionally comprise a polymeric carrier. A wide variety of polymeric carriers may be utilized to contain and or delivery one or more of the therapeutic agents discussed above, including for example both biodegradable and non-biodegradable compositions. Representative examples of biodegradable compositions include albumin, collagen, gelatin, starch, cellulose (methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextrans, polysaccharides, fibrinogen, poly(D,L lactide), poly(D,L-lactide-co-glycolide), poly (glycolide), poly(hydroxybutyrate), poly(alkylcarbonate) and poly(orthoesters), polyesters, poly(hydroxyvaleric acid), polydioxanone, poly(ethylene terephthalate), poly (malic acid), poly(tartronic acid), polyanhydrides, polyphosphazenes, poly(amino acids and their copolymers (see generally Illum, L., Davids, S. S. (eds.) "Polymers in controlled Drug Delivery" Wright, Bristol, 1987; Arshady, *J. Controlled Release* 17:1–22, 1991; Pitt, *Int. J. Phar.* 59:173–196, 1990; Holland et al., *J. Controlled Release* 4:155–0180, 1986). Representative examples of nondegradable polymers include EVA copolymers, silicone rubber, acrylic polymers (polyacrylic acid, polymethylacrylic acid, polymethylmethacrylate, polyalkylcynoacrylate), polyethylene, polyproplene, polyamides (nylon 6,6), polyurathane, poly(ester urathanes), poly(ether urathanes), poly(ester-urea), polyethers (poly(ethylene oxide), poly (propylene oxide), pluronics, poly(tetramethylene glycol)) xxx,silicone rubbers and vinyl polymers [polyvinylpyrrolidone, poly(vinyl alcohol), poly(vinyl acetate phthalate. Polymers may also be developed which are either anionic (e.g., alginate, carrageenin, caboxymethyl cellulose and poly(acrylic acid), or cationic (e.g., Chitosan, poly-1-lysine, polyethylenimine, and poly (allyl amine)) (see generally, Dunn et al., *J. Applied Polymer Sci.* 50:353–365, 1993; Cascone et al., *J. Materials Sci.: Materials in Medicine* 5:770–774, 1994; Shiraishi et al., *Biol. Pharm. Bull.* 16(11):1164–1168, 1993; Thacharodi and Rao, *Int'l J. Pharm.* 120:115–118, 1995; Miyazaki et al., *Int'l J. Pharm.* 118:257–263, 1995). Particularly preferred polymeric carriers include poly(ethylene-vinyl acetate) (40% cross-linked), poly (D,L-lactic acid) oligomers and polymers, poly (L-lactic acid) oligomers and polymers, poly (glycolic acid), copolymers of lactic acid and glycolic acid, poly (caprolactone), poly (valerolactone), polyanhydrides, copolymers of poly (caprolactone) or poly (lactic acid) with polyethylene glycol and blends thereof.

Polymeric carriers can be fashioned in a variety of forms, with desired release characteristics and/or with specific desired properties. For example, polymeric carriers may be fashioned to release a therapeutic agent upon exposure to a specific triggering event such as pH (see, e.g., Heller et al., "Chemically Self-Regulated Drug Delivery Systems," in *Polymers in Medicine III*, Elsevier Science Publishers B.V., Amsterdam, 1988, pp. 175–188; Kang et al., *J. Applied Polymer Sci.* 48:343–354, 1993; Dong et al., *J. Controlled Release* 19:171–178, 1992; Dong and Hoffman, *J. Controlled Release* 15:141–152, 1991; Kim et al., *J. Controlled Release* 28:143–152, 1994; Cornejo-Bravo et al., *J. Controlled Release* 33:223–229, 1995; Wu and Lee, *Pharm. Res.* 10(10):1544–1547, 1993; Serres et al., *Pharm. Res.* 13(2): 196–201, 1996; Peppas, "Fundamentals of pH- and Temperature-Sensitive Delivery Systems," in Gumy et al. (eds.), *Pulsatile Drug Delivery,* Wissenschaftliche Verlagsgesellschaft mbH, Stuttgart, 1993, pp. 41–55; Doelker, "Cellulose Derivatives," 1993, in Peppas and Langer (eds.), *Biopolymers* 1, Springer-Verlag, Berlin). Representative examples of pH-senstive polymers include poly(acrylic acid) and its derivatives (including for example, homopolymers such as poly(aminocarboxylic acid); poly(acrylic acid); poly(methyl acrylic acid)), copolymers of such homopolymers, and copolymers of poly(acrylic acid) and acrylmonomers such as those discussed above. Other pH sensitive polymers include polysaccharides such as cellulose acetate phthalate; hydroxypropylmethylcellulose phthalate; hydroxypropylmethylcellulose acetate succinate; cellulose acetate trimellilate; and chitosan. Yet other pH sensitive polymers include any mixture of a pH sensitive polymer and a water soluble polymer.

Likewise, polymeric carriers can be fashioned which are temperature sensitive (see, e.g., Chen et al., "Novel Hydrogels of a Temperature-Sensitive Pluronic Grafted to a Bioadhesive Polyacrylic Acid Backbone for Vaginal Drug Delivery," in *Proceed. Intern. Symp. Control. Rel. Bioact. Mater.* 22:167–168, Controlled Release Society, Inc., 1995; Okano, "Molecular Design of Stimuli-Responsive Hydrogels for Temporal Controlled Drug Delivery," in *Proceed. Intern. Symp. Control Rel. Bioact. Mater.* 22:111–112, Controlled Release Society, Inc., 1995; Johnston et al., *Pharm. Res.* 9(3):425–433, 1992; Tung, *Int'l J. Pharm.* 107:85–90, 1994; Harsh and Gehrke, *J. Controlled Release* 17:175–186, 1991; Bae et al., *Pharm. Res.* 8(4):531–537, 1991; Dinarvand and D'Emanuele, *J. Controlled Release* 36:221–227, 1995; Yu and Grainger, "Novel Thermo-sensitive Amphiphilic Gels: Poly N-isopropylacrylamide-co-sodium acrylate-co-n-N-alkylacrylamide Network Synthesis and Physicochemical Characterization," Dept. of Chemical & Bioligal Sci., Oregon Graduate Institute of Science & Technology, Beaverton, Oreg., pp. 820–821; Zhou and Smid, "Physical Hydrogels of Associative Star Polymers," Polymer Research Institute, Dept. of Chemistry, College of Environmental Science and Forestry, State Univ. of New York, Syracuse, N.Y., pp. 822–823; Hoffman et al., "Characterizing Pore Sizes and Water 'Structure' in Stimuli-Responsive Hydrogels," Center for Bioengineering, Univ. of Washington, Seattle, Wash., p. 828; Yu and Grainger, "Thermo-sensitive Swelling Behavior in Crosslinked N-isopropylacrylamide Networks: Cationic, Anionic and Ampholytic Hydrogels," Dept. of Chemical & Biological Sci., Oregon Graduate Institute of Science & Technology, Beaverton, Oreg., pp. 829–830; Kim et al., *Pharm. Res.* 9(3):283–290, 1992; Bae et al., *Pharm. Res.* 8(5):624–628, 1991; Kono et al., *J. Controlled Release* 30:69–75, 1994; Yoshida et al., *J. Controlled Release* 32:97–102, 1994; Okano et al., *J. Controlled Release* 36:125–133, 1995; Chun and Kim, *J. Controlled Release* 38:39–47, 1996; D'Emanuele and Dinarvand, *Int'l J. Pharm.* 118:237–242, 1995; Katono et al., *J. Controlled Release* 16:215–228, 1991; Hoffman, "Thermally Reversible Hydrogels Containing Biologically Active Species," in Migliaresi et al. (eds.), *Polymers in Medicine III,* Elsevier Science Publishers B.V., Amsterdam, 1988, pp. 161–167; Hoffmnan, "Applications of Thermally Reversible Polymers and Hydrogels in Therapeutics and Diagnostics," in *Third International Symposium on Recent Advances in Drug Delivery Systems,* Salt Lake City, Utah, Feb. 24–27, 1987, pp. 297–305; Gutowska et al., *J. Controlled Release* 22:95–104, 1992; Palasis and Gehrke, *J. Controlled Release* 18:1–12, 1992; Paavola et al., *Pharm. Res.* 12(12):1997–2002, 1995).

Representative examples of thermogelling polymers, and their gelatin temperature (LCST (° C.)) include homopolymers such as poly(N-methyl-N-n-propylacrylamide), 19.8; poly(N-n-propylacrylamide), 21.5; poly(N-methyl-N-isopropylacrylamide), 22.3; poly(N-n- propylmethacrylamide), 28.0; poly(N-isopropylacrylamide), 30.9; poly(N,n-diethylacrylamide), 32.0; poly(N-isopropylmethacrylamide), 44.0; poly(N-cyclopropylacrylamide), 45.5; poly(N-ethylmethyacrylamide), 50.0; poly(N-methyl-N-ethylacrylamide), 56.0; poly(N-cyclopropylmethacrylamide), 59.0; poly(N-ethylacrylamide), 72.0. Moreover thermogelling polymers may be made by preparing copolymers between (among) monomers of the above, or by combining such homopolymers with other water soluble polymers such as acrylmonomers (e.g., acrylic acid and derivatives thereof such as methylacrylic acid, acrylate and derivatives thereof such as butyl methacrylate, acrylamide, and N-n-butyl acrylamide).

Other representative examples of thermogelling polymers include cellulose ether derivatives such as hydroxypropyl cellulose, 41° C.; methyl cellulose, 55° C.; hydroxypropylmethyl cellulose, 66° C.; and ethylhydroxyethyl cellulose, and pluronics such as F-127, 10–15° C.; L-122, 19° C.; L-92, 26° C.; L-81, 20° C.; and L-61, 24° C.

A wide variety of forms may be fashioned by the polymeric carriers of the present invention, including for example, rod-shaped devices, pellets, slabs, or capsules (see, e.g., Goodell et al., *Am. J. Hosp. Pharm.* 43:1454–1461, 1986; Langer et al., "Controlled release of macromolecules from polymers", in *Biomedical polymers, Polymeric materials and pharmaceuticals for biomedical use*, Goldberg, E. P., Nakagim, A. (eds.) Academic Press, pp. 113–137, 1980; Rhine et al., *J. Pharm. Sci.* 69:265–270, 1980; Brown et al., *J. Pharm. Sci.* 72:1181–1185, 1983; and Bawa et al., *J. Controlled Release* 1:259–267, 1985). Therapeutic agents may be linked by occlusion in the matrices of the polymer, bound by covalent linkages, or encapsulated in microcapsules. Within certain preferred embodiments of the invention, therapeutic compositions are provided in non-capsular formulations such as microspheres (ranging from nanometers to micrometers in size), pastes, threads of various size, films and sprays.

Preferably, therapeutic compositions of the present invention are fashioned in a manner appropriate to the intended use. Within certain aspects of the present invention, the therapeutic composition should be biocompatible, and release one or more therapeutic agents over a period of several days to months. For example, "quick release" or "burst" therapeutic compositions are provided that release greater than 10%, 20%, or 25% (w/v) of a therapeutic agent (e.g., paclitaxel) over a period of 7 to 10 days. Such "quick release" compositions should, within certain embodiments, be capable of releasing chemotherapeutic levels (where applicable) of a desired agent. Within other embodiments, "low release" therapeutic compositions are provided that release less than 1% (w/v) of a therapeutic agent over a period of 7 to 10 days. Further, therapeutic compositions of the present invention should preferably be stable for several months and capable of being produced and maintained under sterile conditions.

Within certain aspects of the present invention, therapeutic compositions may be fashioned in any size ranging from 50 nm to 500 µm, depending upon the particular use. Alternatively, such compositions may also be readily applied as a "spray", which solidifies into a film or coating. Such sprays may be prepared from microspheres of a wide array of sizes, including for example, from 0.1 µm to 3 µm, from 10 µm to 30 µm, and from 30 µm to 100 µm.

Therapeutic compositions of the present invention may also be prepared in a variety of "paste" or gel forms. For example, within one embodiment of the invention, therapeutic compositions are provided which are liquid at one temperature (e.g., temperature greater than 37° C., such as 40° C., 45° C., 50° C., 55° C. or 60° C.), and solid or semi-solid at another temperature (e.g., ambient body temperature, or any temperature lower than 37° C.). Such "thermopastes" may be readily made given the disclosure provided herein.

Within yet other aspects of the invention, the therapeutic compositions of the present invention may be formed as a film. Preferably, such films are generally less than 5, 4, 3, 2, or 1, mm thick, more preferably less than 0.75 mm or 0.5 mm thick, and most preferably less than 500 µm to 100 µm thick. Such films are preferably flexible with a good tensile strength (e.g., greater than 50, preferably greater than 100, and more preferably greater than 150 or 200 N/cm$^2$), good adhesive properties (i.e., readily adheres to moist or wet surfaces), and have controlled permeability.

Within certain embodiments of the invention, the therapeutic compositions may also comprise additional ingredients such as surfactants (e.g. pluronics such as F-127, L-122, L-92, L-81, and L-61).

Within further aspects of the present invention, polymeric carriers are provided which are adapted to contain and release a hydrophobic compound, the carrier containing the hydrophobic compound in combination with a carbohydrate, protein or polypeptide. Within certain embodiments, the polymeric carrier contains or comprises regions, pockets, or granules of one or more hydrophobic compounds. For example, within one embodiment of the invention, hydrophobic compounds may be incorporated within a matrix which contains the hydrophobic compound, followed by incorporation of the matrix within the polymeric carrier. A variety of matrices can be utilized in this regard, including for example, carbohydrates and polysaccharides such as starch, cellulose, dextran, methylcellulose, and hyaluronic acid, proteins or polypeptides such as albumin, collagen and gelatin. Within alternative embodiments, hydrophobic compounds may be contained within a hydrophobic core, and this core contained within a hydrophilic shell. For example, as described within the Examples, paclitaxel may be incorporated into a hydrophobic core (e.g., of the poly D,L lactic acid-PEG or MePEG aggregate) which has a hydrophilic shell.

A wide variety of hydrophobic compounds may be released from the polymeric carriers described above, including for example: certain hydrophobic compounds which disrupt microtubule function such as paclitaxel and estramustine; hydrophobic proteins such as myelin basic protein, proteolipid proteins of CNS myelin, hydrophobic cell wall protein, porins, membrane proteins (*EMBO J.* 12(9):3409–3415, 1993), myelin oligodendrocyte glycoprotein ("MOG") (*Biochem. and Mol. Biol. Int.* 30(5):945–958, 1993, P27 *Cancer Res.* 53(17):4096–4101, 1913, bacterioopsin, human surfactant protein ("HSB"; *J. Biol. Chem.* 268(15):11160–11166, 1993), and SP-B or SP-C (*Biochimica et Biophysica Acta* 1105(1):161–169, 1992).

Representative examples of the incorporation of therapeutic agents such as those described above into a polymeric carriers to form a therapeutic composition, is described in more detail below in the Examples.

Other Carriers

Other carriers that may likewise be utilized to contain and deliver the therapeutic agents described herein include: hydroxypropyl β cyclodextrin (Cserhati and Hollo, *Int. J.*

*Pharm.* 108:69–75, 1994), liposomes (see e.g., Sharma et al., *Cancer Res.* 53:5877–5881, 1993; Sharma and Straubinger, *Pharm. Res.* 11(60):889–896, 1994; WO 93/18751; U.S. Pat. No. 5,242,073), liposome/gel (WO 94/26254), nanocapsules (Bartoli et al., *J. Microencapsulation* 7(2):191–197, 1990), micelles (Alkan-Onyuksel et al., *Pharm. Res.* 11(2):206–212, 1994), implants (Jampel et al., *Invest. Ophthalm. Vis. Science* 34(11):3076–3083, 1993; Walter et al., *Cancer Res.* 54:22017–2212, 1994) nanoparticles(Violante and Lanzafame PAACR), nanoparticles—modified (U.S. Pat. No. 5,145,684), nanoparticles (surface modified) (U.S. Pat. No. 5,399,363), taxol emulsion/solution (U.S. Pat. No. 5,407,683), micelle (surfactant) (U.S. Pat. No. 5,403,858), synthetic phospholipid compounds (U.S. Pat. No. 4,534,899), gas borne dispersion (U.S. Pat. No. 5,301,664), liquid emulsions, foam spray, gel lotion cream, ointment, dispersed vesicles, particles or droplets solid- or liquid-aerosols, microemulsions (U.S. Pat. No. 5,330,756), polymeric shell (nano- and microcapsule) (U.S. Pat. No. 5,439,686), taxoid-based compositions in a surface-active agent (U.S. Pat. No. 5,438,072), emulsion (Tarr et al., *Pharm Res.* 4: 62–165, 1987), nanospheres (Hagan et al., *Proc. Intern. Symp. Control Rel. Bioact. Mater.* 22, 1995; Kwon et al., *Pharm Res.* 12(2):192–195; Kwon et al., *Pharm Res.* 10(7):970–974; Yokoyama et al., *J. Contr. Rel.* 32:269–77, 1994; Gref et al., *Science* 263:1600–1603, 1994; Bazile et al., *J. Pharm. Sci.* 84:493–498, 1994) and implants (U.S. Pat. No. 4,882,168).

As discussed in more detail below, therapeutic agents of the present invention, which are optionally incorporated within one of the carriers described herein to form a therapeutic composition, may be prepared and utilized to treat or prevent a wide variety of diseases.

Treatment or Prevention of Disease

As noted above, the present invention provides methods for treating or preventing a wide variety of diseases associated with the obstruction of body passageways, including for example, vascular diseases, neoplastic obstructions, inflammatory diseases, and infectious diseases.

For example, within one aspect of the present invention a wide variety of therapeutic compositions as described herein may be utilized to treat vascular diseases that cause obstruction of the vascular system. Representative examples of such diseases include artherosclerosis of all vessels (around any artery, vein or graft) including, but not restricted to: the coronary arteries, aorta, iliac arteries, carotid arteries, common femoral arteries, superficial femoral arteries, popliteal arteries, and at the site of graft anastomosis; vasospasms (e.g, coronary vasospasms and Raynaud's Disease); restenosis (obstruction of a vessel at the site of a previous intervention such as balloon angioplasty, bypass surgery, stent insertion and graft insertion); inflammatory and autoimmune conditions (e.g. Temporal Arteritis, vasculitis).

Briefly, in vascular diseases such as atherosclerosis, white cells, specifically monocytes and T lymphocytes adhere to endothelial cells, especially at locations of arterial branching. After adhering to the endothelium, leukocytes migrate across the endothelial cell lining in response to chemostatic stimuli, and accumulate in the intima of the arterial wall, along with smooth muscle cells. This initial lesion of athersosclerosis development is known as the "fatty streak". Monocytes within the fatty streak differentiate into macrophages; and the macrophages and smooth muscle cells progressively take up lipids and lipoprotein to become foam cells.

As macrophages accumulate, the overlying endothelium becomes mechanically disrupted and chemically altered by oxidized lipid, oxygen-derived free radicals and proteases which are released by macrophages. Foam cells erode through the endothelial surface causing micro-ulcerations of the vascular wall. Exposure of potentially thrombogenic subendothelial tissues (such as collagen and other proteins) to components of the bloodstream results in adherence of platelets to regions of disrupted endothelium. Platelet adherence and other events triggers the elaboration and release of growth factors into this mileau, including platelet-derived growth factor (PDGF), platelet activating factor (PAF), and interleukins 1 and 6 (IL-1, IL-6). These paracrine factors are thought to stimulate vascular smooth muscle cell (VSMC) migration and proliferation.

In the normal (non-diseased) blood vessel wall, vascular smooth muscle cells have a contractile phenotype and low index of mitotic activity. However, under the influence of cytokines and growth factors released by platelets, macrophages and endothelial cells, VSMC undergo phenotypic alteration from mature contractile cells to immature secretory cells. The transformed VSMC proliferate in the media of the blood vessel wall, migrate into the intima, continue to proliferate in the intima and generate large quantities of extracellular matrix. This transforms the evolving vascular lesion into a fibrous plaque. The extracellular matrix elaborated by secretory VSMC includes collagen, elastin, glycoprotein and glycosaminoglycans, with collagen comprising the major extracellular matrix component of the atherosclerotic plaque. Elastin and glycosaminoglycans bind lipoproteins and also contribute to lesion growth. The fibrous plaque consists of a fibrous cap of dense connective tissue of varying thickness containing smooth muscle cells and overlying macrophages, T cells and extracellular material.

In addition to PDGF, IL-1 and IL-6, other mitogenic factors are produced by cells which infiltrate the vessel wall including: transforming growth factor beta (TGF-$\beta$), fibroblast growth factor (FGF), thrombospondin, serotonin, thromboxane $A_2$, norepenephrine, and angiotensin II. This results in the recruitment of more cells, elaboration of further extracellular matrix and the accumulation of additional lipid. This progressively enlarges the atherosclerotic lesion until it significantly encroaches upon the vascular lumen. Initially, obstructed blood flow through the vascular tube causes ischemia of the tissues distal to the atherosclerotic plaque only when increased flow is required—later as the lesion further blocks the artery, ischemia occurs at rest.

Macrophages in the enlarging atherosclerotic plaque release oxidized lipid, free radicals, elastases, and collageneses that cause cell injury and necrosis of neighbouring tissues. The lesion develops a necrotic core and is transformed into a complex plaque. Complex plaques are unstable lesions that can: break off causing embolization; local hemorrhage (secondary to rupture of the vasa vasora supplying the plaque which results in lumen obstruction due to rapid expansion of the lesion); or ulceration and fissure formation (this exposes the thrombogenic necrotic core to the blood stream producing local thrombosis or distal embolization). Even should none of the above sequela occur, the adherent thrombus may become organized and incorporated into the plaque, thereby accelerating its growth. Furthermore, as the local concentrations of fibrinogen and thrombin increase, proliferation of vascular smooth muscle cells within the media and intima is stimulated; a process which also ultimately leads to additional narrowing of the vessel.

The intima and media of normal arteries are oxygenated and supplied with nutrition from the lumen of the artery or from the vasa vasorum in the adventitia. With the development of atherosclerotic plaque, microvessels arising from the adventitial vasa vasorum extend into the thickened intima and media. This vascular network becomes more extensive as the plaque worsens and diminishes with plaque regression.

Hemorrhage from these microvessels may precipitate sudden expansion and rupture of plaque in association with arterial dissection, ulceration, or thrombosis. It has also been postulated that the leakage of plasma proteins from these microvessels may attract inflammatory infiltrates into the region and these inflammatory cells may contribute to the rapid growth of atherosclerotic plaque and to associated complications (through local edema and inflammation).

In order to treat vascular diseases, such as those discussed above, a wide variety of therapeutic agents (either with or without a carrier) may be delivered to the external portion of the body passageway, or to smooth muscle cells via the adventia of the body passageway. Particularly preferred therapeutic agents in this regard include anti-angiogenic factors, inhibitors of platelet adhesion/aggregation (e.g., aspirin, dipyridamole, thromboxane synthesis inhibitors, fish oils that result in production of thromboxane AE rather than the more potent thromboxane A2, antibodies against the platelet IIb/IIIa receptors that binds fibrinogen and prostacyclin), vasodilators (e.g., calcium entry blockers, and the nitric oxide donors nitroglycerine, nitroprusside, and molsidomine) and anthithrombotics and thrombin antagonists (e.g., heparin (low-molecular-weight heparins, warfarin andudin). Other therapeutics which may be utilized include anti-inflammatory agents (e.g., glucorticoids, dexamethasone and methylprednisolone), growth factor inhibitors (e.g., PDGF antagonist such as trapidil; receptor inhibitors (e.g., inhibitors of the receptors for FGF, VEGF, PDGF and TNF), including inhibitors of tyrosine kinase and promoters of tyrosine phosphatase; somatostatin analogs, including angiopeptin; angiotensin converting enzyme inhibitors; and $5HT_2$ serotenergic receptor antagonists such as ketanserin). Yet other therapeutic agents include anti-proliferative agents (e.g., colchicine, heparin, beta (e.g., P-32) or gamma emitters (e.g., Ir-192), calcium-entry blockers such as verapamil, diltiazem and nifedipine, cholesterol-lowering HMB Co-A reductase inhibitors such as lovastatin, compounds which disrupt microtubule function such as paclitaxel and nitric oxide donors as discussed above), and promoters of re-endothelialization (e.g., bFGF and vascular endothelial cell growth factor).

Within other aspects of the invention, the therapeutic agents or compositions described herein may be utilized to treat neoplastic obstructions. Briefly, as utilized herein, a "neoplastic obstruction" should be understood to include any neoplastic (benign or malignant) obstruction of a bodily tube regardless of tube location or histological type of malignancy present. Representative examples include gastrointestinal diseases (e.g., oral-pharyngeal carcinoma (adenocarcinoma, esophageal carcinoma (squamous cell, adenocarcinoma, lymphoma, melanoma), gastric carcinoma (adenocarcinoma, linitis plastica, lymphoma, leiomyosarcoma), small bowel tumors (adenomas, leiomyomas, lipomas, adenocarcinomas, lymphomas, carcinoid tumors), colon cancer (adenocarcinoma) and anorectal cancer); biliary tract diseases (e.g., neoplasms resulting in biliary obstruction such as pancreatic carcinoma (ductal adenocarcinoma, islet cell tumors, cystadenocarcinoma), cholangiocarcinoma and hepatocellular carcinoma); pulmonary diseases (e.g., carcinoma of the lung and/or tracheal/bronchial passageways (small cell lung cancer, non-small cell lung cancer); female reproductive diseases (e.g., malignancies of the fallopian tubes, uterine cancer, cervical cancer, vaginal cancer); male reproductive diseases (e.g,. testicular cancer, cancer of the epididymus, tumors of the vas deferens, prostatic cancer, benign prostatic hypertrophy); and urinary tract diseases (e.g., renal cell carcinoma, tumors of the renal pelvis, tumors of the urinary collection system such as transitional cell carcinoma, bladder carcinoma, and urethral obstructions due to benign strictures, or malignancy).

As an example, benign prostatic hyperplasia (BPH) is the enlargement of the prostate, particularly the central portion of the gland which surrounds the urethra, which occurs in response to prolonged androgenic stimulation. It affects more than 80% of the men over 50 years of age. This enlargement can result in compression of the portion of the urethra which runs through the prostate, resulting in bladder outflow tract obstruction, i.e., an abnormally high bladder pressure is required to generate urinary flow. In 1980, 367,000 transurethral resections of the prostate were performed in the United States as treatment for BPH. Other treatments include medication, transurethral sphincterotomy, transurethral laser or microwave, transurethral hyperthermia, transurethral ultrasound, transrectal microwave, transrectal hyperthermia, transrectal ultrasound and surgical removal. All have disadvantages including interruption of the sphincter mechanism resulting in incontinence and stricture formation.

In order to treat neoplastic diseases, such as those discussed above, a wide variety of therapeutic agents (either with or without a polymeric carrier) may be delivered to the external portion of the body passageway, or to smooth muscle cells via the adventia of the body passageway. Particularly preferred therapeutic agents in this regard include anti-angiogenic, anti-proliferative or anti-neoplastic agents discussed above, including for example, compounds which disrupt microtuble function, such as paclitaxel and derivatives or analogues thereof.

For example, within one preferred embodiment a needle or catheter is guided into the prostate gland adjacent to the urethra via the transrectal route (or alternatively transperineally) under ultrasound guidance and through this deliver a therapeutic agent, preferably in several quadrants of the gland, particularly around the urethra. The needle or catheter can also be placed under direct palpation or under endoscopic, fluoroscopic, CT or MRI guidance, and administered at intervals. As an alternative, the placement of pellets via a catheter or trocar can also be accomplished. The above procedures can be accomplished alone or in conjunction with a stent placed in the prostatic urethra. By avoiding urethral instrumentation or damage to the urethra, the sphincter mechanism would be left intact, avoiding incontinence, and a stricture is less likely.

Within other aspects of the invention, methods are provided for preventing or treating inflammatory diseases which affect or cause the obstruction of a body passageway. Inflammatory diseases include both acute and chronic inflammation which result in obstruction of a variety of body tubes. Representative examples include vasculitis (e.g., Giant cell arteritis (temporal arteritis, Takayasu's arteritis), polyarteritis nodosa, allergic angiitis and granulomatosis (Churg-Strauss disease), polyangiitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system), Wegener's granulomatosis, Kawasaki's disease, vasculitis of the central nervous system, Buerger's disease and systemic sclerosis); gastrointestinal tract diseases (e.g., pancreatitis, Crohn's Disease, Ulcerative Colitis, Ulcerative Proctitis, Primary Sclerosing Cholangitis, benign strictures of any cause including ideopathic (e.g., strictures of bile ducts, esophagus, duodenum, small bowel or colon)); respiratory tract diseases (e.g, asthma, hypersensitivity pneumonitis, asbestosis, silicosis, and other forms of pneumoconiosis, chronic bronchitis and chronic obstructive airway disease); nasolacrimal duct diseases (e.g., strictures of all causes including ideopathic); and eustachean tube diseases (e.g., strictures of all causes including ideopathic).

In order to treat inflammatory diseases, such as those discussed above, a wide variety of therapeutic agents (either with or without a carrier) may be delivered to the external portion of the body passageway, or to smooth muscle cells via the adventia of the body passageway. Particularly preferred therapeutic agents in this regard include both nonsteroidal agents ("NSAIDS") and steroidal agents, as well as the anti-angiogenic factors discussed above. Other agents which may also be utilized include a wide variety of anti-angiogenic facts, including for example compounds which disrupt microtubule function, such as paclitaxel, and lighter "d" group transition metals.

Within yet other aspects of the present invention, methods are provided for treating or preventing infectious diseases that are associated with, or causative of, the obstruction of a body passageway. Briefly, infectious diseases include several acute and chronic infectious processes can result in obstruction of body passageways including for example, obstructions of the male reproductive tract (e.g., strictures due to urethritis, epididymitis, prostatitis); obstructions of the female reproductive tract (e.g., vaginitis, cervicitis, pelvic inflammatory disease (e.g., tuberculosis, gonococcus, chlamydia, enterococcus and syphilis); urinary tract obstructions (e.g., cystitis, urethritis); respiratory tract obstructions (e.g., chronic bronchitis, tuberculosis, other mycobacterial infections (MAI, etc.), anaerobic infections, fungal infections and parasitic infections) and cardiovascular obstructions (e.g., mycotic aneurysms and infective endocarditis).

In order to treat infectious diseases, such as those discussed above, a wide variety of therapeutic agents (either with or without a carrier) may be delivered to the external portion of the body passageway, or to smooth muscle cells via the adventia of the body passageway. Particularly preferred therapeutic agents in this regard include a wide variety of antibiotics as discussed above.

Formulation and Administration

As noted above, therapeutic compositions of the present invention may be formulated in a variety of forms (e.g., microspheres, pastes, films or sprays). Further, the compositions of the present invention may be formulated to contain more than one therapeutic agents, to contain a variety of additional compounds, to have certain physical properties (e.g., elasticity, a particular melting point, or a specified release rate). Within certain embodiments of the invention, compositions may be combined in order to achieve a desired effect (e.g., several preparations of microspheres may be combined in order to achieve both a quick and a slow or prolonged release of one or more anti-angiogenic factor).

Therapeutic agents and compositions of the present invention may be administered either alone, or in combination with pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

As noted above, therapeutic agents, therapeutic compositions, or pharmaceutical compositions provided herein may be prepared for administration by a variety of different routes, including for example, directly to a body passageway under direct vision (e.g., at the time of surgery or via endoscopic procedures) or via percutaneous drug delivery to the exterior (adventitial) surface of the body passageway (e.g., perivascular delivery). Other representative routes of administration include gastroscopy, ECRP and colonoscopy, which do not require full operating procedures and hospitalization, but may require the presence of medical personnel.

Briefly, perivascular drug delivery involves percutaneous administration of localized (often sustained release) therapeutic formulations using a needle or catheter directed via ultrasound, CT, fluoroscopic, MRI or endoscopic guidance to the disease site. Alternatively the procedure can be performed intra-operatively under direct vision or with additional imaging guidance. Such a procedure can also be performed in conjunction with endovascular procedures such as angioplasty, atherectomy, or stenting or in association with an operative arterial procedure such as endarterectomy, vessel or graft repair or graft insertion.

For example, within one embodiment, polymeric paclitaxel formulations can be injected into the vascular wall or applied to the adventitial surface allowing drug concentrations to remain highest in regions where biological activity is most needed. This has the potential to reduce local "washout" of the drug that can be accentuated by continuous blood flow over the surface of an endovascular drug delivery device (such as a drug-coated stent). Administration of effective therapeutic agents to the external surface of the vascular tube can reduce obstruction of the tube and reduce the risk of complications associated with intravascular manipulations (such as restenosis, embolization, thrombosis, plaque rupture, and systemic drug toxicity).

For example, in a patient with narrowing of the superficial femoral artery, balloon angioplasty would be performed in the usual manner (i.e., passing a balloon angioplasty catheter down the artery over a guide wire and inflating the balloon across the lesion). Prior to, at the time of, or after angioplasty, a needle would be inserted through the skin under ultrasound, fluoroscopic, or CT guidance and a therapeutic agent (e.g., paclitaxel impregnated into a slow release polymer) would be infiltrated through the needle or catheter in a circumferential manner directly around the area of narrowing in the artery. This could be performed around any artery, vein or graft, but ideal candidates for this intervention include diseases of the carotid, coronary, iliac, common femoral, superficial femoral and popliteal arteries and at the site of graft anastomosis. Logical venous sites include infiltration around veins in which indwelling catheters are inserted.

The therapeutic agents, therapeutic compositions and pharmaceutical compositions provided herein may be placed within containers, along with packaging material which provides instructions regarding the use of such materials. Generally, such instructions include a tangible expression describing the reagent concentration, as well as within certain embodiments, relative amounts of excipient ingredients or diluents (e.g., water, saline or PBS) which may be necessary to reconstitute the anti-angiogenic factor, anti-angiogenic composition, or pharmaceutical composition.

The following examples are offered by way of illustration, and not by way of limitation.

EXAMPLES

Example 1

Manufacture of "Pastes"

As noted above, the present invention provides a variety of polymeric-containing drug compositions that may be utilized within a variety of clinical situations. For example, compositions may be produced: (1) as a "thermopaste" that is applied to a desired site as a fluid, and hardens to a solid of the desired shape at a specified temperature (e.g., body temperature); (2) as a spray (i.e., "nanospray") which may delivered to a desired site either directly or through a specialized apparatus (e.g., endoscopy), and which subsequently hardens to a solid which adheres to the tissue to which it is applied; (3) as an adherent, pliable, resilient, drug-loaded-polymer film applied to a desired site either directly or through a specialized apparatus, and which preferably adheres to the site to which it is applied; and (4) as a fluid composed of a suspension of microspheres in an appropriate carrier medium, which is applied to a desired site either directly or via a specialized apparatus, and which leaves a layer of microspheres at the application site. Representative examples of each of the above embodiments is set forth in more detail below.

A. Procedure for Producing Thermopaste

Reagents and equipment which are utilized within the following experiments include a sterile glass syringe (1 ml), Corning hot plate/stirrer, 20 ml glass scintillation vial, moulds (e.g., 50 µl DSC pan or 50 ml centrifuge tube cap inner portion), scalpel and tweezers, Polycaprolactone ("PCL"—mol wt 10,000 to 20,000; Polysciences, Warrington, Pa. USA), and Paclitaxel (Sigma grade 95% purity minimum).

Weigh 5.00 g of polycaprolactone directly into a 20 ml glass scintillation vial. Place the vial in a 600 ml beaker containing 50 ml of water. Gently heat the beaker to 65° C. and hold it at that temperature for 20 minutes. This allows the polymer to melt. Thoroughly mix a known weight of paclitaxel, or other angiogenesis inhibitor into the melted polymer at 65° C. Pour the melted polymer into a pre-warmed (60° C. oven) mould. Use a spatula to assist with the pouring process. Allow the mould to cool so the polymer solidifies. Cut or break the polymer into small pieces (approximately 2 mm by 2 mm in size). These pieces must fit into a 1 ml glass syringe. Remove the plunger from the 1 ml glass syringe (do not remove the cap from the tip) and place it on a balance. Zero the balance.

Weigh 0.5 g of the pieces directly into the open end of the syringe. Place the glass syringe upright (capped tip downwards) into a 500 ml glass beaker containing distilled water at 65° C. (corning hot plate) so that no water enters the barrel. The polymer melts completely within 10 minutes in this apparatus. When the polymer pieces have melted, remove the barrel from the water bath, hold it horizontally and remove the cap. Insert the plunger into the barrel and compress the melted polymer into a sticky mass at the tip end of the barrel. Cap the syringe and allow it to cool to room temperature.

For application, the syringe may be reheated to 60° C. and administered as a liquid which solidifies when cooled to body temperature.

B. Procedure for Producing Nanospray

Nanospray is a suspension of small microspheres in saline. If the microspheres are very small (ie., under 1 µm in diameter) they form a colloid so that the suspension will not sediment under gravity. As is described in more detail below, a suspension of 0.1 µm to 1 µm microparticles may be created suitable for deposition onto tissue through a finger pumped aerosol. Equipment and materials which may be utilized to produce nanospray include 200 ml water jacketed beaker (Kimax or Pyrex), Haake circulating water bath, overhead stirrer and controller with 2 inch diameter (4 blade, propeller type stainless steel stirrer; Fisher brand), 500 ml glass beaker, hot plate/stirrer (Corning brand), 4×50 ml polypropylene centrifuge tubes (Nalgene), glass scintillation vials with plastic insert caps, table top centrifuge (Beckman), high speed centrifuge—floor model (JS 21 Beckman), Mettler analytical balance (AJ 100, 0.1 mg), Mettler digital top loading balance (AE 163, 0.01 mg), automatic pipetter (Gilson), sterile pipette tips, pump action aerosol (Pfeiffer pharmaceuticals) 20 ml, laminar flow hood, Polycaprolactone ("PCL"—mol wt 10,000 to 20,000; Polysciences, Warrington, Pa. USA), "washed" (see previous) Ethylene Vinyl Acetate ("EVA"), Poly(DL)lactic acid ("PLA" mol wt 15,000 to 25,000; Polysciences), Polyvinyl Alcohol ("PVA"—mol wt 124,000 to 186,000; 99% hydrolyzed; Aldrich Chemical Co., Milwaukee, Wis. USA), Dichloromethane ("DCM" or "methylene chloride;" HPLC grade Fisher scientific), Distilled water, sterile saline (Becton and Dickenson or equivalent)

1. Preparation of 5% (w/v) Polymer Solutions

Depending on the polymer solution being prepared, weigh 1.00 g of PCL or PLA or 0.50 g each of PLA and washed EVA directly into a 20 ml glass scintillation vial. Using a measuring cylinder, add 20 ml of DCM and tightly cap the vial. Leave the vial at room temperature (25° C.) for one hour or until all the polymer has dissolved (occasional hand shaking may be used). Dissolving of the polymer can be determined by a visual check; the solution should be clear. Label the vial with the name of the solution and the date it was produced. Store the solutions at room temperature and use within two weeks.

2. Preparation of 3.5% (w/v) Stock Solution of PVA

The solution can be prepared by following the procedure given below, or by diluting the 5% (w/v) PVA stock solution prepared for production of microspheres (see Example 2). Briefly, 17.5 g of PVA is weighed directly into a 600 ml glass beaker, and 500 ml of distilled water is added. Place a 3 inch Teflon coated stir bar in the beaker. Cover the beaker with a cover glass to reduce evaporation losses. Place the beaker in a 2000 ml glass beaker containing 300 ml of water. This will act as a water bath. Stir the PVA at 300 rpm at 85° C. (Corning hot plate/stirrer) for 2 hours or until fully dissolved. Dissolving of the PVA can be determined by a visual check; the solution should be clear. Use a pipette to transfer the solution to a glass screw top storage container and store at 4° C. for a maximum of two months. This solution should be warmed to room temperature before use or dilution.

3. Procedure for Producing Nanospray

Place the stirring assembly in a fume hood. Place 100 ml of the 3.5% PVA solution in the 200 ml water jacketed beaker. Connect the Haake water bath to this beaker and allow the contents to equilibrate at 27° C. (+/−1° C.) for 10 minutes. Set the start speed of the overhead stirrer at 3000 rpm (+/−200 rpm). Place the blade of the overhead stirrer half way down in the PVA solution and start the stirrer. Drip 10 ml of polymer solution (polymer solution used based on type of nanospray being produced) into the stirring PVA over a period of 2 minutes using a 5 ml automatic pipetter. After 3 minutes, adjust the stir speed to 2500 rpm (+/−200 rpm) and leave the assembly for 2.5 hours. After 2.5 hours, remove the stirring blade from the nanospray preparation and rinse with 10 ml of distilled water. Allow the rinse solution to go into the nanospray preparation.

Pour the microsphere preparation into a 500 ml beaker. Wash the jacketed water bath with 70 ml of distilled water. Allow the 70 ml rinse solution to go into the microsphere preparation. Stir the 180 ml microsphere preparation with a glass rod and pour equal amounts of it into four polypropylene 50 ml centrifuge tubes. Cap the tubes. Centrifuge the capped tubes at 10000 g (+/−1000 g) for 10 minutes. Using a 5 ml automatic pipetter or vacuum suction, draw 45 ml of the PVA solution off of each microsphere pellet and discard it. Add 5 ml of distilled water to each centrifuge tube and use a vortex to resuspend the microspheres in each tube. Using 20 ml of distilled water, pool the four microsphere suspensions into one centrifuge tube. To wash the microspheres, centrifuge the nanospray preparation for 10 minutes at 10000 g (+/−1000 g). Draw the supernatant off of the microsphere pellet. Add 40 ml of distilled water and use a vortex to resuspend the microspheres. Repeat this process two more times for a total of three washes. Do a fourth wash but use only 10 ml (not 40 ml) of distilled water when resuspending the microspheres. After the fourth wash, transfer the microsphere preparation into a preweighed glass scintillation vial.

Cap the vial and let it to sit for 1 hour at room temperature (25° C.) to allow the 2 μm and 3 μm diameter microspheres to sediment out under gravity. After 1 hour, draw off the top 9 ml of suspension using a 5 ml automatic pipetter. Place the 9 ml into a sterile capped 50 ml centrifuge tube. Centrifuge the suspension at 10000 g (+/−1000 g) for 10 minutes. Discard the supernatant and resuspend the pellet in 20 ml of sterile saline. Centrifuge the suspension at 10000 g (+/−1000 g) for 10 minutes. Discard the supernatant and resuspend the pellet in sterile saline. The quantity of saline used is dependent on the final required suspension concentration (usually 10% w/v). Thoroughly rinse the aerosol apparatus in sterile saline and add the nanospray suspension to the aerosol.

C. Manufacture of Paclitaxel Loaded Nanospray

To manufacture nanospray containing paclitaxel, use Paclitaxel (Sigma grade 95% purity). To prepare the polymer drug stock solution, weigh the appropriate amount of paclitaxel directly into a 20 ml glass scintillation vial. The appropriate amount is determined based on the percentage of paclitaxel to be in the nanospray. For example, if nanospray containing 5% paclitaxel was required, then the amount of paclitaxel weighed would be 25 mg since the amount of polymer added is 10 ml of a 5% polymer in DCM solution (see next step).

Add 10 ml of the appropriate 5% polymer solution to the vial containing the paclitaxel. Cap the vial and vortex or hand swirl it to dissolve the paclitaxel (visual check to ensure paclitaxel dissolved). Label the vial with the date it was produced. This is to be used the day it is produced.

Follow the procedures as described above, except that polymer/drug (e.g., paclitaxel) stock solution is substituted for the polymer solution.

D. Procedure for Producing Film

The term film refers to a polymer formed into one of many geometric shapes. The film may be a thin, elastic sheet of polymer or a 2 mm thick disc of polymer. This film is designed to be placed on exposed tissue so that any encapsulated drug is released from the polymer over a long period of time at the tissue site. Films may be made by several processes, including for example, by casting, and by spraying.

In the casting technique, polymer is either melted and poured into a shape or dissolved in dichloromethane and poured into a shape. The polymer then either solidifies as it cools or solidifies as the solvent evaporates, respectively. In the spraying technique, the polymer is dissolved in solvent and sprayed onto glass, as the solvent evaporates the polymer solidifies on the glass. Repeated spraying enables a build up of polymer into a film that can be peeled from the glass.

Reagents and equipment which were utilized within these experiments include a small beaker, Coming hot plate stirrer, casting moulds (e.g., 50 ml centrifuge tube caps) and mould holding apparatus, 20 ml glass scintillation vial with cap (Plastic insert type), TLC atomizer, Nitrogen gas tank, Polycaprolactone ("PCL"—mol wt 10,000 to 20,000; Polysciences), Paclitaxel (Sigma 95% purity), Ethanol, "washed" (see previous) Ethylene vinyl acetate ("EVA"), Poly(DL)lactic acid ("PLA"—mol wt 15,000 to 25,000; Polysciences), Dichloromethane (HPLC grade Fisher Scientific).

1. Procedure for Producing Films—Melt Casting

Weigh a known weight of PCL directly into a small glass beaker. Place the beaker in a larger beaker containing water (to act as a water bath) and put it on the hot plate at 70° C. for 15 minutes or until the polymer has fully melted. Add a known weight of drug to the melted polymer and stir the mixture thoroughly. To aid dispersion of the drug in the melted PCL, the drug may be suspended/dissolved in a small volume (<10% of the volume of the melted PCL) of 100% ethanol. This ethanol suspension is then mixed into the melted polymer. Pour the melted polymer into a mould and let it to cool. After cooling, store the film in a container.

2. Procedure for Producing Films—Solvent Casting

Weigh a known weight of PCL directly into a 20 ml glass scintillation vial and add sufficient DCM to achieve a 10% w/v solution. Cap the vial and mix the solution. Add sufficient paclitaxel to the solution to achieve the desired final paclitaxel concentration. Use hand shaking or vortexing to dissolve the paclitaxel in the solution. Let the solution sit for one hour (to diminish the presence of air bubbles) and then pour it slowly into a mould. The mould used is based on the shape required. Place the mould in the fume hood overnight. This will allow the DCM to evaporate. Either leave the film in the mould to store it or peel it out and store it in a sealed container.

3. Procedure for Producing Films—Sprayed

Weigh sufficient polymer directly into a 20 ml glass scintillation vial and add sufficient DCM to achieve a 2% w/v solution. Cap the vial and mix the solution to dissolve the polymer (hand shaking). Assemble the moulds in a vertical orientation in a suitable mould holding apparatus in the fume hood. Position this mould holding apparatus 6 to 12 inches above the fume hood floor on a suitable support (e.g., inverted 2000 ml glass beaker) to enable horizontal spraying. Using an automatic pipette, transfer a suitable volume (minimum 5 ml) of the 2% polymer solution to a separate 20 ml glass scintillation vial. Add sufficient paclitaxel to the solution and dissolve it by hand shaking the capped vial. To prepare for spraying, remove the cap of this vial and dip the barrel (only) of an TLC atomizer into the polymer solution. Note: the reservoir of the atomizer is not used in this procedure—the 20 ml glass vial acts as a reservoir.

Connect the nitrogen tank to the gas inlet of the atomizer. Gradually increase the pressure until atomization and spraying begins. Note the pressure and use this pressure throughout the procedure. To spray the moulds use 5 second oscillating sprays with a 15 second dry time between sprays. During the dry time, finger crimp the gas line to avoid wastage of the spray. Spraying is continued until a suitable thickness of polymer is deposited on the mould. The thickness is based on the request. Leave the sprayed films attached to the moulds and store in sealed containers.

E. Procedure for Producing Nanopaste

Nanopaste is a suspension of microspheres suspended in a hydrophilic gel. Within one aspect of the invention, the gel or paste can be smeared over tissue as a method of locating drug loaded microspheres close to the target tissue. Being water based, the paste will soon become diluted with bodily fluids causing a decrease in the stickiness of the paste and a tendency of the microspheres to be deposited on nearby tissue. A pool of microsphere encapsulated drug is thereby located close to the target tissue.

Reagents and equipment which were utilized within these experiments include glass beakers, Carbopol 925 (pharmaceutical grade, Goodyear Chemical Co.), distilled water, sodium hydroxide (1 M) in water solution, sodium hydroxide solution (5 M) in water solution, microspheres in the 0.1 lm to 3 lm size range suspended in water at 20% w/v (See previous).

1. Preparation of 5% w/v Carbopol Gel

Add a sufficient amount of carbopol to 1 M sodium hydroxide to achieve a 5% w/v solution. To dissolve the carbopol in the 1 M sodium hydroxide, allow the mixture to sit for approximately one hour. During this time period, stir the mixture using a glass rod. After one hour, take the pH of the mixture. A low pH indicates that the carbopol is not fully dissolved. The pH you want to achieve is 7.4. Use 5 M sodium hydroxide to adjust the pH. This is accomplished by slowly adding drops of 5 M sodium hydroxide to the mixture, stirring the mixture and taking the pH of the mixture. It usually takes approximately one hour to adjust the pH to 7.4. Once a pH of 7.4 is achieved, cover the gel and let it sit for 2 to 3 hours. After this time period, check the pH to ensure it is still at 7.4. If it has changed, adjust back to pH 7.4 using 5 M sodium hydroxide. Allow the gel to sit for a few hours to ensure the pH is stable at 7.4. Repeat the process until the desired pH is achieved and is stable. Label the container with the name of the gel and the date. The gel is to be used to make nanopaste within the next week.

2. Procedure for Producing Nanopaste

Add sufficient 0.1 $\mu$m to 3 $\mu$m microspheres to water to produce a 20% suspension of the microspheres. Put 8 ml of the 5% w/v carbopol gel in a glass beaker. Add 2 ml of the 20% microsphere suspension to the beaker. Using a glass rod or a mixing spatula, stir the mixture to thoroughly disperse the microspheres throughout the gel. This usually takes 30 minutes. Once the microspheres are dispersed in the gel, place the mixture in a storage jar. Store the jar at 4° C. It must be used within a one month period.

Example 2

Manufacture of Microspheres

Equipment which is preferred for the manufacture of microspheres described below include: 200 ml water jacketed beaker (Kimax or Pyrex), Haake circulating water bath, overhead stirrer and controller with 2 inch diameter (4 blade, propeller type stainless steel stirrer—Fisher brand), 500 ml glass beaker, hot plate/stirrer (Coming brand), 4×50 ml polypropylene centrifuge tubes (Nalgene), glass scintillation vials with plastic insert caps, table top centrifuge (GPR Beckman), high speed centrifuge—floor model (JS 21 Beckman), Mettler analytical balance (AJ 100, 0.1 mg), Mettler digital top loading balance (AE 163, 0.01 mg), automatic pipetter (Gilson). Reagents include Polycaprolactone ("PCL"—mol wt 10,000 to 20,000; Polysciences, Warrington Pa., USA), "washed" (see later method of "washing") Ethylene Vinyl Acetate ("EVA"), Poly(DL) lactic acid ("PLA"—mol wt 15,000 to 25,000; Polysciences), Polyvinyl Alcohol ("PVA"—mol wt 124,000 to 186,000; 99% hydrolyzed; Aldrich Chemical Co., Milwaukee Wis., USA), Dichloromethane ("DCM" or "methylene chloride"; HPLC grade Fisher scientific), and distilled water.

A. Preparation of 5% (w/v) Polymer Solutions

Depending on the polymer solution being prepared, 1.00 g of PCL or PLA, or 0.50 g each of PLA and washed EVA is weighed directly into a 20 ml glass scintillation vial. Twenty milliliters of DCM is then added, and the vial tightly capped. The vial is stored at room temperature (25° C.) for one hour (occasional shaking may be used), or until all the polymer has dissolved (the solution should be clear). The solution may be stored at room temperature for at least two weeks.

B. Preparation of 5% (w/v) Stock Solution of PVA

Twenty-five grams of PVA is weighed directly into a 600 ml glass beaker. Five hundred milliliters of distilled water is added, along with a 3 inch Teflon coated stir bar. The beaker is covered with glass to decrease evaporation losses, and placed into a 2000 ml glass beaker containing 300 ml of water (which acts as a water bath). The PVA is stirred at 300 rpm at 85° C. (Coming hot plate/stirrer) for 2 hours or until fully dissolved. Dissolution of the PVA may be determined by a visual check; the solution should be clear. The solution is then transferred to a glass screw top storage container and stored at 4° C. for a maximum of two months. The solution, however should be warmed to room temperature before use or dilution.

C. Procedure for Producing Microspheres

Based on the size of microspheres being made (see Table I), 100 ml of the PVA solution (concentrations given in Table I) is placed into the 200 ml water jacketed beaker. Haake circulating water bath is connected to this beaker and the contents are allowed to equilibrate at 27° C. (+/−1° C.) for 10 minutes. Based on the size of microspheres being made (see Table I), the start speed of the overhead stirrer is set, and the blade of the overhead stirrer placed half way down in the PVA solution. The stirrer is then started, and 10 ml of polymer solution (polymer solution used based on type of microspheres being produced) is then dripped into the stirring PVA over a period of 2 minutes using a 5 ml automatic pipetter. After 3 minutes the stir speed is adjusted (see Table I), and the solution stirred for an additional 2.5 hours. The stirring blade is then removed from the microsphere preparation, and rinsed with 10 ml of distilled water so that the rinse solution drains into the microsphere preparation. The microsphere preparation is then poured into a 500 ml beaker, and the jacketed water bath washed with 70 ml of distilled water, which is also allowed to drain into the microsphere preparation. The 180 ml microsphere preparation is then stirred with a glass rod, and equal amounts are poured into four polypropylene 50 ml centrifuge tubes. The tubes are then capped, and centrifuged for 10 minutes (force given in Table I). A 5 ml automatic pipetter or vacuum suction is then utilized to draw 45 ml of the PVA solution off of each microsphere pellet.

TABLE I

PVA concentrations, stir speeds, and centrifugal force requirements for each diameter range of microspheres.

| PRO-<br>DUCTION<br>STAGE | MICROSPHERE DIAMETER RANGES | | |
|---|---|---|---|
| | 30 $\mu$m to 100 $\mu$m | 10 $\mu$m to 30 $\mu$m | 0.1 $\mu$m to 3 $\mu$m |
| PVA concentration | 2.5% (w/v) (i.e.,) dilute 5% stock with distilled water | 5% (w/v) (i.e., undiluted stock) | 3.5% (w/v) (i.e., dilute 5% stock with distilled water |
| Starting Stir Speed | 500 rpm +/− 50 rpm | 500 rpm +/− 50 rpm | 3000 rpm +/− 200 rpm |
| Adjusted Stir Speed | 500 rpm +/− 50 rpm | 500 rpm +/− 50 rpm | 2500 rpm +/− 200 rpm |
| Centrifuge Force | 1000 g +/− 100 g (Table top model) | 1000 g +/− 100 g (Table top model) | 10 000 g +/− 1000 g (High speed model) |

Five milliliters of distilled water is then added to each centrifuge tube, which is then vortexed to resuspend the microspheres. The four microsphere suspensions are then pooled into one centrifuge tube along with 20 ml of distilled water, and centrifuged for another 10 minutes (force given in Table I). This process is repeated two additional times for a total of three washes. The microspheres are then centrifuged a final time, and resuspended in 10 ml of distilled water. After the final wash, the microsphere preparation is transferred into a preweighed glass scintillation vial. The vial is capped, and left overnight at room temperature (25° C.) in order to allow the microspheres to sediment out under gravity. Microspheres which fall in the size range of 0.1 um to 3 um do not sediment out under gravity, so they are left in the 10 ml suspension.

D. Drying of 10 $\mu$m to 30 $\mu$m or 30 $\mu$m to 100 $\mu$m Diameter Microspheres After the microspheres have sat at room temperature overnight, a 5 ml automatic pipetter or vacuum suction is used to draw the supernatant off of the sedimented microspheres. The microspheres are allowed to dry in the uncapped vial in a drawer for a period of one week or until they are fully dry (vial at constant weight). Faster drying may be accomplished by leaving the uncapped vial under a slow stream of nitrogen gas (flow approx. 10 ml/min.) in the fume hood. When fully dry (vial at constant weight), the vial is weighed and capped. The labeled, capped vial is stored at room temperature in a drawer. Microspheres are normally stored no longer than 3 months.

E. Drying of 0.1 $\mu$m to 3 $\mu$m Diameter Microspheres

This size range of microspheres will not sediment out, so they are left in suspension at 4° C. for a maximum of four weeks. To determine the concentration of microspheres in the 10 ml suspension, a 200 $\mu$l sample of the suspension is pipetted into a 1.5 ml preweighed microfuge tube. The tube is then centrifuged at 10,000 g (Eppendorf table top microfuge), the supernatant removed, and the tube allowed to dry at 50° C. overnight. The tube is then reweighed in order to determine the weight of dried microspheres within the tube.

F. Manufacture of Paclitaxel Loaded Microsphere

In order to prepare paclitaxel containing microspheres, an appropriate amount of weighed paclitaxel (based upon the percentage of paclitaxel to be encapsulated) is placed directly into a 20 ml glass scintillation vial. Ten milliliters of an appropriate polymer solution is then added to the vial containing the paclitaxel, which is then vortexed until the paclitaxel has dissolved.

Microspheres containing paclitaxel may then be produced essentially as described above in steps (C) through (E).

Example 3

Surfactant Coated Microspheres

A. Materials and Methods

Microspheres were manufactured from Poly (DL) lactic acid (PLA), poly methylmethacrylate (PMMA), polycaprolactone (PCL) and 50:50 Ethylene vinyl acetate (EVA):PLA essentially as described in Example 2. Size ranged from 10 to 100 um with a mean diameter 45 um.

Human blood was obtained from healthy volunteers. Neutrophils (white blood cells) were separated from the blood using dextran sedimentation and Ficoll Hypaque centrifugation techniques. Neutrophils were suspended at 5 million cells per ml in Hanks Buffered Salt Solution ("HBSS").

Neutrophil activation levels were determined by the generation of reactive oxygen species as determined by chemiluminescence. In particular, chemiluminescence was determined by using an LKB luminometer with 1 uM luminol enhancer. Plasma precoating (or opsonization) of microspheres was performed by suspending 10 mg of microspheres in 0.5 ml of plasma and tumbling at 37° C. for 30 min.

Microspheres were then washed in 1 ml of HBSS and the centrifuged microsphere pellet added to the neutrophil suspension at 37° C. at time t=0. Microsphere surfaces were modified using a surfactant called Pluronic F127 (BASF) by suspending 10 mg of microspheres in 0.5 ml of 2% w/w solution of F127 in HBSS for 30 min at 37° C. Microspheres were then washed twice in 1 ml of HBSS before adding to neutrophils or to plasma for further precoating.

B. Results

FIG. 1 shows that the untreated microspheres give chemiluminescence values less than 50 mV. These values represent low levels of neutrophil activation. By way of comparison, inflammatory microcrystals might give values close to 1000 mV, soluble chemical activators might give values close to 5000 mV. However, when the microspheres are precoated with plasma, all chemiluminescence values are amplified to the 100 to 300 mV range (see FIG. 1). These levels of neutrophil response or activation can be considered mildly inflammatory. PMMA gave the biggest response and could be regarded as the most inflammatory. PLA and PCL both become three to four times more potent in activating neutrophils after plasma pretreatment (or opsonization) but there is little difference between the two polymers in this regard. EVA:PLA is not likely to be used in angiogenesis formulations since the microspheres are difficult to dry and resuspend in aqueous buffer. This effect of plasma is termed opsonization and results from the adsorption of antibodies or complement molecules onto the surface. These adsorbed species interact with receptors on white blood cells and cause an amplified cell activation.

FIGS. 2–5 describe the effects of plasma precoating of PCL, PMMA, PLA and EVA:PLA respectively as well as showing the effect of pluronic F127 precoating prior to plasma precoating of microspheres. These figures all show the same effect: (1) plasma precoating amplifies the response; (2) Pluronic F127 precoating has no effect on its own; (3) the amplified neutrophil response caused by plasma precoating can be strongly inhibited by pretreating the microsphere surface with 2% pluronic F127.

The nature of the adsorbed protein species from plasma was also studied by electrophoresis. Using this method, it was shown that pretreating the polymeric surface with Pluronic F127 inhibited the adsorption of antibodies to the polymeric surface.

FIGS. 6–9 likewise show the effect of precoating PCL, PMMA, PLA or EVA:PLA microspheres (respectively) with either IgG (2 mg/ml) or 2% pluronic F127 then IgG (2 mg/ml). As can be seen from these figures, the amplified response caused by precoating microspheres with IgG can be inhibited by treatment with pluronic F127.

This result shows that by pretreating the polymeric surface of all four types of microspheres with Pluronic F127, the "inflammatory" response of neutrophils to microspheres may be inhibited.

Example 4

Encapsulation of Paclitaxel

Five hundred micrograms of either paclitaxel or baccatin (a paclitaxel analog, available from Inflazyme Pharmaceuticals Inc., Vancouver, British Columbia, Canada) are dissolved in 1 ml of a 50:50 ELVAX:poly-1-lactic acid mixture in dcm. Microspheres are then prepared in a dissolution machine (Six-spindle dissolution tester, VanderKanp, Van Kell Industries Inc., U.S.A.) in triplicate at 200 rpm, 42° C., for 3 hours. Microspheres so prepared are washed twice in water and sized on the microscope.

Determination of paclitaxel encapsulation is undertaken in a uv/vis assay (uv/vis lambda max. at 237 nm, fluorescence assay at excitation 237, emission at 325 nm; Fluorescence results are presented in square brackets [ ]). Utilizing the procedures described above, 58 µg (+/−12 µg) [75 µg (+/−25 µg)] of paclitaxel may be encapsulated from a total 500 µg of starting material. This represents 12% (+/−2.4%) [15% (+/−5%)] of the original weight, or 1.2% (+/−0.25%) [1.5% (+/−0.5%)] by weight of the polymer. After 18 hours of tumbling in an oven at 37° C., 10.3% (+/−10%) [6% (+/−5.6%)] of the total paclitaxel had been released from the microspheres.

For baccatin, 100 +/−15 µg [83 +/−23 µg] of baccatin can be encapsulated from a total of 500 µg starting material. This represents a 20% (+/−3%) [17% (+/−5%) of the original weight of baccatin, and 2% (+/−0.3%) [1.7% (+/−0.5%)] by weight of the polymer. After 18 hours of tumbling in an oven at 37° C., 55% (+/−13%) [60% (+/−23%)] of the baccatin is released from the microspheres.

Example 5

Controlled Delivery of Paclitaxel from Microspheres Composed of a Blend of Ethylene-vinyl-acetate Copolymer and Poly (D,L Lactic Acid). In vivo Testing of the Microspheres on the CAM Assay This example describes the preparation of paclitaxel-loaded microspheres composed of a blend of biodegradable poly (d,l-lactic acid) (PLA) polymer and nondegradable ethylene-vinyl acetate (EVA) copolymer. In addition, the in vitro release rate and anti-angiogenic activity of paclitaxel released from microspheres placed on a CAM are demonstrated.

Reagents which were utilized in these experiments include paclitaxel, which is purchased from Sigma Chemical Co. (St. Louis, Mo.); PLA (molecular weight 15,000–25,000) and EVA (60% vinyl acetate) (purchased from Polysciences (Warrington, Pa.); polyvinyl alcohol (PVA) (molecular weight 124,000–186,000, 99% hydrolysed, purchased from Aldrich Chemical Co. (Milwaukee, Wis.)) and Dichloromethane (DCM) (HPLC grade, obtained from Fisher Scientific Co). Distilled water is used throughout.

A. Preparation of Microspheres

Microspheres are prepared essentially as described in Example 2 utilizing the solvent evaporation method. Briefly, 5% w/v polymer solutions in 20 mL DCM are prepared using blends of EVA:PLA between 35:65 to 90:10. To 5 mL of 2.5% w/v PVA in water in a 20 mL glass vial is added 1 mL of the polymer solution dropwise with stirring. Six similar vials are assembled in a six position overhead stirrer, dissolution testing apparatus (Vanderkamp) and stirred at 200 rpm. The temperature of the vials is increased from room temperature to 40° C. over 15 min and held at 40° C. for 2 hours. Vials are centrifuged at 500×g and the microspheres washed three times in water. At some EVA:PLA polymer blends, the microsphere samples aggregated during the washing stage due to the removal of the dispersing or emulsifying agent, PVA. This aggregation effect could be analyzed semi-quantitatively since aggregated microspheres fused and the fused polymer mass floated on the surface of the wash water. This surface polymer layer is discarded during the wash treatments and the remaining, pelleted microspheres are weighed. The % aggregation is determined from $$\% \text{ aggregation} = 1 - \frac{(\text{weight of pelleted microspheres}) \times 100}{\text{initial polymer weight}}$$

Paclitaxel loaded microspheres (0.6% w/w paclitaxel) are prepared by dissolving the paclitaxel in the 5% w/v polymer solution in DCM. The polymer blend used is 50:50 EVA:PLA. A "large" size fraction and "small" size fraction of microspheres are produced by adding the paclitaxel/polymer solution dropwise into 2.5% w/v PVA and 5% w/v PVA, respectively. The dispersions are stirred at 40° C. at 200 rpm for 2 hours, centrifuged and washed 3 times in water as described previously. Microspheres are air dried and samples are sized using an optical microscope with a stage micrometer. Over 300 microspheres are counted per sample. Control microspheres (paclitaxel absent) are prepared and sized as described previously.

B. Encapsulation efficiency

Known weights of paclitaxel-loaded microspheres are dissolved in 1 mL DCM, 20 mL of 40% acetonitrile in water at 50° C. are added and vortexed until the DCM had been evaporated. The concentration of paclitaxel in the 40% acetonitrile is determined by HPLC using a mobile phase of water:methanol:acetonitrile (37:5:58) at a flow rate of 1 mL/min (Beckman isocratic pump), a C8 reverse phase column (Beckman) and UV detection at 232 nm. To determine the recovery efficiency of this extraction procedure, known weights of paclitaxel from 100–1000 µg are dissolved in 1 mL of DCM and subjected to the same extraction procedure in triplicate as described previously. Recoveries are always greater than 85% and the values of encapsulation efficiency are corrected appropriately.

C. Drug release studies

In 15 mL glass, screw capped tubes are placed 10 mL of 10 mM phosphate buffered saline (PBS), pH 7.4 and 35 mg paclitaxel-loaded microspheres. The tubes are tumbled at 37° C. and at given time intervals, centrifuged at 1500×g for 5 min and the supernatant saved for analysis. Microsphere pellets are resuspended in fresh PBS (10 mL) at 37° C. and reincubated. Paclitaxel concentrations are determined by extraction into 1 mL DCM followed by evaporation to dryness under a stream of nitrogen, reconstitution in 1 mL of 40% acetonitrile in water and analysis using HPLC as previously described.

D. Scanning Electron Microscopy (SEM)

Microspheres are placed on sample holders, sputter coated with gold and micrographs obtained using a Philips 501B SEM operating at 15 kV.

E. CAM Studies

Fertilized, domestic chick embryos are incubated for 4 days prior to shell-less culturing. The egg contents are incubated at 90% relative humidity and 3% $CO_2$ for 2 days. On day 6 of incubation, 1 mg aliquots of 0.6% paclitaxel loaded or control (paclitaxel free) microspheres are placed directly on the CAM surface. After a 2 day exposure the vasculature is examined using a stereomicroscope interfaced with a video camera; the video signals are then displayed on a computer and video printed.

F. Results

Microspheres prepared from 100% EVA are freely suspended in solutions of PVA but aggregated and coalesced or fused extensively on subsequent washing in water to remove the PVA. Blending EVA with an increasing proportion of PLA produced microspheres showing a decreased tendency to aggregate and coalesce when washed in water, as described in FIG. 10A. A 50:50 blend of EVA:PLA formed microspheres with good physical stability, that is the microspheres remained discrete and well suspended with negligible aggregation and coalescence.

The size range for the "small" size fraction microspheres is determined to be >95% of the microsphere sample (by weight) between 10–30 mm and for the "large" size fraction, >95% of the sample (by weight) between 30–100 mm. Representative scanning electron micrographs of paclitaxel loaded 50:50 EVA:PLA microspheres in the "small" and "large" size ranges are shown in FIGS. 10B and 10C, respectively. The microspheres are spherical with a smooth surface and with no evidence of solid drug on the surface of the microspheres. The efficiency of loading 50:50 EVA:PLA microspheres with paclitaxel is between 95–100% at initial paclitaxel concentrations of between 100–1000 mg paclitaxel per 50 mg polymer. There is no significant difference (Student t-test, $p<0.05$) between the encapsulation efficiencies for either "small" or "large" microspheres.

Figure 10A:
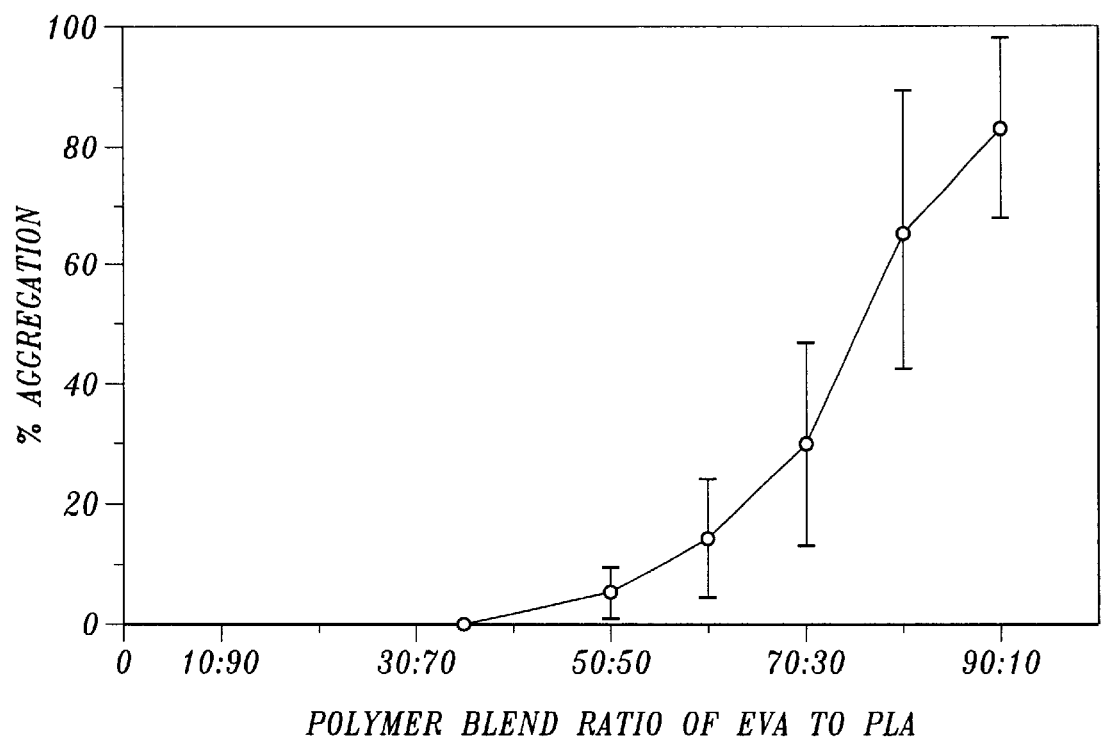
FIG. 10A is a graph which shows the effect of the EVA:PLA polymer blend ratio upon aggregation of microspheres.
Figure 10B:
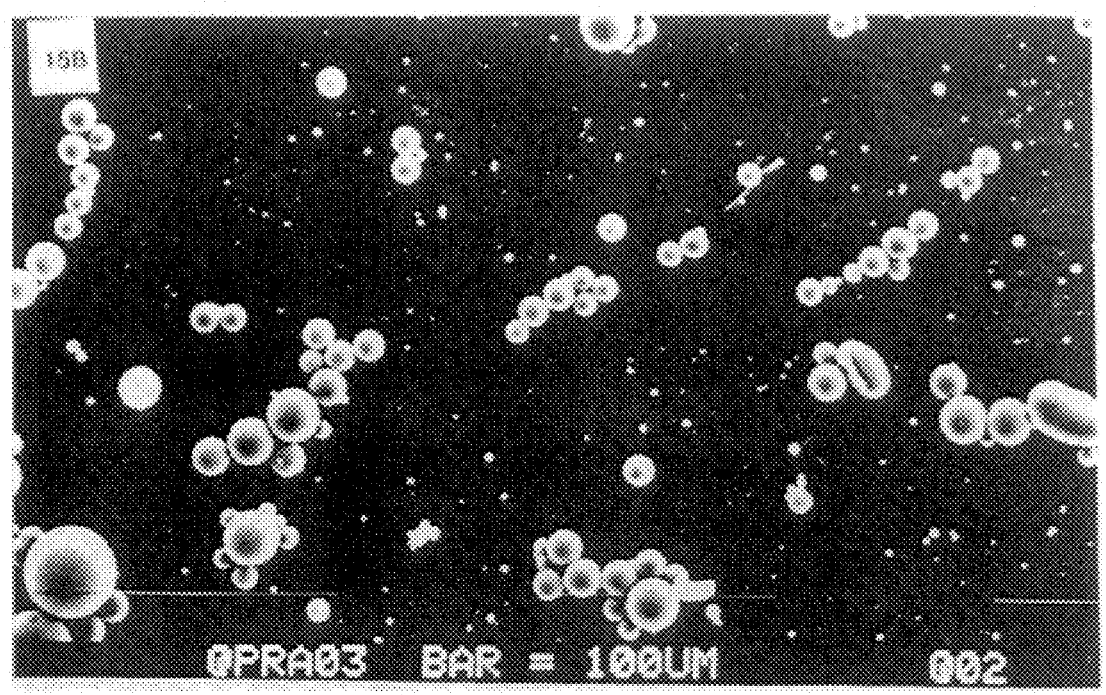
FIG. 10B is a scanning electron micrograph which shows the size of "small" microspheres.
Figure 10C:
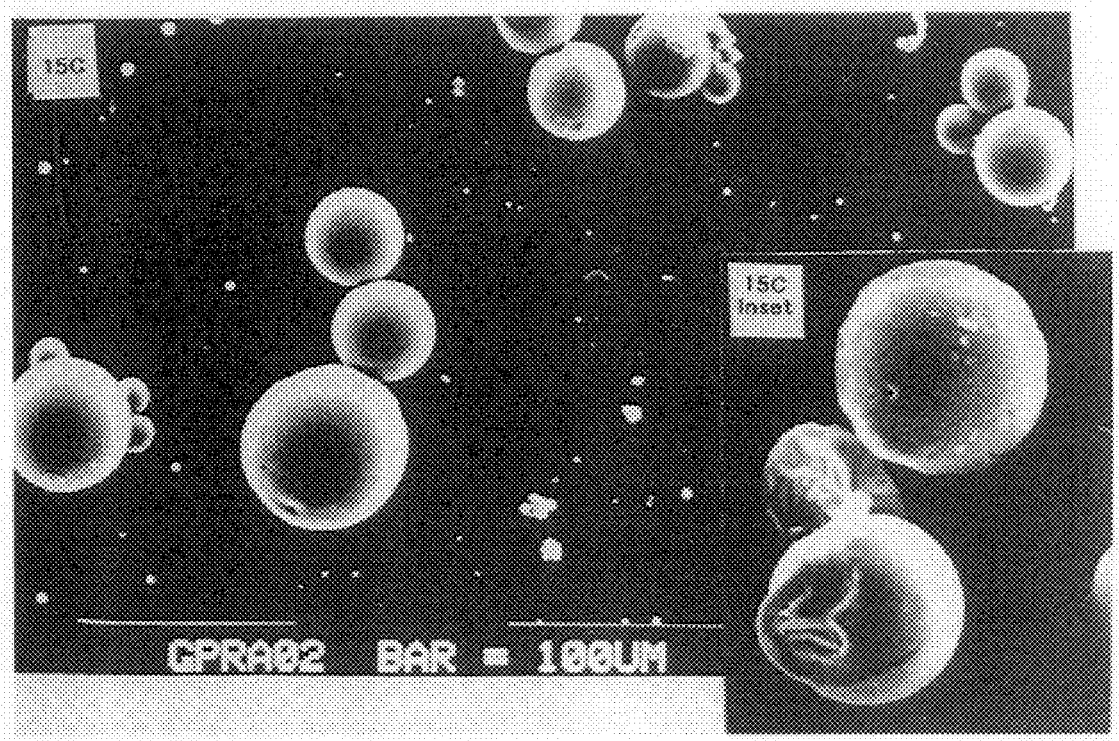
FIG. 10C (which includes a magnified inset—labelled "10C-inset") is a scanning electron micrograph which shows the size of "large" microspheres.
Figure 10D:
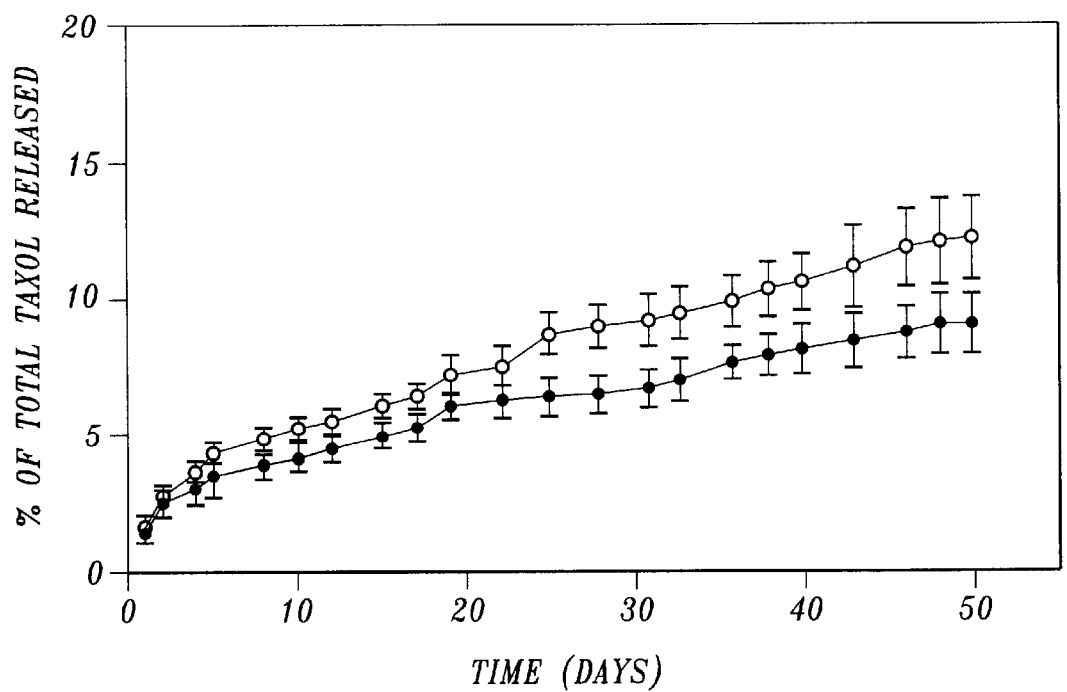
FIG. 10D is a graph which depicts the time course of in vitro paclitaxel release from 0.6% w/v paclitaxel-loaded 50:50 EVA:PLA polymer blend microspheres into phosphate buffered saline (pH 7.4) at 37° C. Open circles are "small" sized microspheres, and closed circles are "large" sized microspheres.

The time course of paclitaxel release from 0.6% w/v loaded 50:50 EVA:PLA microspheres is shown in FIG. 10D for "small" size (open circles) and "large" size (closed circles) microspheres. The release rate studies are carried out in triplicate tubes in 3 separate experiments. The release profiles are biphasic with an initial rapid release of paclitaxel or "burst" phase occurring over the first 4 days from both size range microspheres. This is followed by a phase of much slower release. There is no significant difference between the release rates from "small" or "large" microspheres. Between 10–13% of the total paclitaxel content of the microspheres is released in 50 days.

Figure 10E:
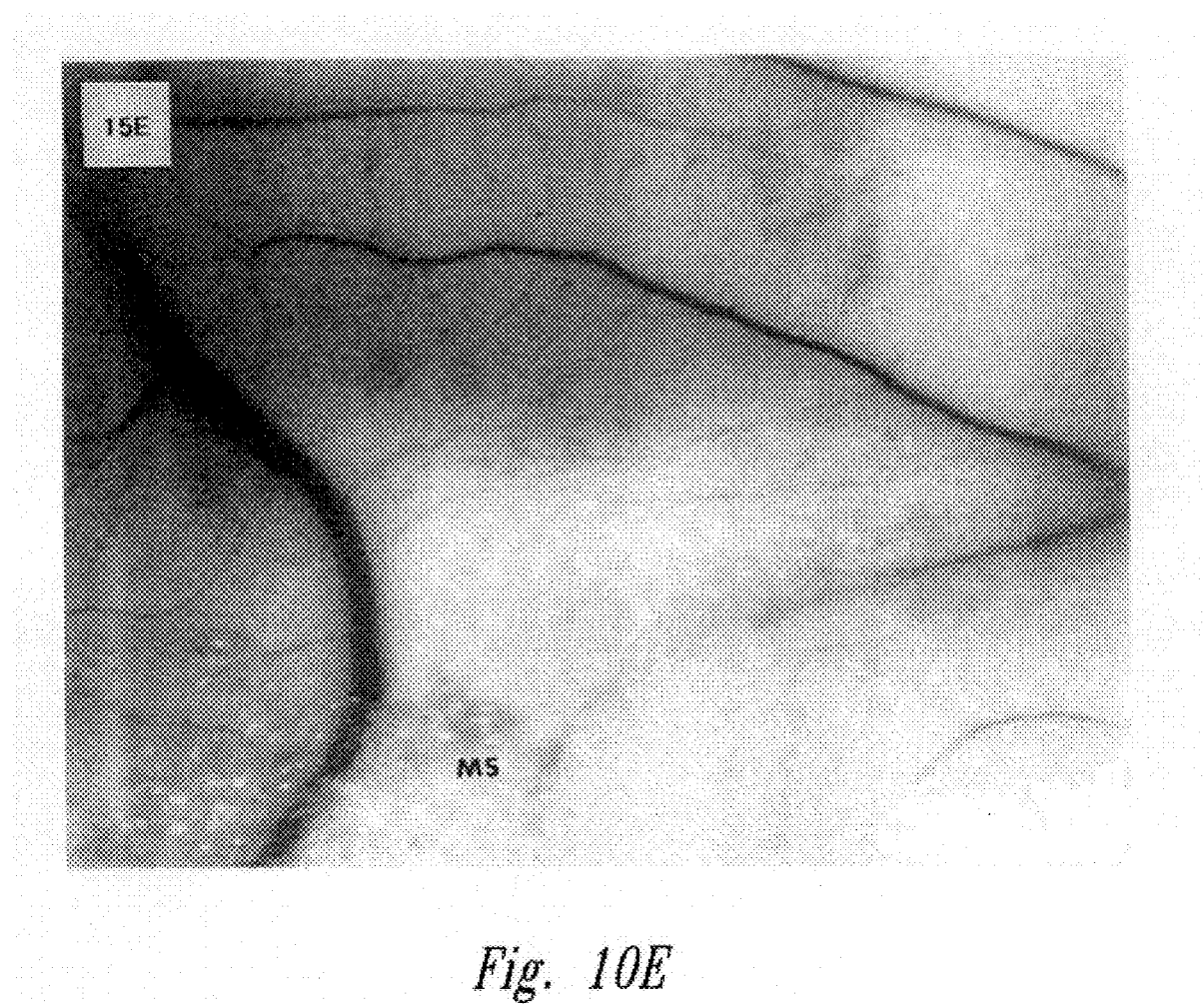
FIG. 10E is a photograph of a CAM which shows the results of paclitaxel release by microspheres ("MS").
Figure 10F:
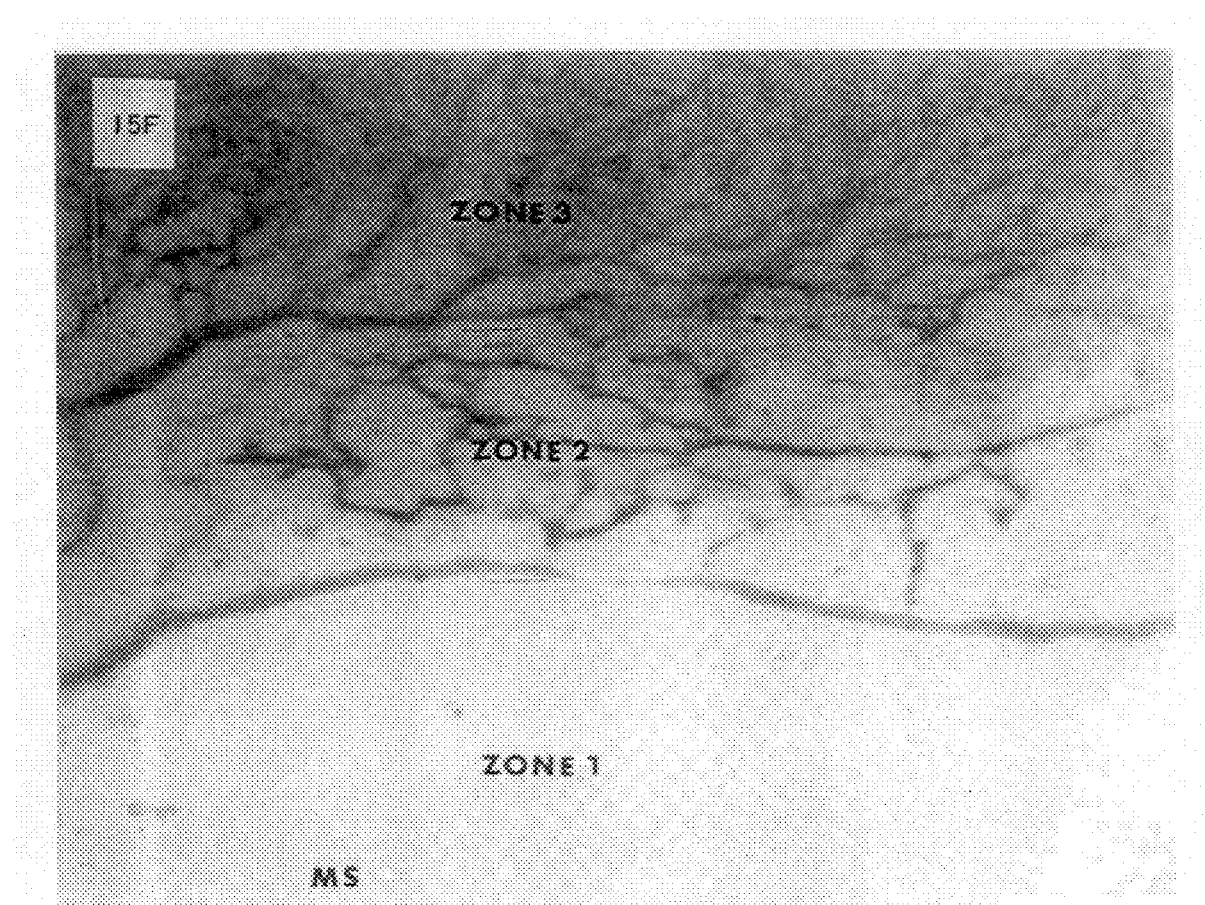
FIG. 10F is a photograph similar to that of 10E at increased magnification.

The paclitaxel loaded microspheres (0.6% w/v loading) are tested using the CAM assay and the results are shown in FIG. 10E. The paclitaxel microspheres released sufficient drug to produce a zone of avascularity in the surrounding tissue (FIG. 10F). Note that immediately adjacent to the microspheres ("MS" in FIGS. 10E and 10F) is an area in which blood vessels are completely absent (Zone 1); further from the microspheres is an area of disrupted, non-functioning capillaries (Zone 2); it is only at a distance of approximately 6 mm from the microspheres that the capillaries return to normal. In CAMs treated with control microspheres (paclitaxel absent) there is a normal capillary network architecture (figure not shown.)

Discussion

Peritubular drug administration is a mildly invasive surgical technique. Therefore, ideally, a perivascular formulation of an anti-proliferative drug such as paclitaxel would release the drug at the tumor or disease site at concentrations sufficient for activity for a prolonged period of time, of the order of several months. EVA is a tissue compatible nondegradable polymer which has been used extensively for the controlled delivery of macromolecules over long time periods (>100 days).

EVA is initially selected as a polymeric biomaterial for preparing microspheres with paclitaxel dispersed in the polymer matrix. However, microspheres prepared with 100% EVA aggregated and coalesced almost completely during the washing procedure.

Polymers and copolymers based on lactic acid and glycolic acid are physiologically inert and biocompatible and degrade by hydrolysis to toxicologically acceptable products. Copolymers of lactic acid and glycolic acids have faster degradation rates than PLA and drug loaded microspheres prepared using these copolymers are unsuitable for prolonged, controlled release over several months.

FIG. 10A shows that increasing the proportion of PLA in a EVA:PLA blend decreased the extent of aggregation of the microsphere suspensions. Blends of 50% or less EVA in the EVA:PLA matrix produced physically stable microsphere suspensions in water or PBS. A blend of 50:50 EVA:PLA is selected for all subsequent studies.

Different size range fractions of microspheres could be prepared by changing the concentration of the emulsifier, PVA, in the aqueous phase. "Small" microspheres are produced at the higher PVA concentration of 5% w/v whereas "large" microspheres are produced at 2.5% w/v PVA. All other production variables are the same for both microsphere size fractions. The higher concentration of emulsifier gave a more viscous aqueous dispersion medium and produced smaller droplets of polymer/paclitaxel/DCM emulsified in the aqueous phase and thus smaller microspheres. The paclitaxel loaded microspheres contained between 95–100% of the initial paclitaxel added to the organic phase encapsulated within the solid microspheres. The low water solubility of paclitaxel favoured partitioning into the organic phase containing the polymer.

Release rates of paclitaxel from the 50:50 EVA:PLA microspheres are very slow with less than 15% of the loaded paclitaxel being released in 50 days. The initial burst phase of drug release may be due to diffusion of drug from the superficial region of the microspheres (close to the microsphere surface).

The mechanism of drug release from nondegradable polymeric matrices such as EVA is thought to involve the diffusion of water through the dispersed drug phase within the polymer, dissolution of the drug and diffusion of solute through a series of interconnecting, fluid filled pores. Blends of EVA and PLA have been shown to be immiscible or bicontinuous over a range of 30 to 70% EVA in PLA. In degradation studies in PBS buffer at 37° C., following an induction or lag period, PLA hydrolytically degraded and eroded from the EVA:PLA polymer blend matrix leaving an inactive sponge-like skeleton. Although the induction period and rate of PLA degradation and erosion from the blended matrices depended on the proportion of PLA in the matrix and on process history, there is consistently little or no loss of PLA until after 40–50 days.

Although some erosion of PLA from the 50:50 EVA:PLA microspheres may have occurred within the 50 days of the in vitro release rate study (FIG. 10C), it is likely that the primary mechanism of drug release from the polymer blend is diffusion of solute through a pore network in the polymer matrix.

At the conclusion of the release rate study, the microspheres are analyzed from the amount of drug remaining. The values for the percent of paclitaxel remaining in the 50 day incubation microsphere samples are 94% +/−9% and 89% +/−12% for "large" and "small" size fraction microspheres, respectively.

Microspheres loaded with 6 mg per mg of polymer (0.6%) provided extensive inhibition of angiogenesis when placed on the CAM of the embryonic chick (FIGS. 10E and 10F).

Example 6

Therapeutic Agent Encapsulation in Poly($\epsilon$-caprolactone) Microspheres. Inhibition of Angiogenesis on the CAM Assay by Paclitaxel-loaded Microspheres This example evaluates the in vitro release rate profile of paclitaxel from biodegradable microspheres of poly($\epsilon$-caprolactone) and demonstrates the in vivo anti-angiogenic activity of paclitaxel released from these microspheres when placed on the CAM.

Reagents which were utilized in these experiments include: poly($\epsilon$-caprolactone) ("PCL") (molecular weight 35,000–45,000; purchased from Polysciences (Warrington, Pa.)); dichloromethane ("DCM") from Fisher Scientific Co., Canada; polyvinyl alcohol (PVP) (molecular weight 12,000–18,000, 99% hydrolysed) from Aldrich Chemical Co. (Milwaukee, Wis.), and paclitaxel from Sigma Chemical Co. (St. Louis, Mo.). Unless otherwise stated all chemicals and reagents are used as supplied. Distilled water is used throughout.

A. Preparation of Microspheres

Microspheres are prepared essentially as described in Example 2 utilizing the solvent evaporation method. Briefly, 5%w/w paclitaxel loaded microspheres are prepared by dissolving 10 mg of paclitaxel and 190 mg of PCL in 2 ml of DCM, adding to 100 ml of 1% PVP aqueous solution and stirring at 1000 rpm at 25° C. for 2 hours. The suspension of microspheres is centrifuged at 1000×g for 10 minutes (Beckman GPR), the supernatant removed and the microspheres washed three times with water. The washed microspheres are air-dried overnight and stored at room temperature. Control microspheres (paclitaxel absent) are prepared as described above. Microspheres containing 1% and 2% paclitaxel are also prepared. Microspheres are sized using an optical microscope with a stage micrometer.

B. Encapsulation Efficiency

A known weight of drug-loaded microspheres (about 5 mg) is dissolved in 8 ml of acetonitrile and 2 ml distilled water is added to precipitate the polymer. The mixture is centrifuged at 1000 g for 10 minutes and the amount of paclitaxel encapsulated is calculated from the absorbance of the supernatant measured in a UV spectrophotometer (Hewlett-Packard 8452A Diode Array Spectrophotometer) at 232 nm.

C. Drug Release Studies

About 10 mg of paclitaxel-loaded microspheres are suspended in 20 ml of 10 mM phosphate buffered saline, pH 7.4 (PBS) in screw-capped tubes. The tubes are tumbled end-over-end at 37° C. and at given time intervals 19.5 ml of supernatant is removed (after allowing the microspheres to settle at the bottom), filtered through a 0.45 um membrane filter and retained for paclitaxel analysis. An equal volume of PBS is replaced in each tube to maintain sink conditions throughout the study. The filtrates are extracted with 3×1 ml DCM, the DCM extracts evaporated to dryness under a stream of nitrogen, redissolved in 1 ml acetonitrile and analyzed by HPLC using a mobile phase of water:methanol:acetonitrile (37:5:58) at a flow rate of 1 ml min$^{-1}$ (Beckman Isocratic Pump), a C8 reverse phase column (Beckman), and UV detection (Shimadzu SPD A) at 232 nm.

D. CAM Studies

Fertilized, domestic chick embryos are incubated for 4 days prior to shell-less culturing. On day 6 of incubation, 1 mg aliquots of 5% paclitaxel-loaded or control (paclitaxel-free) microspheres are placed directly on the CAM surface. After a 2-day exposure the vasculature is examined using a stereomicroscope interfaced with a video camera; the video signals are then displayed on a computer and video printed.

E. Scanning Electron Microscopy

Microspheres are placed on sample holders, sputter-coated with gold and then placed in a Philips 501B Scanning Electron Microscope operating at 15 kV.

F. Results

The size range for the microsphere samples is between 30–100 um, although there is evidence in all paclitaxel-loaded or control microsphere batches of some microspheres falling outside this range. The efficiency of loading PCL microspheres with paclitaxel is always greater than 95% for all drug loadings studied. Scanning electron microscopy demonstrated that the microspheres are all spherical and many showed a rough or pitted surface morphology. There appeared to be no evidence of solid drug on the surface of the microspheres.

Figure 11A:
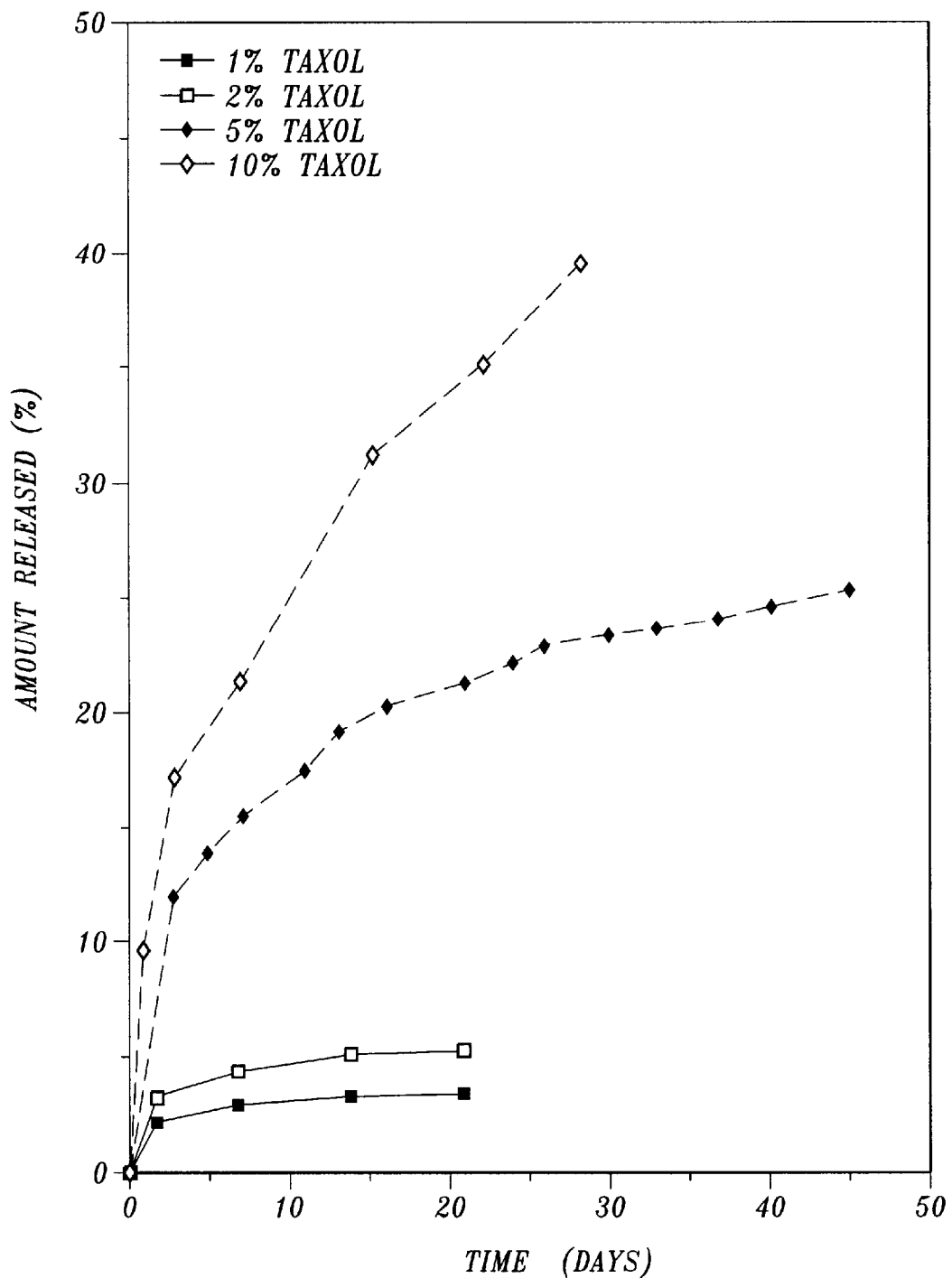
FIG. 11A is a graph which shows release rate profiles from polycaprolactone microspheres containing 1%, 2%, 5% or 10% paclitaxel into phosphate buffered saline at 37° C.

The time courses of paclitaxel release from 1%, 2% and 5% loaded PCL microspheres are shown in FIG. 11A. The release rate profiles are bi-phasic. There is an initial rapid release of paclitaxel or "burst phase" at all drug loadings. The burst phase occurred over 1–2 days at 1% and 2% paclitaxel loading and over 3–4 days for 5% loaded microspheres. The initial phase of rapid release is followed by a phase of significantly slower drug release. For microspheres containing 1% or 2% paclitaxel there is no further drug release after 21 days. At 5% paclitaxel loading, the microspheres had released about 20% of the total drug content after 21 days.

Figure 11B:
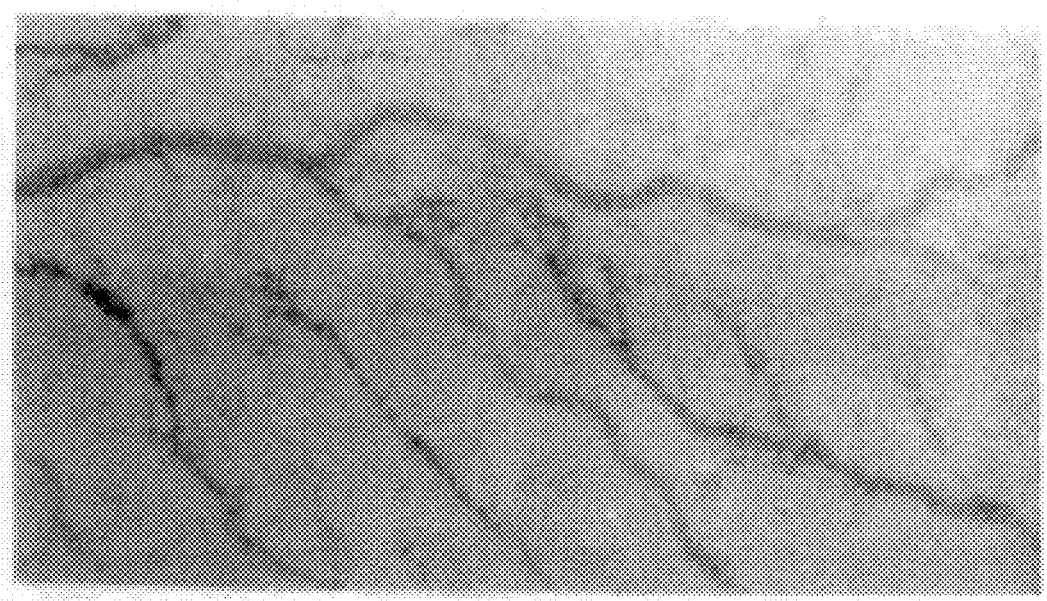
FIG. 11B is a photograph which shows a CAM treated with control microspheres.
Figure 11C:
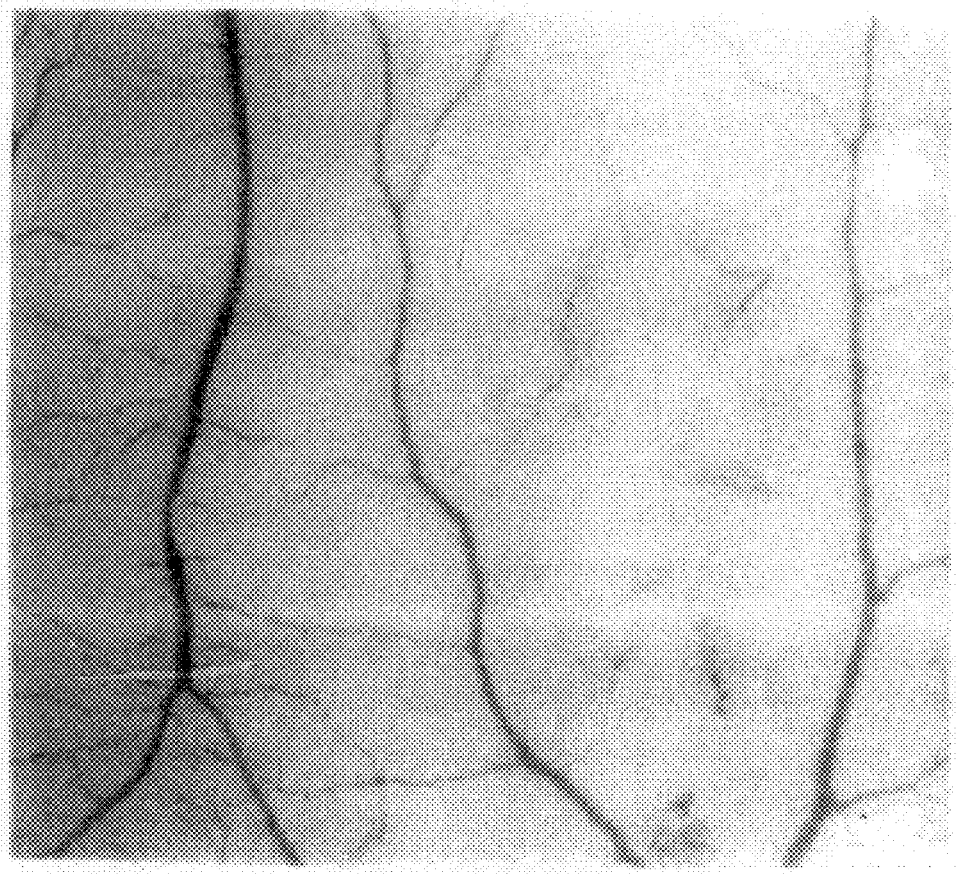
FIG. 11C is a photograph which shows a CAM treated with 5% paclitaxel loaded microspheres.

FIG. 11B shows CAMs treated with control PCL microspheres, and FIG. 11C shows treatment with 5% paclitaxel loaded microspheres. The CAM with the control microspheres shows a normal capillary network architecture. The CAM treated with paclitaxel-PCL microspheres shows marked vascular regression and zones which are devoid of a capillary network.

G. Discussion

The solvent evaporation method of manufacturing paclitaxel-loaded microspheres produced very high paclitaxel encapsulation efficiencies of between 95–100%. This is due to the poor water solubility of paclitaxel and its hydrophobic nature favouring partitioning in the organic solvent phase containing the polymer.

The biphasic release profile for paclitaxel is typical of the release pattern for many drugs from biodegradable polymer matrices. Poly($\epsilon$-caprolactone) is an aliphatic polyester which can be degraded by hydrolysis under physiological conditions and it is non-toxic and tissue compatible. The degradation of PCL is significantly slower than that of the extensively investigated polymers and copolymers of lactic and glycolic acids and is therefore suitable for the design of long-term peritubular drug delivery systems. The initial rapid or burst phase of paclitaxel release is thought to be due to diffusional release of the drug from the superficial region of the microspheres (close to the microsphere surface). Release of paclitaxel in the second (slower) phase of the release profiles is not likely due to degradation or erosion of PCL because studies have shown that under in vitro conditions in water there is no significant weight loss or surface erosion of PCL over a 7.5-week period. The slower phase of paclitaxel release is probably due to dissolution of the drug within fluid-filled pores in the polymer matrix and diffusion through the pores. The greater release rate at higher paclitaxel loading is probably a result of a more extensive pore network within the polymer matrix.

Paclitaxel microspheres with 5% loading have been shown to release sufficient drug to produce extensive inhibition of angiogenesis when placed on the CAM. The inhibition of blood vessel growth resulted in an avascular zone as shown in FIG. 11C.

Example 7

Therapeutic Agent-loaded Peritubular Polymeric Films Composed of Ethylene Vinyl Acetate and a Surfactant Two types of films are investigated within this example: pure EVA films loaded with paclitaxel and EVA/surfactant blend films loaded with paclitaxel.

The surfactants being examined are two hydrophobic surfactants (Span 80 and Pluronic L101) and one hydrophilic surfactant (Pluronic F127). The pluronic surfactants are themselves polymers, which is an attractive property since they can be blended with EVA to optimize various drug delivery properties. Span 80 is a smaller molecule which is in some manner dispersed in the polymer matrix, and does not form a blend.

Figure 12A:
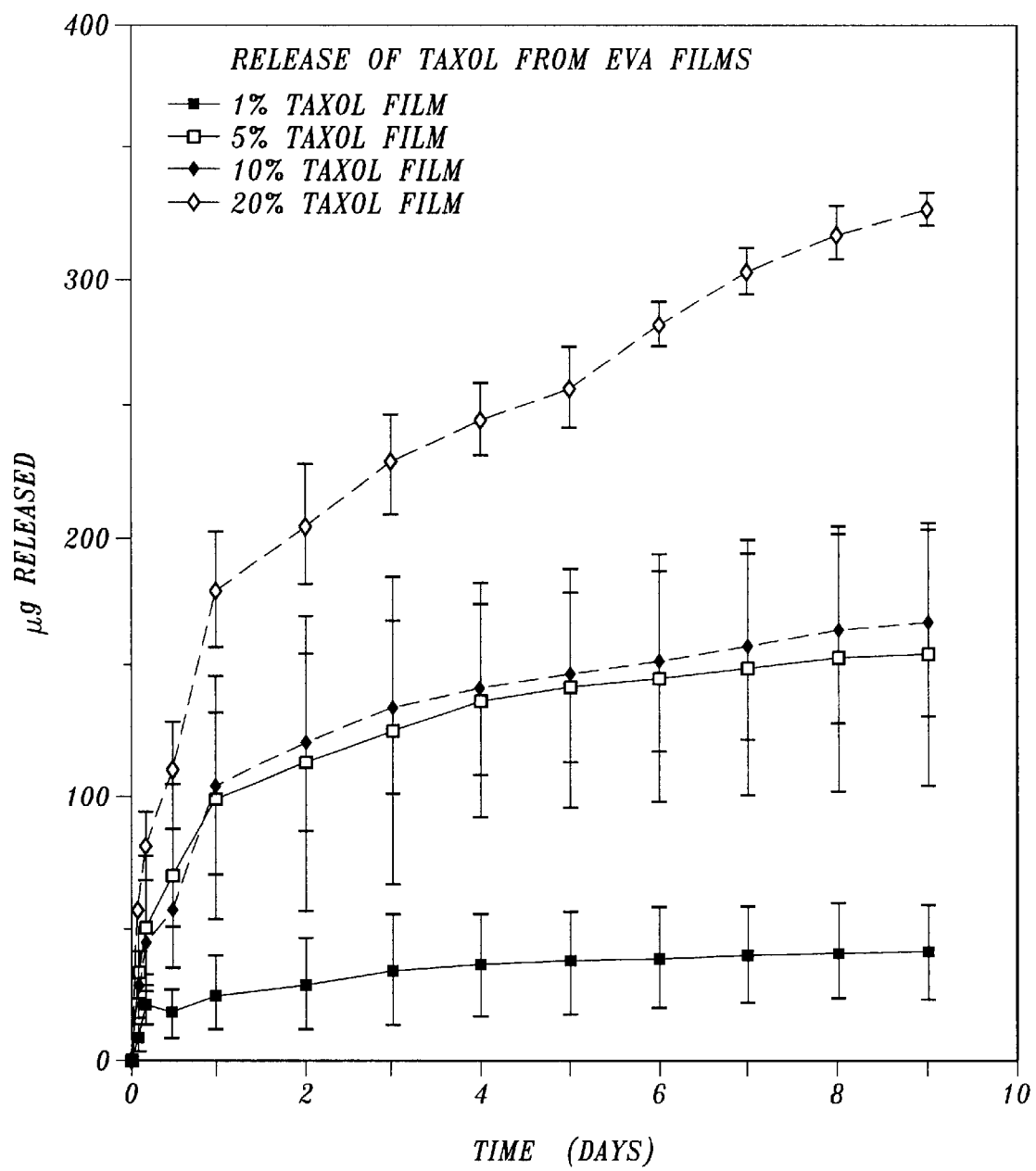
FIGS. 12A and 12B, respectively, are two graphs which show the release of paclitaxel from EVA films, and the percent paclitaxel remaining in those same films over time.
Figure 12B:
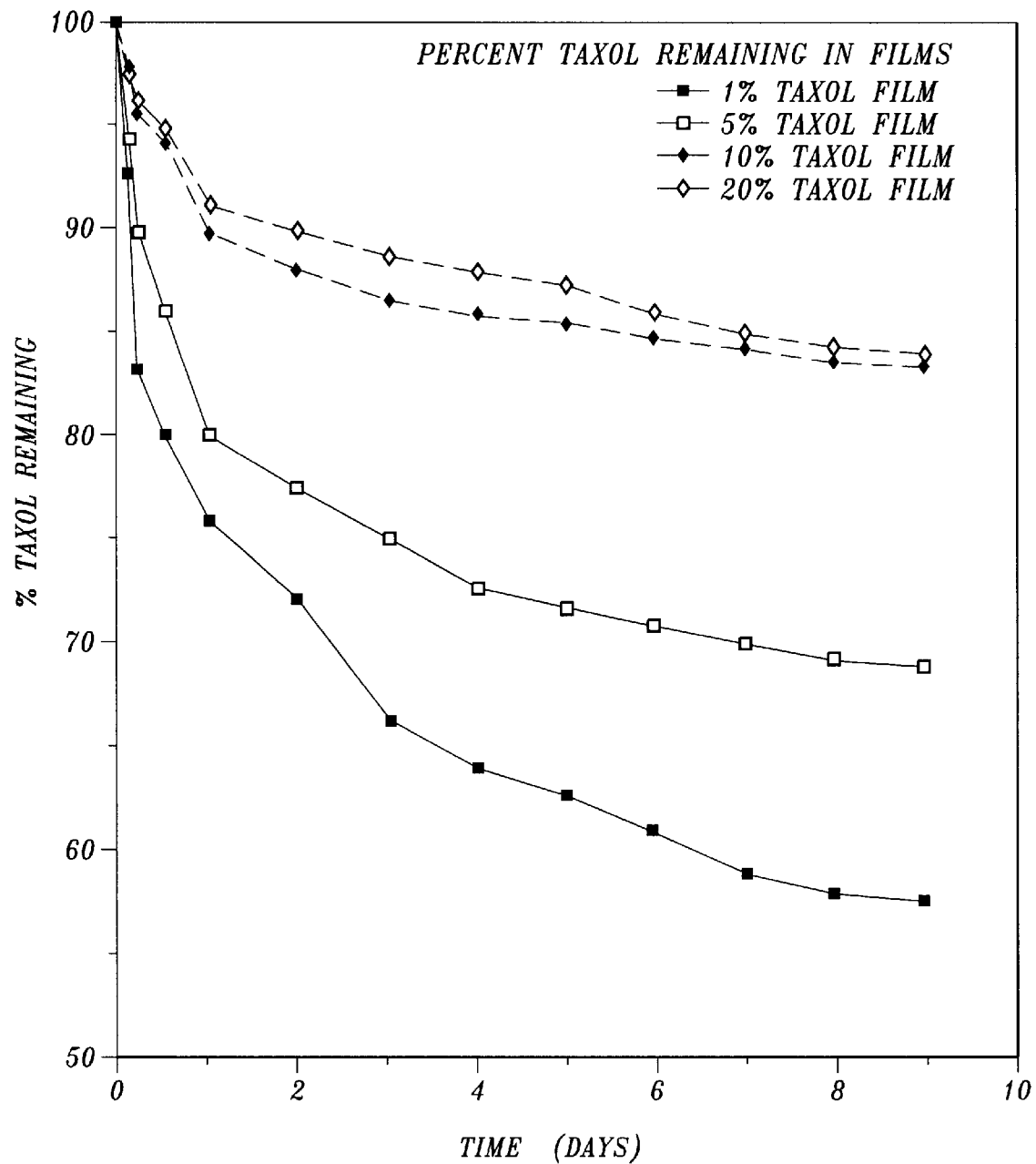
Figure 12C:
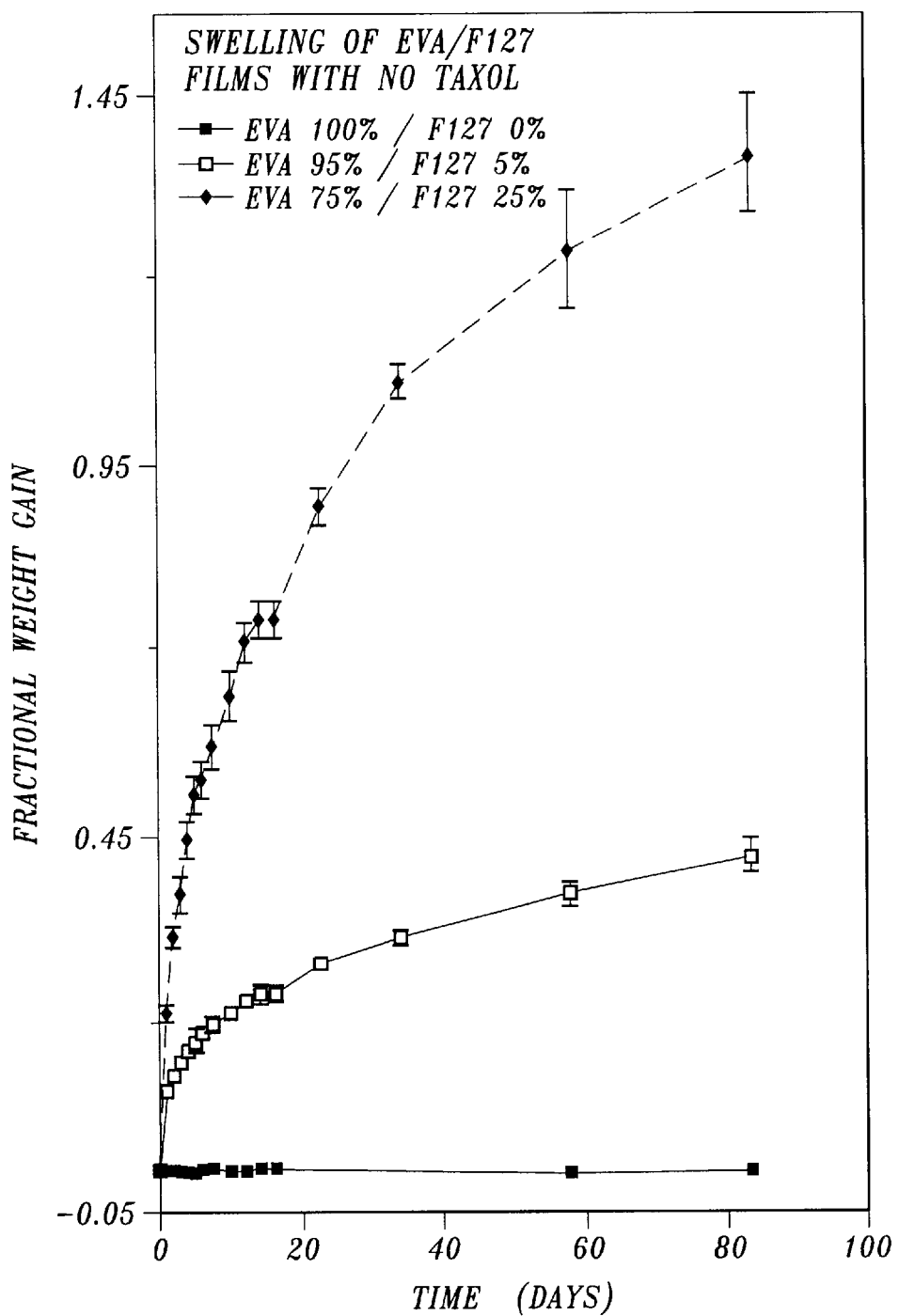
FIG. 12C is a graph which shows the swelling of EVA/F127 films with no paclitaxel over time.
Figure 12D:
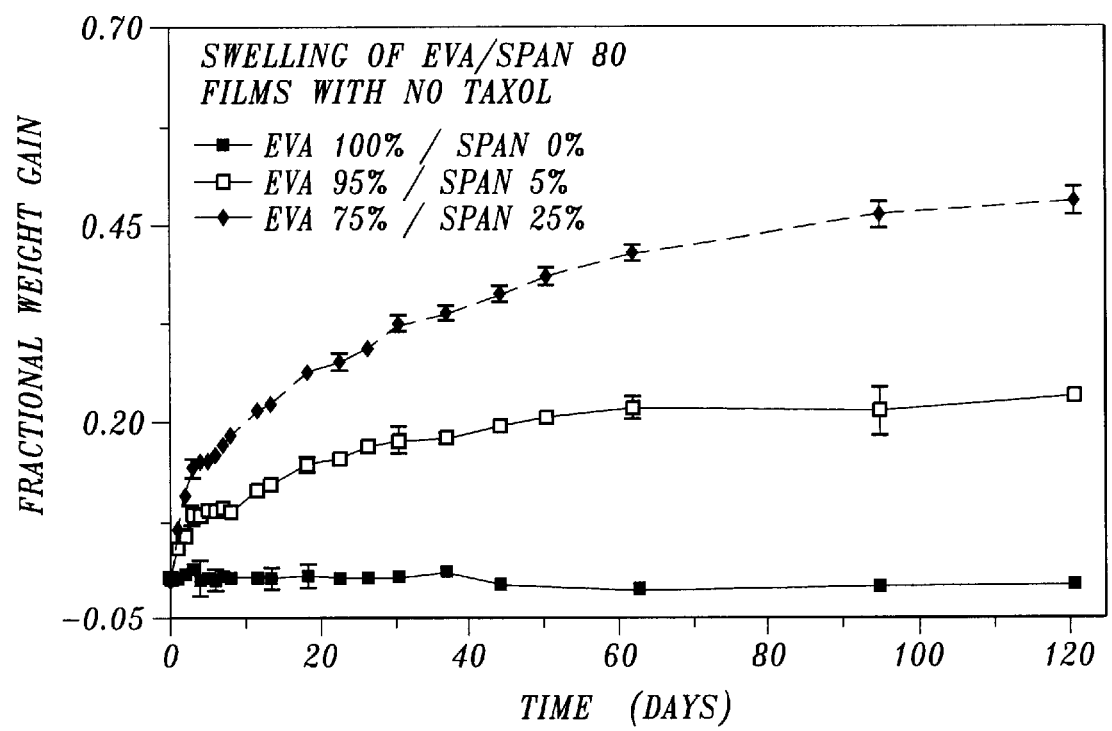
FIG. 12D is a graph which shows the swelling of EVA/Span 80 films with no paclitaxel over time.

Surfactants is useful in modulating the release rates of paclitaxel from films and optimizing certain physical parameters of the films. One aspect of the surfactant blend films which indicates that drug release rates can be controlled is the ability to vary the rate and extent to which the compound will swell in water. Diffusion of water into a polymer-drug matrix is critical to the release of drug from the carrier. FIGS. 12C and 12D show the degree of swelling of the films as the level of surfactant in the blend is altered. Pure EVA films do not swell to any significant extent in over 2 months. However, by increasing the level of surfactant added to the EVA it is possible to increase the degree of swelling of the compound, and by increasing hydrophilicity swelling can also be increased.

Results of experiments with these films are shown below in FIGS. 12A–E. Briefly, FIG. 12A shows paclitaxel release (in mg) over time from pure EVA films. FIG. 12B shows the percentage of drug remaining for the same films. As can be seen from these two figures, as paclitaxel loading increases (i.e., percentage of paclitaxel by weight is increased), drug release rates increase, showing the expected concentration dependence. As paclitaxel loading is increased, the percent paclitaxel remaining in the film also increases, indicating that higher loading may be more attractive for long-term release formulations.

Figure 12E:
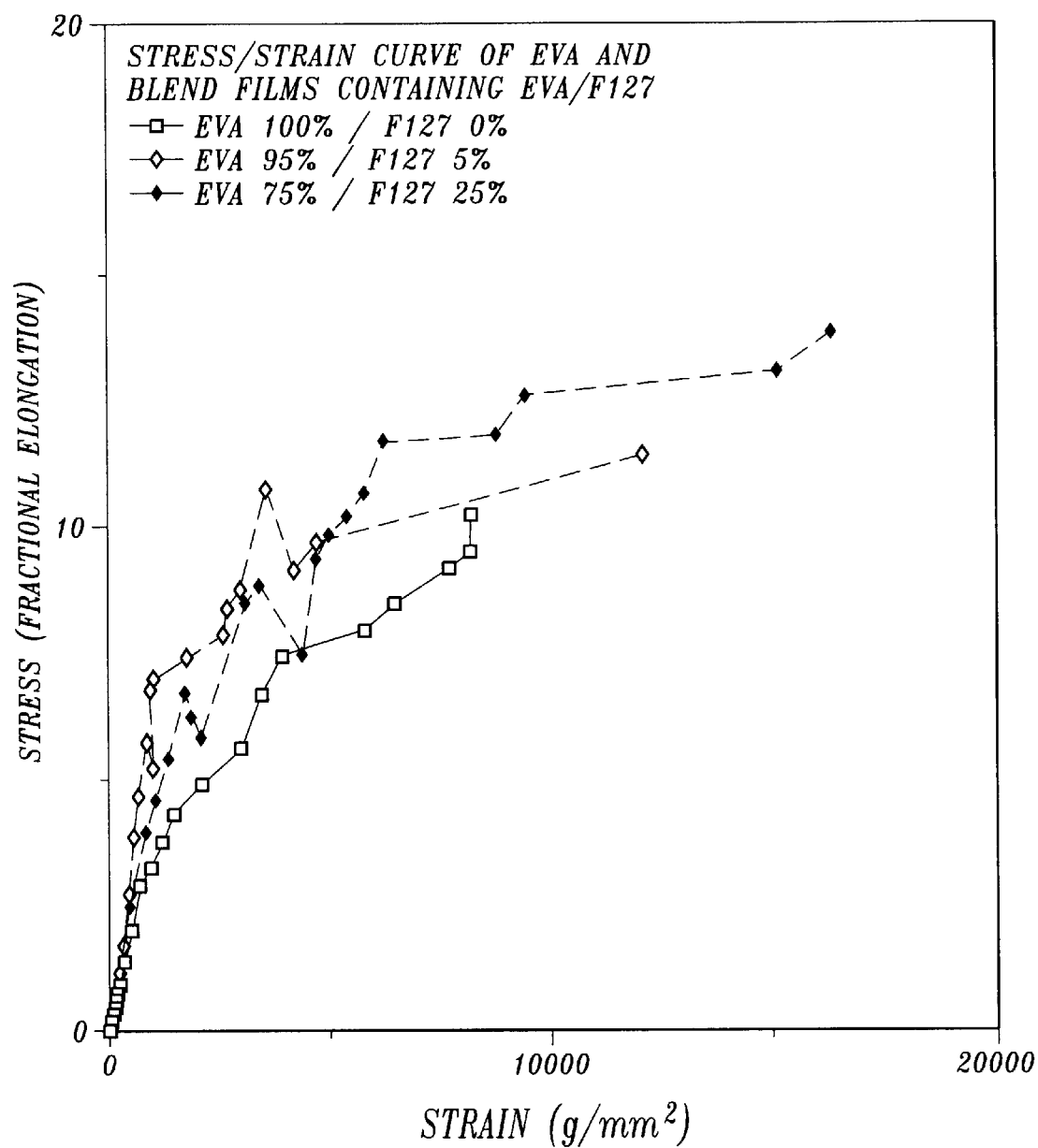
FIG. 12E is a graph which depicts a stress vs. strain curve for various EVA/F127 blends.

Physical strength and elasticity of the films is assessed in FIG. 12E. Briefly, FIG. 12E shows stress/strain curves for pure EVA and EVA-Surfactant blend films. This crude measurement of stress demonstrates that the elasticity of films is increased with the addition of Pluronic F127, and that the tensile strength (stress on breaking) is increased in a concentration dependent manner with the addition of Pluronic F127. Elasticity and strength are important considerations in designing a film which can be manipulated for particular peritubular clinical applications without causing permanent deformation of the compound.

The above data demonstrates the ability of certain surfactant additives to control drug release rates and to alter the physical characteristics of the vehicle.

Example 8

Incorporating Methoxypolyethylene Glycol 350 (MePEG) into Poly(E-caprolactone) to Develop a Formulation for the Controlled Delivery of Therapeutic Agents from a Paste Reagents and equipment which were utilized within these experiments include methoxypolyethylene glycol 350 ("MePEG"—Union Carbide, Danbury, Conn.). MePEG is liquid at room temperature, and has a freezing point of 10° C. to −5° C.

A. Preparation of a MePEG/PCL Paclitaxel-containing Paste

MePEG/PCL paste is prepared by first dissolving a quantity of paclitaxel into MePEG, and then incorporating this into melted PCL. One advantage with this method is that no DCM is required.

B. Analysis of Melting Point

Figure 13A:
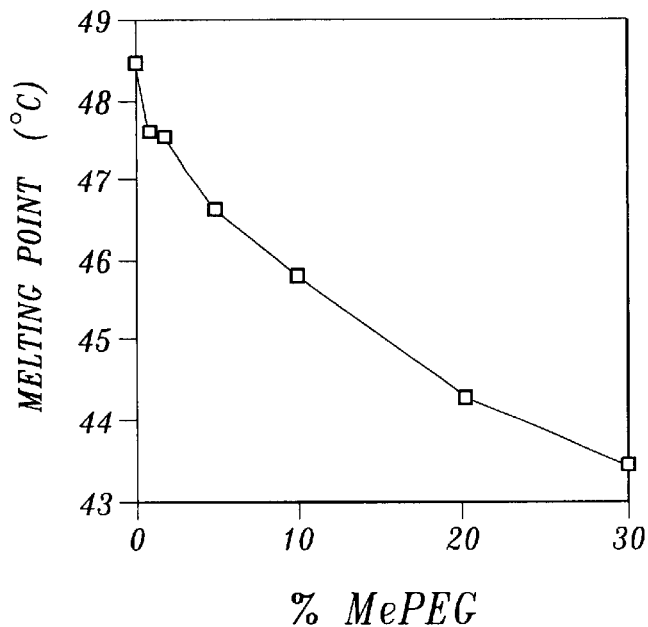
FIGS. 13A and 13B are two graphs which show the melting point of PCL/MePEG polymer blends as a function of % MePEG in the formulation (13A), and the percent increase in time needed for PCL paste at 60° C. to being to solidify as a function of the amount of MePEG in the formulation (13B).
Figure 13B:
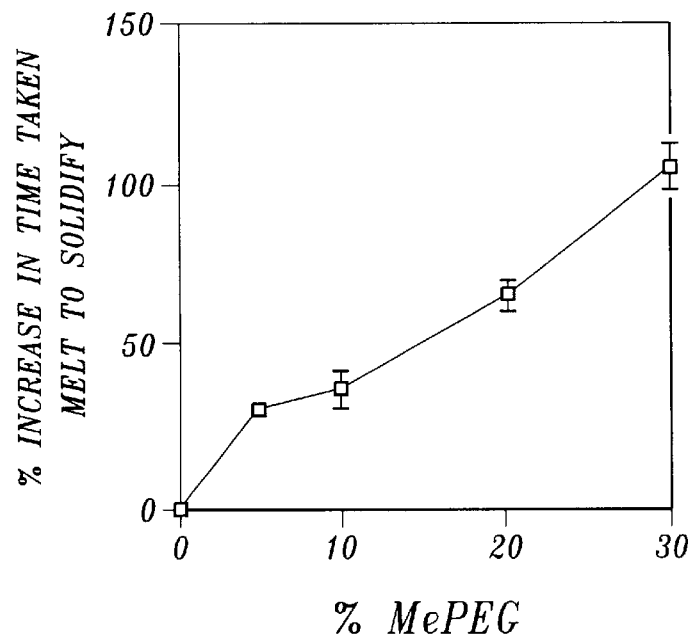

The melting point of PCL/MePEG polymer blends may be determined by differential scanning calorimetry from 30° C. to 70° C. at a heating rate of 2.5° C. per minute. Results of this experiment are shown in FIGS. 13A and 13B. Briefly, as shown in FIG. 13A the melting point of the polymer blend (as determined by thermal analysis) is decreased by MePEG in a concentration dependent manner. The melting point of the polymer blends as a function of MePEG concentration is shown in FIG. 13A. This lower melting point also translates into an increased time for the polymer blends to solidify from melt as shown in FIG. 13B. A 30:70 blend of MePEG: PCL takes more than twice as long to solidify from the fluid melt than does PCL alone.

C. Measurement of Brittleness

Figure 13C:
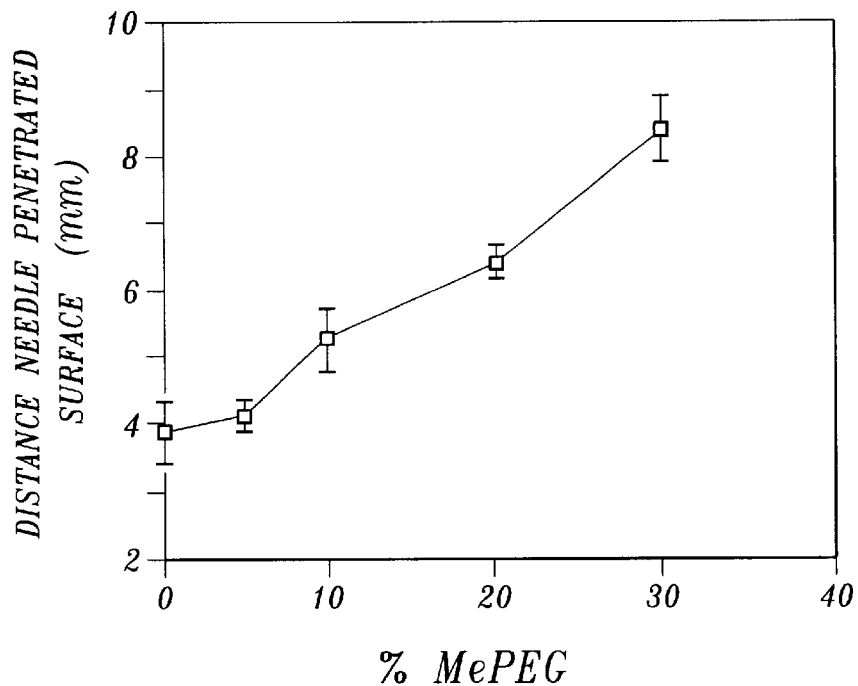
FIG. 13C is a graph which depicts the softness of varying PCL/MePEG polymer blends.

Incorporation of MePEG into PCL appears to produce a less brittle solid, as compared to PCL alone. As a "rough" way of quantitating this, a weighted needle is dropped from an equal height into polymer blends containing from 0% to 30% MePEG in PCL, and the distance that the needle penetrates into the solid is then measured. The resulting graph is shown as FIG. 13C. Points are given as the average of four measurements +/−1 S.D.

For purposes of comparison, a sample of paraffin wax is also tested and the needle penetrated into this a distance of 7.25 mm+/−0.3 mm.

D. Measurement of Paclitaxel Release

Figure 13D:
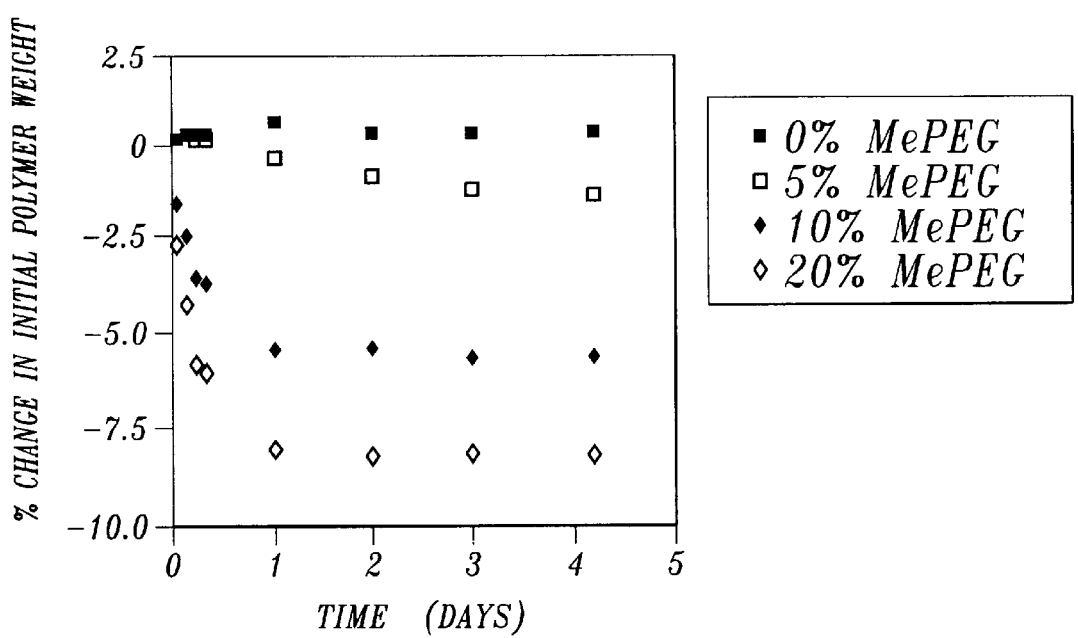
FIG. 13D is a graph which shows the percent weight change over time for polymer blends of various MePEG concentrations.

Pellets of polymer (PCL containing 0%, 5%, 10% or 20% MePEG) are incubated in phosphate buffered saline (PBS, pH 7.4) at 37° C., and % change in polymer weight is measured over time. As can be seen in FIG. 13D, the amount of weight lost increases with the concentration of MePEG originally present in the blend. It is likely that this weight loss is due to the release of MePEG from the polymer matrix into the incubating fluid. This would indicate that paclitaxel will readily be released from a MePEG/PCL blend since paclitaxel is first dissolved in MePEG before incorporation into PCL.

E. Effect of Varying Quantities of MePEG on Paclitaxel Release

Figure 13E:
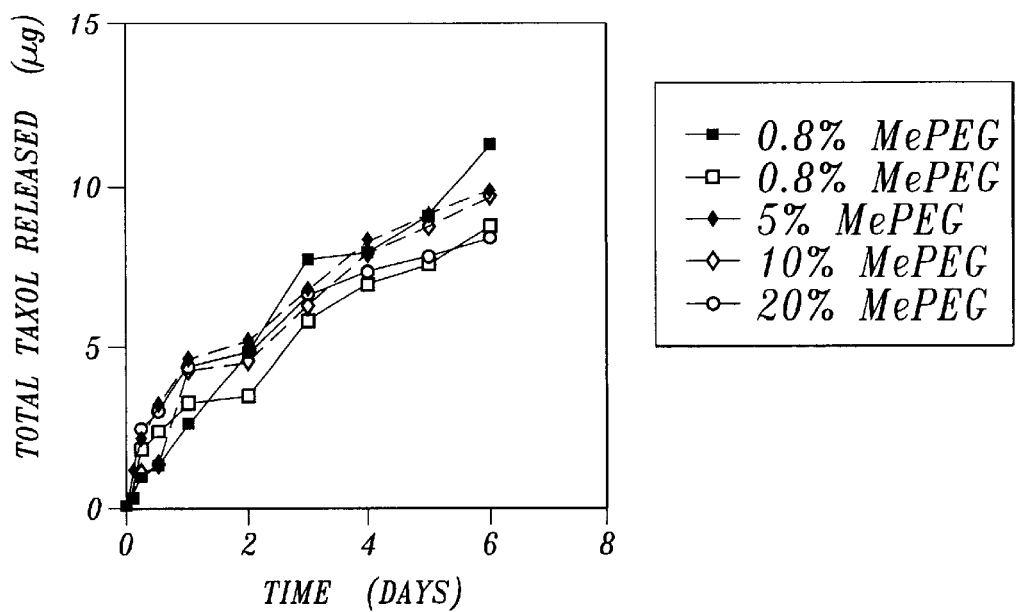
FIG. 13E is a graph which depicts the rate of paclitaxel release over time from various polymer blends loaded with 1% paclitaxel.

Thermopastes are made up containing between 0.8% and 20% MePEG in PCL. These are loaded with 1% paclitaxel. The release of paclitaxel over time from 10 mg pellets in PBS buffer at 37° C. is monitored using HPLC. As is shown in FIG. 13E, the amount of MePEG in the formulation does not affect the amount of paclitaxel that is released.

Figure 13F:
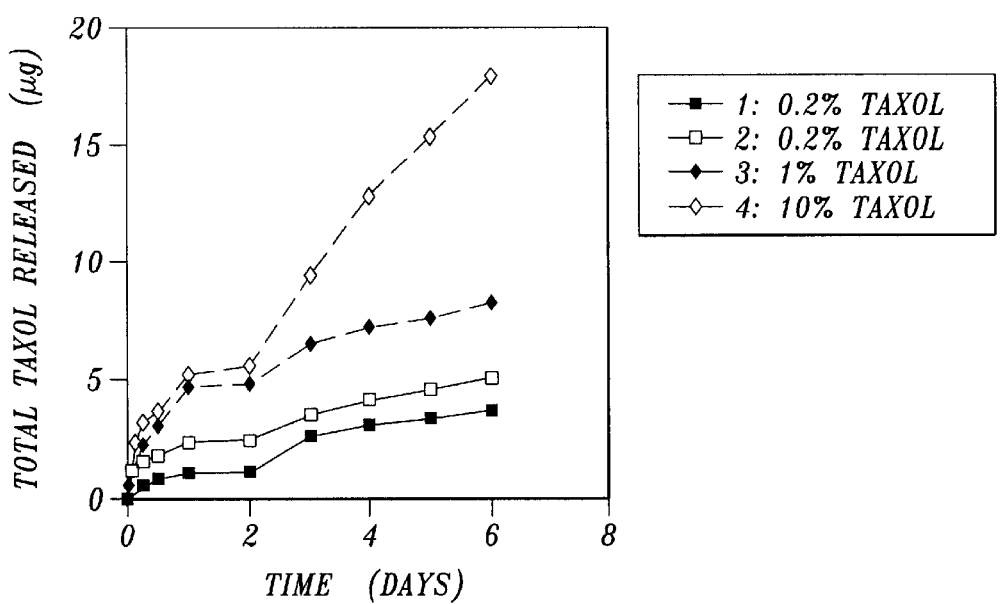
FIGS. 13F and 13G are graphs which depict the effect of varying quantities of paclitaxel on the total amount of paclitaxel released from a 20% MePEG/PCL blend.
Figure 13G:
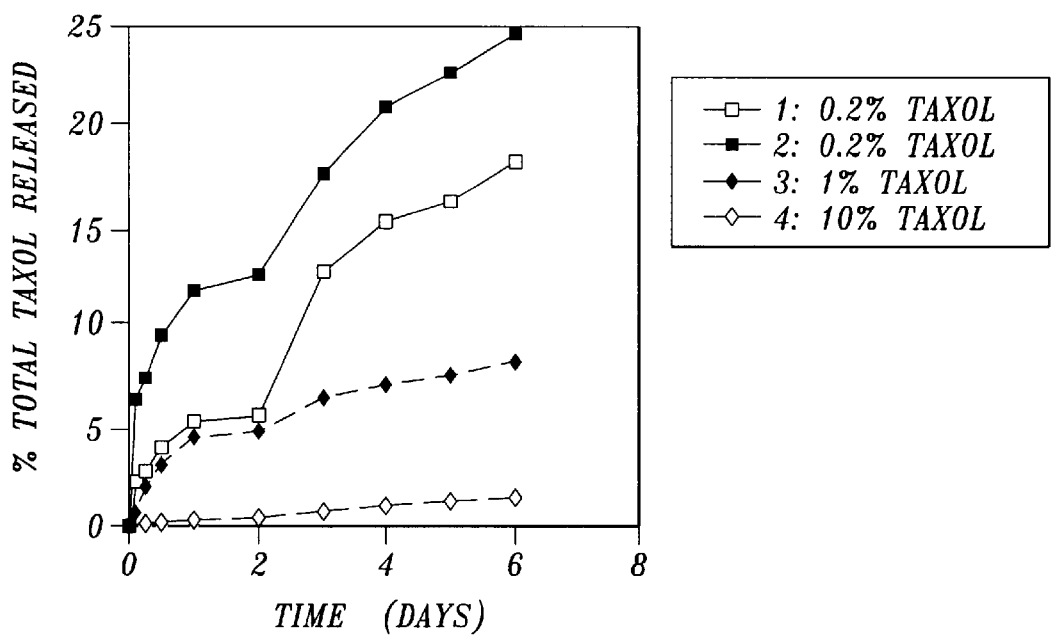

F. Effect of Varying Quantities of Paclitaxel on the Total Amount of Paclitaxel Released from a 20% MePEG/PCL Blend Thermopastes are made up containing 20% MePEG in PCL and loaded with between 0.2% and 10% paclitaxel. The release of paclitaxel over time is measured as described above. As shown in FIG. 13F, the amount of paclitaxel released over time increases with increased paclitaxel loading. When plotted as the percent total paclitaxel released, however, the order is reversed (FIG. 13G). This gives information about the residual paclitaxel remaining in the paste and allows for a projection of the period of time over which paclitaxel may be released from the 20% MePEG Thermopaste.

G. Strength Analysis of Various MePEG/PCL Blends

A CT-40 mechanical strength tester is used to measure the strength of solid polymer "tablets" of diameter 0.88 cm and an average thickness of 0.560 cm. The polymer tablets are blends of MePEG at concentrations of 0%, 5%, 10% or 20% in PCL.

Figure 13H:
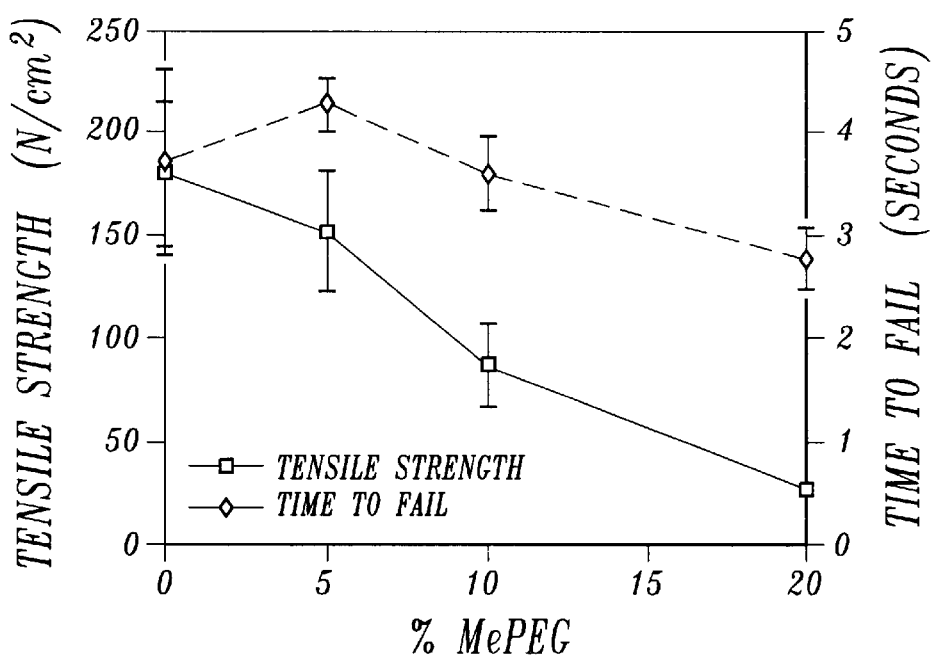
FIG. 13H is a graph which depicts the effect of MePEG on the tensile strength of a MePEG/PCL polymer.

Results of this test are shown in FIG. 13H, where both the tensile strength and the time to failure are plotted as a function of %MePEG in the blend. Single variable ANOVA indicated that the tablet thicknesses within each group are not different. As can be seen from FIG. 13H, the addition of MePEG into PCL decreased the hardness of the resulting solid.

Example 9

Alteration of Therapeutic Agent Release from Thermopaste Using Low Molecular Weight Poly(D, L, Lactic Acid)

As discussed above, depending on the desired therapeutic effect, either quick release or slow release polymeric carriers may be desired. For example, polycaprolactone (PCL) and mixtures of PCL with poly(ethylene glycol) (PEG) produce compositions which release paclitaxel over a period of several months. In particular, the diffusion of paclitaxel in the polymers is very slow due to its large molecular size and extreme hydrophobicity.

On the other hand, low molecular weight poly(DL-lactic acid) (PDLLA) gives fast degradation, ranging from one day to a few months depending on its initial molecular weight. The release of paclitaxel, in this case, is dominated by polymer degradation. Another feature of low molecular weight PDLLA is its low melting temperature, (i.e., 40° C.–60° C.), which makes it suitable material for making Thermopaste. As described in more detail below, several different methods can be utilized in order to control the polymer degradation rate, including, for example, by changing molecular weight of the PDLLA, and/or by mixing it with high mol wt. PCL, PDLLA, or poly(lactide-co-glyocide) (PLGA).

A. Experimental Materials

D,L-lactic acid was purchased from Sigma Chemical Co., St. Louis, Mo. PCL (molecular weight 10–20,000) was obtained from Polysciences, Warrington, Pa. High molecular weight PDLLA (intrinsic viscosity 0.60 dl/g) and PLGA (50:50 composition, viscosity 0.58 dl/g) were from Birmingham Polymers.

B. Synthesis of Low Molecular Weight PDLLA

Low molecular weight PDLLA was synthesized from DL-lactic acid through polycondensation. Briefly, DL-lactic acid was heated in a glass beaker at 200° C. with nitrogen purge and magnetic stirring for a desired time. The viscosity increased during the polymerization, due to the increase of molecular weight. Three batches were obtained with different polymerization times, i.e., 40 min (molecular weight 800), 120 min, 160 min.

C. Formulation of Paclitaxel Thermopastes

Paclitaxel was loaded, at 20%, into the following materials by hand mixing at a temperature about 60° C.

1. low molecular weight PDLLA with polymerization time of 40 min.

2. low molecular weight PDLLA with polymerization time of 120 min.

3. low mol. wt PDLLA with polymerization time of 160 min.

4. a mixture of 50:50 high molecular weight PDLLA and low molecular weight PDLLA 40 min.

5. a mixture of 50:50 high molecular weight PLGA and low molecular weight PDLLA 40 min.

6. mixtures of high molecular weight PCL and low molecular weight. PDLLA 40 min with PCL:PDLLA of 10:90, 20:80, 40:60, 60:40, and 20:80. Mixtures of high molecular weight PDLLA or PLGA with low molecular weight. PDLLA were obtained by dissolving the materials in acetone followed by drying.

D. Release Study

The release of paclitaxel into PBS albumin buffer at 37° C. was measured as described above with HPLC at various times.

E. Results

Low molecular weight PDLLA 40 min was a soft material with light yellow color. The color is perhaps due to the oxidation during the polycondensation. Low molecular weight PDLLA 120 min (yellow) and 160 min (brown) were brittle solids at room temperature. They all become melts at 60° C. Mixtures of 50:50 high molecular weight PDLLA or PLGA with low molecular weight PDLLA 40 min also melted about 60° C.

During the release, low molecular weight PDLLA 40 min and 120 min broke up into fragments within one day, other materials were intact up to this writing (3 days).

Figure 14:
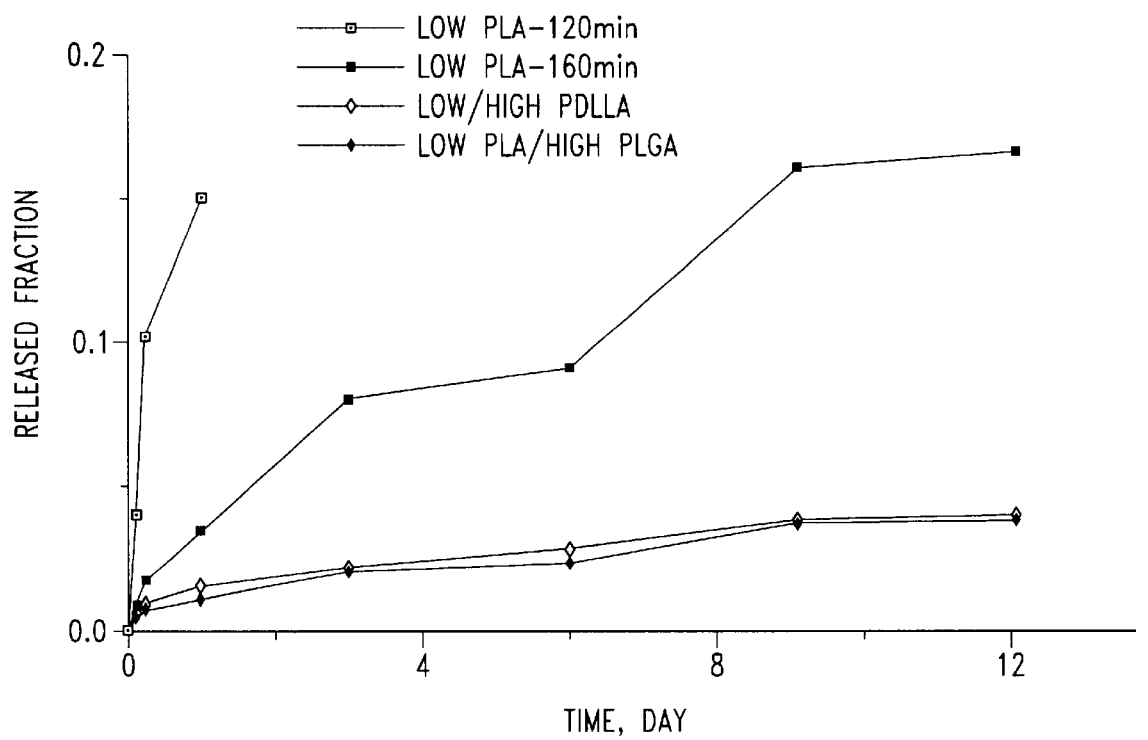
FIG. 14 is a graph which shows paclitaxel release from various polymeric formulations.

The release of paclitaxel from formulations 2–5 were shown in FIG. 14. Low molecular weight PDLLA 40 min and 120 min gave the fastest release due to the break up of the paste. The release was perhaps solubility limited. Low molecular weight PDLLA 160 min. also gave a fast release yet maintained an intact pellet. For example, 10% of loaded paclitaxel was released with one day. The 50:50 mixtures of high molecular weight PDLLA or PLGA with low molecular weight PDLLA 40 min were slower, i.e., 3.4% and 2.2% release within one day.

Although not specifically set forth above, a wide variety of other polymeric carriers may be manufactured, including for example, (1) low molecular weight (500–10,000) poly (D,L-lactic acid), poly(L-lactic acid), poly(glycolic acid), poly(6-hydroxycaproic acid), poly(5-hydroxyvaleric acid), poly(4-hydroxybutyric acid), and their copolymers; (2) blends of above (#1) above; (3) blends of (#1) above with high molecular weight poly(DL-lactic acid), poly(L-lactic acid), poly(glycolic acid), poly(6-hydroxycaproic acid), poly(5-hydroxyvaleric acid), poly(4-hydroxybutyric acid), and their copolymers; and (4) copolymers of poly(ethylene glycol) and pluronics with poly(D,L-lactic acid), poly(L-lactic acid), poly(glycolic acid), poly(6-hydroxycaproic acid), poly(5-hydroxyvaleric acid), poly(4-hydroxybutyric acid), and their copolymers.

Example 10

Preparation of Polymeric Compositions Containing Water Soluble Additives and Paclitaxel

A. Preparation of Polymeric Compositions

Microparticles of co-precipitates of paclitaxel/additive were prepared and subsequently added to PCL to form pastes. Briefly, paclitaxel (100 mg) was dissolved in 0.5 ml of ethanol (95%) and mixed with the additive (100 mg) previously dissolved or dispersed in 1.0 ml of distilled water. The mixture was triturated until a smooth paste was formed. The paste was spread on a Petri dish and air-dried overnight at 37° C. The dried mass was pulverized using a mortar and pestle and passed through a mesh #140 (106 $\mu$m) sieve (Endecotts Test Sieves Ltd, London, England). The microparticles (40%) were then incorporated into molten PCL (60%) at 65° C. corresponding to a 20% loading of paclitaxel. The additives used in the study were gelatin (Type B, 100 bloom, Fisher Scientific), methylcellulose, (British Drug Houses), dextran, T500 (Pharmacia, Sweden), albumin (Fisher Scientific), and sodium chloride (Fisher Scientific). Microparticles of paclitaxel and gelatin or albumin were prepared as described above but were passed through a mesh # 60 (270 $\mu$m) sieve (Endecotts Test Sieves Ltd, London, England) to evaluate the effect of microparticle size on the release of paclitaxel from the paste. Pastes were also prepared to contain 10, 20 or 30% gelatin and 20% paclitaxel in PCL to study the effect of the proportion of the additive on drug release. Unless otherwise specified, pastes containing 20% paclitaxel dispersed in PCL were prepared to serve as controls for the release rate studies.

B. Drug Release Studies

Approximately 2.5 mg pellet of paclitaxel-loaded paste was suspended in 50 ml of 10 mM phosphate buffered saline, pH 7.4 (PBS) in screw-capped tubes. The tubes were tumbled end-over-end at 37° C. and at given time intervals 49.5 ml of supernatant was removed, filtered through a 0.45 $\mu$m membrane filter and retained for paclitaxel analysis. An equal volume of PBS was replaced in each tube to maintain sink conditions throughout the study. For analysis, the filtrates were extracted with 3×1 ml dichloromethane (DCM), the DCM extracts evaporated to dryness under a stream of nitrogen and redissolved in 1 ml acetonitrile. The analysis was by HPLC using a mobile phase of water:methanol:acetonitrile (37:5:58:) at a flow rate of 1 ml min$^{-1}$ (Beckman Isocratic Pump), a C18 reverse phase column (Beckman), and UV detection (Shimadzu SPD A) at 232 nm.

C. Sweling Studies

Paclitaxel/additive/PCL pastes, prepared using paclitaxel-additive microparticles of mesh size #140 (and #60 for gelatin only), were extruded to form cylinders, pieces were cut, weighed and the diameter and length of each piece were measured using a micrometer (Mitutoyo Digimatic). The pieces were suspended in distilled water (10 ml) at 37° C. and at predetermined intervals the water was discarded and the diameter and the length of the cylindrical pieces were measured and the samples weighed. The morphology of the samples (before and after suspending in water) was examined using scanning electron microscopy (SEM) (Hitachi F-2300). The samples were coated with 60% Au and 40% Pd (thickness 10–15 nm) using a Hummer Instrument (Technics, USA).

D. Chick Embryo Chorioallantoic Membrane (CAM) Studies

Fertilized, domestic chick embryos were incubated for 4 days prior to shell-less culturing. The egg contents were incubated at 90% relative humidity and 3% $CO_2$ and on day 6 of incubation, 1 mg pieces of the paclitaxel-loaded paste containing 6% paclitaxel, 24% gelatin and 70% PCL) or control (30% gelatin in PCL) pastes were placed directly on the CAM surface. After a 2-day exposure the vasculature was examined using a stereomicroscope interfaced with a video camera; the video signals were then displayed on a computer and video printed.

E. In Vivo Anti-tumor Activity

Pastes, prepared as described above (using mesh size 140 fractions of the paclitaxel-gelatin microparticles) containing 20% paclitaxel, 20% gelatin and 60% PCL were filled into 8×1 ml syringes (BD Insulin Syringe, ½ cc) each syringe containing 150 mg of the paste (equivalent to 30 mg of paclitaxel). Ten week old DBA/2j female mice (16) weighing 18–20 g were acclimatized for 4 days after arrival and each mouse was injected in the posteriolateral flank with MDAY-D2 tumor cells, (10 ×10$^6$ ml$^{-1}$) in 100 $\mu$l of phosphate buffered saline on day 1. On day 6, the mice were divided into two groups of eight, the tumor site opened under anesthesia and 150 mg of the paste, previously heated to about 60° C. was extruded at the tumor site and the wound closed. One group was implanted with the paclitaxel-loaded paste and the other group with control paste containing gelatin and PCL only. On day 16, the mice were sacrificed and the weight of the mice and the excised tumor were measured.

F. Results and Discussion

Microparticles of co-precipitated paclitaxel and gelatin or albumin were hard and brittle and were readily incorporated into PCL while the other additives produced soft particles which showed a tendency to break up during the preparation of the paste.

Figure 15:
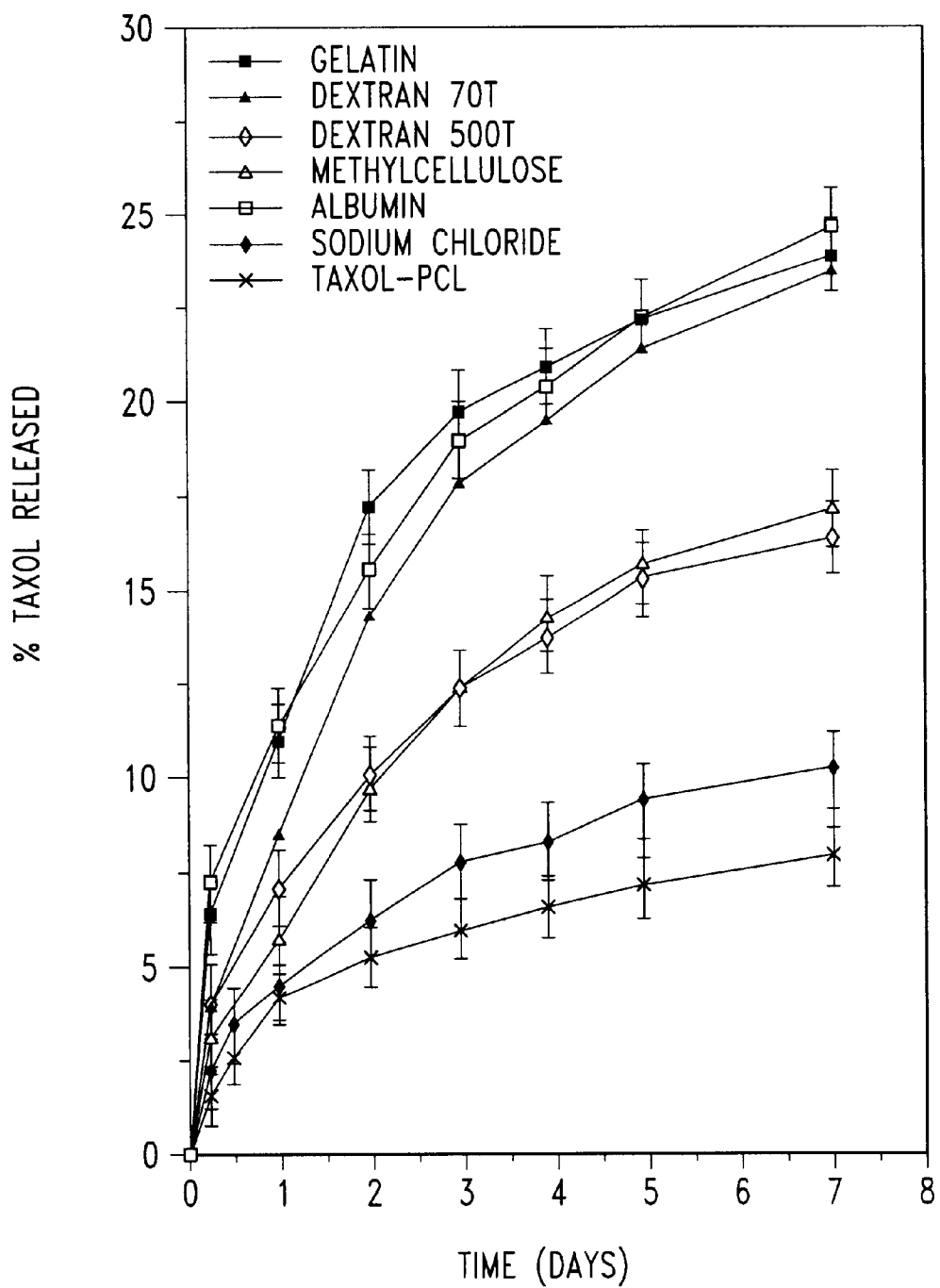
FIG. 15 is a graph which depicts, over a time course the release of paclitaxel from PCL pastes into PBS at 37° C. The PCL pastes contain microparticles of paclitaxel and various additives prepared using mesh #140. The error bars represent the standard deviation of 3 samples.

FIG. 15 shows the time courses of paclitaxel release from pastes containing 20% paclitaxel in PCL or 20% paclitaxel, 20% additive and 60% PCL. The release of paclitaxel from PCL with or without additives followed a bi-phasic release pattern; initially, there was a faster drug release rate followed by a slower drug release of the drug. The initial period of faster release rate of paclitaxel from the pastes was thought to be due to dissolution of paclitaxel located on the surface or diffusion of paclitaxel from the superficial regions of the paste. The subsequent slower phase of the release profiles may be attributed to a decrease in the effective surface area of the drug particles in contact with the solvent, a slow ingress of the solvent into the polymer matrix or an increase in the mean diffusion paths of the drug through the polymer matrix.

Figure 16:
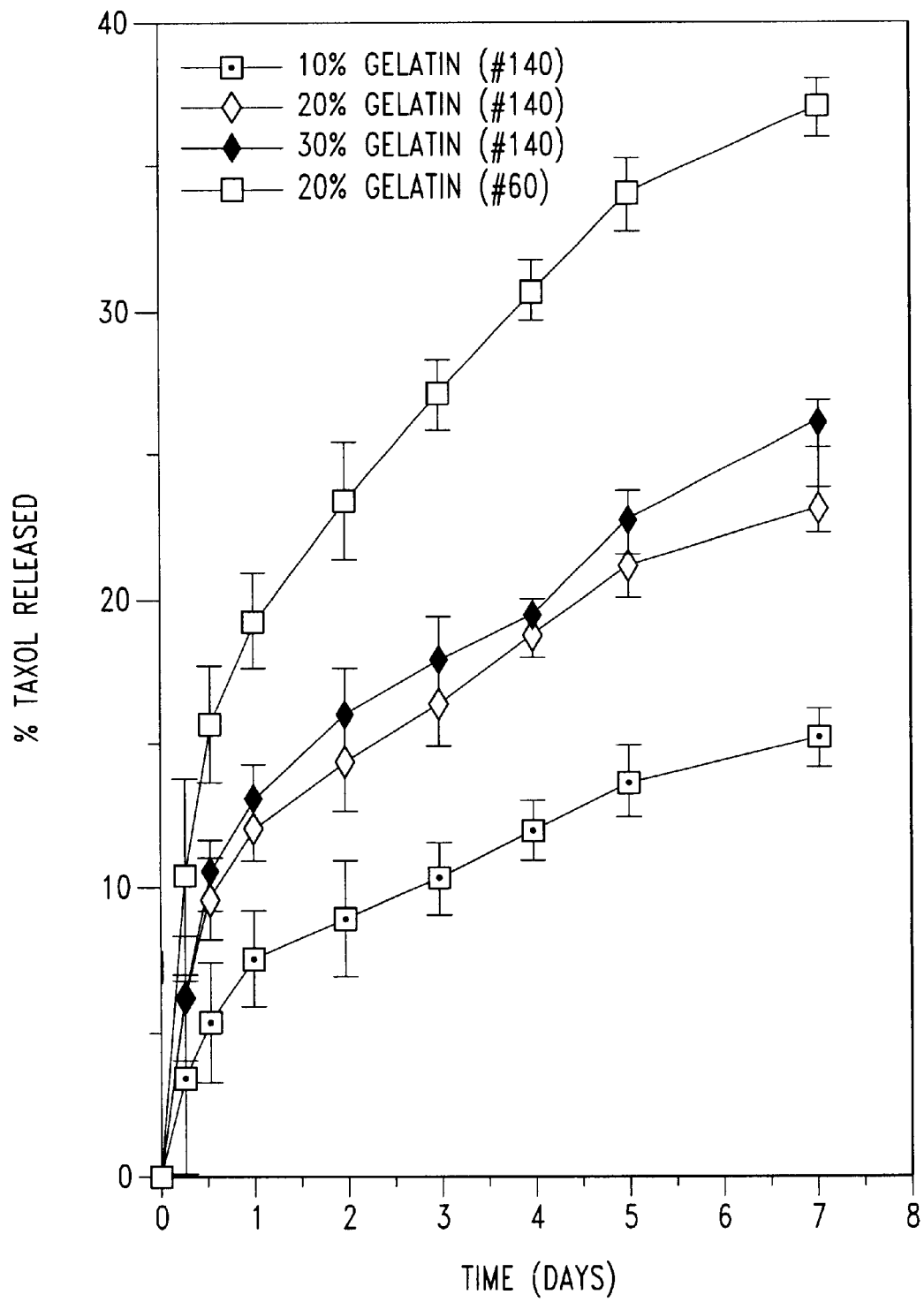
FIG. 16 is a graph which depicts time courses of paclitaxel release from paclitaxel-gelatin-PCL pastes into PBS at 37° C. This graph shows the effects of gelatin concentration (mesh #140) and the size of paclitaxel-gelatin (1:1) microparticles prepared using mesh #140 or mesh #60. The error bars represent the standard deviation of 3 samples.
Figure 17A:
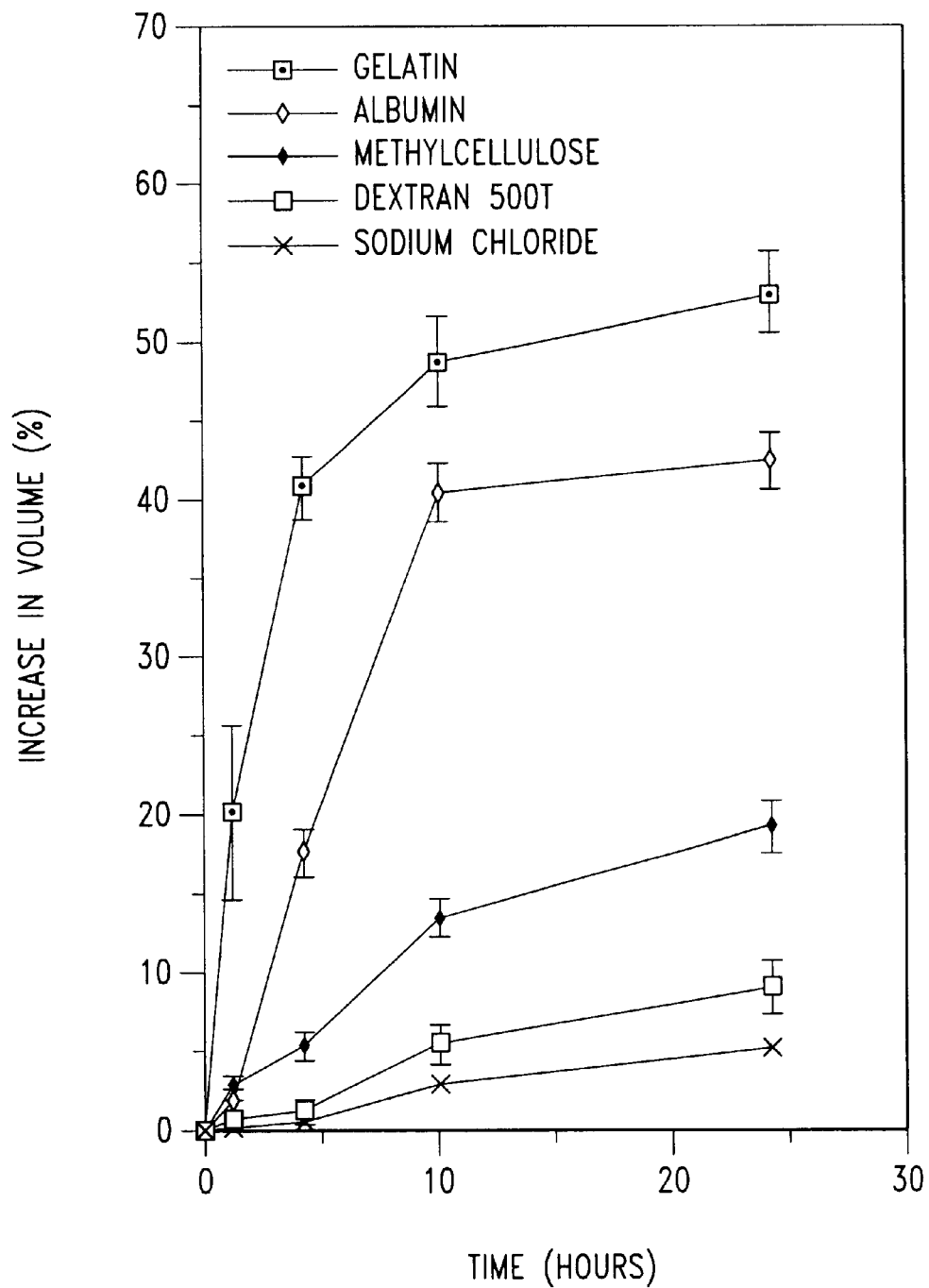
FIGS. 17A and 17B are graphs which depict the effect of additives (17A; mesh #140) and the size of microparticles (17B; mesh #140 or #60) and the proportion of the additive (mesh #140) on the swelling behavior of PCL pastes containing 20% paclitaxel following suspension in distilled water at 37° C. Measurements for the paste prepared with 270 μm microparticles in paclitaxel-gelatin and paste containing 30% gelatin were discontinued after 4 hours due to disintegration of the matrix. The error bars represent the standard deviation of 3 samples.
Figure 17B:
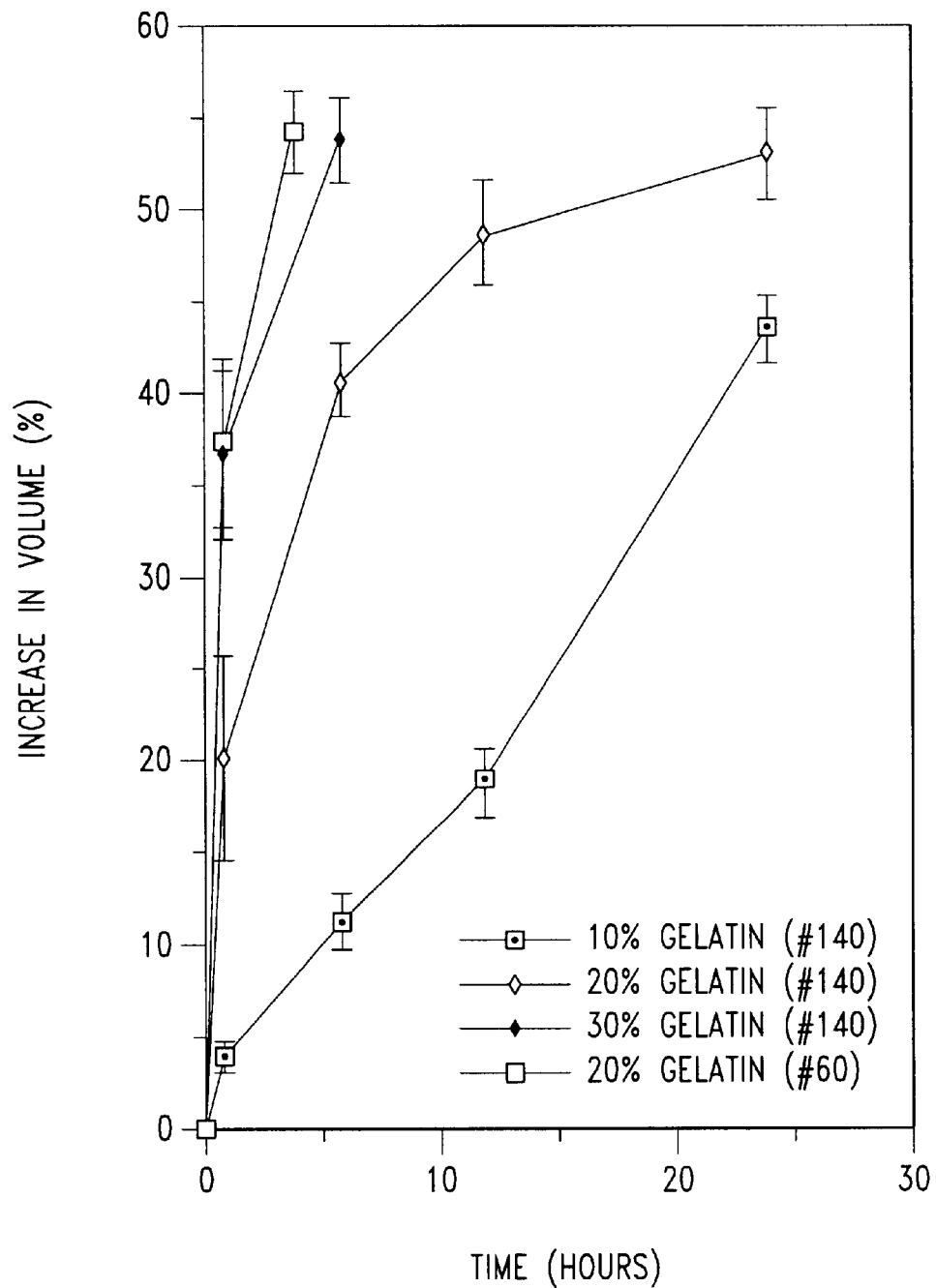
Figure 18A:
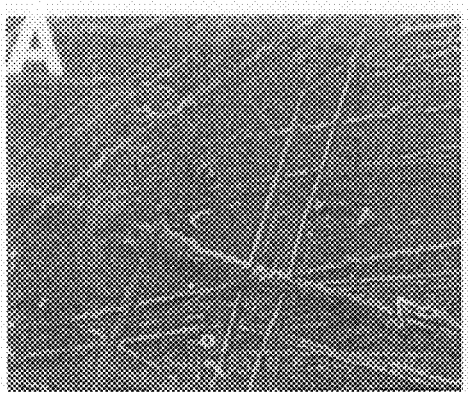
FIGS. 18A, 18B, 18C and 18D are representative scanning electron micrographs of paclitaxel-gelatin-PCL (20:20:60) pastes before (18A) and after (18B) suspending in distilled water at 37° C. for 6 hours. Micrographs 18C and 18D are higher magnifications of 18B, showing intimate association of paclitaxel (rod shaped) and gelatin matrix.
Figure 18B:
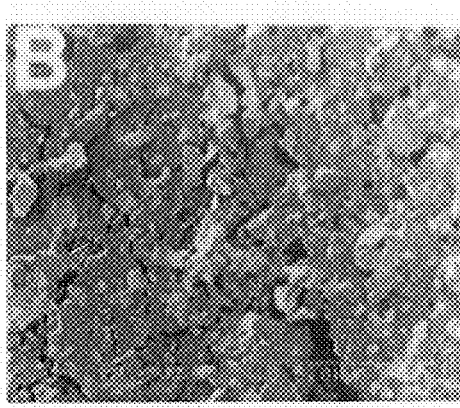
Figure 18C:
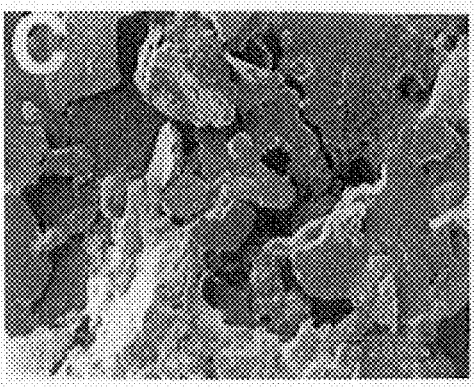
Figure 18D:
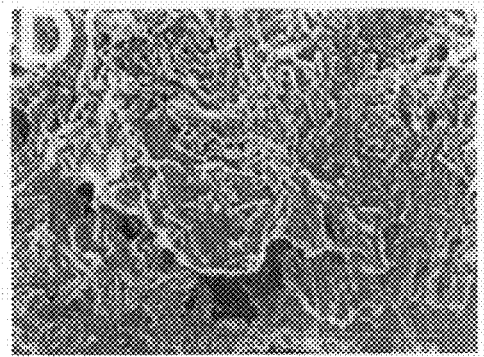

Both phases of the release profiles of paclitaxel from PCL increased in the presence of the hydrophilic additives with gelatin, albumin and methylcellulose producing the greatest increase in drug release rates (FIG. 15). There were further increases in the release of paclitaxel from the polymer matrix when larger paclitaxel-additive particles (270 $\mu$m) were used to prepare the paste compared with the smaller paclitaxel-additive particles (106 $\mu$m) were used (FIG. 16). Increases in the amount of the additive (e.g., gelatin) produced a corresponding increase in drug release (FIG. 16). FIG. 17A shows the swelling behavior of pastes containing 20% paclitaxel, 20% additive and 60% PCL. The rate of swelling followed the order gelatin>albumin>methylcellulose>dextran>sodium chloride. In addition, the rate of swelling increased when a higher proportion of the water-soluble polymer was added to the paste (FIG. 17B). The pastes containing gelatin or albumin swelled rapidly within the first 8–10 hours and subsequently the rate of swelling decreased when the change in the volume of the sample was greater than 40%. The paste prepared using the larger (270 $\mu$m) paclitaxel-gelatin particles swelled at a faster rate than those prepared with the smaller (106 μm) paclitaxel-gelatin particles. All pastes disintegrated when the volume increases were greater than 50%. The SEM studies showed that the swelling of the pastes was accompanied by the cracking of the matrix (FIG. 18). At high magnifications (FIGS. 18C and 18D) there was evidence of needle or rod shaped paclitaxel crystals on the surface of the paste and in close association with gelatin following swelling (FIGS. 18C and 18D).

Osmotic or swellable, hydrophilic agents embedded as discrete particles in the hydrophobic polymer result in drug release by a combination of the erosion of the matrix, diffusion of drug through the polymer matrix, and/or diffusion and/or convective flow through pores created in the matrix by the dissolution of the water soluble additives. Osmotic agents and swellable polymers dispersed in a hydrophobic polymer would imbibe water (acting as wicking agents), dissolve or swell and exert a turgor pressure which could rupture the septa (the polymer layer) between adjacent particles, creating microchannels and thus facilitate the escape of the drug molecules into the surrounding media by diffusion or convective flow. The swelling and cracking of the paste matrix (FIG. 18) likely resulted in the formation of microchannels throughout the interior of the matrix. The different rates and extent of swelling of the polymers (FIG. 17) may account for the differences in the observed paclitaxel release rates (FIGS. 15 and 16).

Figure 19A:
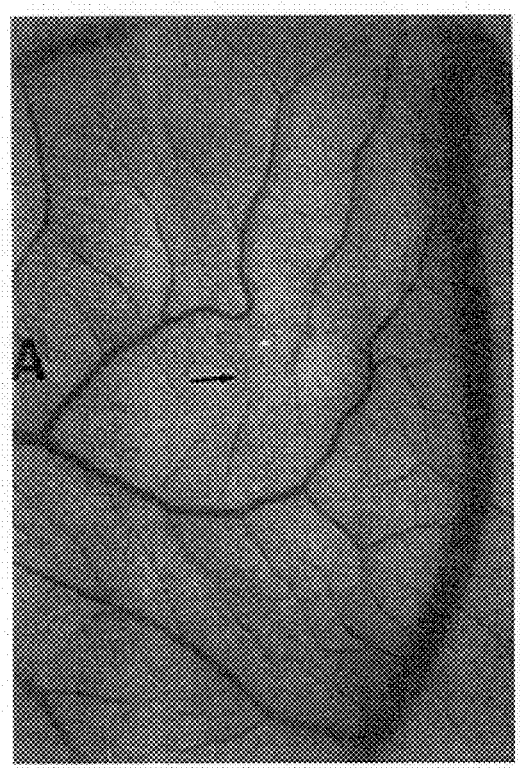
FIGS. 19A and 19B are representative photomicrographs of CAMs treated with gelatin-PCL (19A) and paclitaxel-gelatin-PCL (20:20:60; 19B) pastes showing zones of avascularity in the paclitaxel treated CAM.
Figure 19B:
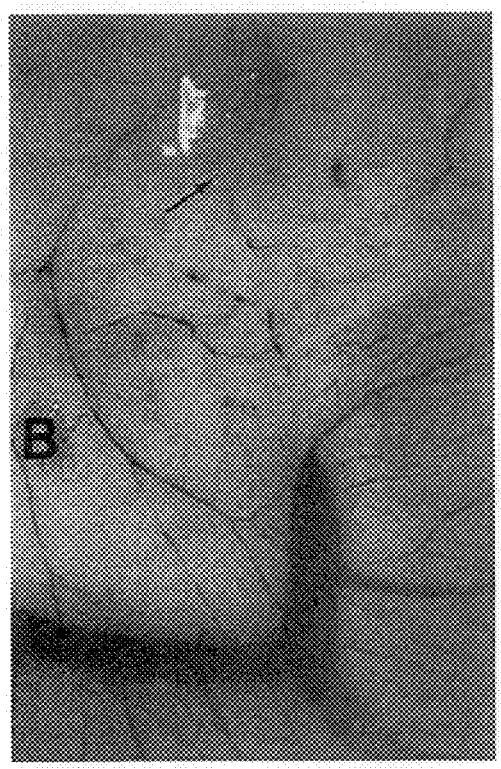

FIG. 19 shows CAMs treated with control gelatin-PCL paste (FIG. 19A) and 20% paclitaxel-gelatin-PCL paste (FIG. 19B). The paste on the surface of the CAMs are shown by the arrows in the figures. The CAM with the control paste shows a normal capillary network architecture. The CAMs treated with paclitaxel-PCL paste consistently showed vascular regression and zones which were devoid of a capillary network. Incorporation of additives in the paste markedly increased the diameter of the zone of avascularity (FIG. 19).

The results of the in vivo study are shown in FIG. 20. Briefly, peri-tumoral injection of paclitaxel-gelatin-PCL paste into mice with established and palpable tumors showed that this preparation produced a mean reduction of 63% in tumor mass compared with controls. In addition, there was no significant effect on the weights of the mice following treatment. Paclitaxel-PCL pastes (without additives) did not produce any significant reduction in tumor mass.

This study showed that the in vitro release of paclitaxel from PCL could be increased by the incorporation of paclitaxel/hydrophilic polymer microparticles into PCL matrix. In vivo studies evaluating the efficacy of the formulation in treating subcutaneous tumors in mice also showed that the paclitaxel/gelatin/PCL paste significantly reduced the tumor mass. Factors such as the type of water soluble agent, the microparticle size and the proportion of the additives were shown to influence the release characteristics of the drug.

Peritubular injection of a chemotherapeutic paste into the adventitia of a tube obstructed by malignant overgrowth can reduce local tumor growth and could relieve symptoms of obstruction without invasive surgical procedures.

Example 11

Modification of Paclitaxel Release from Thermopaste Using PDLLA-PEG-PDLLA and Low Molecular Weight Poly(D,L, Lactic Acid)

A. Preparation of PDLLA-PEG-PDLLA and Low Molecular Weight PDLLA

DL-lactide was purchased from Aldrich. Polyethylene glycol (PEG) with molecular weight 8,000, stannous octoate, and DL-lactic acid were obtained from Sigma. Poly-ε-caprolactone (PCL) with molecular weight 20,000 was obtained from Birmingham Polymers (Birmingham, Ala.). Paclitaxel was purchased from Hauser Chemicals (Boulder, Colo.). Polystyrene standards with narrow molecular weight distributions were purchased from Polysciences (Warrington, Pa.). Acetonitrile and methylene chloride were HPLC grade (Fisher Scientific).

The triblock copolymer of PDLLA-PEG-PDLLA was synthesized by a ring opening polymerization. Monomers of DL-lactide and PEG in different ratios were mixed and 0.5 wt % stannous octoate was added. The polymerization was carried out at 150° C. for 3.5 hours. Low molecular weight PDLLA was synthesized through polycondensation of DL-lactic acid. The reaction was performed in a glass flask under the conditions of gentle nitrogen purge, mechanical stirring, and heating at 180° C. for 1.5 hours. The PDLLA molecular weight was about 800 measured by titrating the carboxylic acid end groups.

B. Manufacture of Paste Formulations

Paclitaxel at loadings of 20% or 30% was thoroughly mixed into either the PDLLA-PEG-PDLLA copolymers or blends of PDLLA:PCL 90:10, 80:20 and 70:30 melted at about 60° C. The paclitaxel loaded pastes were weighed into 1 ml syringes and stored at 4° C.

C. Characterization of PDLLA-PEG-PDLLA and the Paste Blends

The molecular weights and distributions of the PDLLA-PEG-PDLLA copolymers were determined at ambient temperature by GPC using a Shimadzu LC-LOAD HPLC pump and a Shimadzu RID-6A refractive index detector (Kyoto, Japan) coupled to a $10^4$ Å Hewlett Packard Plgel column. The mobile phase was chloroform with a flow rate of 1 ml/min. The injection volume of the sample was 20 μl at a polymer concentration of 0.2% (w/v). The molecular weights of the polymers were determined relative to polystyrene standards. The intrinsic viscosity of PDLLA-PEG-PDLLA in $CHCl_3$ at 25° C. was measured with a Cannon-Fenske viscometer.

Thermal analysis of the copolymers was carried out by differential scanning calorimetry (DSC) using a TA Instruments 2000 controller and DuPont 910S DSC (Newcastle, Del.). The heating rate was 10° C./min and the copolymer and paclitaxel/copolymer matrix samples were weighed (3–5 mg) into crimped open aluminum sample pans.

$^1H$ Nuclear magnetic resonance (NMR) was used to determine the chemical composition of the polymer. $^1H$ NMR spectra of paclitaxel loaded PDLLA-PEG-PDLLA were obtained in $CDCl_3$ using an NMR instrument (Bruker, AC-200E) at 200 MHz. The concentration of the polymer was 1–2%.

The morphology of the paclitaxel/PDLLA-PEG-PDLLA paste was investigated using scanning electron microscopy (SEM) (Hitachi F-2300). The sample was coated with 60% Au and 40% Pd (thickness 10–15 nm) using a Hummer instrument (Technics, USA).

D. In Vitro Release of Paclitaxel

A small pellet of 20% paclitaxel loaded PDLLA:PCL paste (about 2 mg) or a cylinder (made by extrusion melten paste through a syringe without needle) of 20% paclitaxel loaded PDLLA-PEG-PDLLA paste were put into capped 14 ml glass tubes containing 10 ml phosphate buffered saline (PBS, pH 7.4) with 0.4 g/L albumin. The tube was incubated at 37° C. with gentle rotational mixing. The supernatant was withdrawn periodically for paclitaxel analysis and replaced with fresh PBS/albumin buffer. The supernatant (10 ml) was extracted with 1 ml methylene chloride. The water phase was decanted and the methylene chloride phase was dried under a stream of nitrogen at 60° C. The dried residue was reconstituted in a 40:60 water:acetonitrile mixture and centrifuged at 10,000 g for about 1 min. The amount of the paclitaxel in the supernatant was then analyzed by HPLC. HPLC analysis was performed using a 110A pump and C-8 ultrasphere column (Beckman), and a SPD-6A uv detector set at 232 nm, a SIL-9A autoinjector and a C-R3A integrator (Shimadzu). The injection volume was 20 $\mu$l and the flow rate was 1 ml/min. The mobile phase was 58% acetonitrile, 5% methanol, and 37% distilled water.

E. In Vivo Animal Studies

Ten week old DBA/2j female mice were acclimatized for 3–4 days after arrival. Each mouse was injected subcutaneously in the posterior lateral flank with $10\times10^5$ MDAY-D2 tumor cells in 100 $\mu$l of PBS on day 1. On day 6, the mice were randomly divided into two groups. Group 1 were implanted with paste alone (control), and group 2 were implanted with paste loaded with paclitaxel. A subcutaneous pocket near the tumor was surgically formed under anaesthesia and approximately 100 mg of molten paste (warmed to 50° C.–60° C.) was placed in the pocket and the wound closed. On day 16, the mice were sacrificed, and the tumors were removed and weighed. Day 16 was selected to allow the tumor growing into a easily measurable size within the ethical limit.

F. Results and Discussion

The molecular weight and molecular weight distribution of PDLLA-PEG-PDLLA, relative to polystyrene standards, were measured by GPC (FIG. 21). The intrinsic viscosity of the copolymer in $CHCl_3$ at 25° C. was determined using a Canon-Fenske viscometer. The molecular weight and intrinsic viscosity decreased with increasing PEG content. The polydispersities of PDLLA-PEG-PDLLA with PEG contents of 10%–40% were from 2.4 to 3.5. However, the copolymer with 70% PEG had a narrow molecular weight distribution with a polydispersity of 1.21. This might be because a high PEG content reduced the chance of side reactions such as transesterfication which results in a wide distribution of polymer molecular weight. Alternatively, a coiled structure of the hydrophobic-hydrophilic block copolymers may result in an artificial low polydispersity value.

Figure 22:
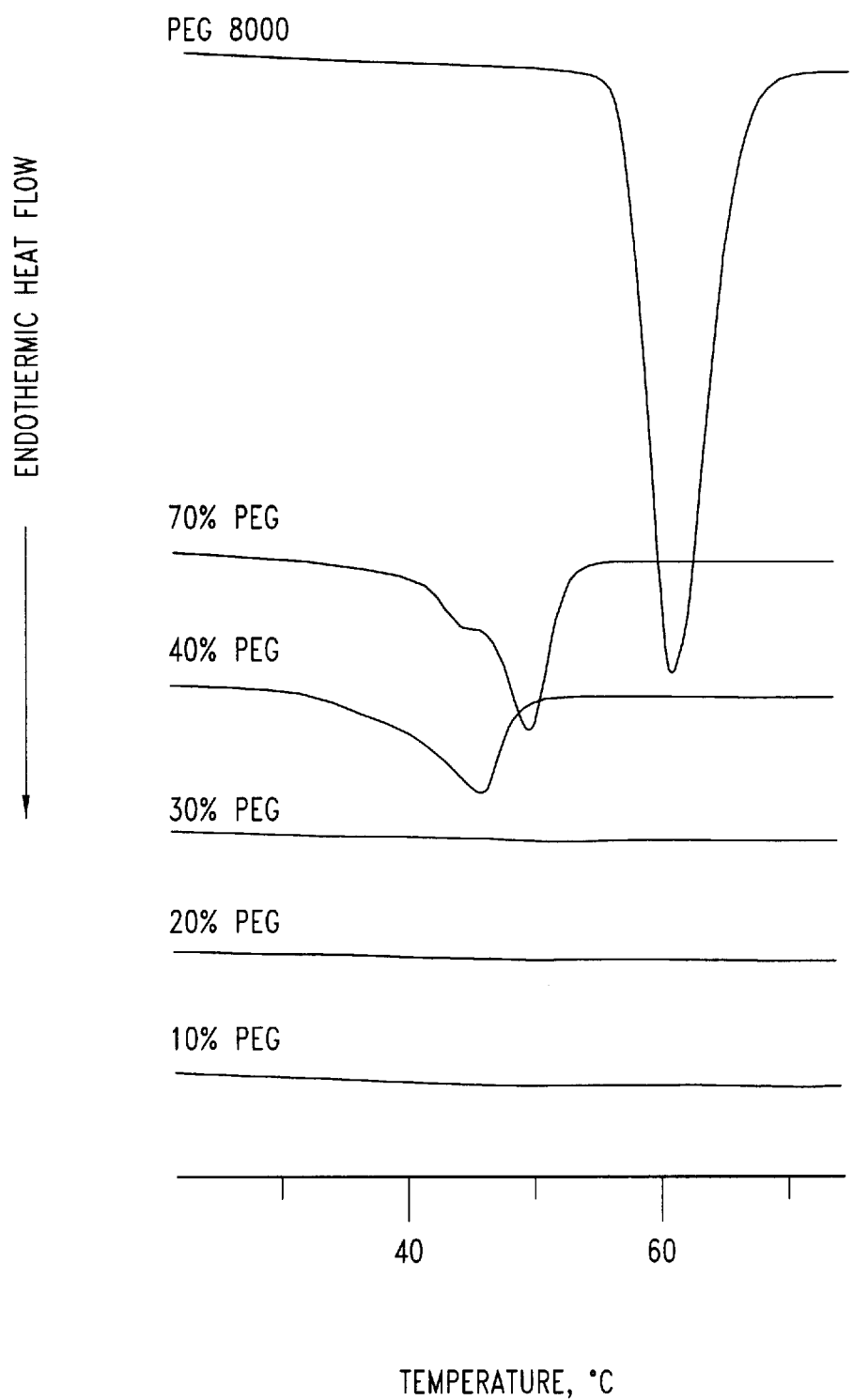
FIG. 22 is a graph which depicts DSC thermograms of PDLLA-PEG-PDLLA and PEG. The heating rate was 10° C./min. See FIG. 21 for melting temperatures and enthalpies.

DSC scans of pure PEG and PDLLA-PEG-PDLLA copolymers are given in FIGS. 21 and 22. The PEG and PDLLA-PEG-PDLLA with PEG contents of 70% and 40% showed endothermic peaks with decreasing enthalpy and temperature as the PEG content of the copolymer decreased. The endothermic peaks in the copolymers of 40% and 70% PEG were probably due to the melting of the PEG region, indicating the occurrence of phase separation. While pure PEG had a sharp melting peak, the copolymers of both 70% and 40% PEG showed broad peaks with a distinct shoulder in the case of 70% PEG. The broad melting peaks may have resulted from the interference of PDLLA with the crystallization of PEG. The shoulder in the case of 70% PEG might represent the glass transition of the PDLLA region. No thermal changes occurred in the copolymers with PEG contents of 10%, 20% and 30% in a temperature range of 10–250° C., indicating that no significant crystallization (therefore may be the phase separation) had occurred.

DSC thermograms of PDLLA:PCL (70:30, 80:20, 90:10) blends without paclitaxel or with 20% paclitaxel showed an endothermic peak at about 60° C., resulting from the melting of PCL. Due to the amorphous nature of the PDLLA and its low molecular weight (800), melting and glass transitions of PDLLA were not observed. No thermal changes due to the recrystallization or melting of paclitaxel was observed.

PDLLA-PEG-PDLLA copolymers of 20% and 30% PEG content were selected as optimum formulation materials for the paste for the following reasons. PDLLA-PEG-PDLLA of 10% PEG could not be melted at a temperature of about 60° C. The copolymers of 40% and 70% PEG were readily melted at 60° C., and the 20% and 30% PEG copolymer became a viscous liquid between 50° C. to 60° C. The swelling of 40% and 70% PEG copolymers in water was very high resulting in rapid dispersion of the pastes in water.

Figure 23:
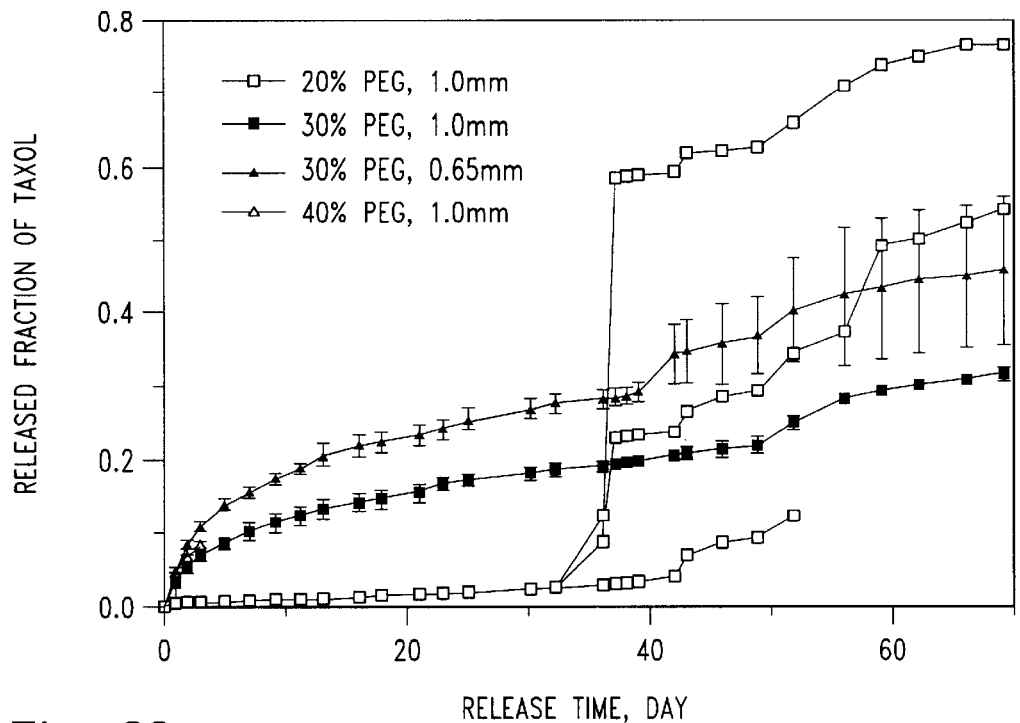
FIG. 23 is a graph which depicts the cumulative release of paclitaxel from 20% paclitaxel loaded PDLLA-PEG-PDLLA cylinders into PBS albumin buffer at 37° C. The error bars represent the standard deviation of 4 samples. Cylinders of 40% PEG were discontinued at 4 days due to disintegration.

The in vitro release profiles of paclitaxel from PDLLA-PEG-PDLLA cylinders are shown in FIG. 23. The experiment measuring release from the 40% PEG cylinders was terminated since the cylinders had a very high degree of swelling (about 200% water uptake within one day) and disintegrated in a few days. The released fraction of paclitaxel from the 30% PEG cylinders gradually increased over 70 days. The released fraction from the 20% PEG cylinders slowly increased up to 30 days and then abruptly increased, followed by another period of gradual increase. A significant difference existed in the extent to which each individual cylinder (20% PEG content) showed the abrupt change in paclitaxel release. Before the abrupt increase, the release fraction of paclitaxel was lower for copolymers of lower PEG content at the same cylinder diameter (1 mm). The 40% and 30% PEG cylinders showed much higher paclitaxel release rates than the 20% PEG cylinders. For example, the cylinder of 30% PEG released 17% paclitaxel in 30 days compared to a 2% release from the 20% PEG cylinder. The cylinders with smaller diameters resulted in faster release rates, e.g., in 30 days, the 30% PEG cylinders with 0.65 mm and 1 mm diameters released 26% and 17% paclitaxel, respectively (FIG. 23).

The above observations may be explained by the release mechanisms of paclitaxel from the cylinders. Paclitaxel was dispersed in the polymer as crystals as observed by optical microscopy. The crystals began dissolving in the copolymer matrix at 170° C. and completely dissolved at 180° C. as observed by hot stage microscope. DSC thermograms of 20% paclitaxel loaded PDLLA-PEG-PDLLA (30% PEG) paste revealed a small recrystallization exotherm (16 J/g, 190° C.) and a melting endotherm (6 J/g, 212° C.) for paclitaxel (FIG. 21) indicating the recrystallization of paclitaxel from the copolymer melt after 180° C. In this type of drug/polymer matrix, paclitaxel could be released via diffusion and/or polymer erosion.

In the diffusional controlled case, drug may be released by molecular diffusion in the polymer and/or through open channels formed by connected drug particles. Therefore at 20% loading, some particles of paclitaxel were isolated and paclitaxel may be released by dissolution in the copolymer followed by diffusion. Other particles of paclitaxel could form clusters connecting to the surface and be released through channel diffusion. In both cases, the cylinders with smaller dimension gave a faster drug release due to the shorter diffusion path (FIG. 23).

Figure 24A:
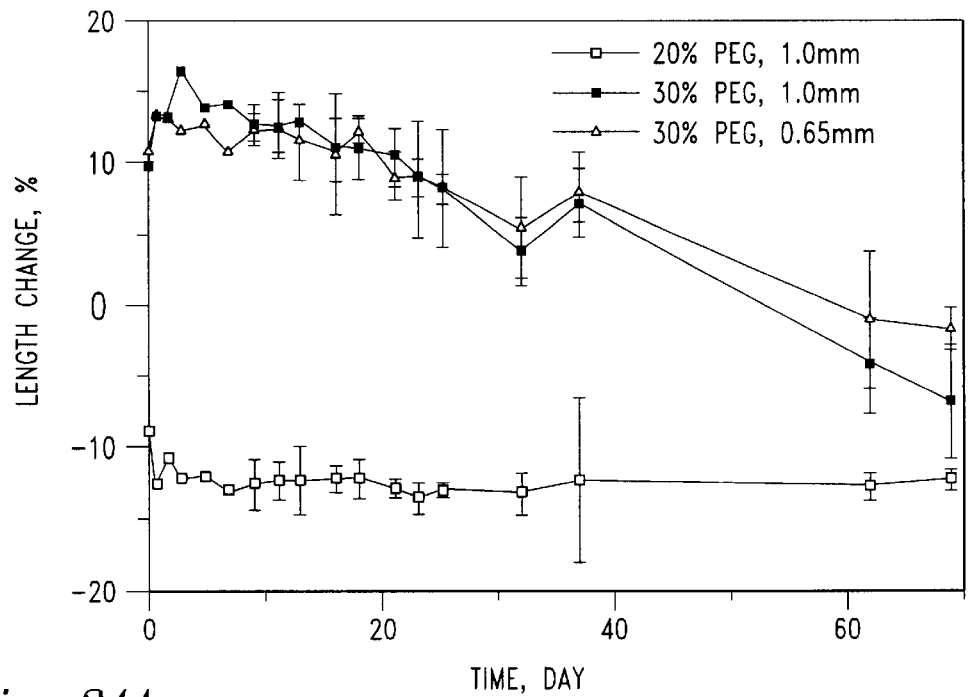
FIGS. 24A, 24B and 24C are graphs which depict the change in dimensions, length (A), diameter (B) and wet weight (C) of 20% paclitaxel laded PDLLA-PEG-PDLLA cylinders during the in vitro release of paclitaxel at 37° C.
Figure 24B:
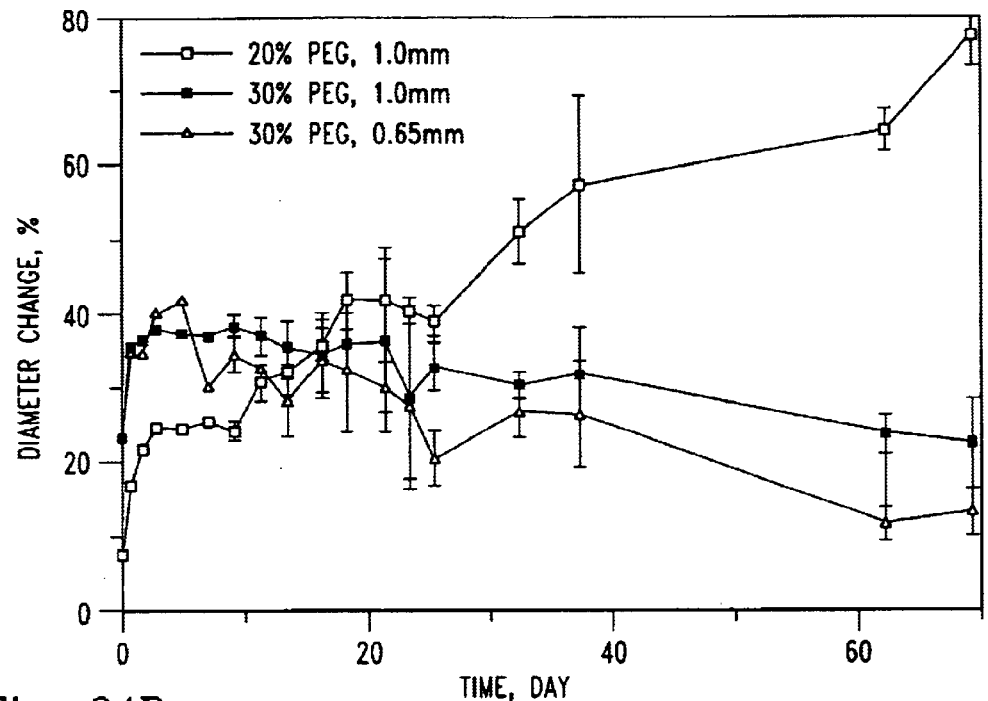
Figure 24C:
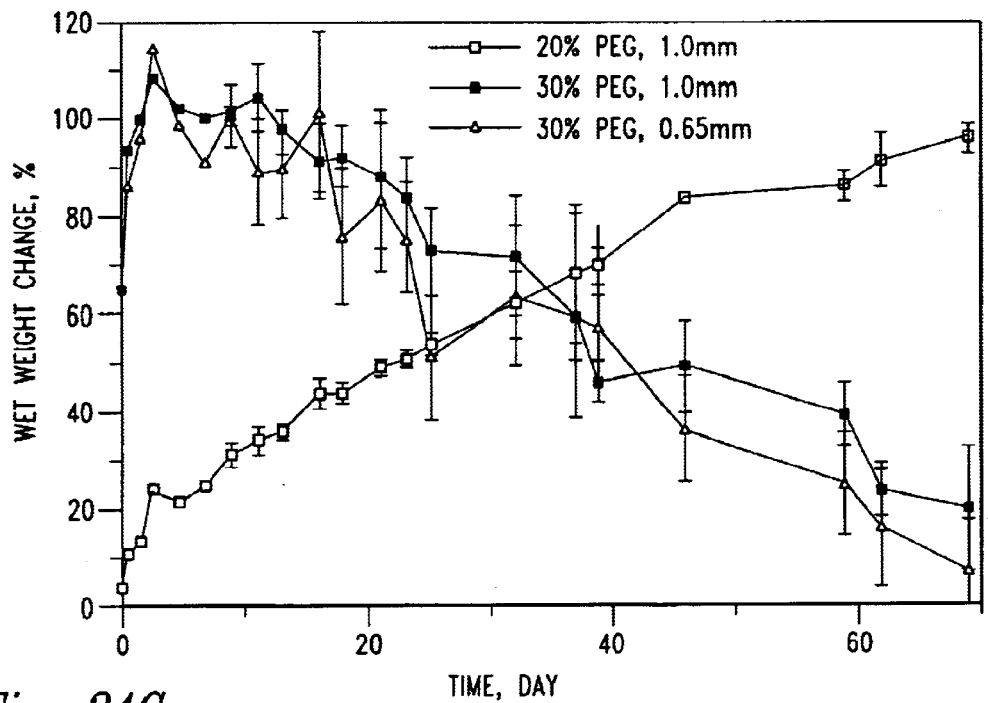

The dimension changes and water uptake of the cylinders were recorded during the release (FIG. 24). The changes in length, diameter and wet weight of the 30% PEG cylinders increased rapidly to a maximum within 2 days, remained unchanged for about 15 days, then decreased gradually. The initial diameter of the cylinder did not affect the swelling behavior. For the cylinder of 20% PEG, the length decreased by 10% in one day and leveled off, while the diameter and water uptake gradually increased over time. Since more PEG in the copolymer uptaken more water to facilitate the diffusion of paclitaxel, a faster release was observed (FIG. 23).

Figure 25:
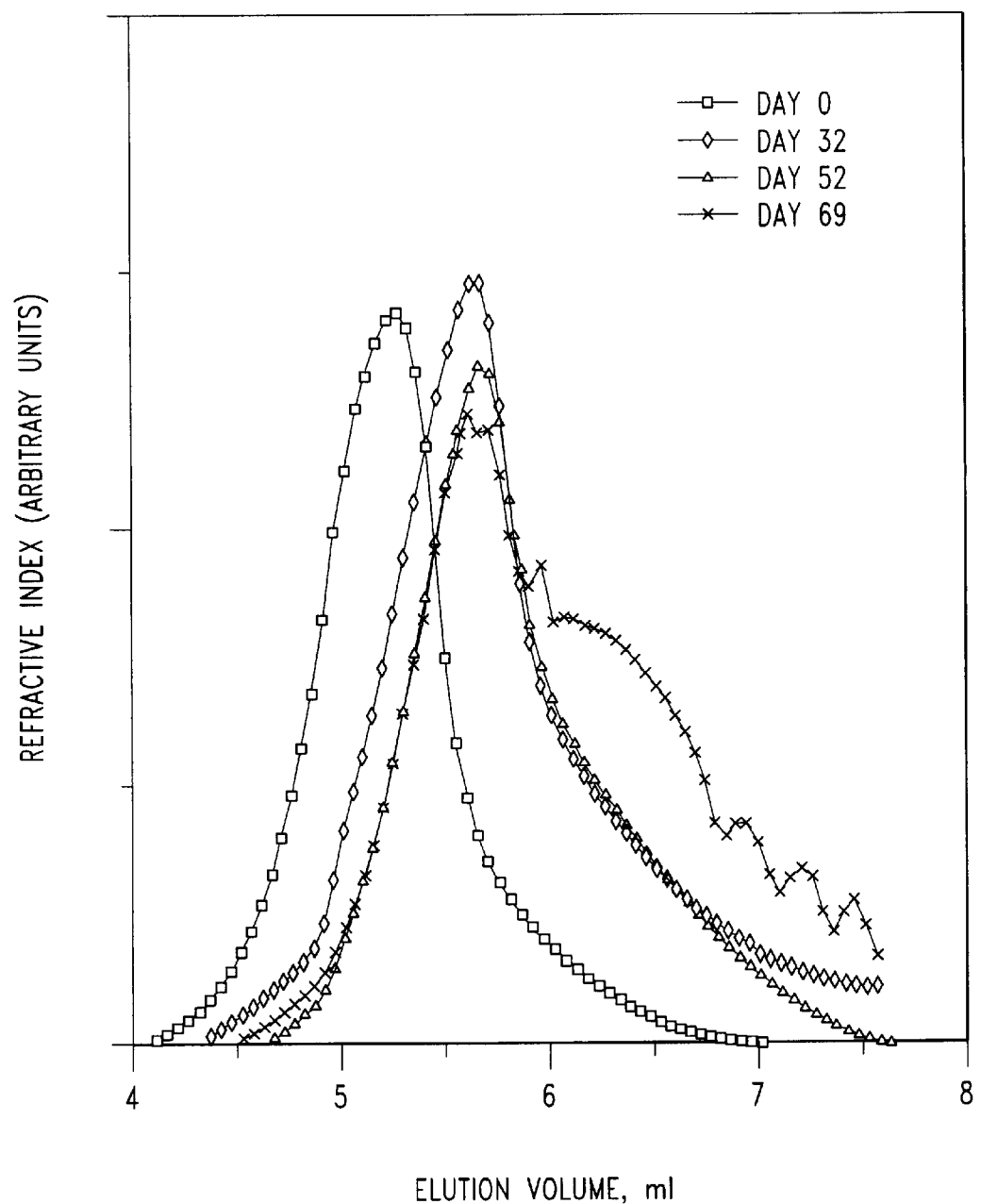
FIG. 25 is a graph which shows gel permeation chromatograms of PDLLA-PEG-PDLLA cylinders (20% PEG, 1 mm diameter) loaded with 20% paclitaxel during the release in PBS albumin buffer at 37° C.
Figure 27A:
FIGS. 27A, 27B, 27C and 27D are SEMs of dried PDLLA-PEG-PDLLA cylinders (loaded with 20% paclitaxel, 1 mm in diameter) before and during paclitaxel release. A: 20% PEG, day 0; B: 30% PEG, day 0; C: 20% PEG, day 69; D: 30% PEG, day 69.
Figure 27B:
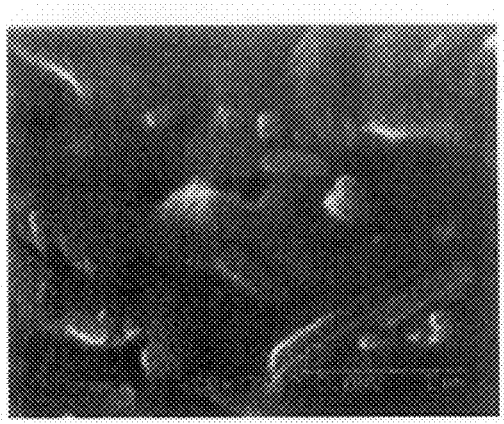
Figure 27C:
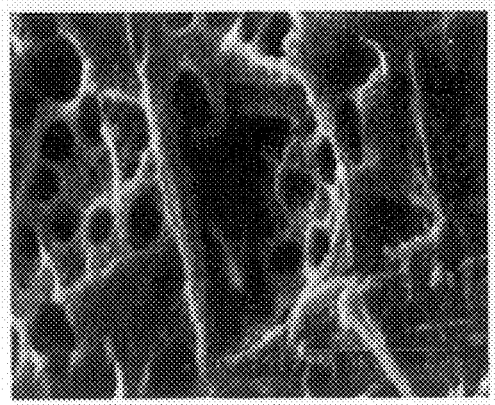
Figure 27D:
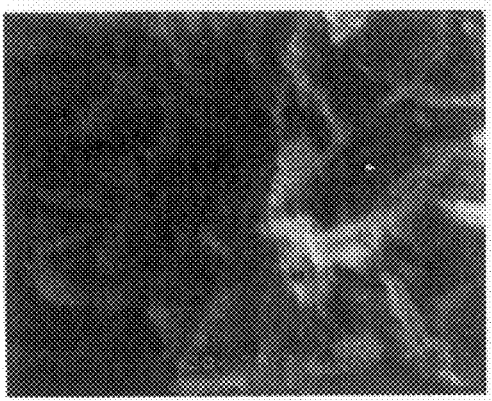

The copolymer molecular weight degradation of PDLLA-PEG-PDLLA paste was monitored by GPC. For the 20% PEG cylinder, the elution volume at the peak position increased with time indicating a reduced polymer molecular weight during the course of the release experiment (FIG. 25). A biphasic molecular weight distribution was observed at day 69. Polymer molecular weight was also decreased for 30% PEG cylinders (1 mm and 0.65 mm). However no biphasic distribution was observed.

NMR spectra revealed a PEG peak at 3.6 ppm and PDLLA peaks at 1.65 ppm and 5.1 ppm. The peak area of PEG relative to PDLLA in the copolymer decreased significantly after 69 days (FIG. 26), indicating the dissolution of PEG after its dissociation from PDLLA. The dry mass loss of the cylinders was also recorded (FIG. 26) and shows a degradation rate decreasing in the order 30%PEG-0.65 mm>30%PEG-1 mm>20%PEG-1 mm.

The morphological changes of the dried cylinders before and during paclitaxel release were observed using SEM (FIG. 27). Briefly, solid paclitaxel crystals and non-porous polymer matrices were seen before the release (FIGS. 27A and 27B). After 69 days of release, no paclitaxel crystals were observed and the matrices contained many pores due to polymer degradation and water uptake (FIGS. 27C and 27D).

The 30% PEG cylinders showed extensive swelling after only two days in water (FIG. 24) and therefore the hindrance to diffusion of the detached water soluble PEG block and degraded PDLLA (i.e., DL-lactic acid oligomers) was reduced. Since the mass loss and degradation of the 30% PEG cylinders was continuous, the contribution of erosion release gradually increased resulting in a sustained release of paclitaxel without any abrupt change (FIG. 23). For the 20% PEG cylinders, the swelling was low initially (FIG. 24) resulting in a slow diffusion of the degradation products. Therefore the degradation products in the interior region are primarily retained while there are much less degradation products in the outer region due to the short diffusion path. The degradation products accelerated the degradation rate since the carboxylic acid end groups of the oligomers catalyzed the hydrolytic degradation. This results in a high molecular weight shell and a low molecular weight interior as indicated by the biphasic copolymer molecular weight distribution (FIG. 25, day 69). Since the shell rupture was dependent on factors such as the strength, thickness and defects of the shell and interior degradation products, the onset and the extent of the loss of interior degradation products are very variable. Because the shell rupture is not consistent and the drug in the polymer is not microscopically homogenous, the time point for the release burst and the extent of the burst were different for the 4 samples tested (FIG. 23).

Figure 28:
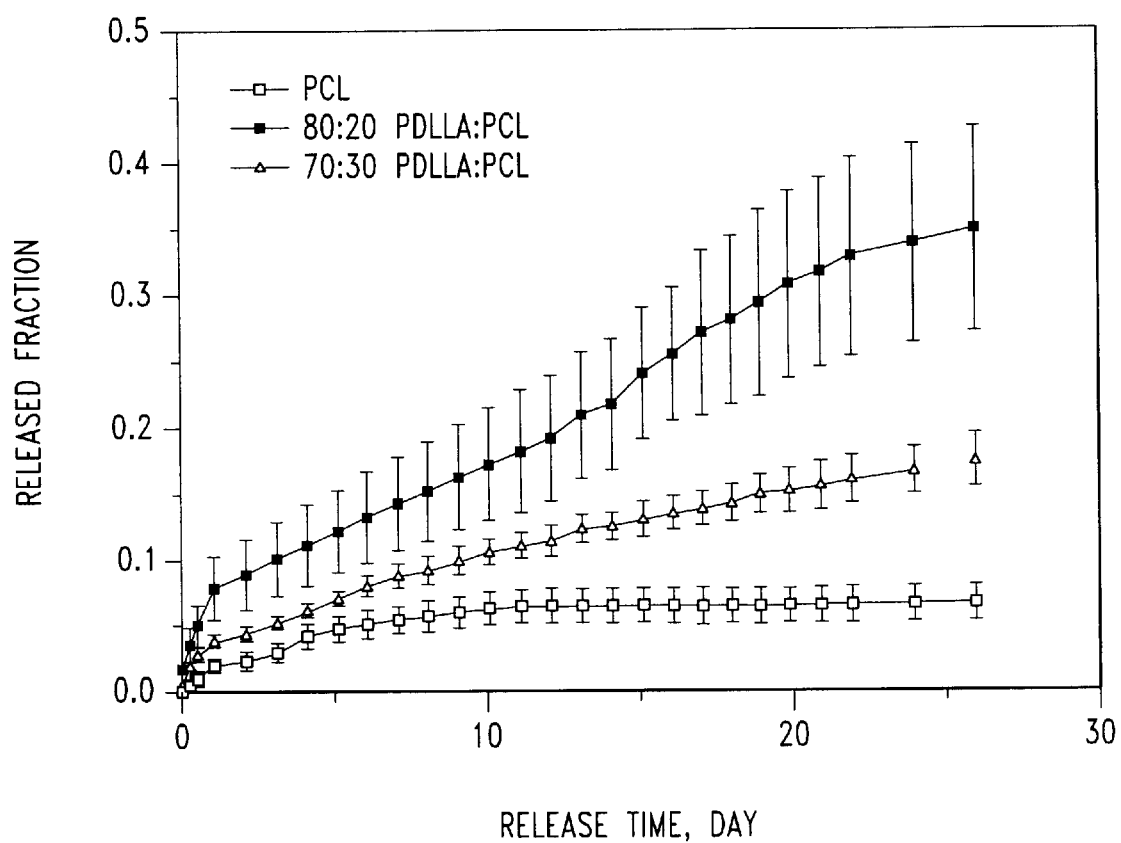
FIG. 28 is a graph which depicts the cumulative release of paclitaxel from 20% paclitaxel loaded PDLLA:PCL blends and PCL into PBS albumin buffer at 37° C. The error bars represent the standard deviations of 4 samples.

The release of paclitaxel from PDLLA and PCL blends and pure PCL are shown in FIG. 28. Briefly, the released fraction increased with PDLLA content in the blend. For example, within 10 days, the released paclitaxel from 80:20, 70:30, and 0:100 PDLLA:PCL were 17%, 11%, and 6%, respectively. After an initial burst in one day, approximately constant release was obtained from 80:20 PDLLA:PCL paste. No significant degree of swelling was observed during the release. For the PDLLA:PCL blends, since PDLLA had a very low molecular weight of about 800, it was hydrolyzed rapidly into water soluble products without a long delay in mass loss. PCL served as the "holding" material to keep the paste from rapidly disintegrating. Therefore the release rate increased with PDLLA content in the blend due to the enhanced degradation. The continuous erosion of the PDLLA controlled the release of paclitaxel and resulted in a constant release. The release of paclitaxel from pure PCL was probably diffusion controlled due to the slow degradation rate (in 1–2 years) of PCL.

Difficulties were encountered in the release study for 20% paclitaxel loaded 90:10 PDLLA:PCL paste due to the disintegration of the paste pellet within 24 hours of incubation. Briefly, during the first 12 hours of incubation, samples were taken every hour in order to ensure sink conditions for paclitaxel release. The released paclitaxel from the 90:10 paste was 25–35% within 10 hours.

The efficacy of the paste formulations for regressing tumor growth in mice were evaluated (FIG. 29). Briefly, pastes examined were PCL±20% paclitaxel, 80:20 PDLLA:PCL±20% paclitaxel, 90:10 PDLLA:PCL±20% paclitaxel and PDLLA-PEG-PDLLA (30% PEG)±20% paclitaxel. The paste formulations, 90:10 PDLLA:PCL and PDLLA-PEG-PDLLA, containing paclitaxel reduced tumor growth in vivo by 54 and 40%, respectively. In contrast, the paste formulations, PCL and 80:20 PDLLA:PCL, containing paclitaxel had little or no effect on tumor growth. All control pastes (drug absent) had no significant effect on tumor growth. The paste formulations with faster release rates of paclitaxel (90:10 PDLLA:PCL and PDLLA-PEG-PDLLA) were also more effective in reducing tumor growth, suggesting that a critical local concentration of paclitaxel is required at the tumor site for tumor growth inhibition. Paste formulations releasing paclitaxel slowly, such as PCL and 80:20 PDLLA:PCL, were not effective. All of the paste formulations examined had no significant effect on the body weights of mice, indicating that the paclitaxel loaded paste was well tolerated in vivo.

These data suggest that local application of paclitaxel at the tumor site is an effective therapeutic strategy to inhibit local tumor growth without increasing systemic toxicity. The inability to the paclitaxel loaded formulations to completely inhibit tumor growth is most likely due to insufficient release of paclitaxel from the polymer and rapid tumor growth of MDAY-D2 tumors. The ability of 90:10 PDLLA:PCL paste containing 30% paclitaxel, which released more paclitaxel than 90:10 PDLLA:PCL paste containing 20% paclitaxel, and which inhibited tumor growth more effectively is consistent in this regard. Thus, modulation of the release rate of paclitaxel, which is regulated by the properties of the polymer and chemotherapeutic agents as well as the site of administration, is in important step in the development of local therapy for inhibiting tumor growth.

Example 12

Manufacture of Polymeric Compositions Containing PCL and MePEG

A. Paclitaxel Release from PCL

Figure 30A:
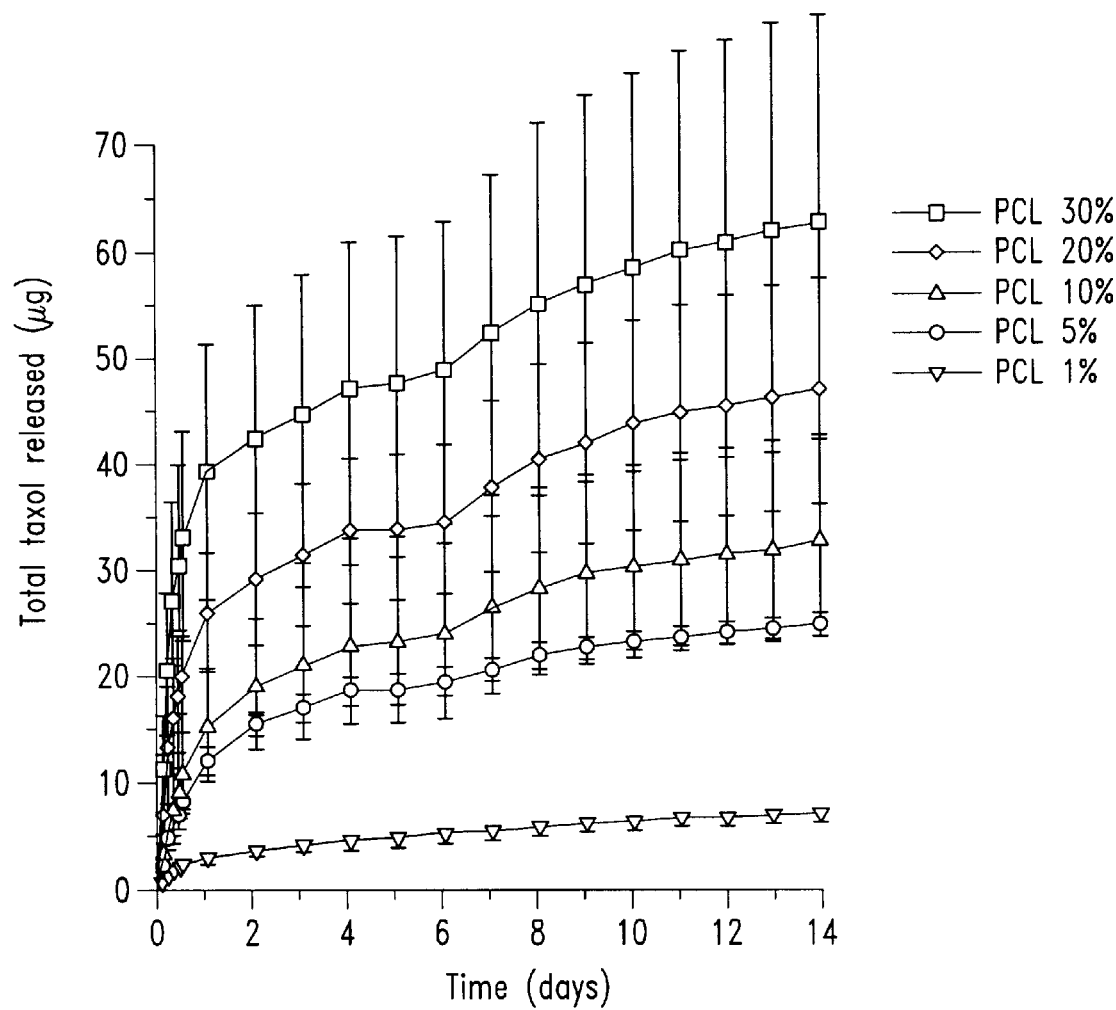
FIG. 30A is a graph which depicts the time course of paclitaxel release from 2.5 mg pellets of PCL.
Figure 30B:
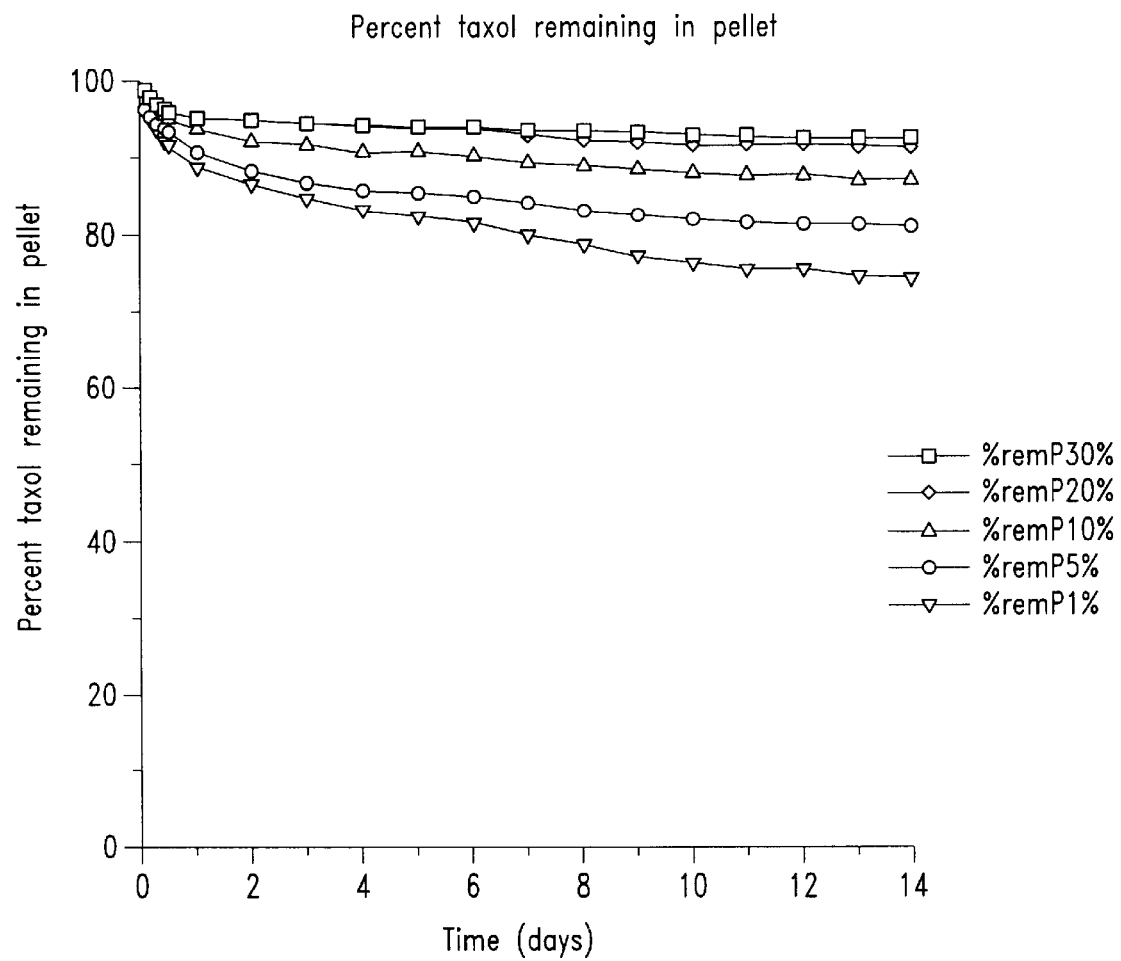
FIG. 30B is a graph which shows the percent paclitaxel remaining in the pellet, over time.

Polycaprolactone containing various concentrations of paclitaxel was prepared as described in Example 1. The release of paclitaxel over time was measured by HPLC essentially as described above. Results are shown in FIG. 30.

B. Effect of MePEG on Paclitaxel Release

Figure 31A:
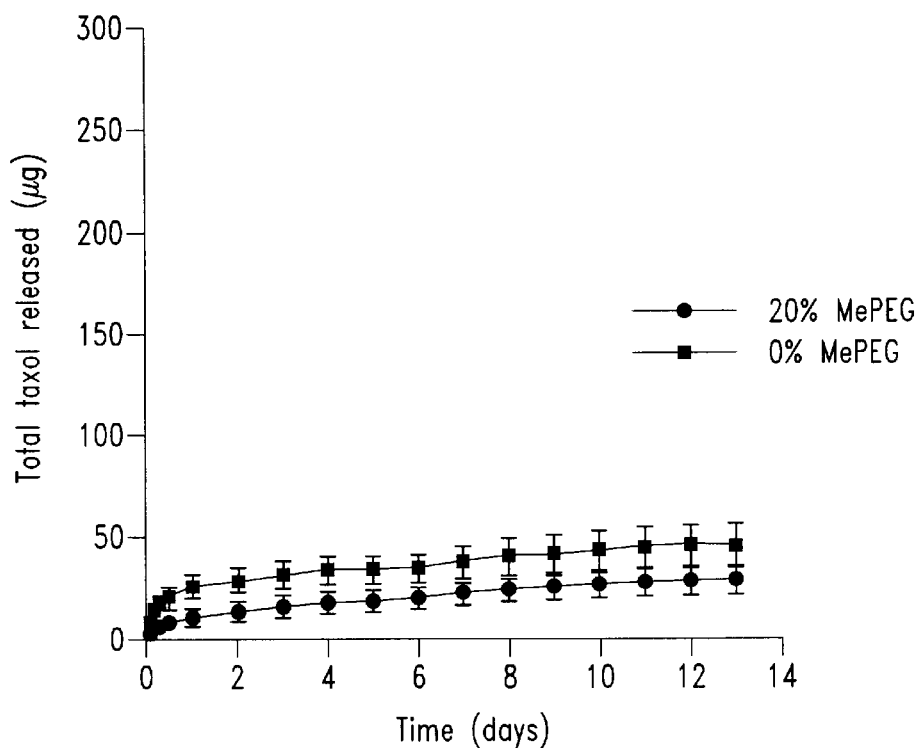
FIG. 31A is a graph which shows the effect of MePEG on paclitaxel release from PCL paste leaded with 20% paclitaxel.
Figure 31B:
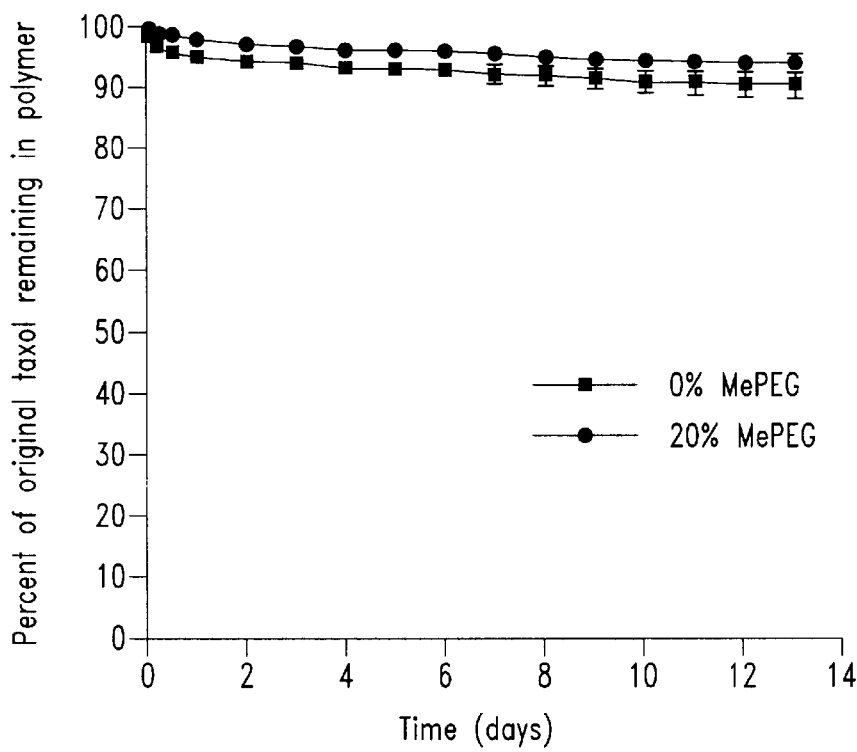
FIG. 31B is a graph which shows the percent paclitaxel remaining in the pellet, over time.

MePEG at various concentrations was formulated into PCL paste containing 20% paclitaxel, utilizing the methods described in Example 1. The release of paclitaxel over time was measured by HPLC essentially as described above. Results of this study are shown in FIG. 31.

C. Effect of MePEG on the Melting Point of PCL

Figure 32A:
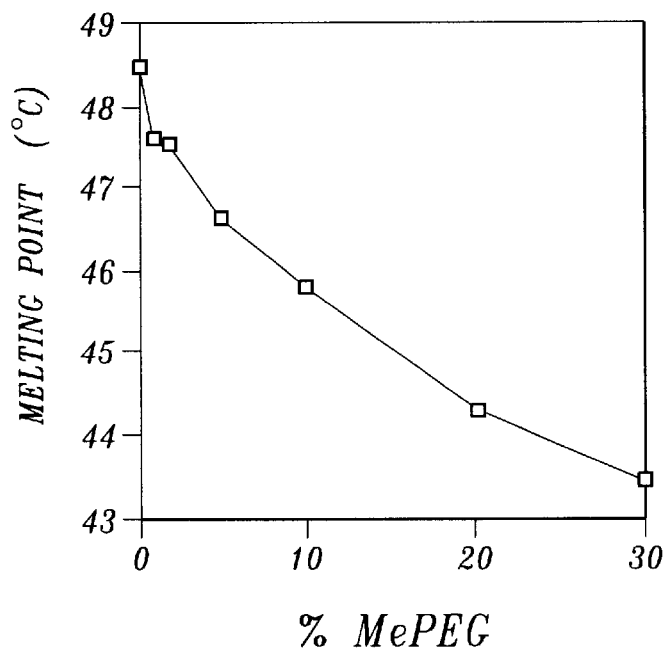
FIGS. 32A and 32B are graphs which show the effect of various concentrations of MePEG in PCL in terms of melting point (32A) and time to solidify (32B).
Figure 32B:
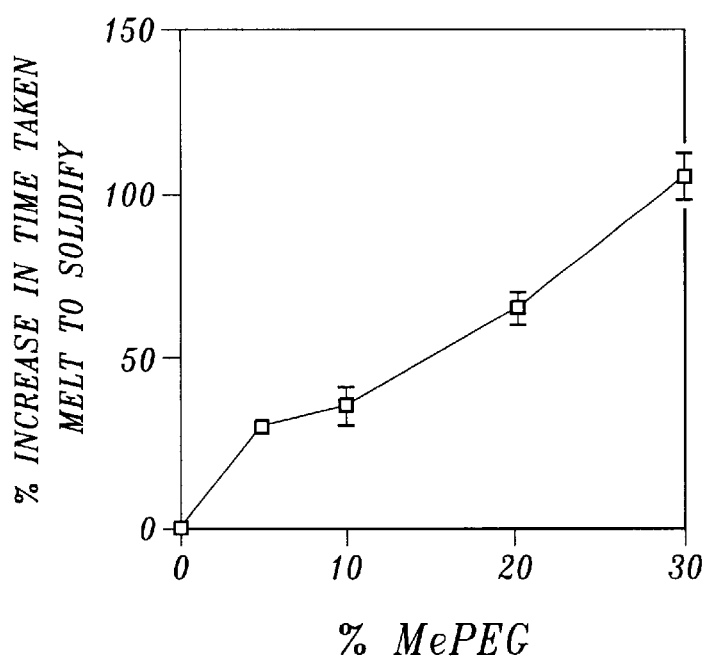

MePEG at various concentrations (formulated into PCL paste containing 20% paclitaxel) was analyzed for melting point using DSC analysis at a heating rate of 2.5° C. per minute. Results are shown in FIGS. 32A (melting point vs. % MePEG) and 32B (percent increase in time to solidify vs. % MePEG).

D. Tensile Strength of MePEG Containing PCL

Figure 33:
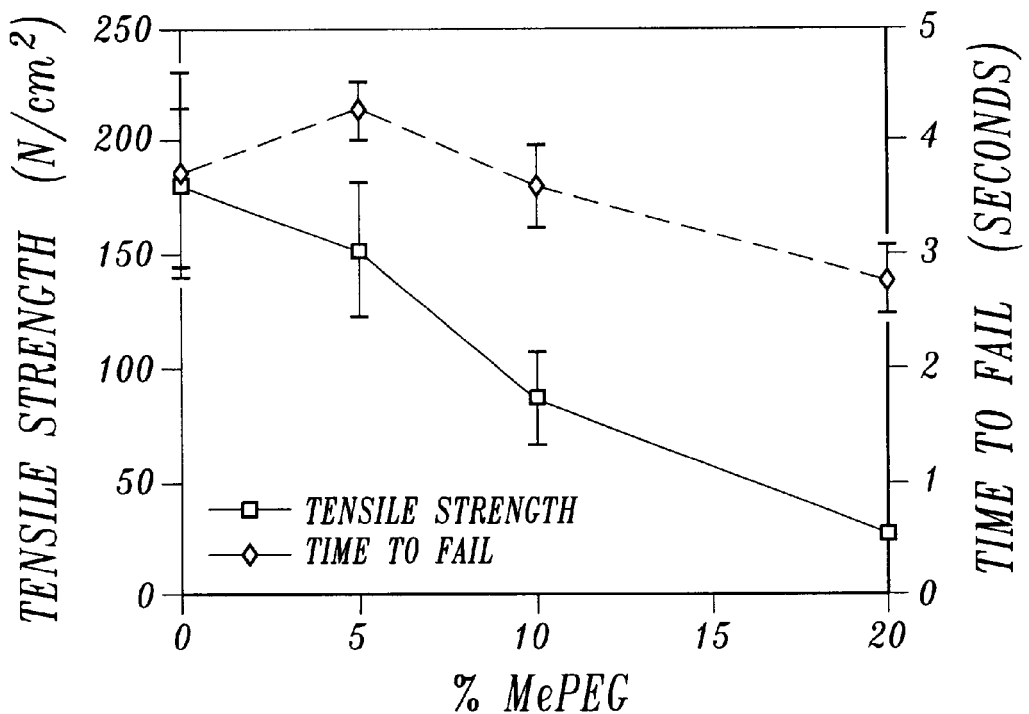
FIG. 33 is a graph which shows the effect of MePEG incorporation into PCL on the tensile strength and time to fail of the polymer.

PCL containing MePEG at various concentrations was tested for tensile strength and time to fail by a CT-40 Mechanical Strength Tester. Results are shown in FIG. 33.

E. Effect of y-irradiation or the Release of Paclitaxel

Figure 34:
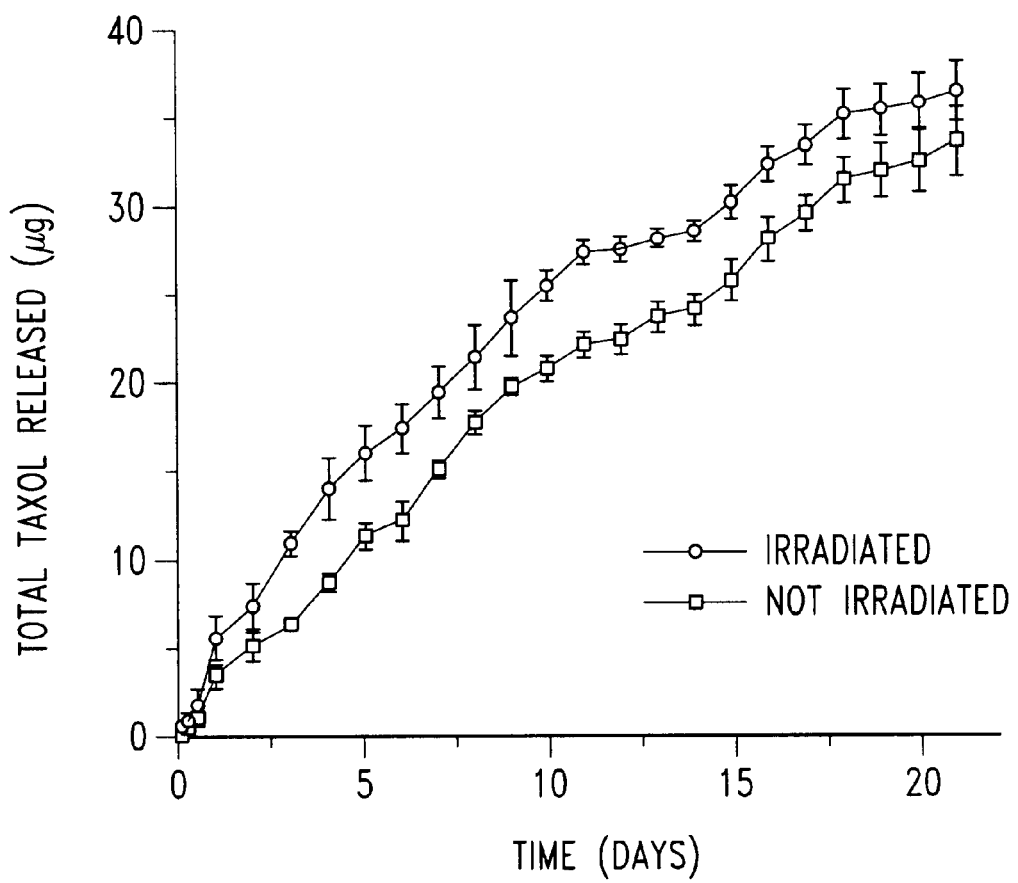
FIG. 34 is a graph which shows the effect of irradiation on paclitaxel release.
Figure 35:
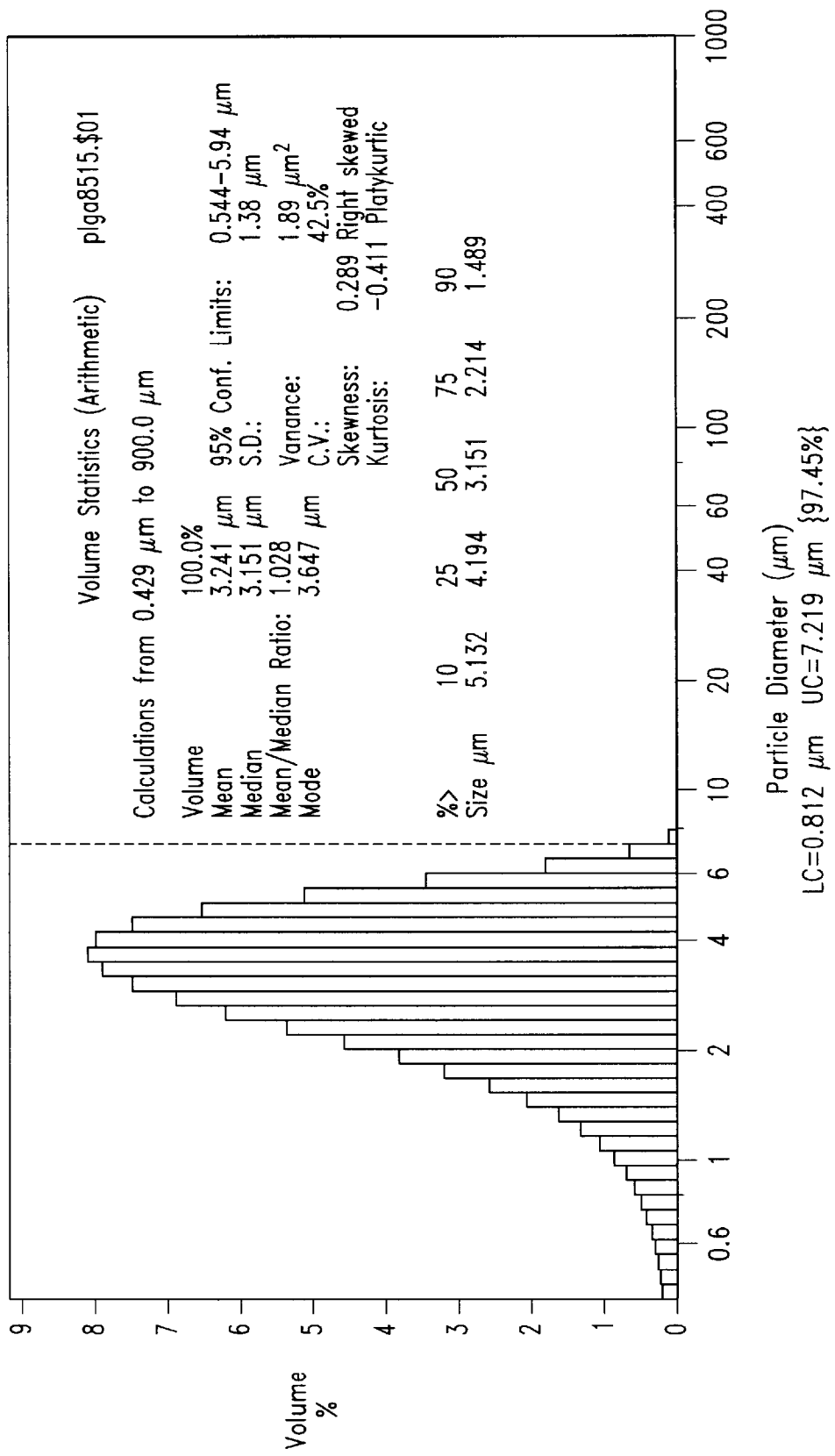
FIG. 35 is a graph which depicts the range of particle sizes for control microspheres (PLLA:GA-85:15).
Figure 36:
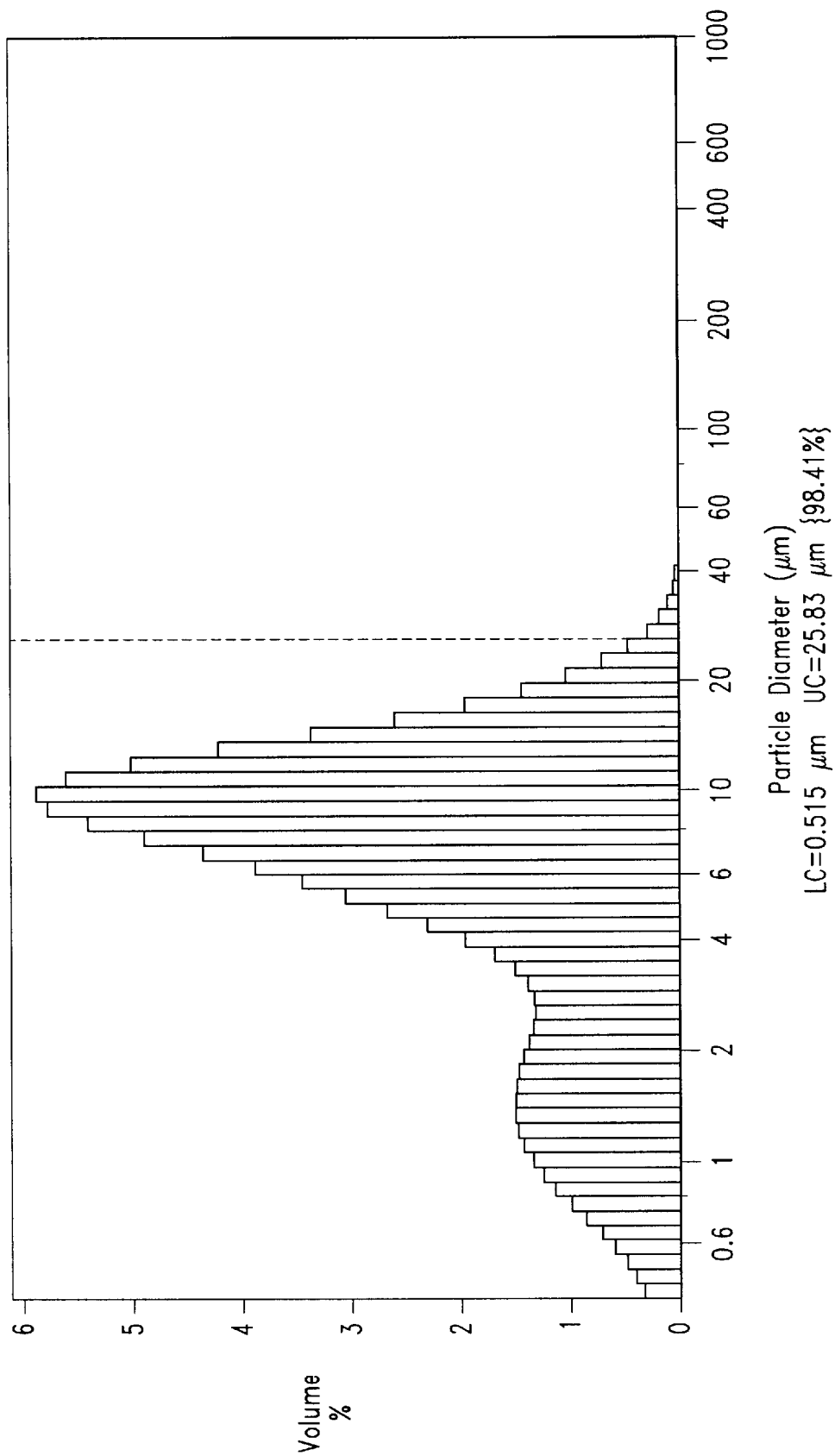
FIG. 36 is a graph which depicts the range of particle sizes for 20% paclitaxel loaded microspheres (PLLA:GA-85-15).
Figure 37:
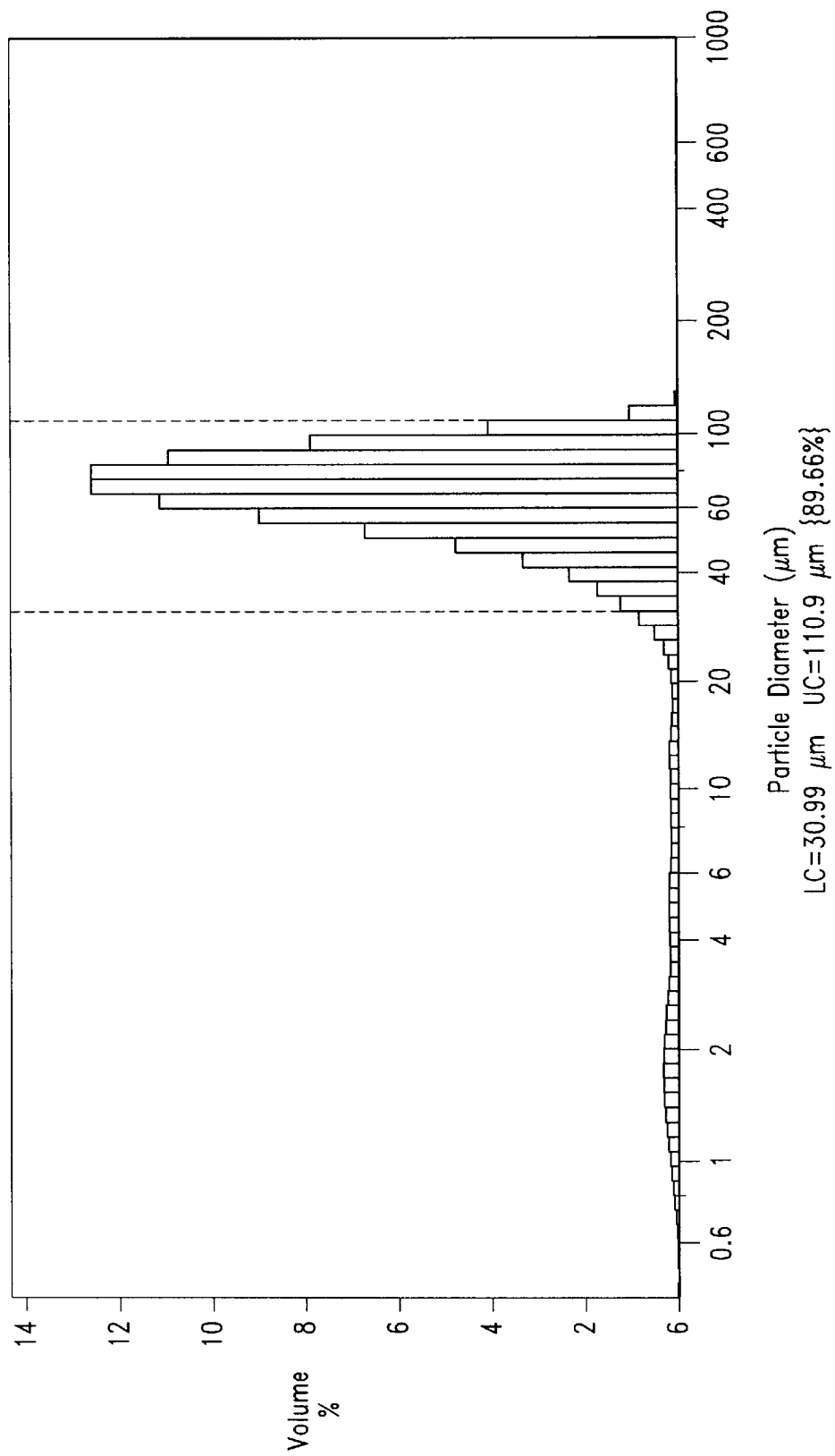
FIG. 37 is a graph which depicts the range of particle sizes for control microspheres (PLLA:GA-85-15).
Figure 38:
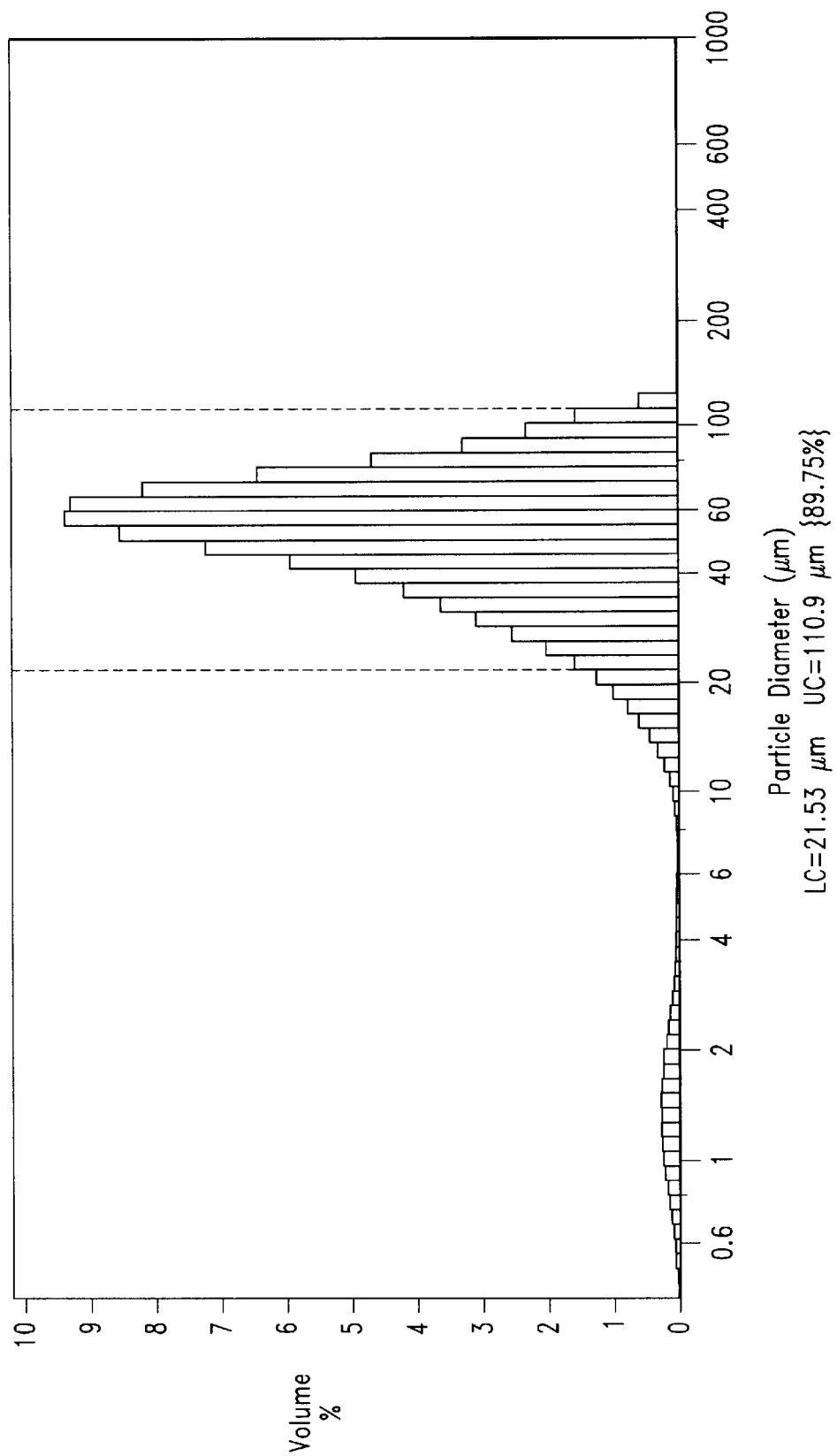
FIG. 38 is a graph which depicts the range of particle sizes for 20% paclitaxel loaded microspheres (PLLA:GA-85-15).
Figure 39C:
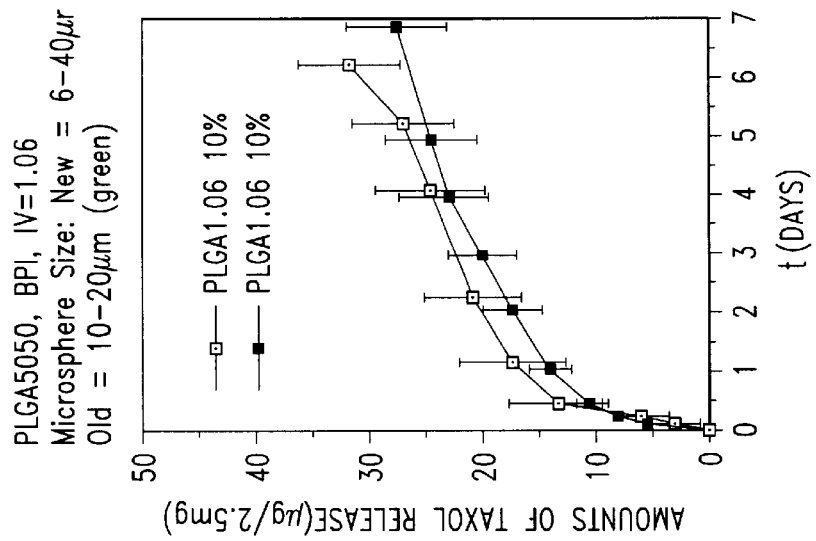
FIGS. 39A, 39B and 39C are graphs which depict the range of particle sizes for various ratios of PLLA and GA.
Figure 39B:
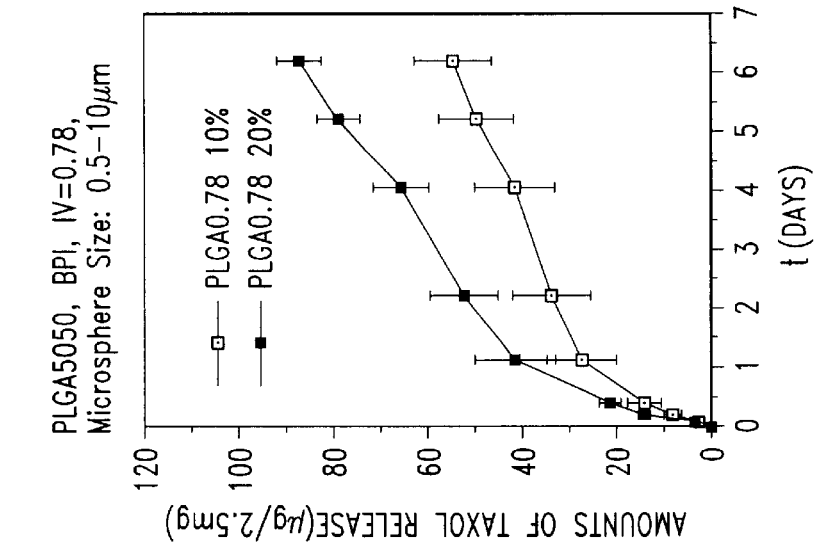
Figure 39A:
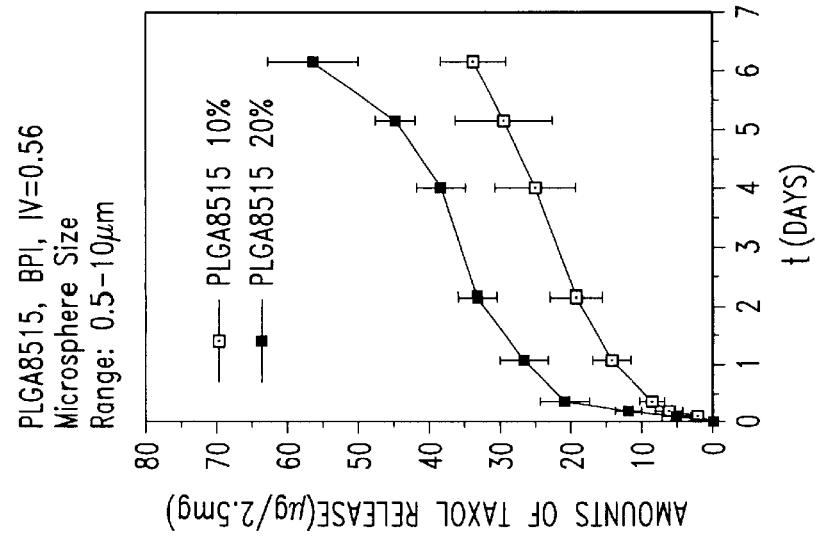
Figure 40B:
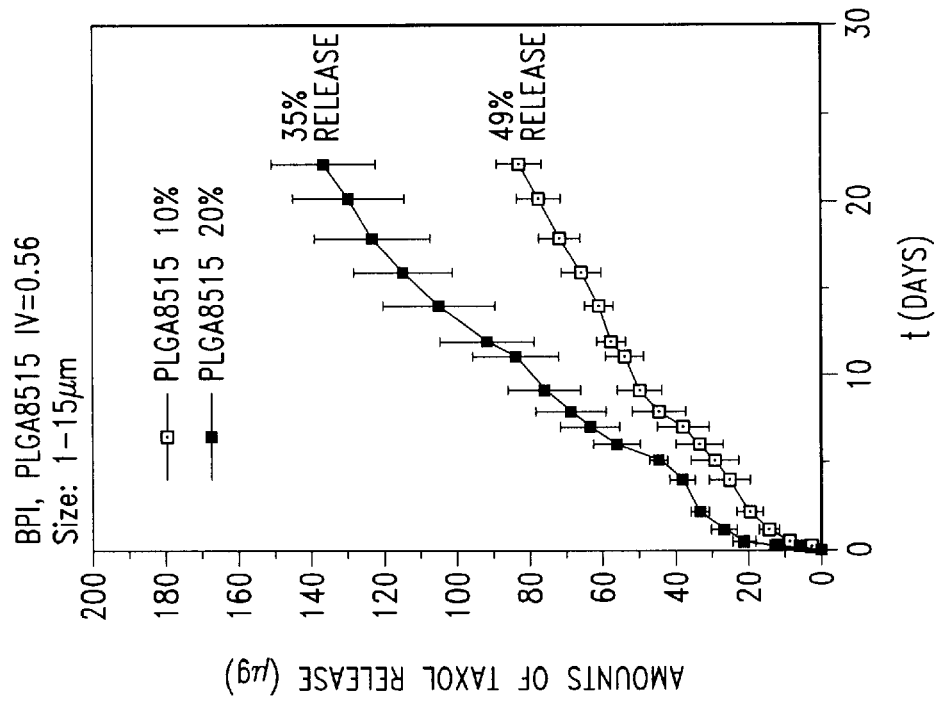
FIGS. 40A and 40B are graphs which depict the range of particle sizes for various ratios of PLLA and GA
Figure 40A:
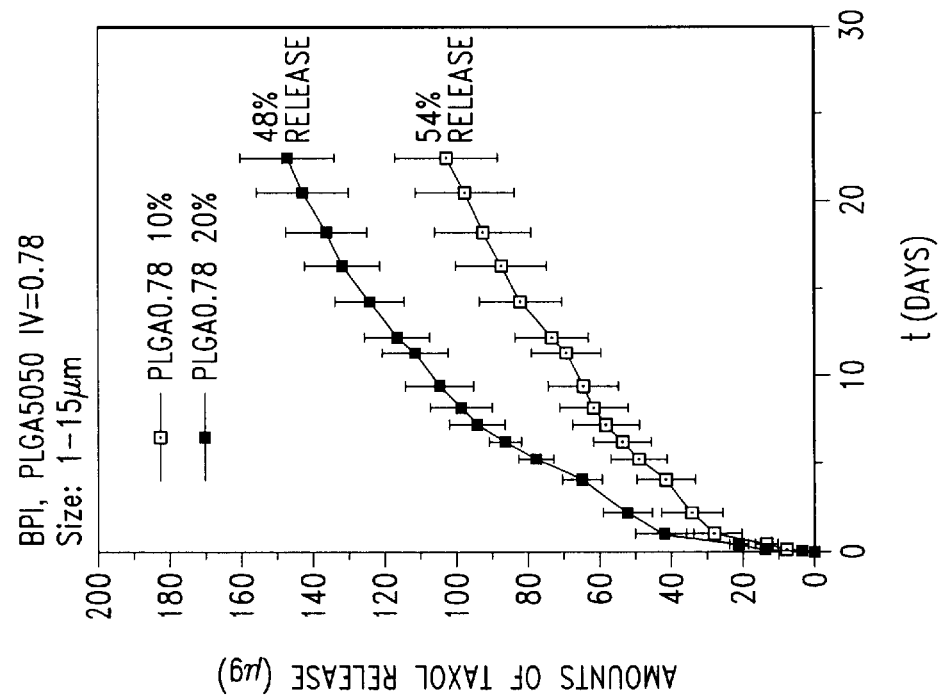
Figure 41B:
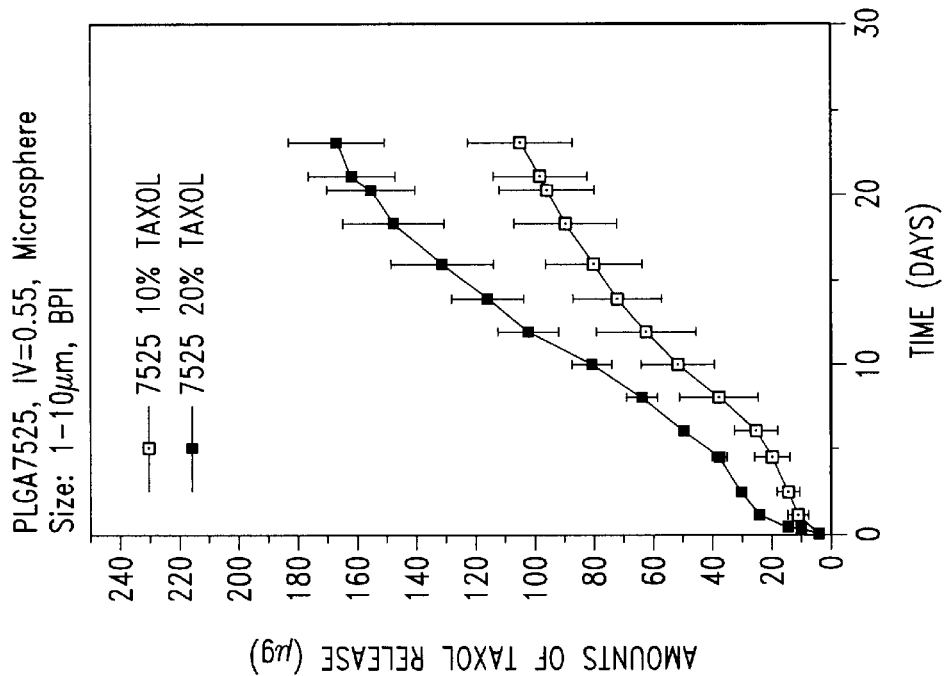
FIGS. 41A, 41B and 41C are graphs which depict the range of particle sizes for various ratios of PLLA and GA.
Figure 41A:
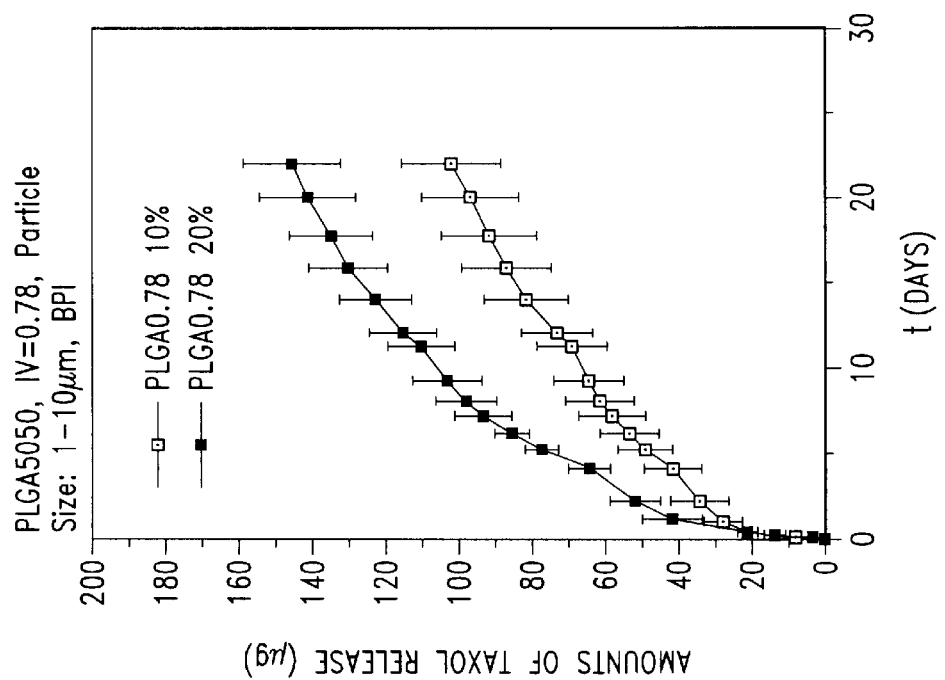
Figure 41C:
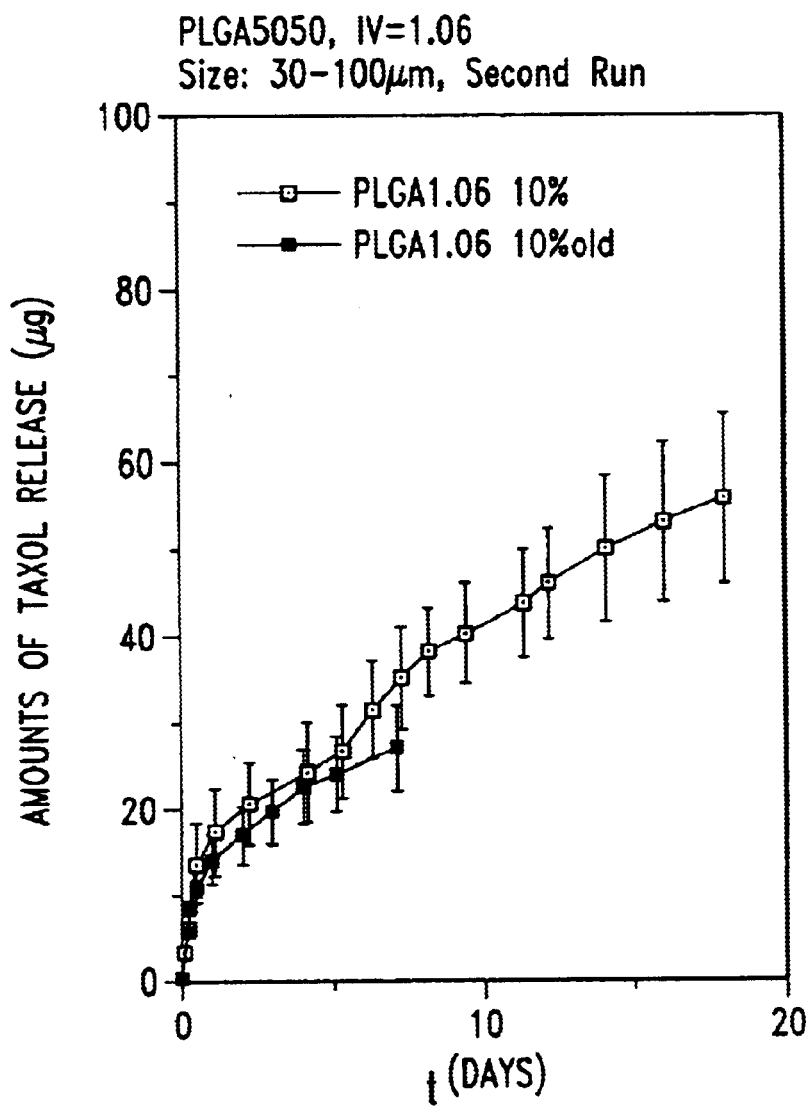
Figure 42B:
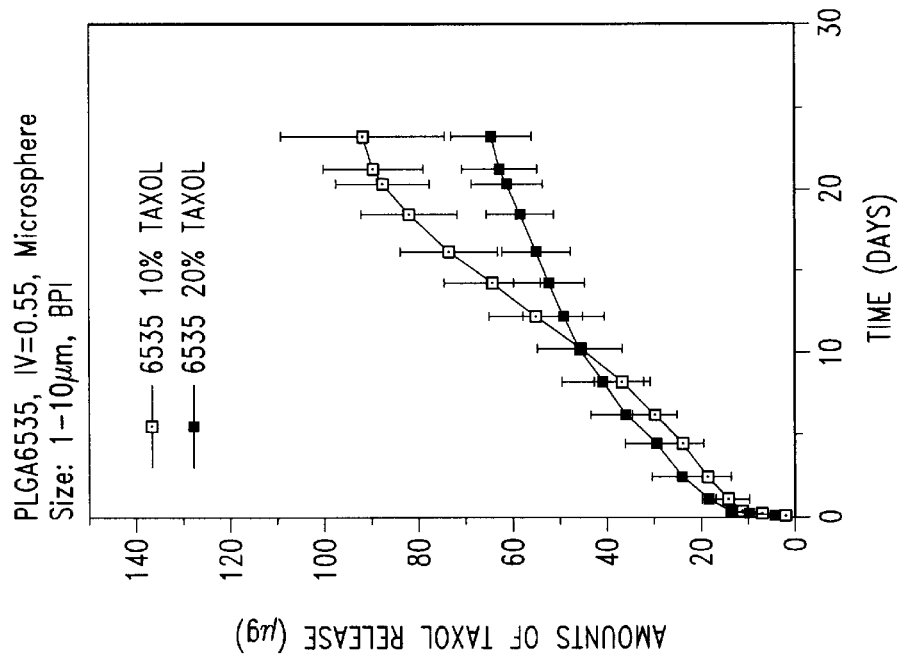
FIGS. 42A and 42B are graphs which depict the range of particle sizes for various ratios of PLLA and GA
Figure 42A:
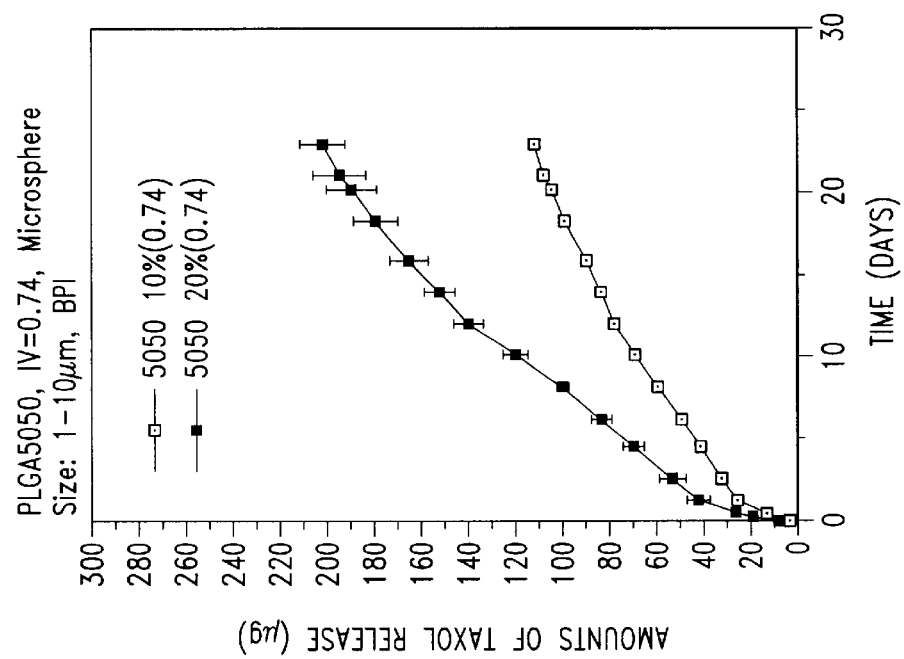

PCL:MePEG (80:20) paste loaded with 20% paclitaxel was y-irradiated and analyzed for paclitaxel release over time. Results are set forth in FIG. 34.

In summary, based on the above experiments it can be concluded that the addition of MePEG makes the polymer less brittle and more wax like, reduces the melting point and increases the solidification time of the polymer. All these factors improve the application properties of the paste. At low concentrations (20%) MePEG has no effect on the release of paclitaxel from PCL. Gamma-irradiation appears to have little effect on paclitaxel release.

Example 13

Preparation of PCL Microspheres: Scale Up Studies

Microspheres (SOg) were prepared using PCL (nominal molecular weight 80,000) using the solvent evaporation method described below.

A. Method

A preparation of 500 ml of 10% PCL in methylene chloride and a 4000 ml solution of 1% PVA (mol. Wt 13,000–23,000; 99% hydrolyzed) were emulsified using the Homo Mixer controlled with a rheostat at 40 setting for 10 hours. The mixture was strained using sieve #140 until the microspheres settled at the bottom then supernatant was decanted. The preparation was then washed 3x with distilled water (using the sedimentation followed by decanting method) and then re-suspended in 250 ml of distilled water and filtered. The microspheres were then air-dried overnight at 37° C.

B. Results

Microsphere yields were as follows:

Initial wt of PCL = 50.1 g
Wt. Of microspheres obtained = 41.2 g
% yield = (43.2/50.0) × 100
= 86.4

Yield (10–50 $\mu$m) about 70%

Mean size 21.4 $\mu$m, median 22.0 $\mu$m mode 24.7 $\mu$m.

Narrower size ranges (20–40 $\mu$m) can be obtained by sieving or by separation using the sedimentation method.

Example 14

Manufacture of PLGA Microspheres

Microspheres were manufactured from (PLLA) lactic acid-glycolic acid (GA) copolymers.

A. Method

Microspheres were manufactured in the size ranges 0.5 to 10 $\mu$m, 10–20 $\mu$m and 30–100 $\mu$m using standard methods (polymer was dissolved in dichloromethane and emulsified in a polyvinyl alcohol solution with stirring as previously described in PCL or PDLLA microspheres manufacture methods). Various ratio's of PLLA to GA were used as the polymers with different molecular weights [given as Intrinsic Viscosity (I.V.)]

B. Result

Microspheres were manufactured successfully from the following tarting polymers:

| PLLA | GA | I.V. |
|------|----|------|
| 50 | 50 | 0.74 |
| 50 | 50 | 0.78 |
| 50 | 50 | 1.06 |
| 65 | 35 | 0.55 |
| 75 | 25 | 0.55 |
| 85 | 15 | 0.56 |

Paclitaxel at 10% or 20% loadings was successfully incorporated into all these microspheres. Examples of size distributions for one starting polymer (85:15, IV=0.56) are given in FIGS. 35–38. Paclitaxel release experiments were performed using microspheres of various sizes and various compositions. Release rates are shown in FIGS. 39–42.

Example 15

Di-block Copolymers

Figures 44A, 44B:
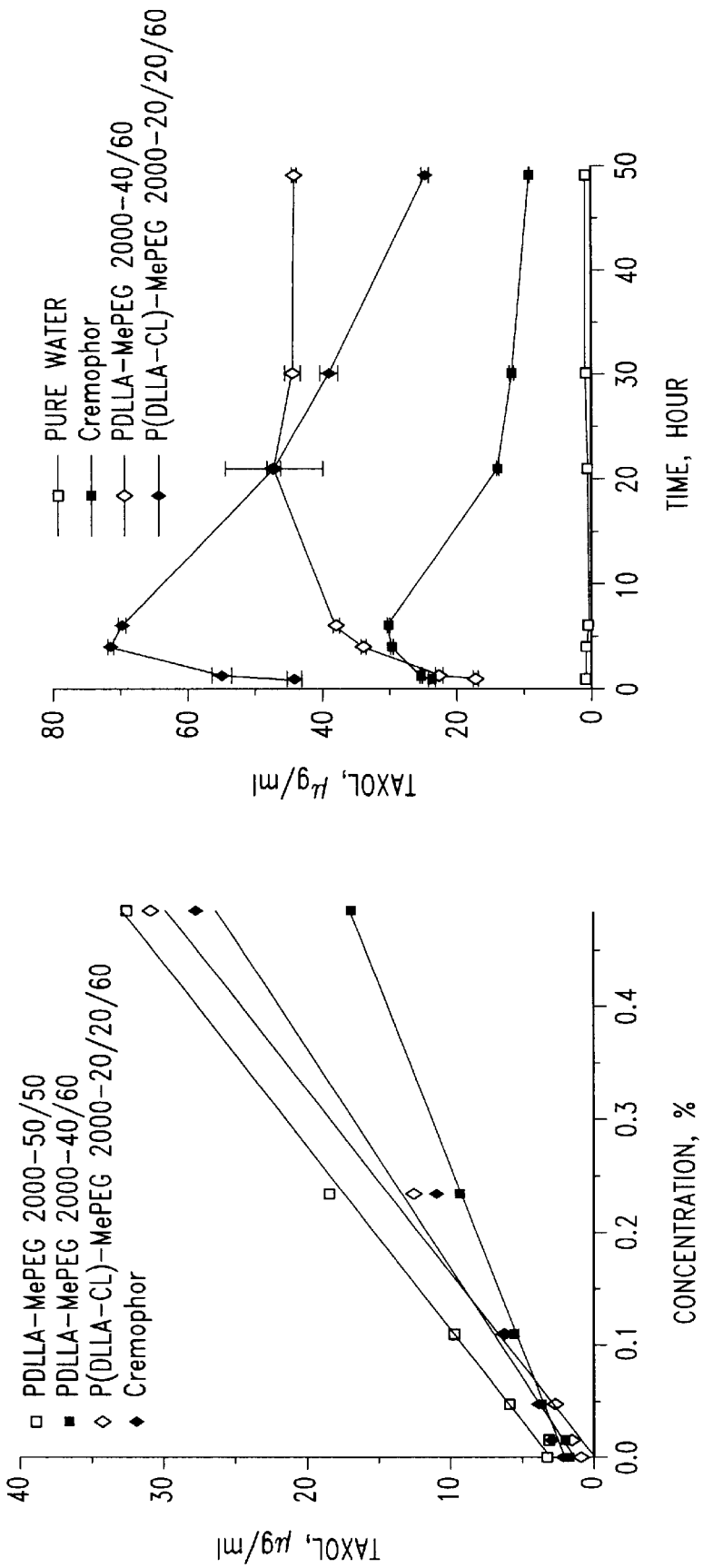
FIGS. 44A and 44B are graphs which depict the solubilization of paclitaxel crystals in water (37° C.) by the copolymers and Cremophor EL. 44A; effect of the concentration of copolymer on Cremophor (20 hours incubation); 44B: effect of time (copolymer or Cremophor concentration 0.5%).
Figure 45B:
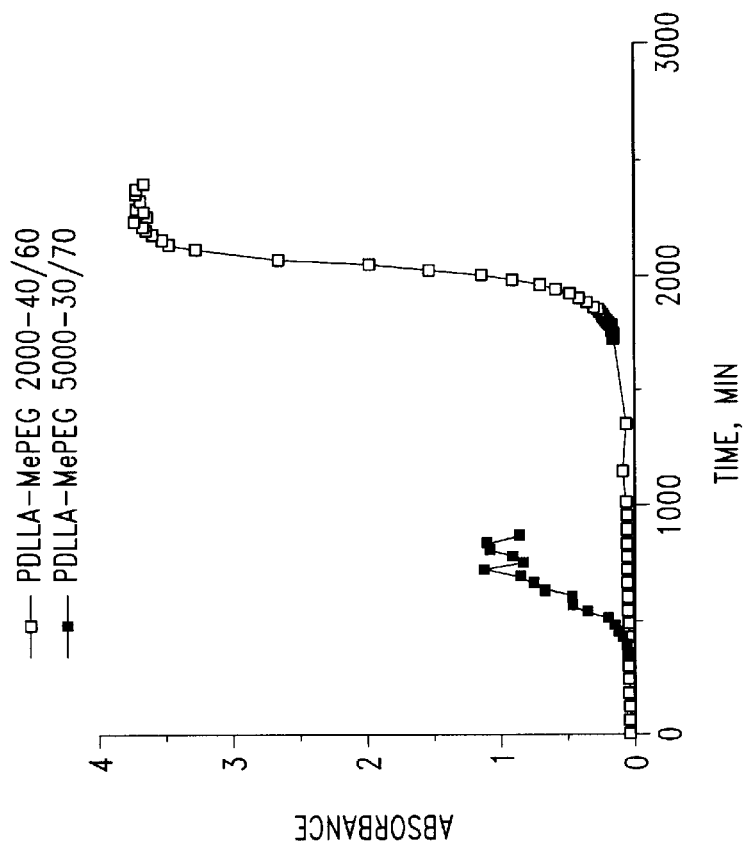
FIGS. 45A and 45B are graphs which depict the turbidity (uv-vis absorbance at 450 µm) of micellar paclitaxel solutions at room temperature (22° C.). Paclitaxel concentration was 2 mg/ml in water. Paclitaxel loading was 10% except MePEG 5000-30/70 where the loading was 5%.
Figure 45A:
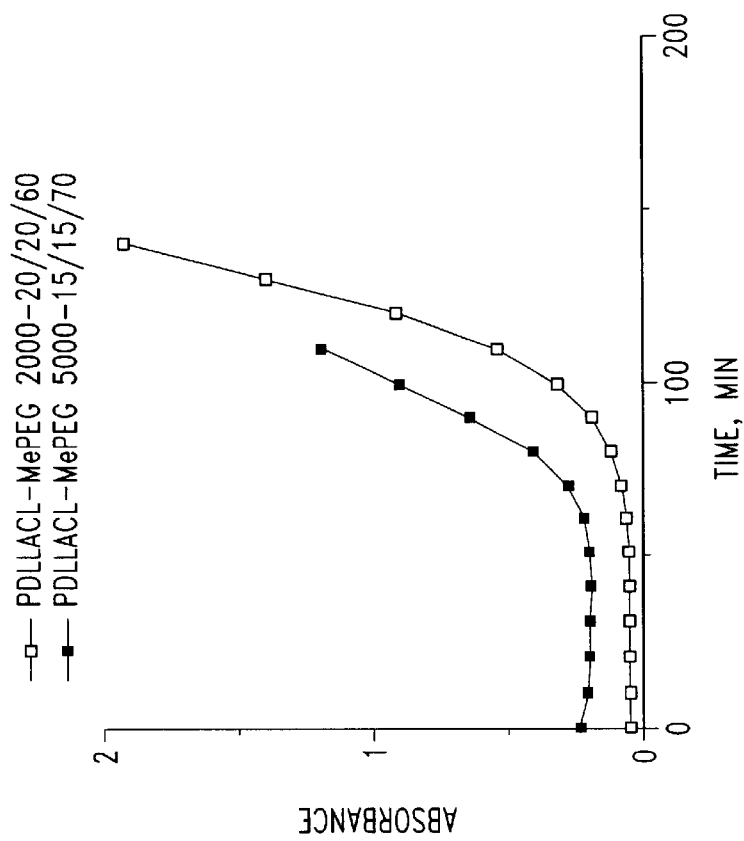

Diblock copolymers of poly(DL-lactide)-block-methoxy polyethylene glycol (PDLLA-MePEG), polycaprolactone-block-methoxy polyethylene glycol (PCL-MePEG) and poly (DL-lactide-co-caprolactone)-block-methoxy polyethylene glycol (PDLLACL-MePEG) were synthesized using a bulk melt polymerization procedure. Briefly, given amounts of monomers DL-lactide, caprolactone, and methoxy polyethylene glycols with different molecular weights were heated (130° C.) to melt under the bubbling of nitrogen and stirring. Catalyst stannous octoate (0.2% w/w) was added to the molten monomers. The polymerization was carried out for 4 hours. The molecular weights, critical micelle concentrations, and the maximum paclitaxel loadings were measured with GPC, fluorescence, and solubilization testing, respectively (FIG. 43). High paclitaxel carrying capacities were obtained. The ability of solubilizing paclitaxel depends on the compositions and concentrations of the copolymers (FIGS. 43 and 44). PDLLA-MePEG gave the most stable solubilized paclitaxel (FIGS. 44 and 45).

Example 16

Encapsulation of Paclitaxel in Nylon Microcapsules

A. Preparation of Paclitaxel-loaded Microcapsules

Paclitaxel was encapsulated into nylon microcapsules using the interfacial polymerization techniques. Briefly, 100 mg of Paclitaxel and 100 mg of Pluronic F-127 was dissolved in 1 ml of dichloromethane (DCM) and 0.4 ml (about 500 mg) of adipoyl chloride (ADC) was added. This solution was homogenized into 2% PVA solution using the Polytron homogenizer (1 setting) for 15 seconds. A solution of 1,6-hexane-diamine (HMD) in 5 ml of distilled water was added dropwise while homogenizing. The mixture was homogenized for a further 10 seconds after the addition of HMD solution. The mixture was transferred to a beaker and stirred with a magnetic stirrer for 3 hours. The mixture was centrifuged, collected and resuspended in 1 ml distilled water.

B. Encapsulation Efficiency/Paclitaxel-loading

About 0.5 ml of the suspension was filtered and the microspheres were dried. About 2.5 mg of the microcapsules was weighed and suspended in 10 ml of acetonitrile for 24 hours. The supernatant analyzed for paclitaxel and the result was expressed as a percentage of paclitaxel. Preliminary studies have shown that paclitaxel could be encapsulated in nylon microcapsules at a high loading (up to 60%) and high encapsulation efficiency (greater than 80%).

C. Paclitaxel Release Studies

Figure 46:
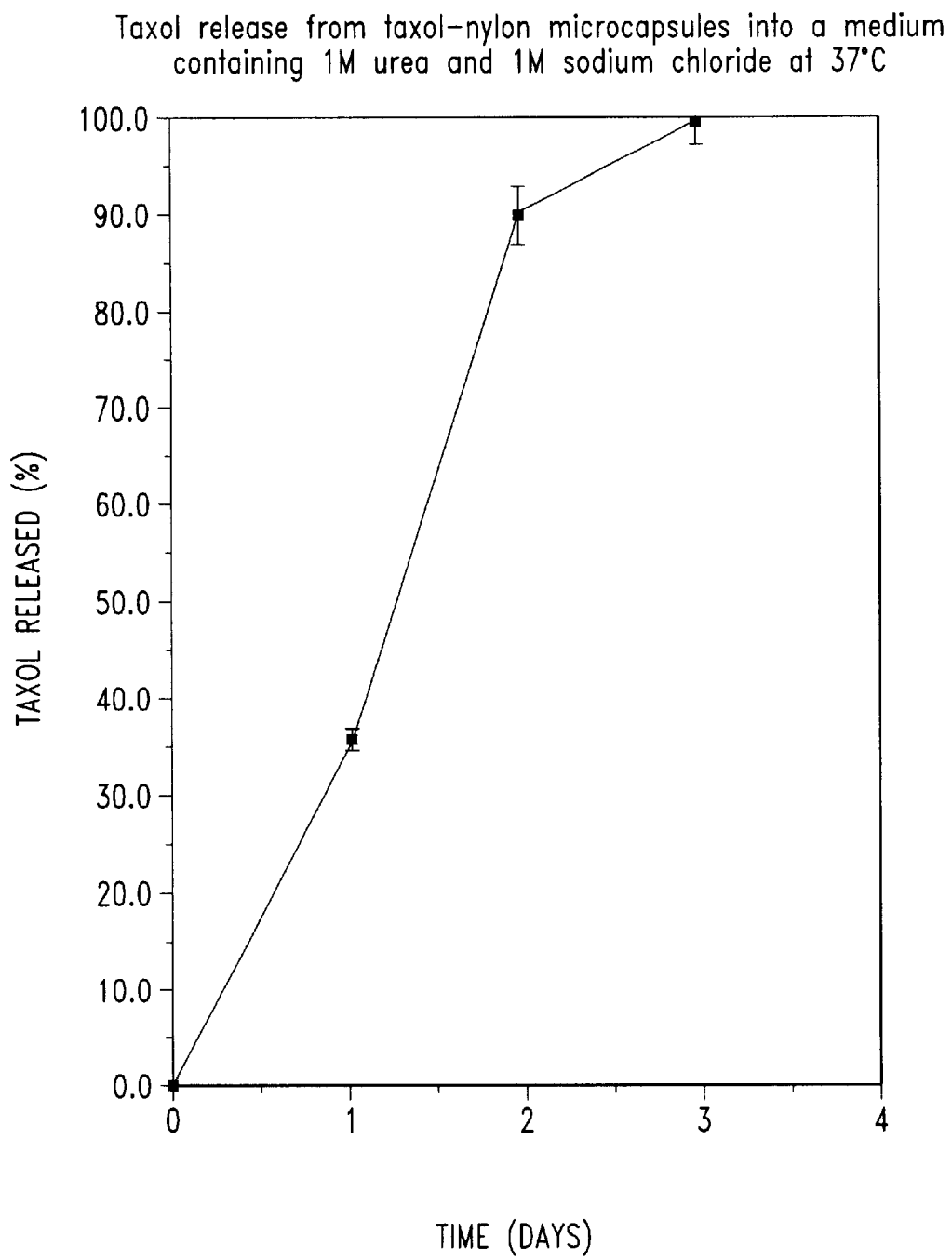
FIG. 46 is a graph which depicts paclitaxel release from paclitaxel-nylon microcapsules.

About 2.5 mg of the paclitaxel-nylon microspheres were suspended in 50 ml water containing 1M each of sodium chloride and urea and analyzed periodically. Release of paclitaxel from the microcapsule was fast with more than 95% of the drug released after 72 hours. (FIG. 46).

Example 17

Complexation of Paclitaxel with Cyclodextrins

A. Materials

Paclitaxel was obtained from Hauser Chemicals Inc., Boulder, Colo. Disodium phosphate (Fisher), citric acid (British Drug Houses), Hydroxypropyl-β-cyclodextrin (HPβCD), γ-cyclodextrin (γ-CD) and hydroxypropyl-γ-cyclodextrin (HPγCD) were obtained from American Maize-Products Company (Hammond, Ind.) and were used as received.

B. Methods

1. Solubility Studies

Excess amounts of paclitaxel (5 mg) were added to aqueous solutions containing various concentrations of γ-CD, HPγ-CD, or HPβ-CD and tumbled gently for about 24 hours at 37° C. After equilibration, aliquots of the suspension were filtered through a 0.45 μm membrane filter (Millipore), suitably diluted and analyzed using HPLC. The mobile phase was composed of a mixture of acetonitrile, methanol and water (58:5:37) at a flow rate of 1.0 ml min$^{-1}$. The solubility of paclitaxel in a solvent composed of 50:50 water and ethanol (95%) containing various concentrations, up to 10%, of HPβ-CD was also investigated. In addition, dissolution rate profiles of paclitaxel were investigated by adding 2 mg of paclitaxel (as received) to 0, 5, 10 or 20% HPγ-CD solutions or 2 mg of previously hydrated paclitaxel (by suspending in water for 7 days) to pure water and tumbling gently at 37° C. Aliquots were taken at various time intervals and assayed for paclitaxel.

2. Stability Studies

The solutions containing 20% HPβCD or HPγCD had pH values of 3.9 and 5.2, respectively. The stability of paclitaxel in cyclodextrin solutions was investigated by assaying paclitaxel in solutions (20 μg ml$^{-1}$) containing 10 or 20% HPγ-CD or HPβ-CD in either water or a 50:50 water-ethanol mixture at 37° C. or 55° C. at various time intervals. In addition, stability of paclitaxel in solutions (1 μg/ml) containing 1%, 2% or 5% HPβCD at 55° C. were determined.

C. Results

1. Solubility Studies

Figure 47:
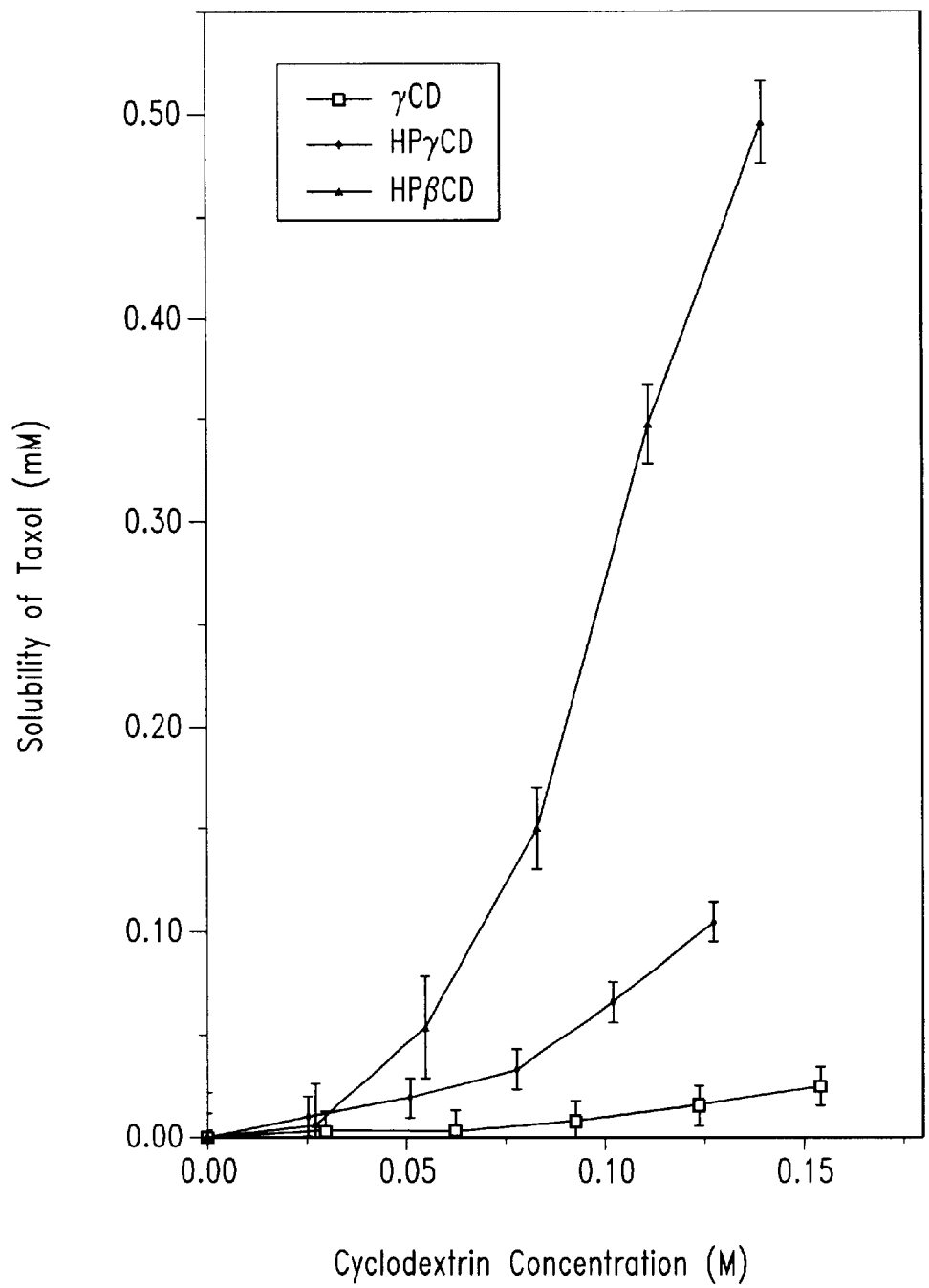
FIG. 47 is a graph which plots the observed pseudo first order kinetic degradation of paclitaxel (20 µg ml$^{-1}$ in 10% HPβCD and 10% HPγCD solutions at 37° C. and pH of 3.7 and 4.9, respectively.
Figure 48:
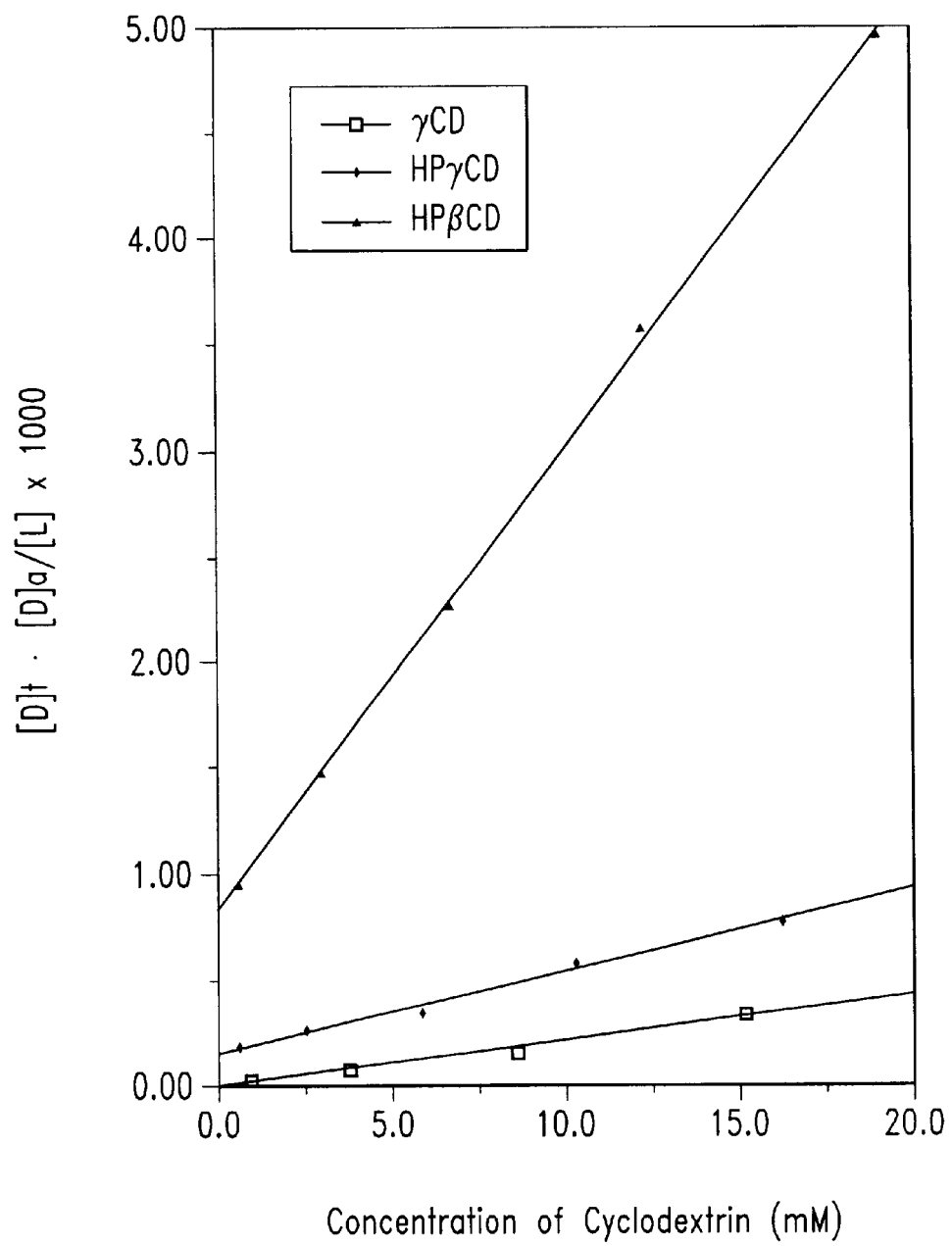
FIG. 48 is a graph which shows the phase solubility for cyclodextrins and paclitaxel in water at 37° C.

The solubility of paclitaxel increased over the entire CD concentration range studied; HPβCD producing the greatest increase in the solubility of paclitaxel (FIG. 47). The shape of the solubility curves suggests that the stoichiometries were of higher order than a 1:1 complex. Paclitaxel formed Type A$_P$ curves with both HPβCD and HPγCD and Type A$_N$ curves with γCD. The solubility of paclitaxel in a 50% solution of HPβCD in water was 3.2 mg ml$^{-1}$ at 37° C. which was about a 2000-fold increase over the solubility of paclitaxel in water. The estimated stability constants (from FIG. 48) for first order complexes of paclitaxel-cyclodextrins were 3.1, 5.8 and 7.2 M$^{-1}$ for γ-CD, HPγCD and HPβCD and those for second order complexes were 0.785×10$^3$, 1.886×10$^3$ and 7.965×10$^3$ M$^{-1}$ for γ-CD, HPγCD and HPβCD respectively. The values of the observed stability constants suggested that the inclusion complexes formed by paclitaxel with cyclodextrins were predominantly second order complexes.

Figure 49:
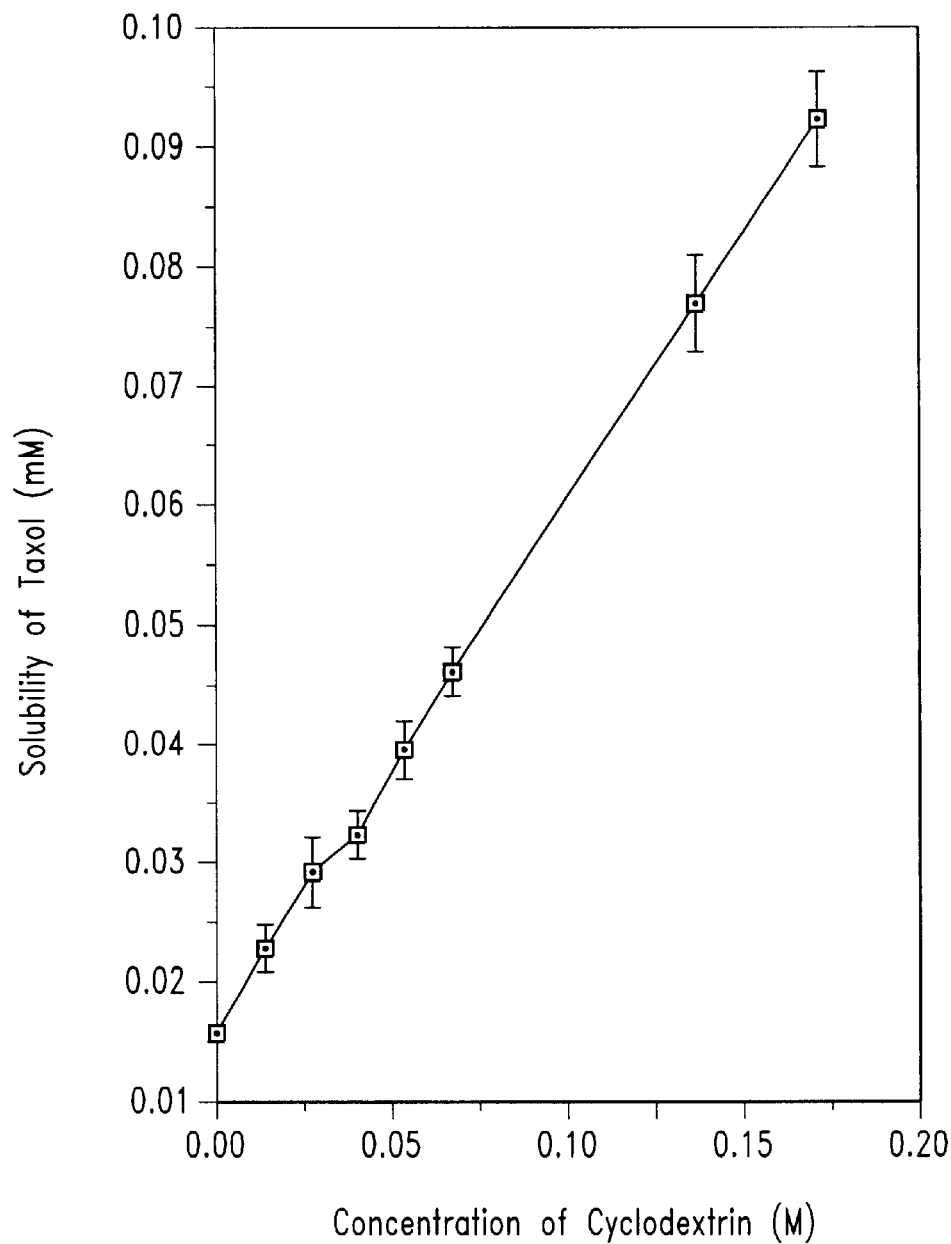
FIG. 49 is a graph which shows second order plots of the complexation of paclitaxel and γCD, HPβCD or HPγCD at 37° C.

The solubility of paclitaxel in 50:50 water:ethanol mixture increased with an increase in the cyclodextrin concentration (FIG. 49) as observed for complexation in pure water. The apparent stability constant for the complexation of paclitaxel and HPβCD in the presence of 50% ethanol (26.57 M$^{-1}$) was significantly lower (about 300 times) than the stability constant in the absence of ethanol. The lower stability constant may be attributed to a change in the dielectric constant or the polarity of the solvent in the presence of ethanol.

Figure 50:
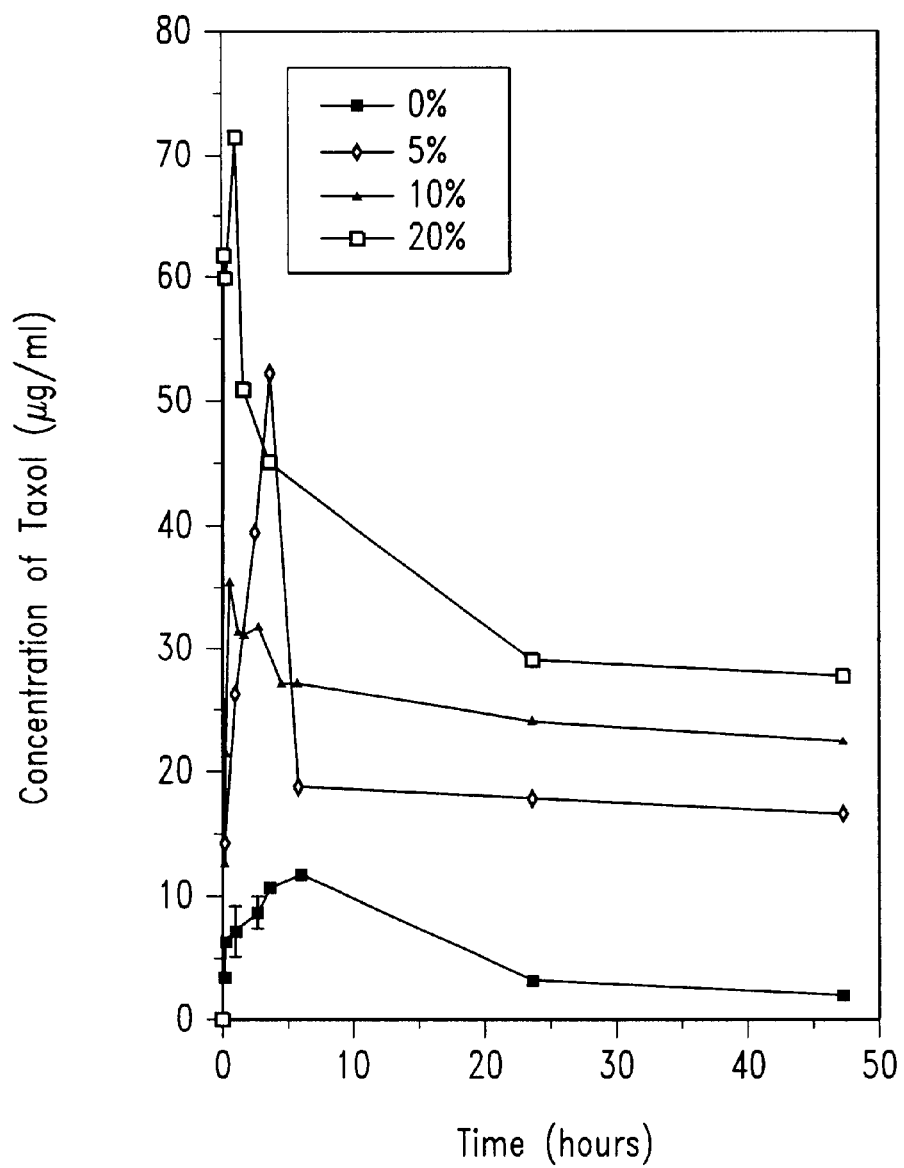
FIG. 50 is a graph which shows the phase solubility for paclitaxel at 37° C. and hydroxypropyl-β-cyclodextrin in 50:50 water:ethanol solutions.

The dissolution profiles of paclitaxel in 0, 5, 10 and 20% γCD solutions (FIG. 50) illustrates the formation of a metastable solution of paclitaxel in pure water or the cyclodextrin solutions; the amount of paclitaxel in solution gradually increased, reached a maximum and subsequently decreased. Dissolution studies using paclitaxel samples which were previously hydrated by suspending in water for 48 hours did not show the formation of the metastable solution. In addition, DSC analysis of the hydrated paclitaxel (dried in a vacuum oven at room temperature) showed two broad endothermic peaks between 60 and 110C. These peaks were accompanied by about 4.5% weight loss (determined by thermogravimetric analysis) indicating the presence of hydrate(s). A loss in weight of about 2.1% would suggest the formation of a paclitaxel monohydrate. Therefore, the occurrence of the DSC peaks between 60° C. and 110° C. and the loss in weight of about 4.5% suggests the presence of a dihydrate. There was no evidence of endothermic peak(s) between 60° C. and 110° C. (DSC results) or a weight loss (TGA results) for paclitaxel samples as received. Therefore, (as received) paclitaxel was anhydrous and on suspension in water it dissolved to form a supersaturated solution which recrystallized as a hydrate of lower solubility (FIG. 50).

2. Stability Studies

Figure 51:
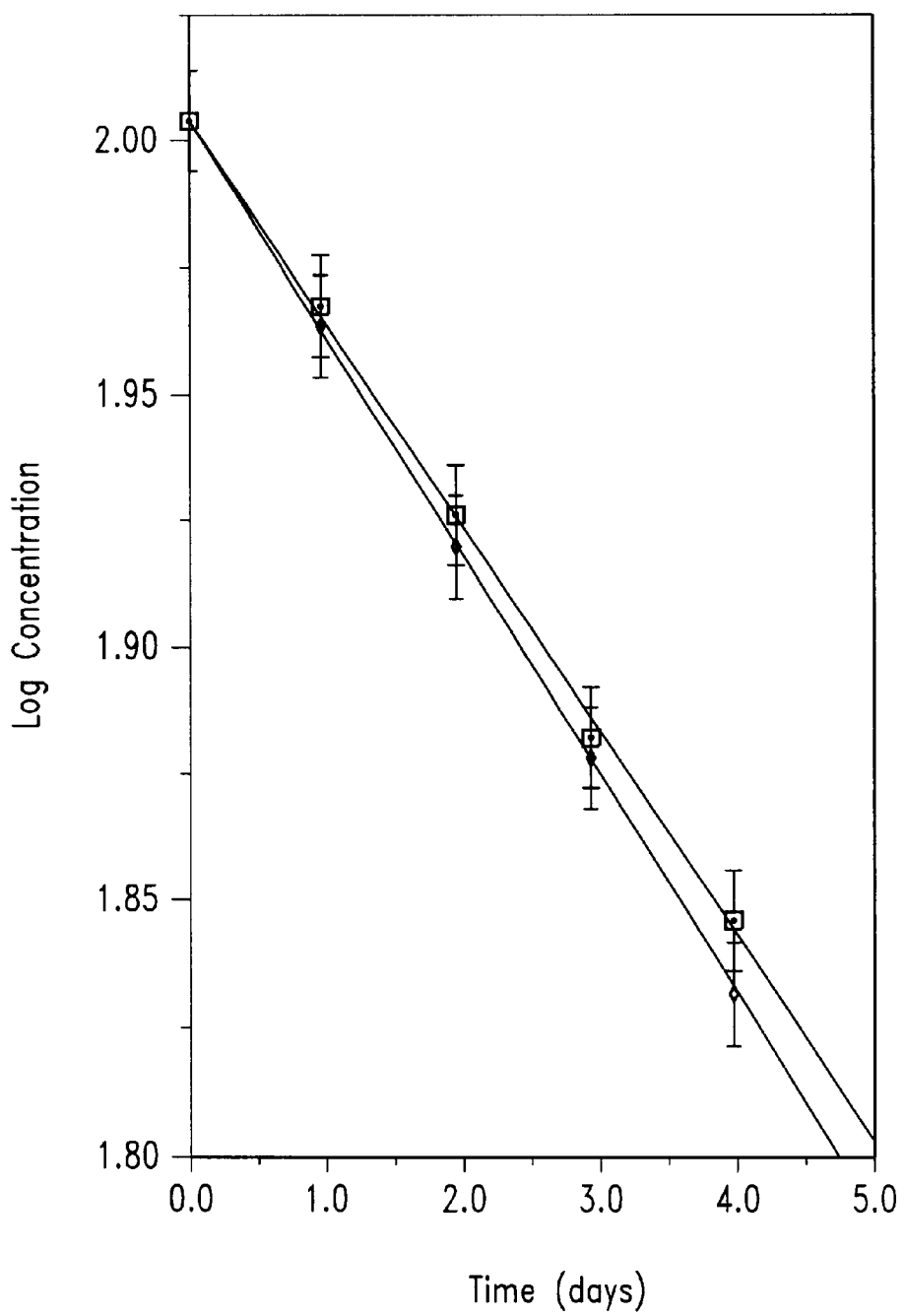
FIG. 51 is a graph which shows dissolution rate profiles of paclitaxel in 0, 5, 10 or 20% HPγCD solutions at 37° C.

Paclitaxel degradation depended on the concentration of the cyclodextrin and followed pseudo-first order degradation kinetics (e.g., FIG. 51). The rate of degradation of paclitaxel in solutions (1 μg/ml paclitaxel) containing 1% HPβCD at 55° C. faster (k=3.38×10$^{-3}$ h$^{-1}$) than the rate at higher cyclodextrin concentrations. Degradation rate constants of 1.78×10$^{-3}$ h$^{-1}$ and 0.96×10$^{-3}$ h$^{-1}$ were observed for paclitaxel in 10% HPβCD and HPγCD, respectively. Paclitaxel solutions (1 μg/ml) containing 2, 4, 6 or 8% HPβCD did not show any significant difference in the rate of degradation from that obtained with the 10 or 20% HPβCD solutions (20 μg/ml). The presence of ethanol did not adversely affect the stability of paclitaxel in the cyclodextrin solutions.

D. Conclusion

This study showed that the solubility of paclitaxel could be increased by complexation with cyclodextrins. These aqueous based cyclodextrin formulations may have potential for peritubular in the treatment of various cancers.

Example 18

Polymeric Compositions with Increased Concentrations of Paclitaxel

PDLLA-MePEG and PDLLA-PEG-PDLLA are block copolymers with hydrophobic (PDLLA) and hydrophilic (PEG or MePEG) regions. At appropriate molecular weights and chemical composition, they may form tiny aggregates of hydrophobic PDLLA core and hydrophilic MePEG shell. Paclitaxel can be loaded into the hydrophobic core, thereby providing paclitaxel with an increased "solubility".

A. Materials

D,L-lactide was purchased from Aldrich, Stannous octoate, poly (ethylene glycol) (mol. wt. 8,000), MePEG (mol. wt. 2,000 and 5,000) were from Sigma. MePEG (mol. wt. 750) was from Union Carbide. The copolymers were synthesized by a ring opening polymerization procedure using stannous octoate as a catalyst (Deng et al, *J. Polym. Sci., Polym, Lett.* 28:411–416, 1990; Cohn et al, *J. Biomed, Mater. Res.* 22: 993–1009, 1988).

For synthesizing PDLLA-MePEG, a mixture of DL-lactide/MePEG/stannous octoate was added to a 10 milliliter glass ampoule. The ampoule was connected to a vacuum and sealed with flame. Polymerization was accomplished by incubating the ampoule in a 150° C. oil bath for 3 hours. For synthesizing PDLLA-PEG-PDLLA, a mixture of D,L-lactide/PEG/stannous octoate was transferred into a glass flask, sealed with a rubber stopper, and heated for 3 hours in a 150° C. oven. The starting compositions of the copolymers are given in Tables II and III. In all the cases, the amount of stannous octoate was 0.5%–0.7%.

B. Methods

The polymers were dissolved in acetonitrile and centrifuged at 10,000 g for 5 minutes to discard any non-dissolvable impurities. Paclitaxel acetonitrile solution was then added to each polymer solution to give a solution with paclitaxel (paclitaxel+polymer)of 10%-wt. The solvent acetonitrile was then removed to obtain a clear paclitaxel/PDLLA-MePEG matrix, under a stream of nitrogen and 60° C. warming. Distilled water, 0.9% NaCl saline, or 5% dextrose was added at four times weight of the matrix. The matrix was finally "dissolved" with the help of vortex mixing and periodic warming at 60° C. Clear solutions were obtained in all the cases. The particle sizes were all below 50 nm as determined by a submicron particle sizer, NICOMP Model 270. The formulations are given in Table II.

TABLE II

Formulations of Paclitaxel/PDLLA-MePEG*

| PDLLA-MePEG | Dissolving Media | Paclitaxel Loading (final paclitaxel concentrate) |
| --- | --- | --- |
| 2000/50/50 | water | 10% (20 mg/ml) |
| 2000/40/60 | water | 10% (20 mg/ml) |
| 2000/50/50 | 0.9% saline | 5% (10 mg/ml) |
| 2000/50/50 | 0.9% saline | 10% (20 mg/ml) |
| 2000/50/50 | 5% dextrose | 10% (10 mg/ml) |
| 2000/50/50 | 5% dextrose | 10% (20 mg/ml) |

In the case of PDLLA-PEG-PDLLA (Table III), since the copolymers cannot dissolve in water, paclitaxel and the polymer were co-dissolved in acetone. Water or a mixture of water/acetone was gradually added to this paclitaxel polymer solution to induce the formation of paclitaxel/polymer spheres.

TABLE III

Composition of PDLLA-PEG-PDLLA

| Copolymer Name | Wt. of PEG (g) | Wt. of DL-lactide (g) |
| --- | --- | --- |
| PDLLA-PEG-PDLLA 90/10 | 1 | 9 |
| PDLLA-PEG-PDLLA 80/20 | 2 | 8 |
| PDLLA-PEG-PDLLA 70/30 | 3 | 7 |
| PDLLA-PEG-PDLLA 60/40 | 4 | 6 |
| PDLLA-PEG-PDLLA 30-/70 | 14 | 6 |

* PEG molecular weight. 8,000.

C. Results

Many of the PDLLA-MePEG compositions form clear solutions in water, 0.9% saline, or 5% dextrose, indicating the formation of tiny aggregates in the range of nanometers. Paclitaxel was loaded into PDLLA-MePEG nanoparticles successfully. For example, at % loading (this represents 10 mg paclitaxel in 1 ml paclitaxel/PDLLA-MePEG/aqueous system), a clear solution was obtained from 2000-50/50 and 2000-40/60. The particle size was about 20 nm.

Example 19

Analysis of Drug Release

A known weight of a polymer (typically a 2.5 mg pellet) is added to a 15 ml test tube containing 14 ml of a buffer containing 10 mm $Na_2HPO_4$—$NaH_2PO_4$, 0.145 m NaCl and 0.4 g/l bovine serum albumin. The tubes are capped and tumbled at 37° C. At specific times all the 14 ml of the liquid buffer are removed and replaced with fresh liquid buffer.

The liquid buffer is added to 1 milliliter of methylene chloride and shaken for 1 minute to extract all the paclitaxel into the methylene chloride. The aqueous phase is then removed and the methylene chloride phase is dried under nitrogen. The residue is then dissolved in 60% acetonitrile: 40% water and the solution is injected on to a HPLC system using the following conditions: C8 column (Beckman Instruments USA), mobile phase of 58%:5%:37% acetonitrile:methanol:water at a flow rate of 1 minute per minute.

For paclitaxel the collected buffer is then analyzed at 232 nm. For MTX the collected buffer is applied directly to the HPLC column with no need for extraction in methylene chloride. MTX is analyzed at 302 nm. For Vanadium containing compounds the liquid buffer is analyzed directly using a UV/VIS spectrometer in the 200 to 300 nm range.

Example 20

Effect of Paclitaxel-loaded Thermopaste on Tumor Growth and Tumor Angiogenesis In Vivo Fertilized domestic chick embryos are incubated for 3 days prior to having their shells removed. The egg contents are emptied by removing the shell located around the airspace, severing the interior shell membrane, perforating the opposite end of the shell and allowing the egg contents to gently slide out from the blunted end. The contents are emptied into round-bottom sterilized glass bowls, covered with petri dish covers and incubated at 90% relative humidity and 3% carbon dioxide.

MDAY-D2 cells (a murine lymphoid tumor) is injected into mice and allowed to grow into tumors weighing 0.5–1.0 g. The mice are sacrificed, the tumor sites wiped with alcohol, excised, placed in sterile tissue culture media, and diced into 1 mm pieces under a laminar flow hood. Prior to placing the dissected tumors onto the 9-day old chick embryos, CAM surfaces are gently scraped with a 30 gauge needle to insure tumor implantation. The tumors are then placed on the CAMs after 8 days of incubation (4 days after deshelling), and allowed to grow on the CAM for four days to establish a vascular supply. Four embryos are prepared utilizing this method, each embryo receiving 3 tumors. For these embryos, one tumor receives 20% paclitaxel-loaded thermopaste, the second tumor unloaded thermopaste, and the third tumor no treatment. The treatments are continued for two days before the results were recorded.

The explanted MDAY-D2 tumors secrete angiogenic factors which induce the ingrowth of capillaries (derived from the CAM) into the tumor mass and allow it to continue to grow in size. Since all the vessels of the tumor are derived from the CAM, while all the tumor cells are derived from the explant, it is possible to assess the effect of therapeutic interventions on these two processes independently. This assay has been used to determine the effectiveness of paclitaxel-loaded thermopaste on: (a) inhibiting the vascularization of the tumor and (b) inhibiting the growth of the tumor cells themselves.

Figure 51A:
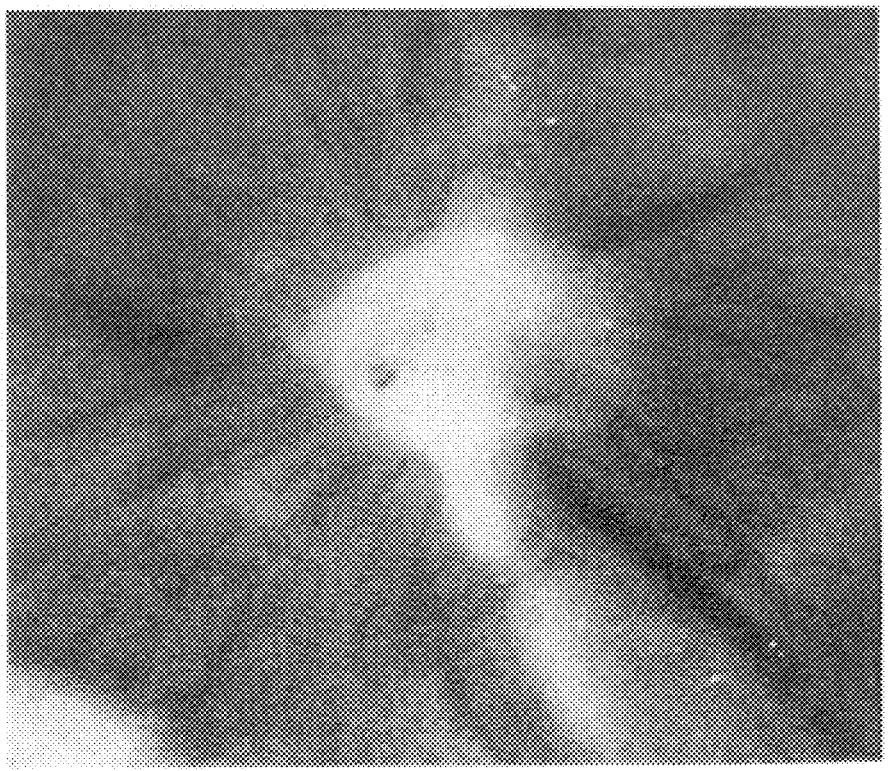
FIGS. 51A and 51B are two photographs of a CAM having a tumor treated with control (unloaded) thermopaste. Briefly, in FIG. 51A the central white mass is the tumor tissue. Note the abundance of blood vessels entering the tumor from the CAM in all directions. The tumor induces the ingrowth of the host vasculature through the production of "angiogenic factors." The tumor tissue expands distally along the blood vessels which supply it.
Figure 51B:
Figure 51C:
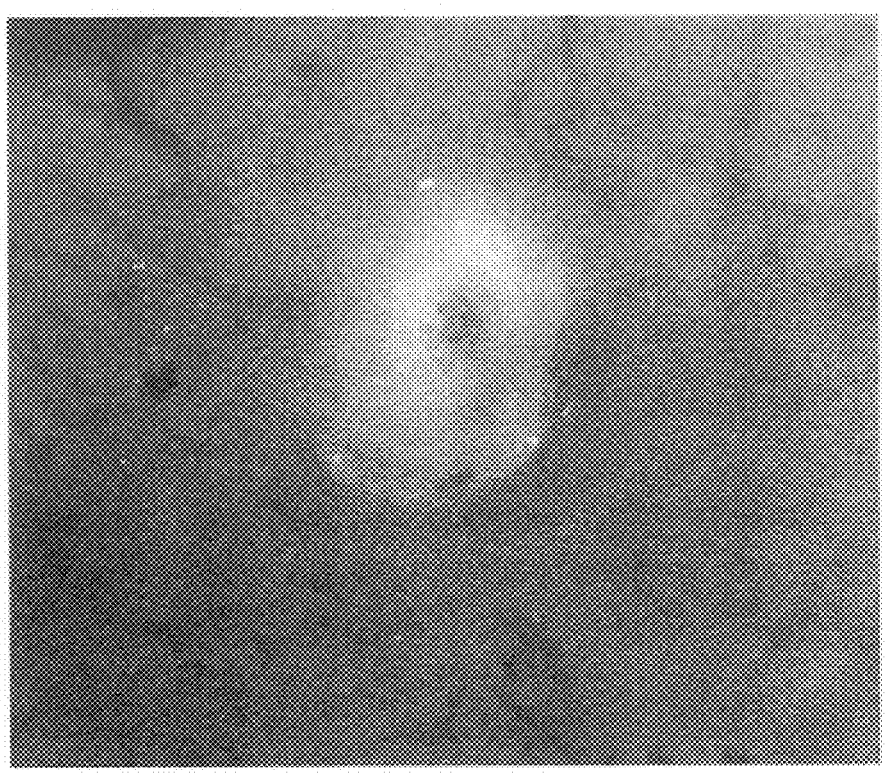
FIGS. 51C and 51D are two photographs of a CAM having a tumor treated with 20% paclitaxel-loaded thermopaste. Briefly, in FIG. 51C the central white mass is the tumor tissue. Note the paucity of blood vessels in the vicinity of the tumor tissue. The sustained release of the angiogenesis inhibitor is capable of overcoming the angiogenic stimulus produced by the tumor. The tumor itself is poorly vascularized and is progressively decreasing in size.
Figure 51D:
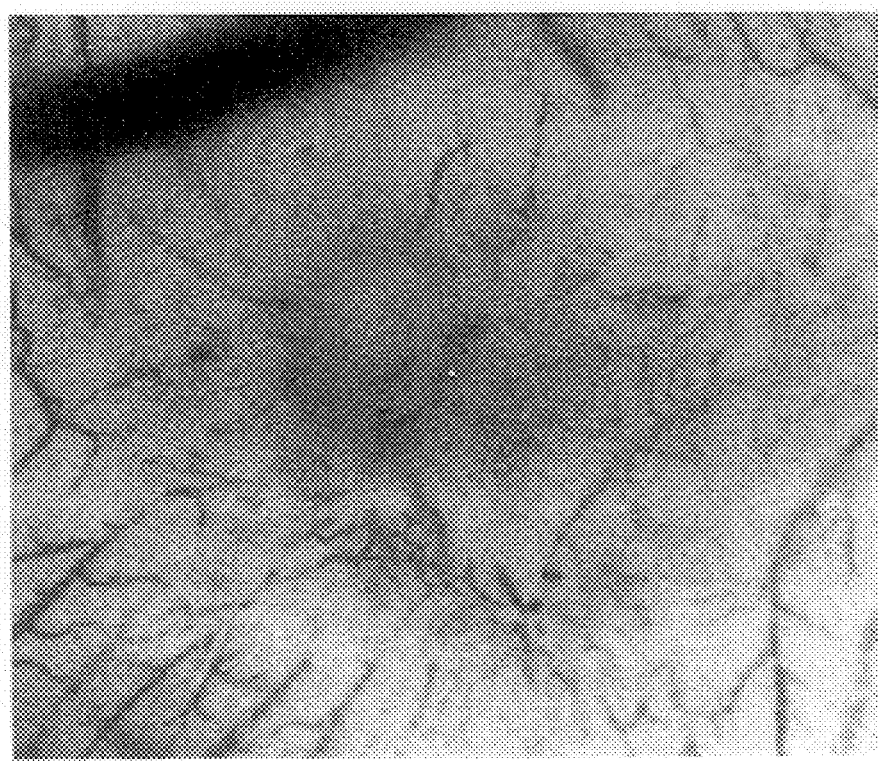

Direct in vivo stereomicroscopic evaluation and histological examination of fixed tissues from this study demonstrated the following. In the tumors treated with 20% paclitaxel-loaded thermopaste, there was a reduction in the number of the blood vessels which supplied the tumor (see FIGS. 51C and 51D), a reduction in the number of blood vessels within the tumor, and a reduction in the number of blood vessels in the periphery of the tumor (the area which is typically the most highly vascularized in a solid tumor) when compared to control tumors (FIGS. 51A and 51B). The tumors began to decrease in size and mass during the two days the study was conducted. Additionally, numerous endothelial cells were seen to be arrested in cell division indicating that endothelial cell proliferation had been affected. Tumor cells were also frequently seen arrested in mitosis. All 4 embryos showed a consistent pattern with the 20% paclitaxel-loaded thermopaste suppressing tumor vascularity while the unloaded thermopaste had no effect.

By comparison, in CAMs treated with unloaded thermopaste, the tumors were well vascularized with an increase in the number and density of vessels when compared to that of the normal surrounding tissue, and dramatically more vessels than were observed in the tumors treated with paclitaxel-loaded paste. The newly formed vessels entered the tumor from all angles appearing like spokes attached to the center of a wheel (see FIGS. 51A and 51B). The control tumors continued to increase in size and mass during the course of the study. Histologically, numerous dilated thin-walled capillaries were seen in the periphery of the tumor and few endothelial were seen to be in cell division. The tumor tissue was well vascularized and viable throughout.

As an example, in two similarly-sized (initially, at the time of explantation) tumors placed on the same CAM the following data was obtained. For the tumor treated with 20% paclitaxel-loaded thermopaste the tumor measured 330 mm×597 mm; the immediate periphery of the tumor has 14 blood vessels, while the tumor mass has only 3–4 small capillaries. For the tumor treated with unloaded thermopaste the tumor size was 623 mm×678 mm; the immediate periphery of the tumor has 54 blood vessels, while the tumor mass has 12–14 small blood vessels. In addition, the surrounding CAM itself contained many more blood vessels as compared to the area surrounding the paclitaxel-treated tumor.

This study demonstrates that thermopaste releases sufficient quantities of anti-proliferative agent (in this case paclitaxel) to inhibit the pathological angiogenesis which accompanies tumor growth and development. Under these conditions angiogenesis is maximally stimulated by the tumor cells which produce angiogenic factors capable of inducing the ingrowth of capillaries from the surrounding tissue into the tumor mass. The 20% paclitaxel-loaded thermopaste is capable of blocking this process and limiting the ability of the tumor tissue to maintain an adequate blood supply. This results in a decrease in the tumor mass both through a cytotoxic effect of the drug on the tumor cells themselves and by depriving the tissue of the nutrients required for growth and expansion.

Example 21

Effect of Therapeutic Agent-loaded Thermopaste on Tumor Growth In Vivo in a Murine Tumor Model The murine MDAY-D2 tumor model may be used to examine the effect of local slow release of an anti-proliferative compound such as paclitaxel on tumor growth, tumor metastasis, and animal survival. Briefly, the MDAY-D2 tumor cell line is grown in a cell suspension consisting of 5% Fetal Calf Serum in alpha mem media. The cells are incubated at 37° C. in a humidified atmosphere supplemented with 5% carbon dioxide, and are diluted by a factor of 15 every 3 days until a sufficient number of cells are obtained. Following the incubation period the cells are examined by light microscopy for viability and then are centrifuged at 1500 rpm for 5 minutes. PBS is added to the cells to achieve a dilution of 1,000,000 cells per ml.

Ten week old DBA/2j female mice are acclimatized for 3–4 days after arrival. Each mouse is then injected subcutaneously in the posteriolateral flank with 100,000 MDAY-D2 cells in 100 ml of PBS. Previous studies have shown that this procedure produces a visible tumor at the injection site in 3–4 days, reach a size of 1.0–1.7 g by 14 days, and produces visible metastases in the liver 19–25 days post-injection. Depending upon the objective of the study a therapeutic intervention can be instituted at any point in the progression of the disease.

Using the above animal model, 20 mice are injected with 140,000 MDAY-D2 cells s.c. and the tumors allowed to grow. On day 5 the mice are divided into groups of 5. The tumor site was surgically opened under anesthesia, the local region treated with the drug-loaded thermopaste or control thermopaste without disturbing the existing tumor tissue, and the wound was closed. The groups of 5 received either no treatment (wound merely closed), polymer (PCL) alone, 10% paclitaxel-loaded thermopaste, or 20% paclitaxel-loaded thermopaste (only 4 animals injected) implanted adjacent to the tumor site. On day 16, the mice were sacrificed, the tumors were dissected and examined (grossly and histologically) for tumor growth, tumor metastasis, local and systemic toxicity resulting from the treatment, effect on wound healing, effect on tumor vascularity, and condition of the paste remaining at the incision site.

The weights of the tumors for each animal is shown in Table IV below:

TABLE IV

| | Tumor Weights (gm) | | | |
|---|---|---|---|---|
| Animal (empty) | No. Control (PCL) | Control Thermopaste | 10% Paclitaxel Thermopaste | 20% Paclitaxel |
| 1 | 1.387 | 1.137 | 0.487 | 0.114 |
| 2 | 0.589 | 0.763 | 0.589 | 0.192 |
| 3 | 0.461 | 0.525 | 0.447 | 0.071 |
| 4 | 0.606 | 0.282 | 0.274 | 0.042 |
| 5 | 0.353 | 0.277 | 0.362 | |
| Mean | 0.6808 | 0.6040 | 0.4318 | 0.1048 |
| Std. Deviation | 0.4078 | 0.3761 | 0.1202 | 0.0653 |
| P Value | 0.7647 | 0.358 | 0.036 | |

Figure 52A:
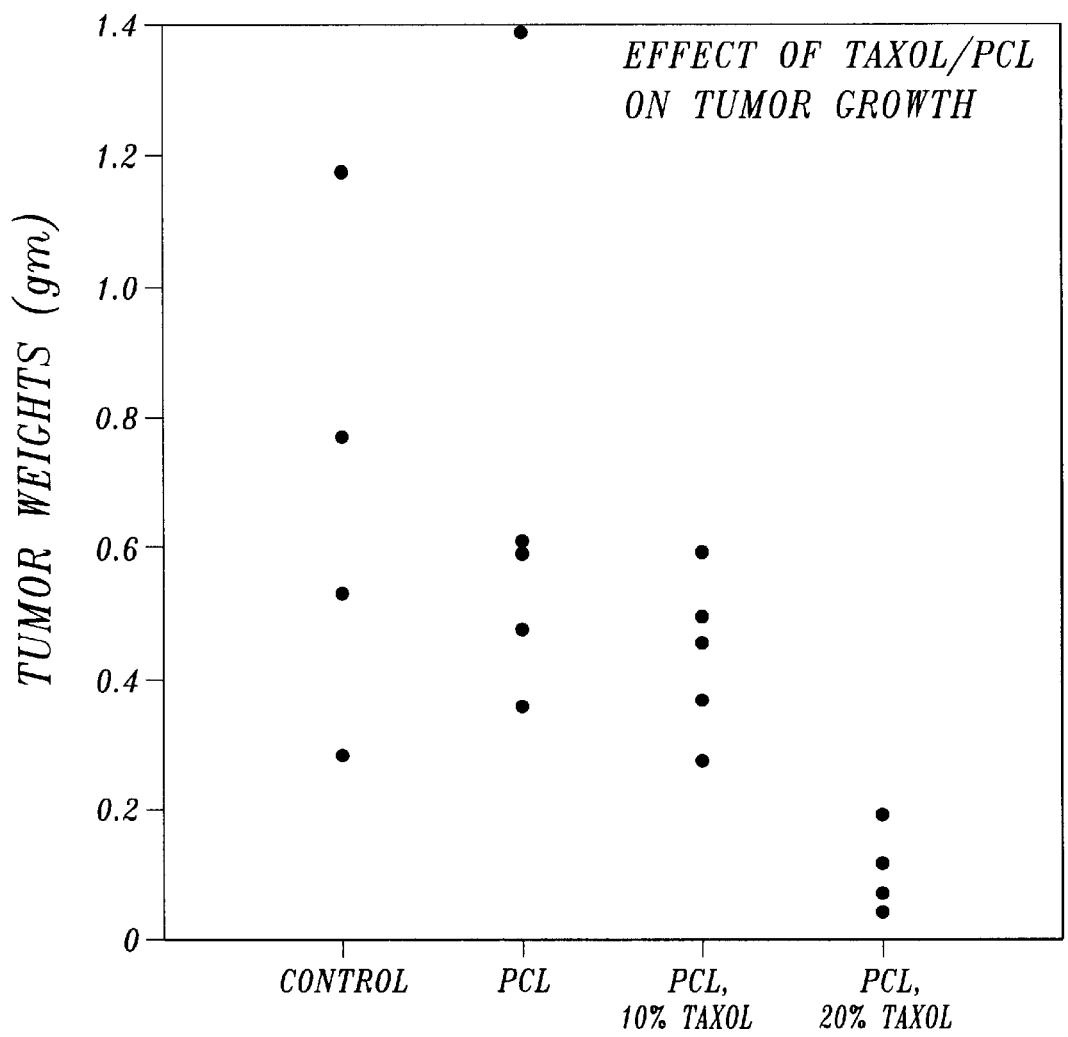
FIG. 52A is a graph which shows the effect of paclitaxel/ PCL on tumor growth.
Figure 52B:
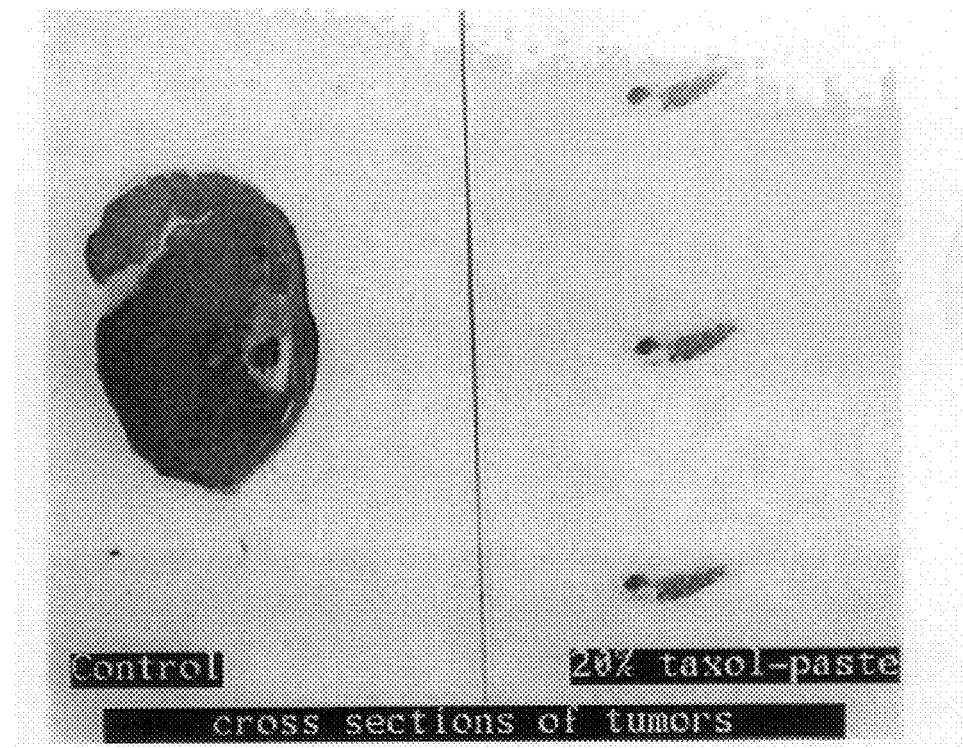
FIGS. 52B and 52C are two photographs which show the effect of control, 10%, and 20% paclitaxel-loaded thermopaste on tumor growth.
Figure 52C:
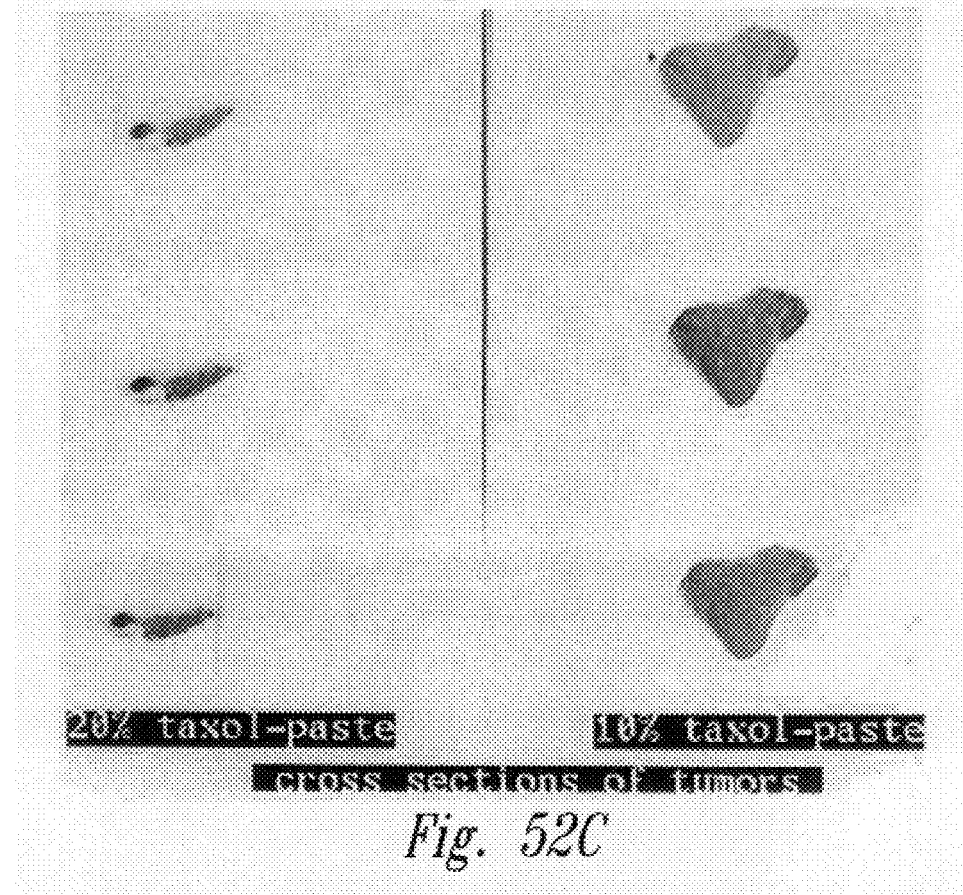
Figure 53:
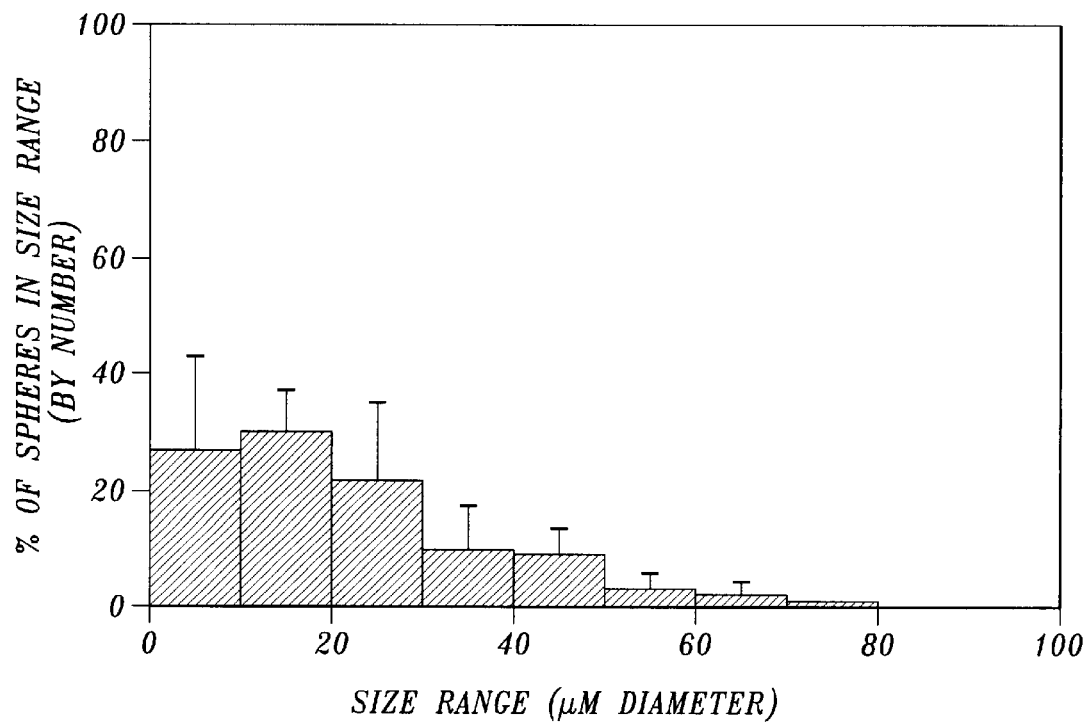
FIG. 53 is a bar graph which depicts the size distribution of microspheres by number (5% poly (ethylene-vinyl acetate) with 10 mg sodium suramin into 5% PVA).
Figure 54:
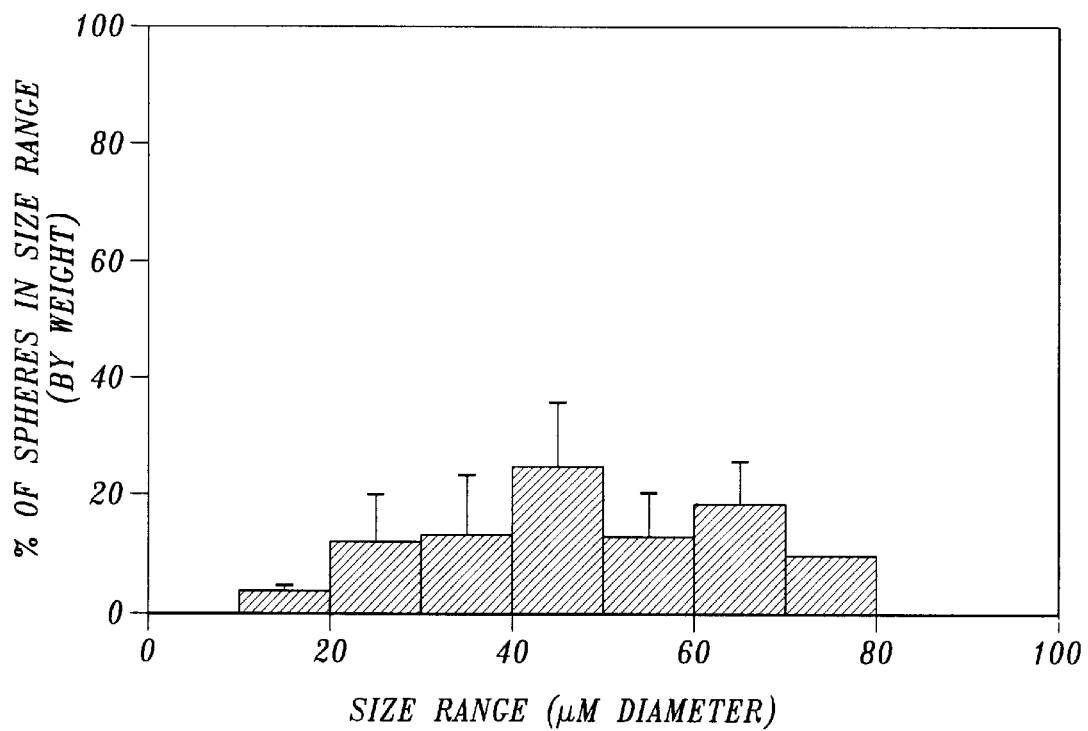
FIG. 54 is a bar graph which depicts the size distribution of microspheres by weight (5% poly (ethylene-vinyl acetate) with 10 mg sodium suramin into 5% PVA).

Thermopaste loaded with 20% paclitaxel reduced tumor growth by over 85% (average weight 0.105) as compared to control animals (average weight 0.681). Animals treated with thermopaste alone or thermopaste containing 10% paclitaxel had only modest effects on tumor growth; tumor weights were reduced by only 10% and 35% respectively (FIG. 52A). Therefore, thermopaste containing 20% paclitaxel was more effective in reducing tumor growth than thermopaste containing 10% paclitaxel (see FIG. 52C; see also FIG. 52B).

Thermopaste was detected in some of the animals at the site of administration. Polymer varying in weight between 0.026 g to 0.078 g was detected in 8 of 15 mice. Every animal in the group containing 20% paclitaxel-loaded thermopaste contained some residual polymer suggesting that it was less susceptible to dissolution. Histologically, the tumors treated with paclitaxel-loaded thermopaste contained lower cellularity and more tissue necrosis than control tumors. The vasculature was reduced and endothelial cells were frequently seen to be arrested in cell division. The paclitaxel-loaded thermopaste did not appear to affect the integrity or cellularity of the skin or tissues surrounding the tumor. Grossly, wound healing was unaffected.

Example 22

Use of Paclitaxel Loaded Surgical Paste to Delay Regrowth of Partially Resected RIF-1 Tumors in Mice The effectiveness of a biodegradable polymeric sustained release surgical paste formulation of paclitaxel in delaying regrowth of partially resected RIF-1 tumors in C3H/HeJ mice was investigated.

A. Methods

Paclitaxel (20%) was incorporated into a 4:1 blend of poly(ε-caprolactone) and methoxypolyethylene glycol. The in vitro release profile for this formulation in phosphate buffered saline containing albumin (0.4 mg/mL) at 37° C. was investigated using an HPLC assay for paclitaxel. Briefly, seventeen mice were injected in the right flank with 100 μl of a RIF-1 cell suspension ($1.0 \times 10^6$ cells) in Hanks Buffer. The tumors were allowed to grow for 5 days following which more than 70% of each tumor was surgically resected and the remaining tumor mass was left untreated or coated with 20–30 μL of either 20% paclitaxel in surgical paste or surgical paste alone (no drug). This was day 0. Dimensions of the visible tumor mass beneath the skin were measured on days 4 through 7 and day 9. The area of this visible cylindrical tumor surface was shown to be correlated to tumor volume (r=0.812).

B. Results

The in vitro release curve of paclitaxel was characterized by an initial 1 day burst phase followed by a long period of slow sustained release. The areas of the visible cylindrical tumor surfaces from each mouse from days 4 through 9 are shown in Table V. All the mice except 1 in each of the two groups which did not receive paclitaxel showed extensive tumor regrowth by day 4. One mouse which received polymer only showed delayed tumor regrowth while one mouse which received no treatment showed no regrowth. In contrast all but one of the mice treated with paclitaxel surgical paste showed no tumor regrowth until at least day 5 and two mice 10 still did not show regrowth until day 6.

C. Conclusion

Paclitaxel loaded paste significantly inhibited tumor regrowth between days 1 to 5. Regrowth occurred after day 6 due to the aggressiveness of the cell line.

TABLE V

RIF-1 cell tumor size (expressed as area of visible tumor mass beneath the skin in mm²) measured on days following tumor resection surgery

| Treatment | Tumor sizes (mm²) | | | | |
|---|---|---|---|---|---|
| | day 4 | day 5 | day 6 | day 7 | day 9 |
| 20% paclitaxel in polymer | 0.0 | 0.0 | 41.3 | 58.8 | * |
| 20% paclitaxel in polymer | 30.7 | 35.3 | 49.0 | 67.9 | * |
| 20% paclitaxel in polymer | 0.0 | 0.0 | 0.0 | * | 42.4 |
| 20% paclitaxel in polymer | 0.0 | 47.2 | 55.4 | 47.8 | * |
| 20% paclitaxel in polymer | 0.0 | 25.5 | 41.9 | 57.1 | * |
| 20% paclitaxel in polymer | 0.0 | 0.0 | 0.0 | * | 46.6 |
| polymer only | 44.2 | 52.8 | * | * | * |
| polymer only | 36.3 | 39.0 | 32.7 | * | 38.5 |
| polymer only | 36.9 | 44.2 | 51.5 | 42.7 | * |
| polymer only | 0.0 | 12.9 | 14.9 | * | 29.2 |
| polymer only | 37.4 | 39.6 | 40.7 | 54.1 | * |
| polymer only | 40.7 | 24.2 | 40.7 | * | 36.9 |
| no treatment | 0.0 | 0.0 | 0.0 | * | * |
| no treatment | 52.2 | 77.8 | * | * | * |
| no treatment | 39.0 | 45.4 | 43.6 | * | * |
| no treatment | 22.1 | 21.2 | 31.2 | * | 26.9 |
| no treatment | 21.2 | 30.7 | 36.3 | * | * |

*Tumor not measured or animal already sacrificed

Example 23

Encapsulation of Suramin

One milliliter of 5% ELVAX (poly(ethylene-vinyl acetate) cross-linked with 5% vinyl acetate) in dichloromethane ("DCM") is mixed with a fixed weight of submicron ground sodium suramin. This mixture is injected into 5 ml of 5% Polyvinyl Alcohol ("PVA") in water in a 30 ml flat bottomed test tube. Tubes containing different weights of the drug are then suspended in a multi-sample water bath at 40° C. for 90 minutes with automated stirring. The mixtures are removed, and microsphere samples taken for size analysis. Tubes are centrifuged at 1000 g for 5 min. The PVA supernatant is removed and saved for analysis (nonencapsulated drug). The microspheres are then washed (vortexed) in 5 ml of water and recentrifuged. The 5 ml wash is saved for analysis (surface bound drug). Microspheres are then wetted in 50 ul of methanol, and vortexed in 1 ml of DCM to dissolve the ELVAX. The microspheres are then warmed to 40° C., and 5 ml of 50° C. water is slowly added with stirring. This procedure results in the immediate evaporation of DCM, thereby causing the release of sodium suramin into the 5 ml of water.

All samples were assayed for drug content by quantification of fluorescence. Briefly, sodium suramin absorbs uv/vis with a lambda max of 312 nm. This absorption is linear in the 0 to 100 ug/ml range in both water and 5% PVA. Sodium suramin also fluoresces strongly with an excitation maximum at 312 nm, and emission maximum at 400 nm. This fluorescence is quantifiable in the 0 to 25 ug/ml range.

The results of these experiments is shown in FIGS. 53–59. Briefly, the size distribution of microspheres by number (FIG. 53) or by weight (FIG. 54) appears to be unaffected by inclusion of the drug in the DCM. Good yields of microspheres in the 20 to 60 μm range may be obtained.

Figure 55:
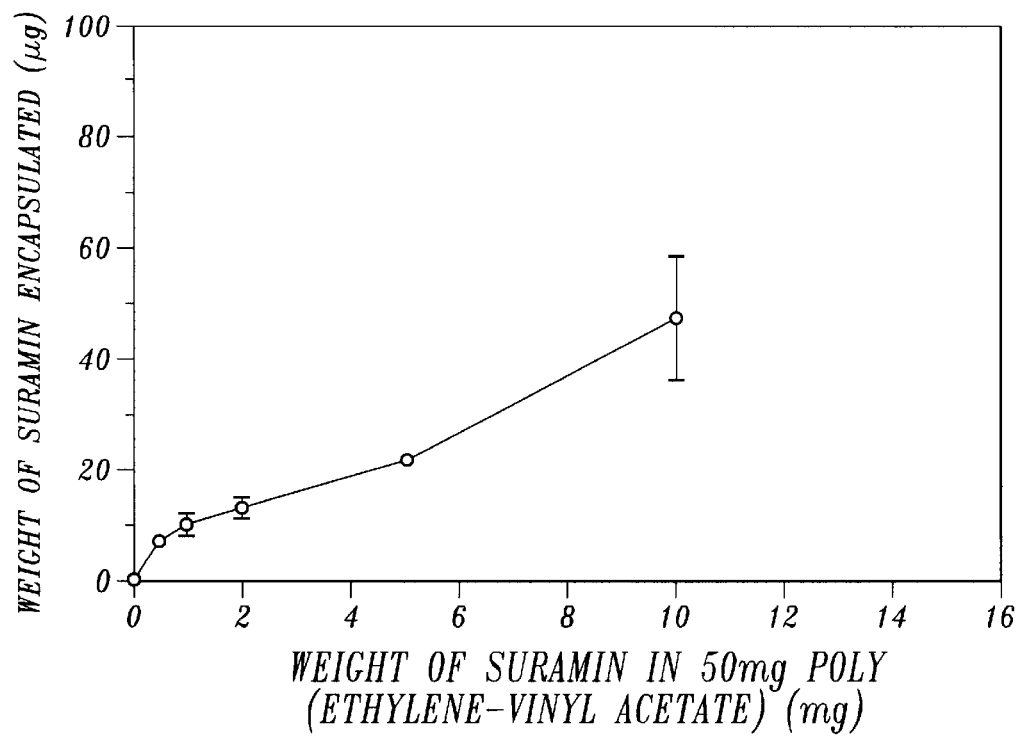
FIG. 55 is a graph which depicts the weight of encapsulation of Sodium Suramin in 50 mg poly (ethylene-vinyl acetate).
Figure 56:
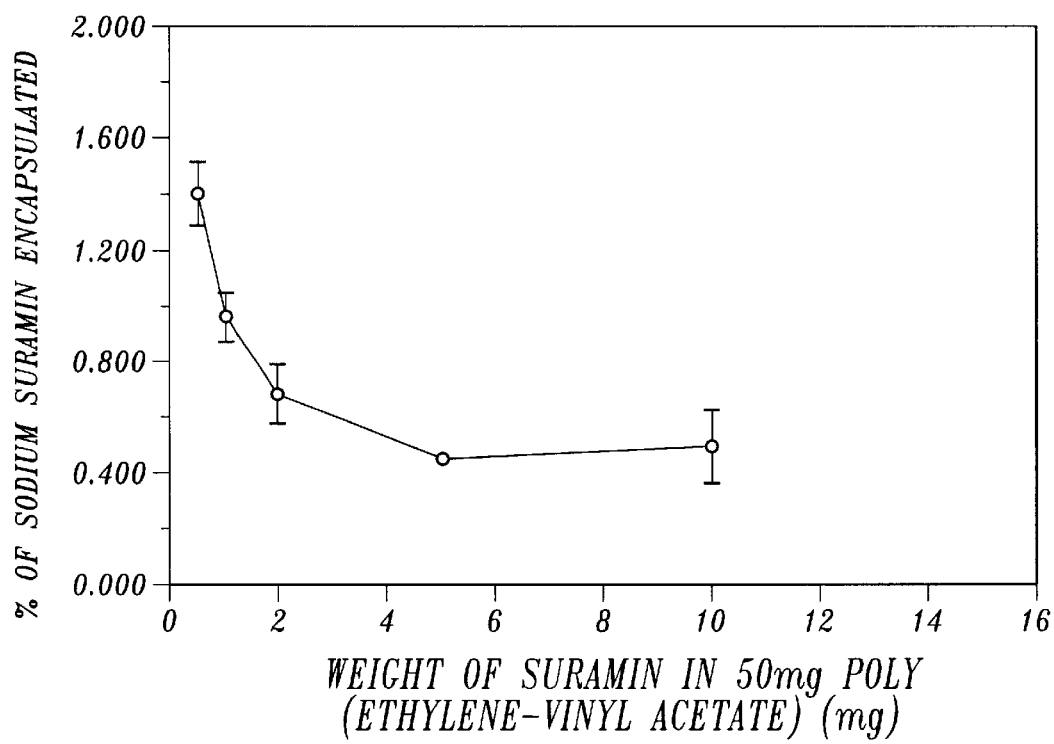
FIG. 56 is a graph which depicts the percent of encapsulation of Sodium Suramin in 50 mg poly (ethylene-vinyl acetate).
Figure 57:
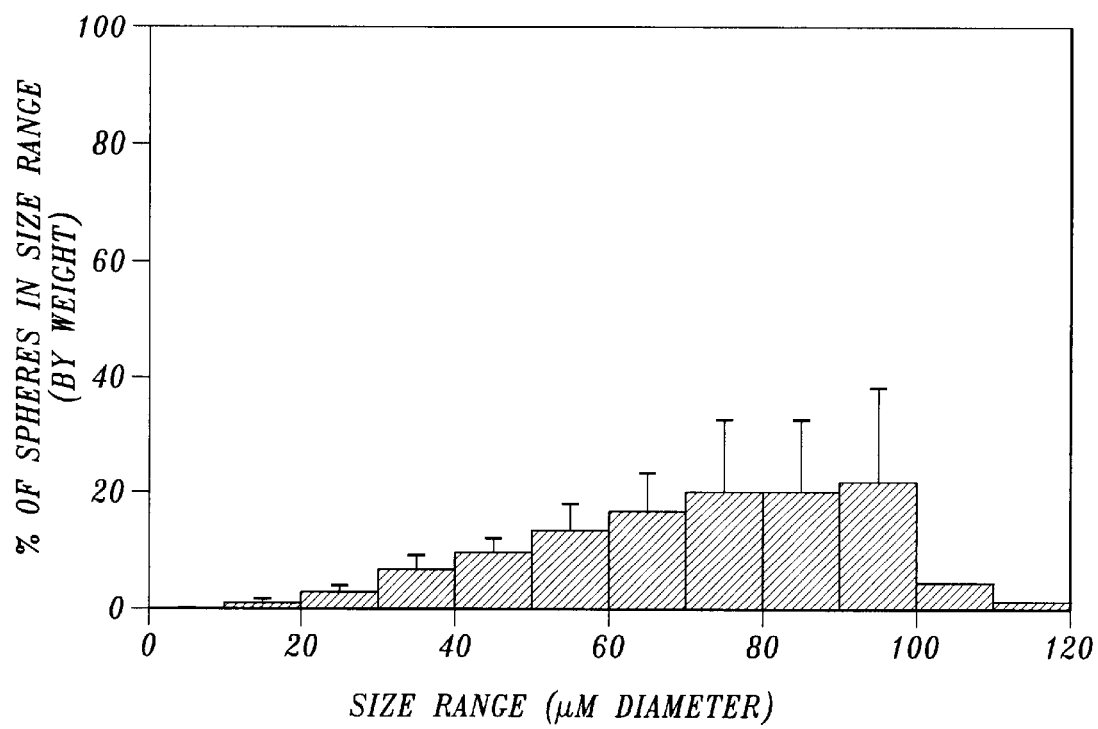
FIG. 57 is a bar graph which depicts the size distribution by weight of 5% ELVAX microspheres containing 10 mg sodium suramin made in 5% PVA containing 10% NaCl.
Figure 58:
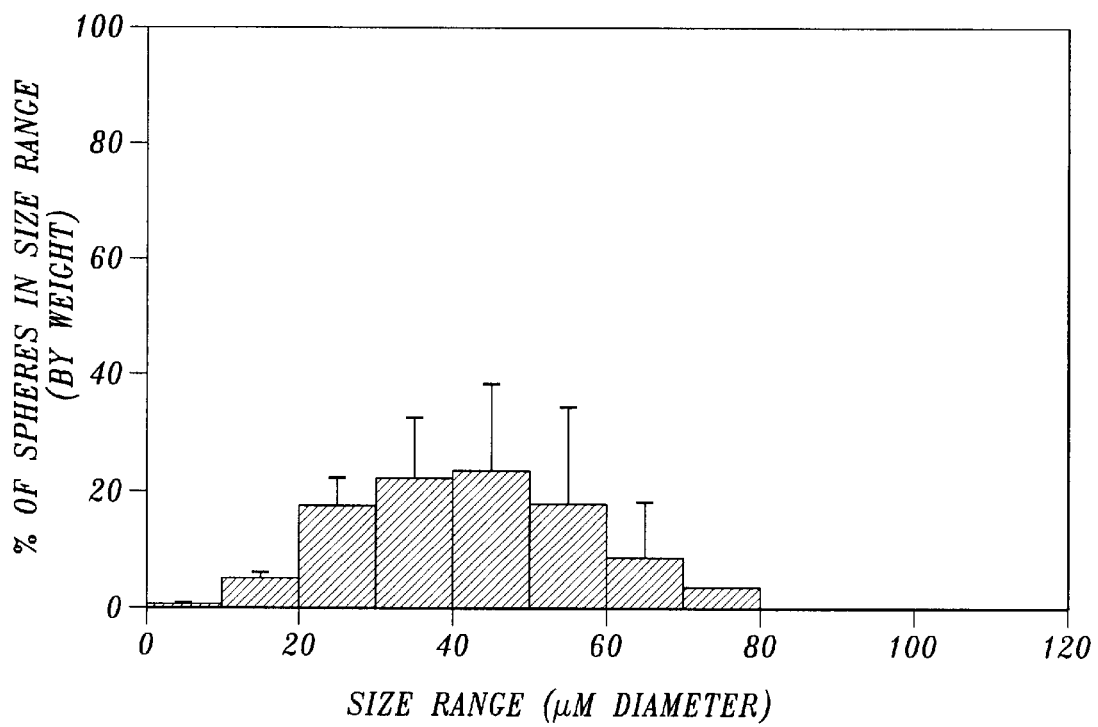
FIG. 58 is a bar graph which depicts the size distribution by weight of 5% microspheres containing 10 mg sodium suramin made in 5% PVA containing 10% NaCl.
Figure 59:
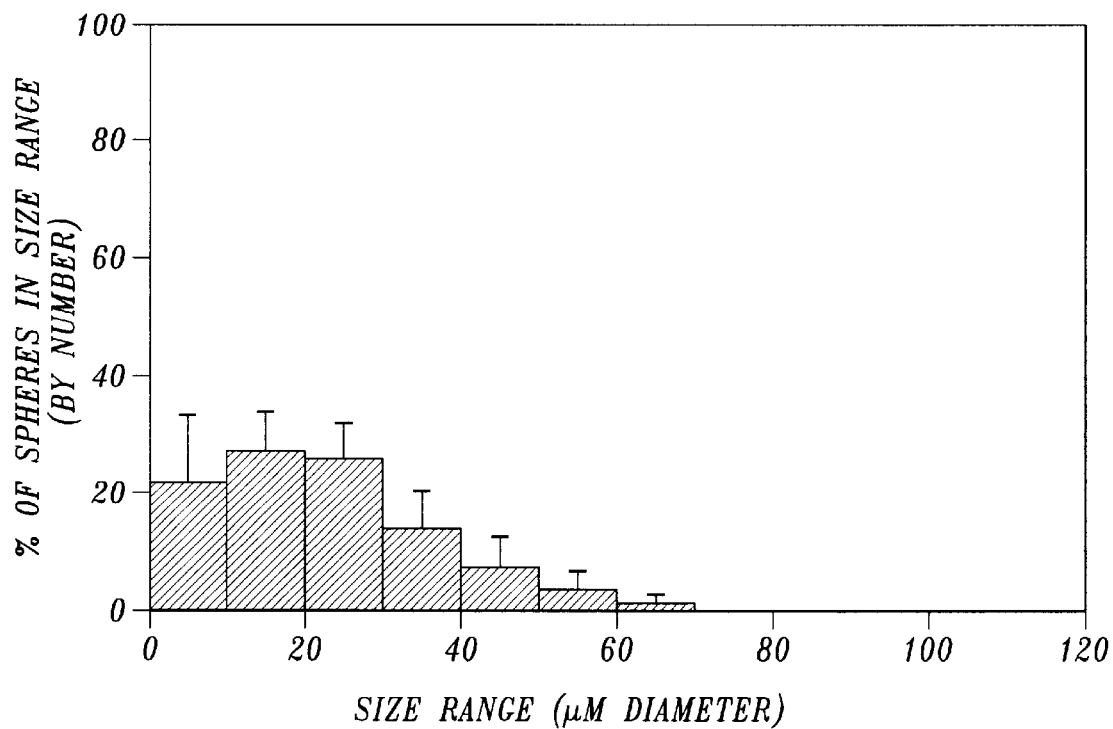
FIG. 59 is a bar graph which depicts the size distribution by number of 5% microspheres containing 10 mg sodium suramin made in 5% PVA containing 10% NaCl.

The encapsulation of suramin is very low (<1%) (see FIG. 56). However as the weight of drug is increased in the DCM the total amount of drug encapsulated increased although the % encapsulation decreased. As is shown in FIG. 55, 50 ug of drug may be encapsulated in 50 mg of ELVAX. Encapsulation of sodium suramin in 2.5% PVA containing 10% NaCl is shown in FIG. 57 (size distribution by weight). Encapsulation of sodium suramin in 5% PVA containing 10% NaCl is shown in FIGS. 58 and 59 (size distribution by weight, and number, respectively).

Figure 60A:
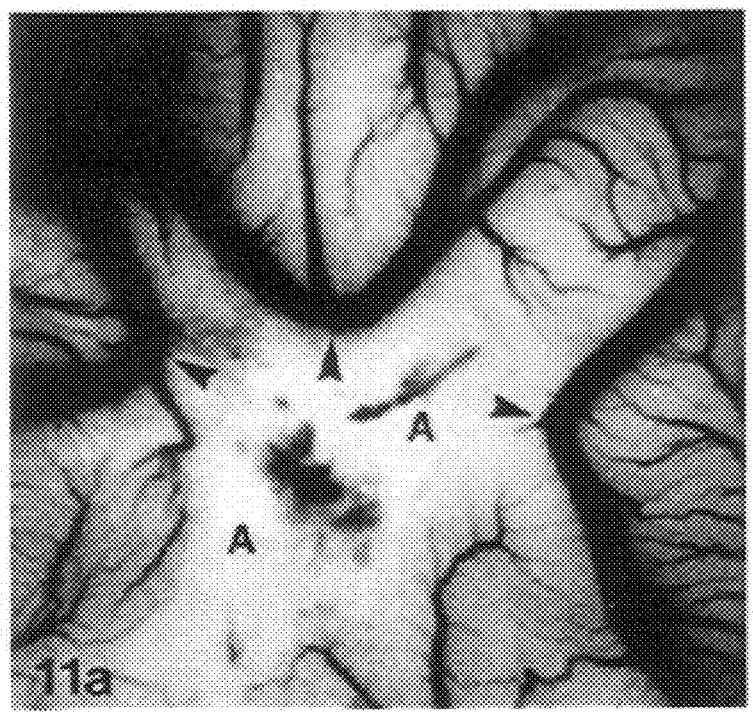
FIG. 60A is a photograph of Suramin and Cortisone Acetate on a CAM (Mag=8×). Briefly, this image shows an avascular zone treated with 20 μg of suramin and 70 μg of cortisone acetate in 0.5% methylcellulose. Note the blood vessels located at the periphery of the avascular zone which are being redirected away from the drug source.
Figure 60B:
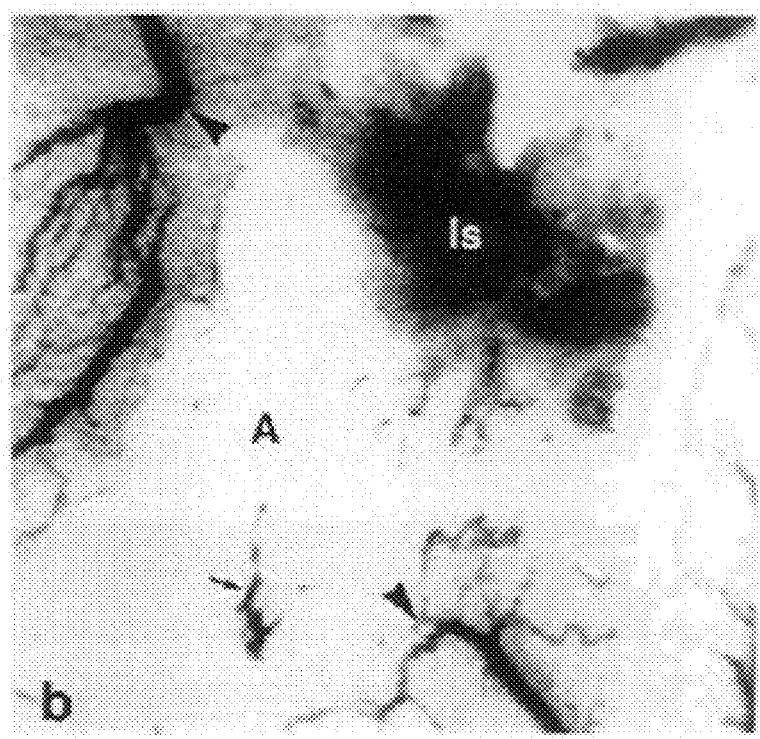
FIG. 60B is a photograph which shows the vascular detail of the effected region at a higher magnification (Mag=20×). Note the avascular regions and the typical "elbowing" effect of the blood vessels bordering the avascular zone.

To assess suramin and cortisone acetate as potential anti-angiogenic agents, each agent was mixed with 0.5% methylcellulose and applied the dried disks containing the agent onto the developing blood vessels of the 6-day old CAM. A combination treatment of suramin (70 µg) with cortisone acetate (20 µg) was successful in inhibiting angiogenesis when tested on the CAM for 48 hours. The resulting avascular region measured 6 mm in diameter and revealed an absence of blood flow and the appearance of sparse blood islands (FIGS. 60A and 60B).

Example 24

Methotrexate-loaded Paste

A. Manufacture of Methotrexate-loaded Paste

Methotrexate ("MTX"; Sigma Chemical Co.) is ground in a pestle and mortar to reduce the particle size to below 5 microns. It is then mixed as a dry powder with polycaprolactone (molecular wt 18000 Birmingham Polymers, AL USA). The mixture is heated to 65° C. for 5 minutes and the molten polymer/methotrexate mixture is stirred into a smooth paste for 5 minutes. The molten paste is then taken into a 1 mL syringe, and extruded as desired.

B. Results

Figure 61A:
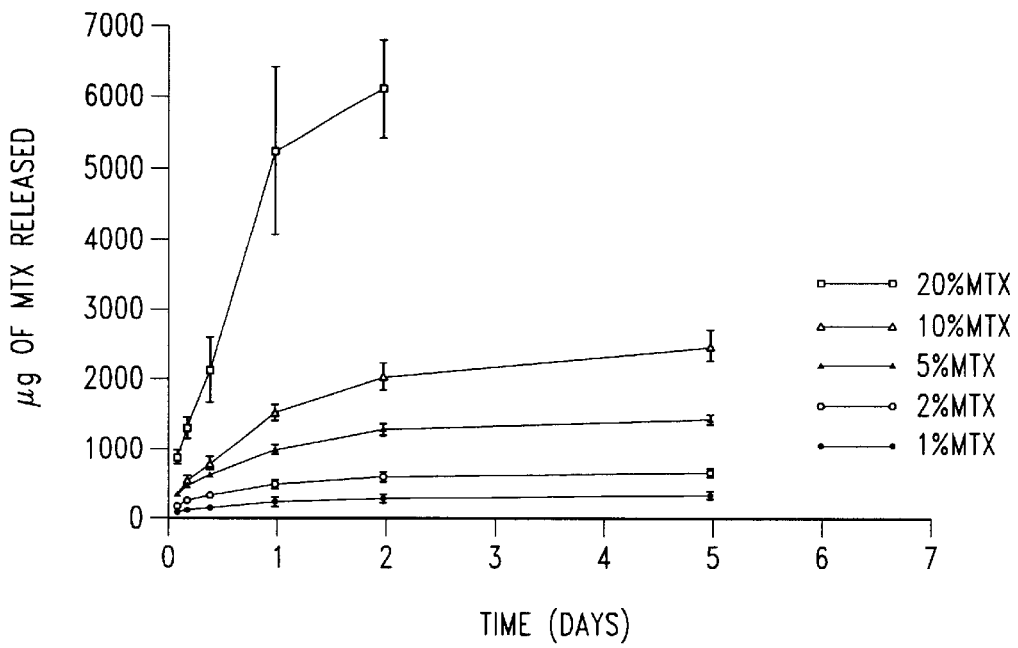
FIGS. 61A, B, C, D and E show the effect of MTX release from PCL over time.
Figure 61B:
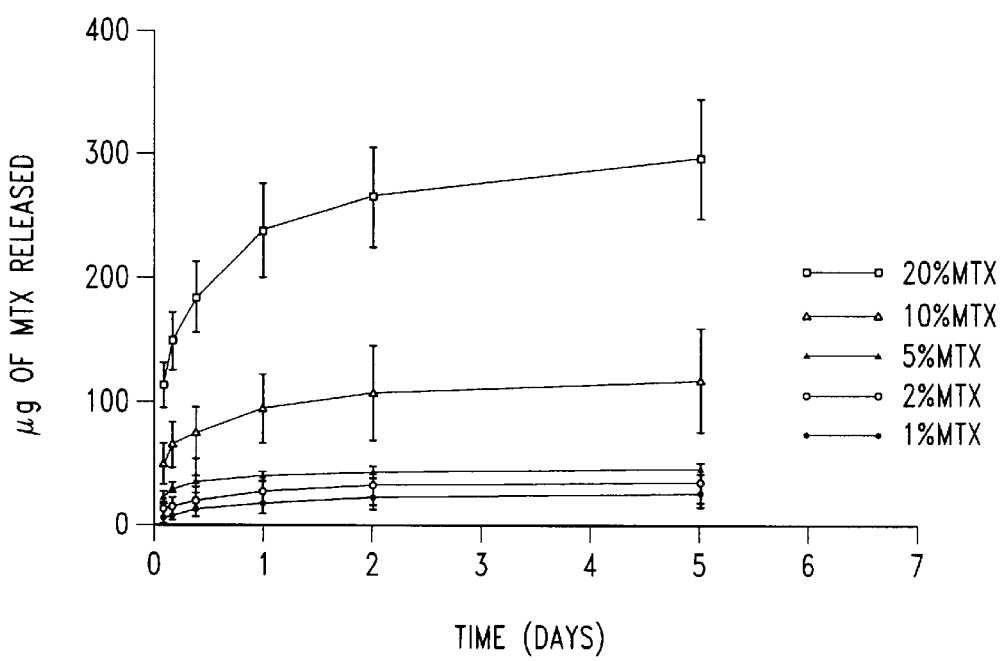

Results are shown in FIGS. 61A–E. Briefly, FIG. 61A shows MTX release from PCL discs containing 20% MePEG and various concentrations of MTX. FIG. 61B shows a similar experiment for paste which does not contain MePEG. FIGS. 61C, D, and E show the amount of MTX remaining in the disk.

As can be seen by the above results, substantial amounts of MTX can be released from the polymer when high MePEG concentrations are utilized.

Example 25

Manufacture of Microspheres Containing Methotrexate

A. Microspheres with MTX Alone

Methotrexate (Sigma) was ground in a pestle and mortar to reduce the particle size to below 5 microns. One hundred milliliters of a 2.5% PVA (w/v) (Aldrich or Sigma) in water was stirred for 15 minutes with 500 mg of unground MTX at 25° C. to saturate the solution with MTX. This solution was then centrifuged at 2000 rpm to remove undissolved MTX and the supernatant used in the manufacture of microspheres.

Briefly, 10 ml of a 5% w/v solution of poly(DL) lactic acid (molecular weight 500,000; Polysciences), Polylactic:glycolic acid (50:50 IV 0.78 polysciences) or polycaprolactone (molecular weight 18,000, BPI) containing 10:90 w/w MTX (ground):POLYMER were slowly dripped into 100 mL of the MTX saturated 2.5% w/v solution of PVA (Aldrich or Sigma) with stirring at 600 rpm. The mixture was stirred at 25° C. for 2 hours and the resulting microspheres were washed and dried.

Figure 62:
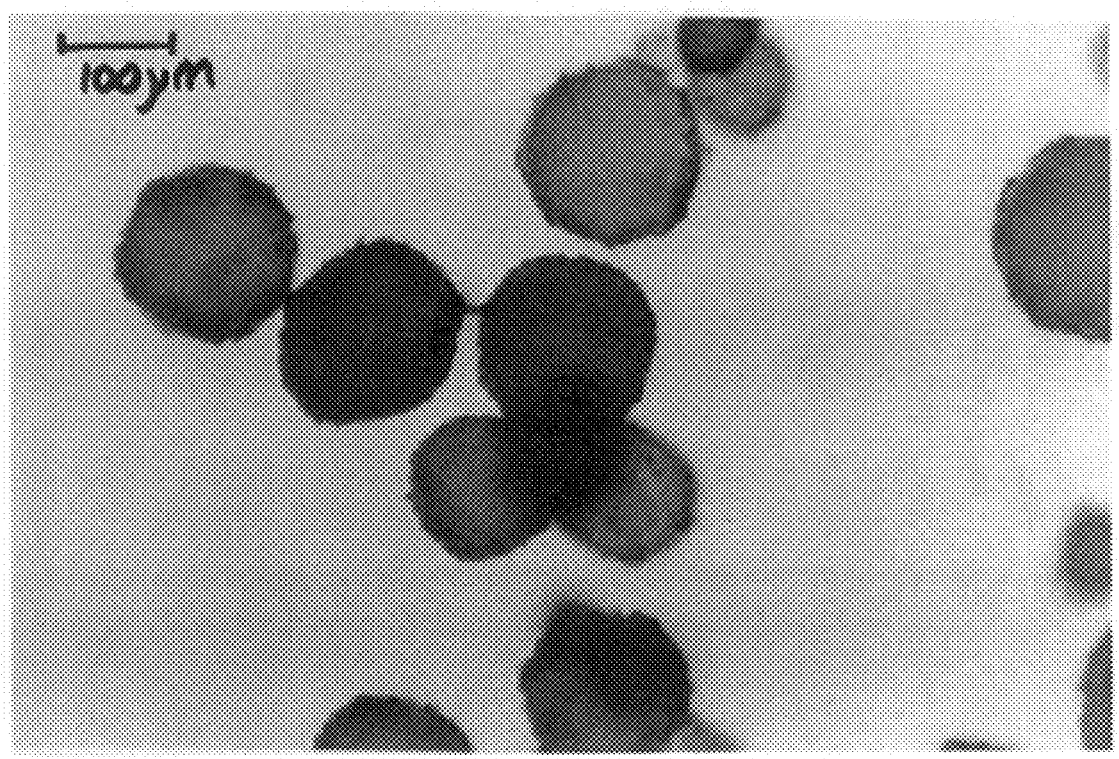
FIG. 62 is a photograph of 10% methotrexate-loaded microspheres made from PLA:GA (50:50); Inherent Viscosity "IV"=0.78.

Using this method MTX loaded microspheres can be reproducibly manufactured in the 30 to 160 micron range (see FIG. 62).

B. Microspheres with MTX and Hyaluronic Acid

MTX loaded microspheres can be made using hyaluronic acid ("HA") as the carrier by a water in oil emulsion manufacture method, essentially as described below. Briefly, 50 ml of Parafin oil (light oil; Fisher Scientific) is warmed to 60° C. with stirring at 200 rpm. A 5 mL solution of sodium hyaluronate (20/mL); source=rooster comb; Sigma) in water containing various amounts MTX is added dropwise into the Parafin oil. The mixture is stirred at 200 rpm for 5 hours, centrifuged at 500×g for 5 minutes. The resulting microspheres are washed in hexane four times, and allowed to dry.

Example 26

Manufacture of Polymeric Compositions Containing Vanadium Compounds

A. Polymeric Paste Containing Vanadyl Sulfate

Vanadyl Sulfate (Fisher Scientific) is first ground in a pestle and mortar to reduce the particle size, then dispersed into melted PCL as described above for MTX. It is then taken up into a syringe to solidify and is ready for use.

Drug release was determined essentially as described above in Example 33, except that a 65 mg pellet of a 10% w/w $VOSO_4$:PCL was suspended in 10 ml of water and the supernatant analyzed for released Vanadyl Sulphate using UV/Vis absorbance spectroscopy of the peak in the 200 to 300 nm range.

Figure 63:
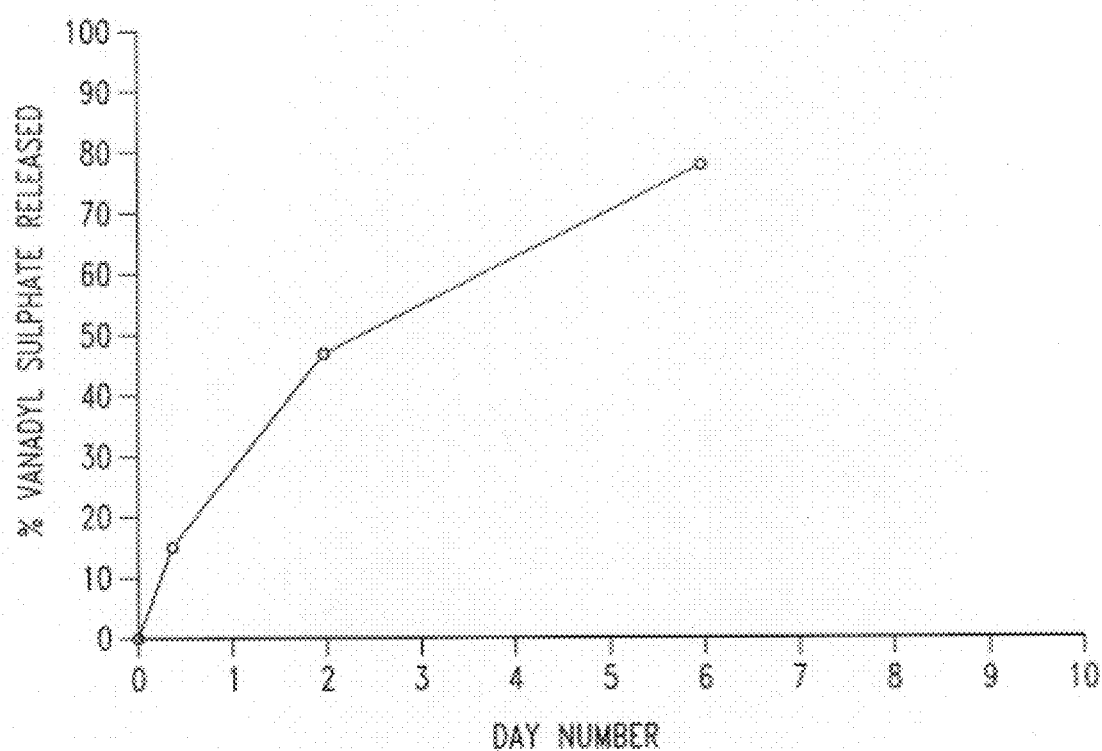
FIG. 63 is a graph which depicts the release of 10% loaded vanadyl sulfate from PCL.

Results are shown in FIG. 63. Briefly, from a polymeric composition containing 10% $VOSO_4$, 1 mg of $VOSO_4$ was released in 6 hours, 3 mg after 2 days and 5 mg by day 6.

B. Polymeric Microspheres Containing Vanadyl Sulfate

Figure 64:
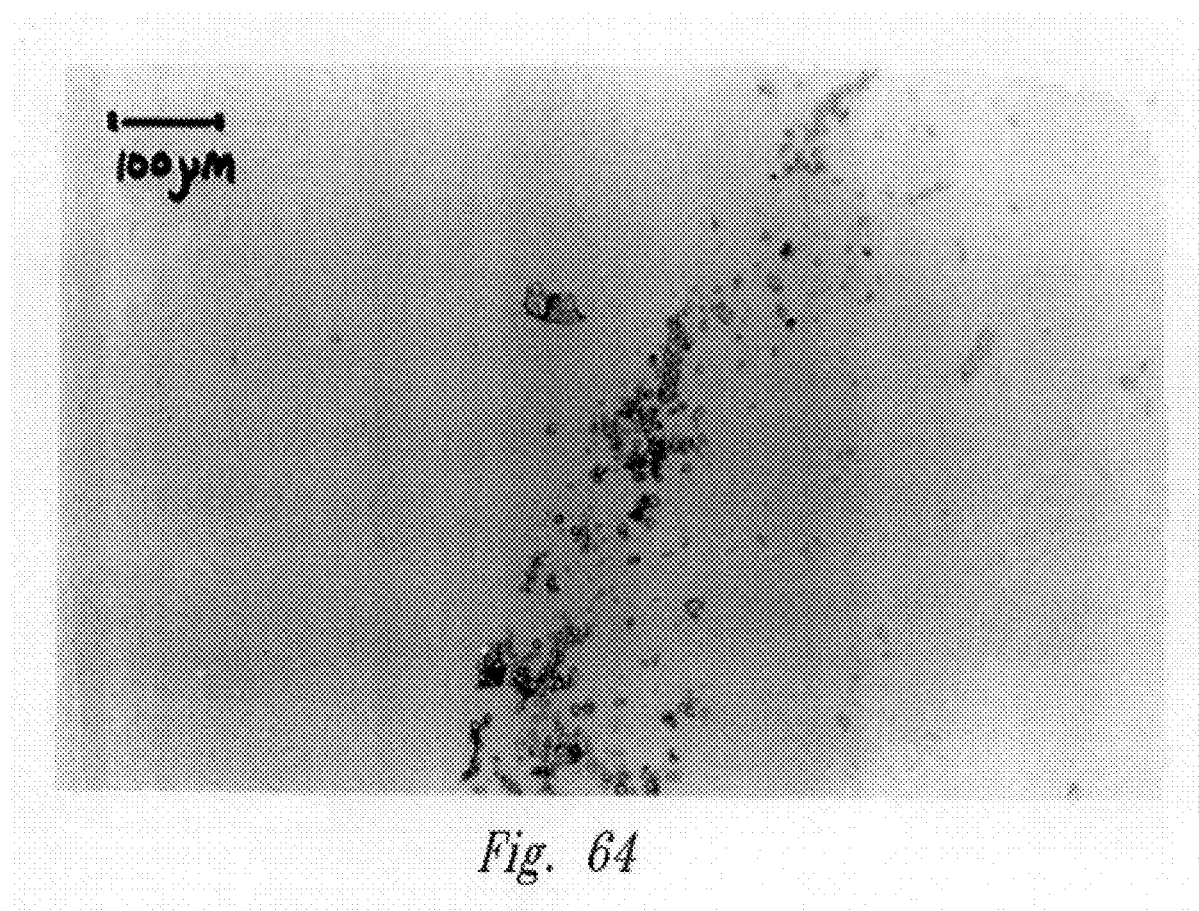
FIG. 64 is a photograph of hyaluronic acid microspheres containing vanadium sulfate.

Vanadyl sulfate was incorporated into microspheres of polylactic acid or hyaluronic acid essentially as described in Example 25. Results are shown in FIG. 64.

C. Polymeric Paste Containing Organic Vanadate

Figure 65A:
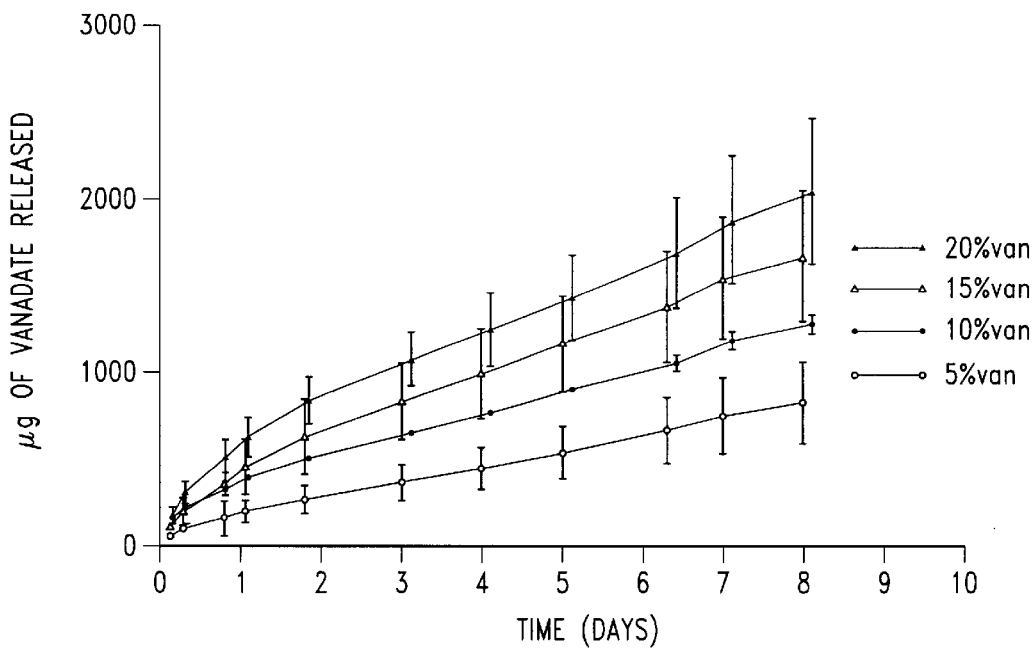
FIG. 65A is a graph which depicts the release of organic vanadate from PCL.
Figure 65B:
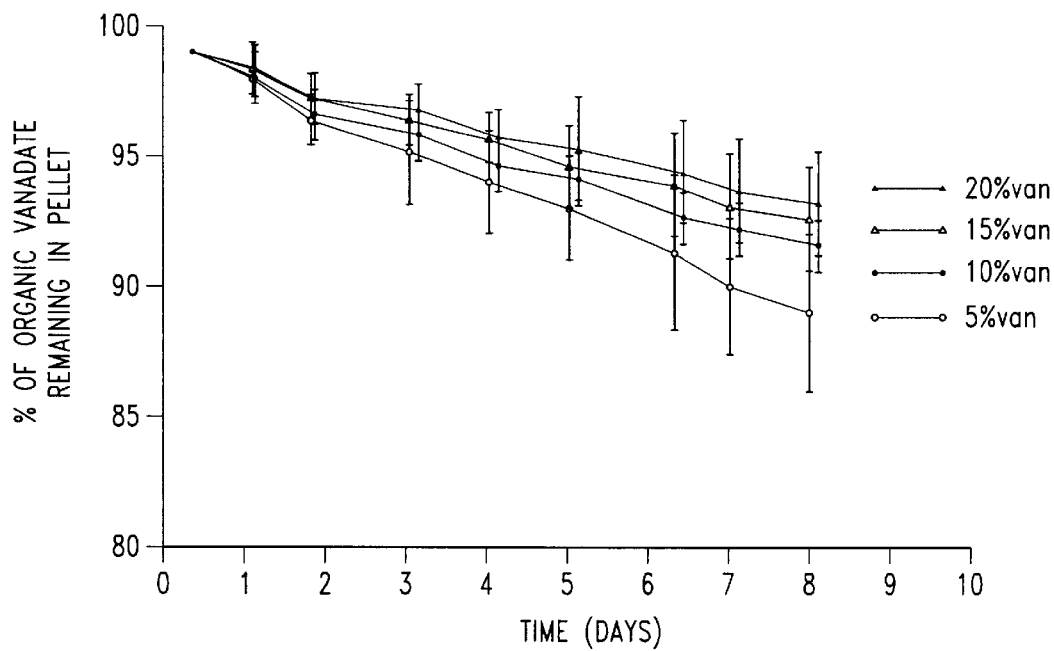
FIG. 65B depicts the percentage of organic vanadate remaining over a time course.

Organic vanadate is loaded into a PCL paste essentially as described above in Example 24. Vanadate release from the microspheres was determined as described above. Results are shown in FIGS. 65A and 65B.

D. Organic Vanadate Containing Microspheres

Figure 66:
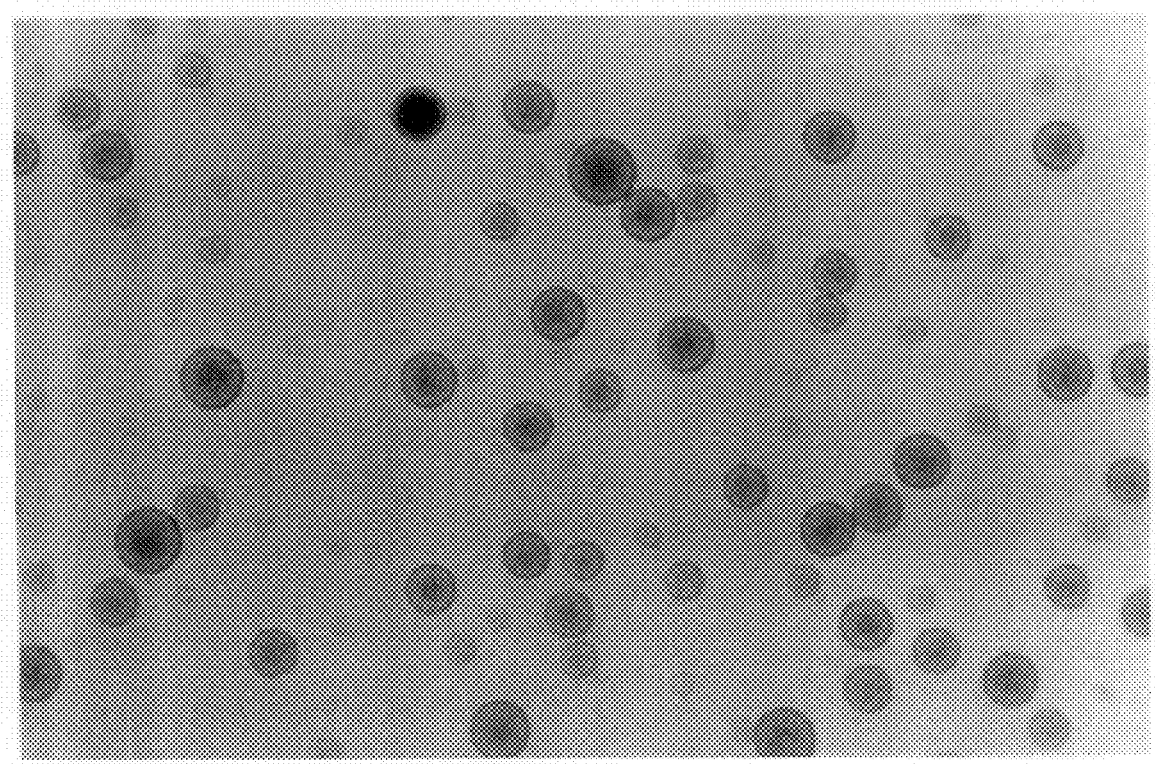
FIG. 66 is a photograph showing poly D,L, lactic acid microspheres containing organic vanadate.

Organic vanadate may also be loaded into microspheres essentially as described in Example 25. Such microspheres are shown in FIG. 66 for poly D,L lactic acid (M.W. 500,000; Polysciences).

Example 27

Polymeric Composition Containing Bis(Maltolato) Oxovanadium (BMOV)

A. Manufacture of bis(maltolato) Oxovanadium Loaded Paste

Poly (E-caprolactone) (Molecular weight 20000) (BPI Birmingham Ala.) and BMOV were weighed directly into a glass beaker in the appropriate proportions. In some formulations methoxypolyethylene glycol (MEPEG) (molecular weight 350) (Union Carbide, Danbury Conn.) was also added to the PCL and BMOV. The beaker and contents were warmed to 55° C. with gentle stirring for 5 minutes until the BMOV was thoroughly dispersed in the molten polymer. The molten mix was then drawn into a prewarmed syringe and stored at 4° C. until use.

B. Drug Release Studies

To tubes containing 15 ml of 10 mM phosphate buffered saline (PBS pH 7.4) and 100 ug/ml bovine serum albumin (fraction 5 Boehringer Mannheim, Germany) were added 150 mg disc-shaped slabs of PCL-BMOV paste. The tubes were sealed and tumbled end over end at 30 rpm at 37° C. At appropriate times the PCL-BMOV slab was allowed to settle under gravity for 5 minutes and all the supernatant was removed. The BMOV concentration was determined in the supernatants by measuring the absorbance at 256 nm (A256) and 276 nm (A276). The supernatant was replaced with 15 ml of fresh PBS and the tubes were retumbled. A linear calibration curve of BMOV concentration vs. A256 or A276 was obtained using BMOV standards in the 0 to 25 ug/ml range. The absorbance values at 256 nm or 276 nm of these standards were shown to be unaffected by storage in sealed tubes at 37° C. for 2 to 3 days (the same conditions used for drug release studies).

At the end of the drug release experiments samples of the PCL-BMOV matrix were assayed for residual drug content by dissolution of a known dried weight of the matrix in 0.5 ml of dichloromethane (DCM) (Fisher). To this solution was added 50 ml of warm water (50° C.) with mixing to evaporate the DCM leaving the BMOV in water for spectrophotometric analysis (A256).

C. Scanning Electron Microscopy (SEM)

Samples of the PCL-BMOV matrix that had been used in the 2 month drug release experiments were examined using SEM. These samples were compared with freshly prepared control samples. Polymer samples were coated (60:40 gold:palladium) (Hummer instruments, Technics, USA) and examined using a Hitachi (model F-2300) scanning electron microscope with a IBM data collection system.

D. Results

Figure 67A:
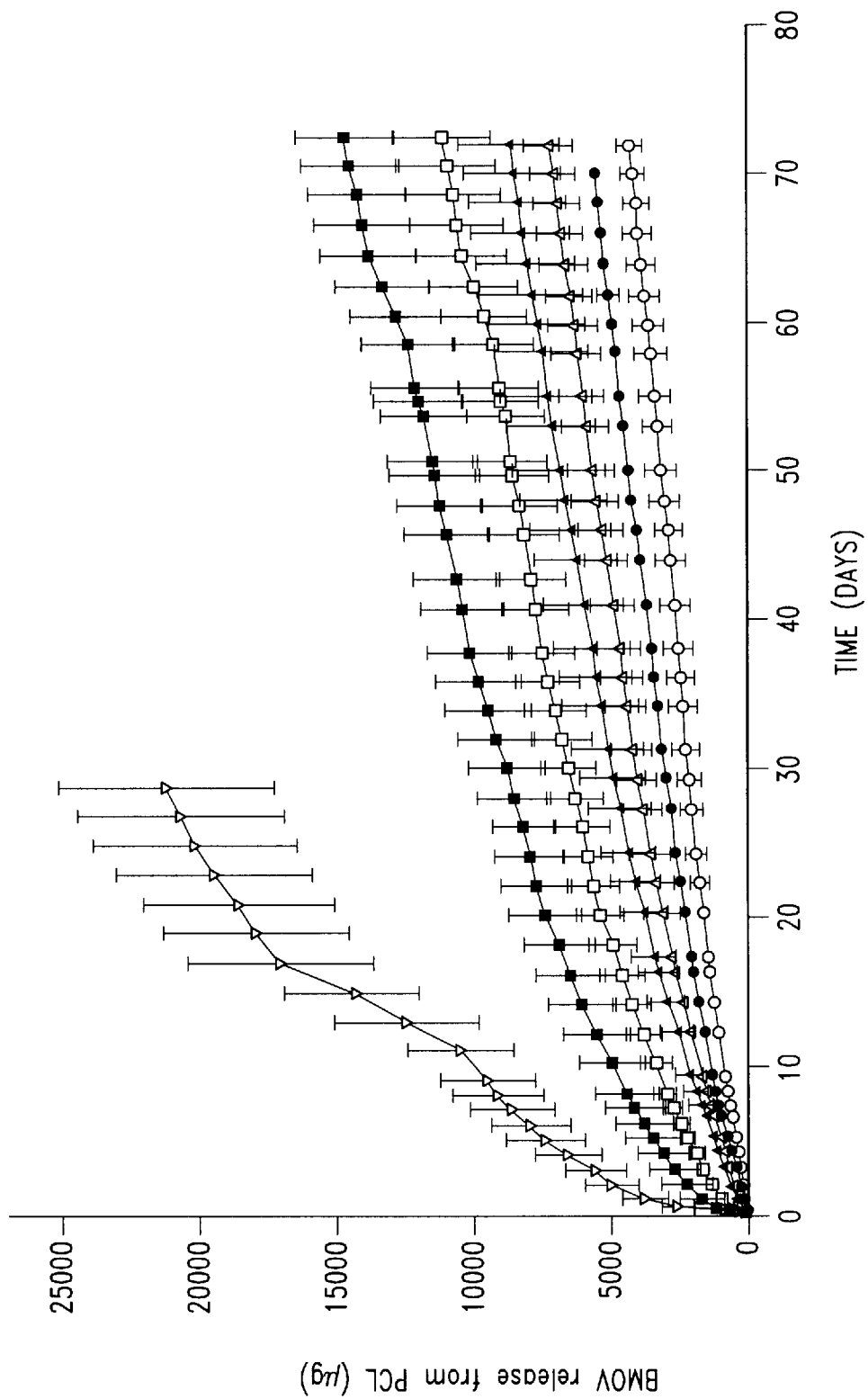
FIGS. 67A and 67B are graphs which show the time course of BMOV release from PCL (150 mg slabs). (A) μg drug released or (B) % of drug remaining in slab. Initial loading of BMOV in PCL given by (○), 5%; (●), 10%; (Δ), 15%; (σ), 20%; ( ), 30% and (∇), 35%.
Figure 67B:
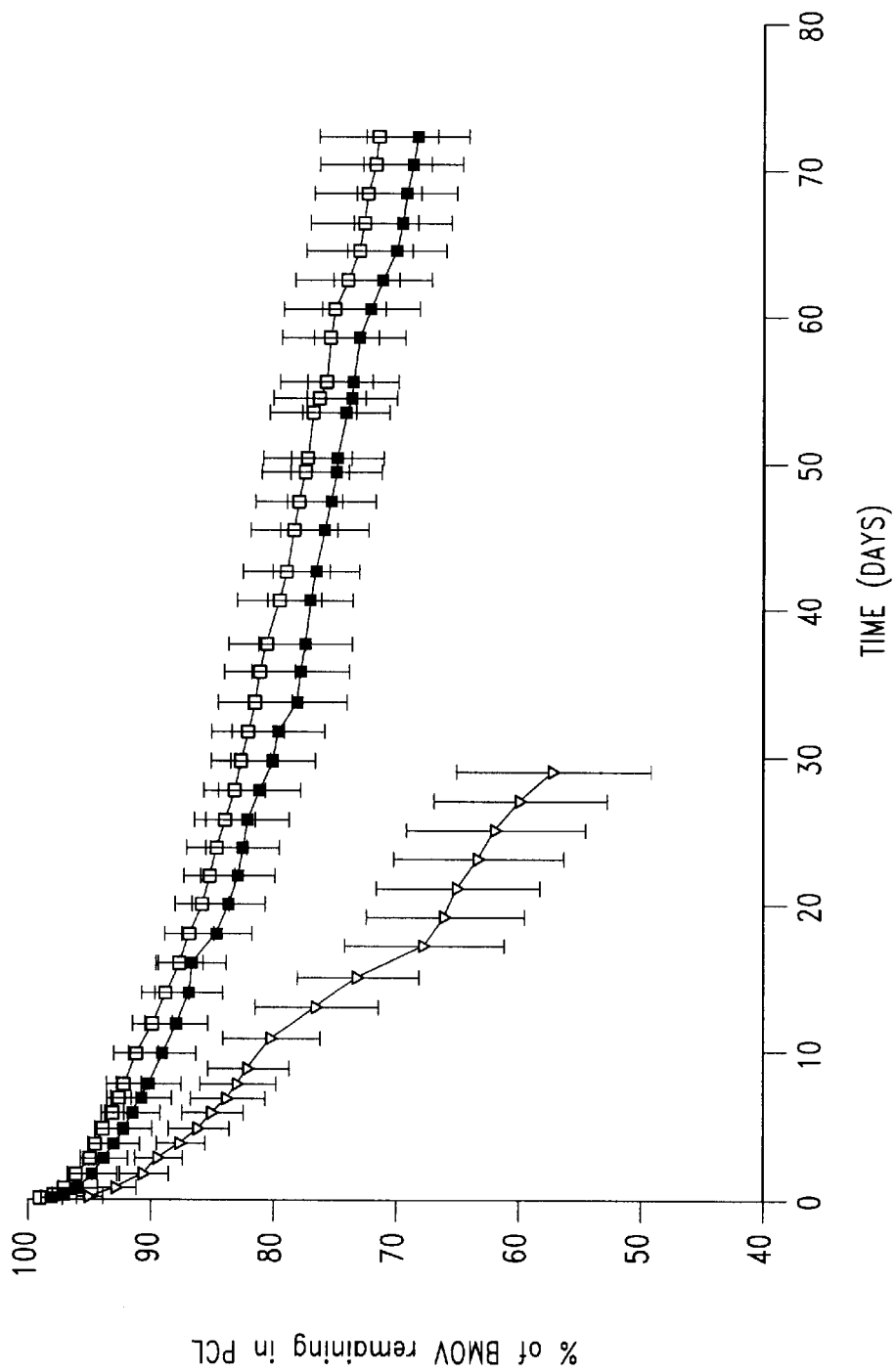

The release of BMOV from the PCL matrix is shown in FIGS. 67A and 67B. Increasing the loading of BMOV from 5% to 35% in the PCL matrix increased the rate of drug release over the two month period (FIG. 67A). At 35% BMOV loading the release rate increased dramatically. The release profiles for the 20% to 30% BMOV loadings showed an initial more rapid phase of drug release in the first two days followed by a controlled, almost zero order release over the next 2 months.

The drug release profiles are also expressed in terms of the % of drug remaining in the pellet (FIG. 67B). Briefly, the % of BMOV remaining in the PCL matrix was almost identical at all time points for all the BMOV loadings up to (and including) 30% so that between 65% and 80% of the original BMOV was still present in the matrix after two months. (Only the data for 25% and 30% BMOV loadings are shown in FIG. 67B for clarity). The percentage of drug remaining in the matrix decreased more rapidly at a loading 35% BMOV so that a little over 50% of the original BMOV was present in the matrix after one month. In order to verify the cumulative drug release data, samples of the PCL-BMOV matrix were assayed for remaining drug content at the end of each drug release experiment. The % drug remaining at 70 days as determined by this residual assay was as follows: 67%+/−10% (5% BMOV), 56%+/−10% (10% BMOV), 80%+/−20% (15% BMOV), 84%+/−20% (20% BMOV), 85%+/−12% (25% BMOV), 77%+/−14% (30% BMOV) and 57%+/−15% (35% BMOV).

Figure 68A:
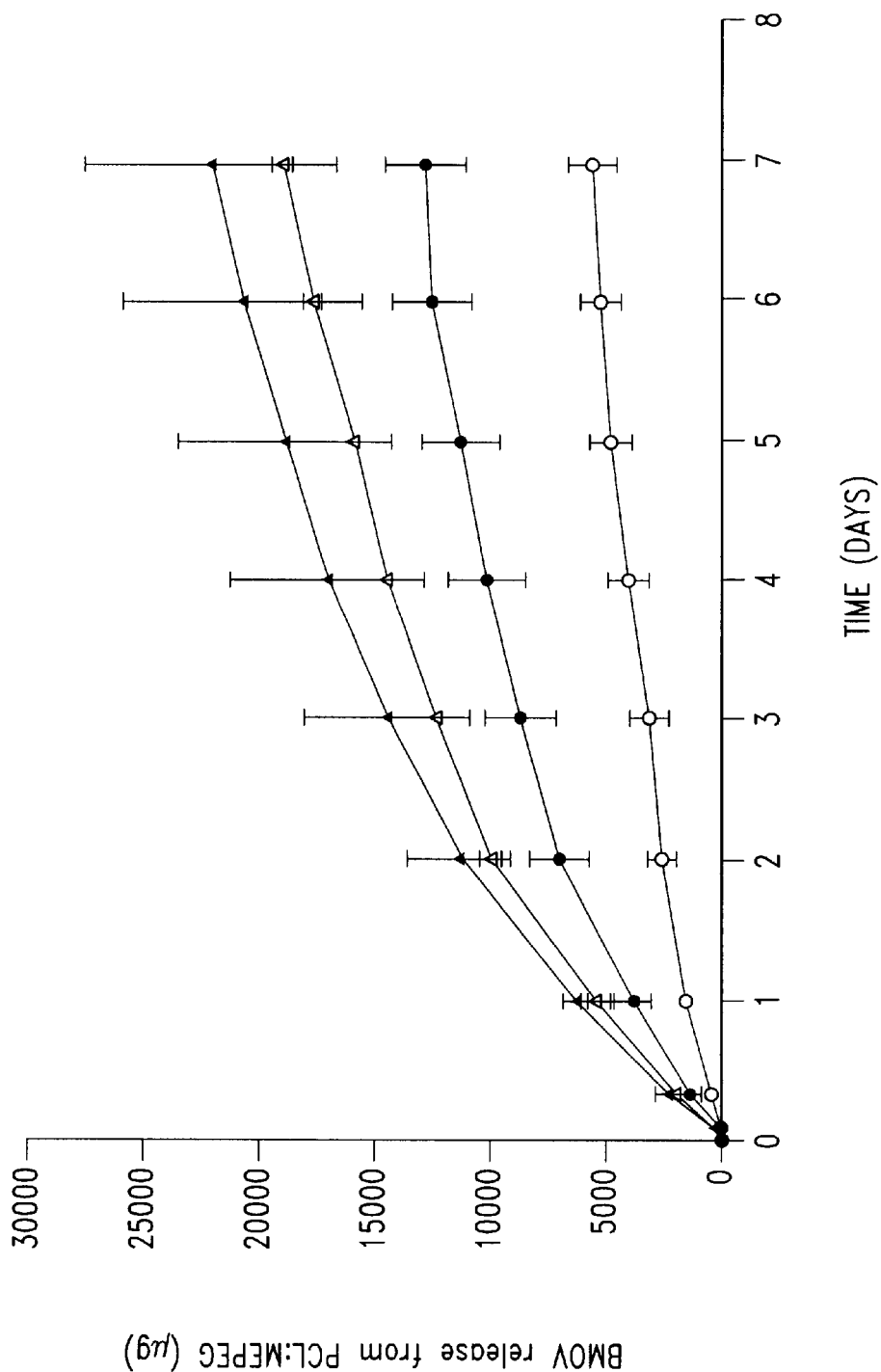
FIGS. 68A and 68B are graphs which show the time course of BMOV release from 150 mg slabs of PCL:ME-PEG (80:20, w:w) expressed as (A) μg drug released or (B) % drug remaining in slab. Initial loading of BMOV in PCL:MEPEG given by (○), 5%; (●), 10%; (Δ), 15%; (σ), 20%.
Figure 68B:
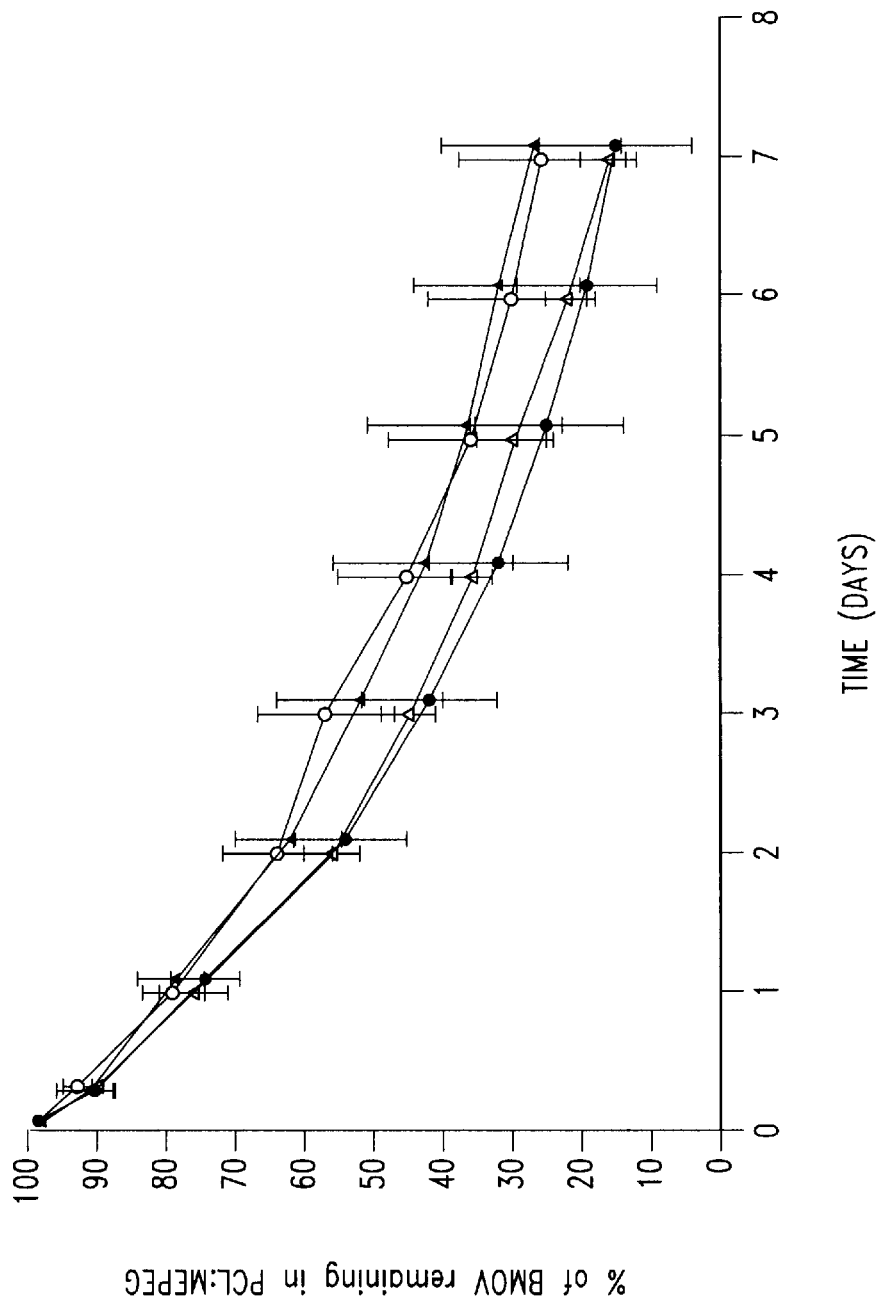

FIGS. 68A and 68B show the effect of adding 20% MEPEG to the PCL matrix on the drug release profiles for various loading concentrations of BMOV. The addition of MEPEG to the matrix increases the release rate of BMOV dramatically compared to the release of BMOV from the PCL alone (FIG. 67). Greater than 50% of the BMOV was released from the polymer matrix within 7 days 1 week at all BMOV loading concentrations. Residual analysis of the PCL-BMOV-MEPEG pellets gave the following values for the % of BMOV remaining at 7 days in the pellets: 24% (+/−9%), 5% BMOV; 25% (+/−8%). 10% BMOV; 22% (+/−4%), 15% BMOV; 27% (+1−7%), 20% BMOV.

Figure 69A:
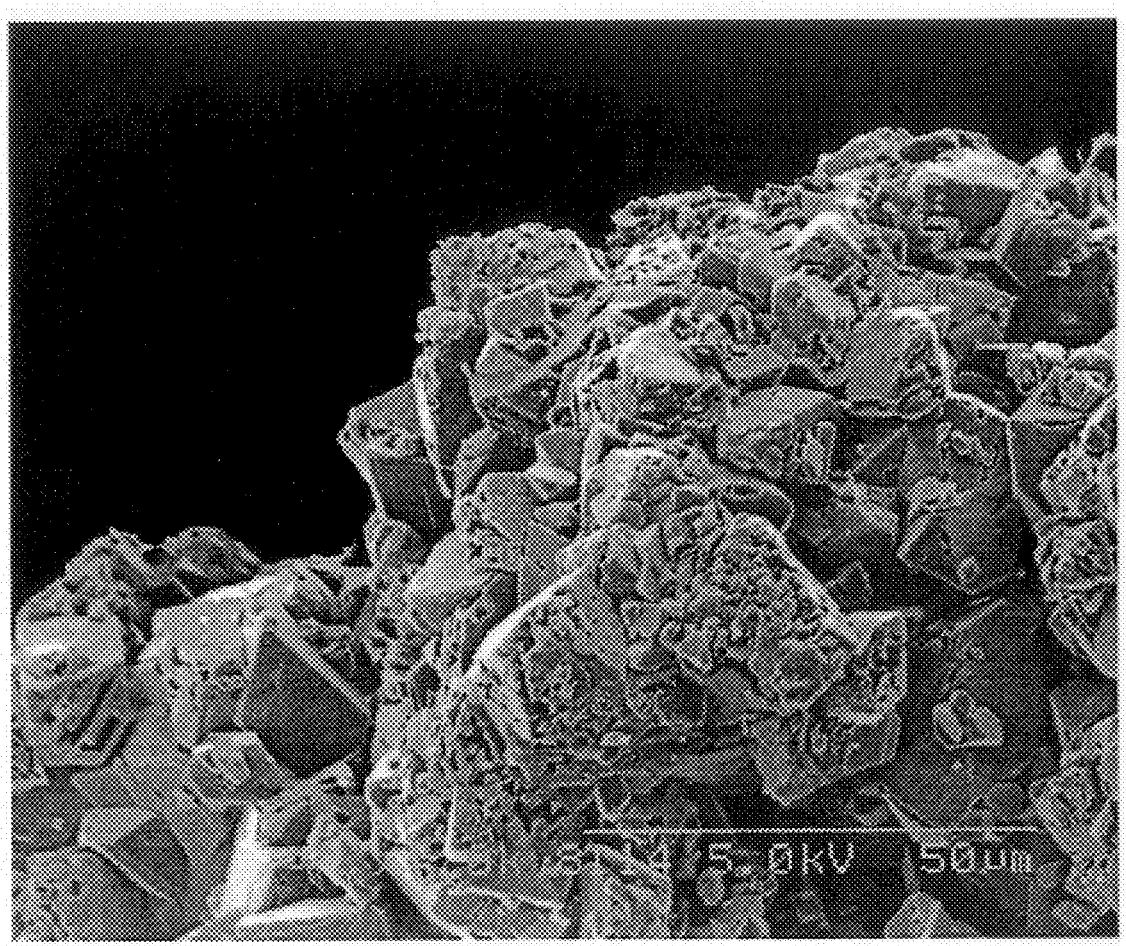
FIGS. 69A, 69B and 69C are Scanning electron micrographs of (69A: top), BMOV crystals; (69B: middle) surface morphology of the PCL slab containing 20% BMOV at the start of the drug release experiment and (69C: bottom), surface morphology of the PCL slab containing 20% BMOV at the end of the drug release experiment (72 days in PBS).
Figure 69B:
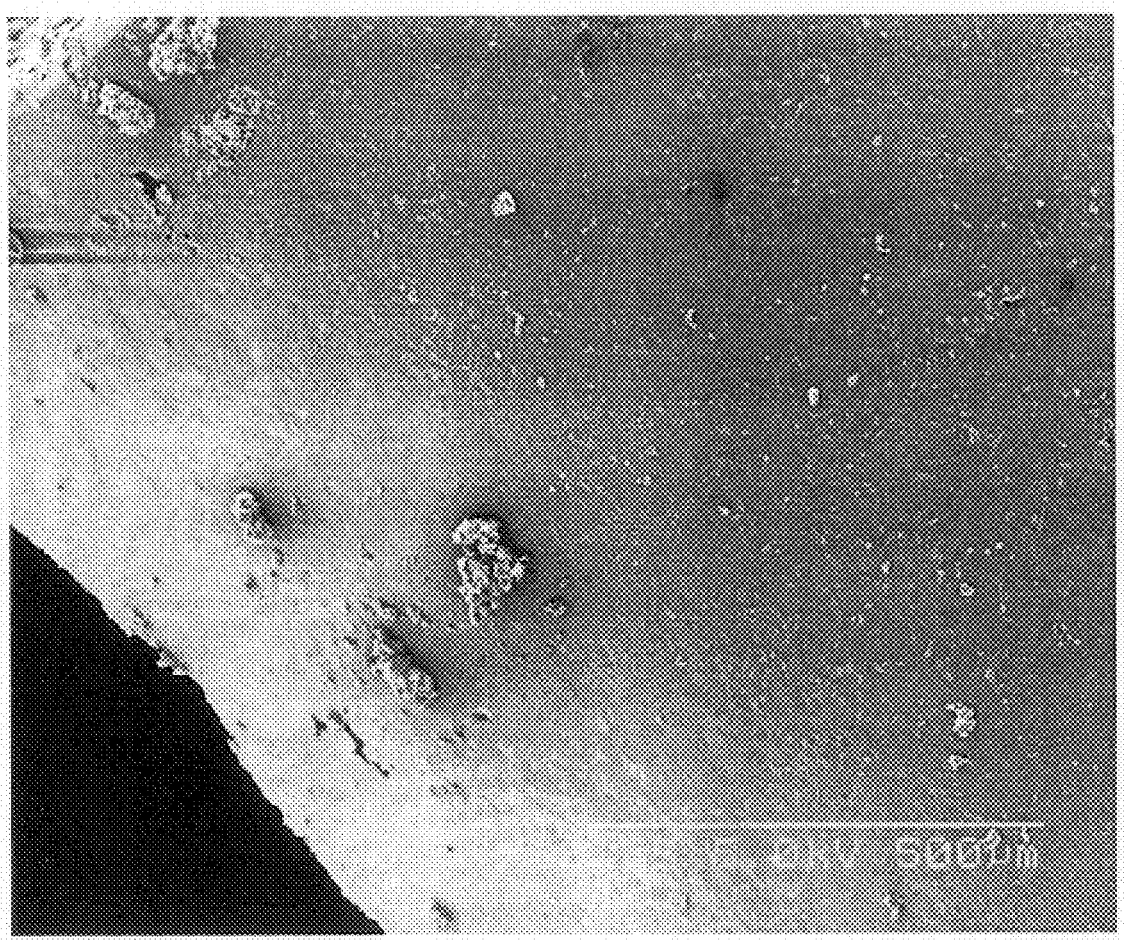
Figure 69C:
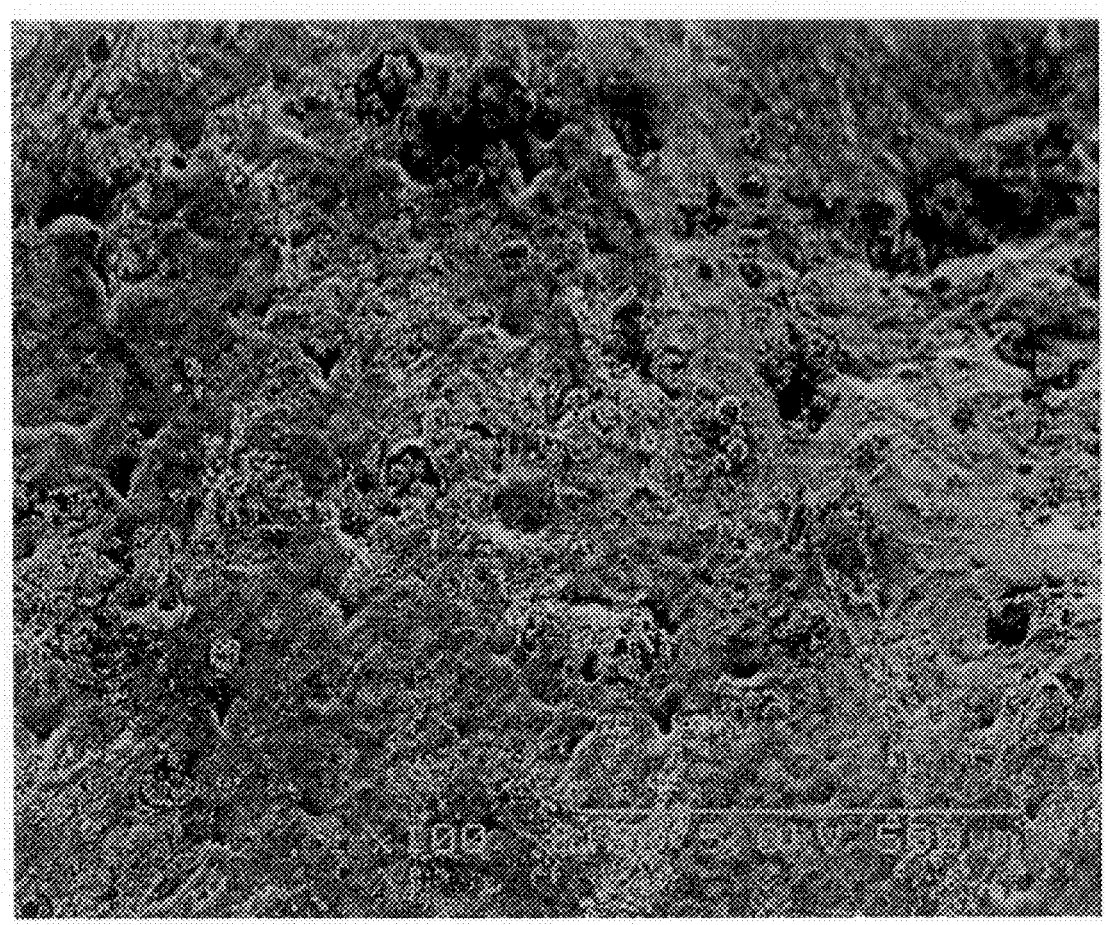
Figure 70B:
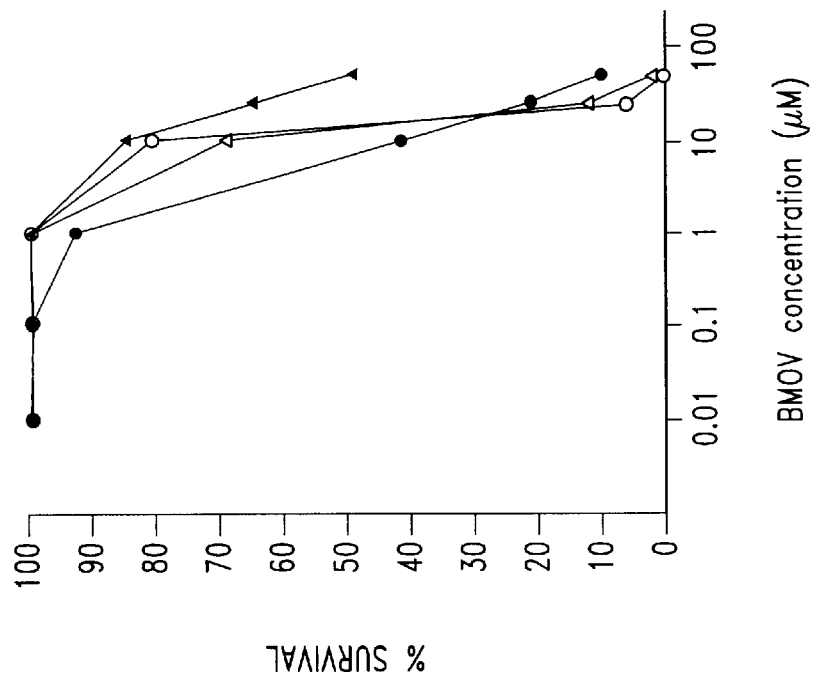
FIGS. 70A and 70B are two graphs which show the effect of increasing concentration of BMOV on cell survival using 1 hour exposure of cells to BMOV (70A), or, continuous exposure to BMOV (70B). Cells described by (○), HT-29 colon cells; (●), MCF-7 breast cells; (Δ), Skmes-1 non-small lung cells and (σ) normal bone marrow cells.
Figure 70A:
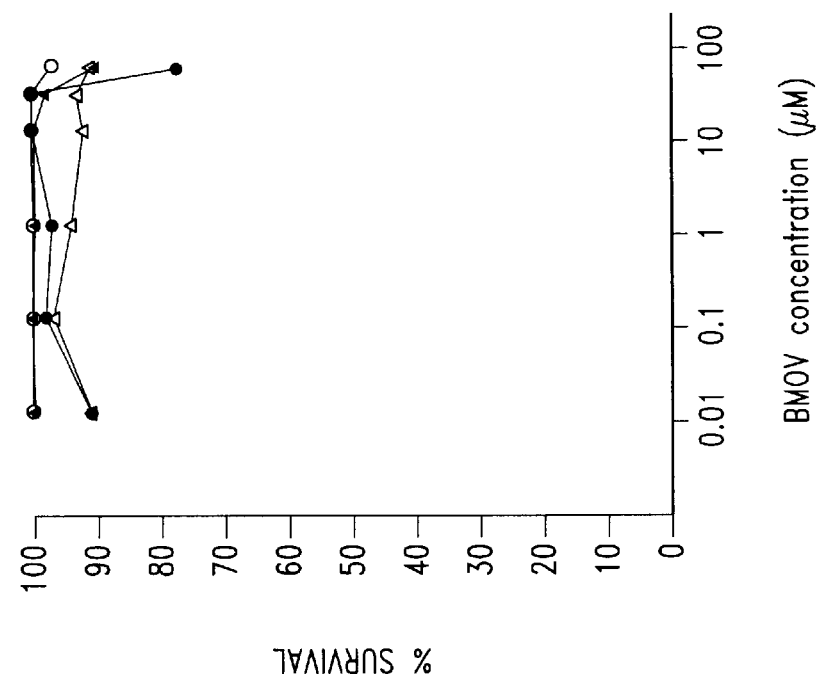
Figure 73A:
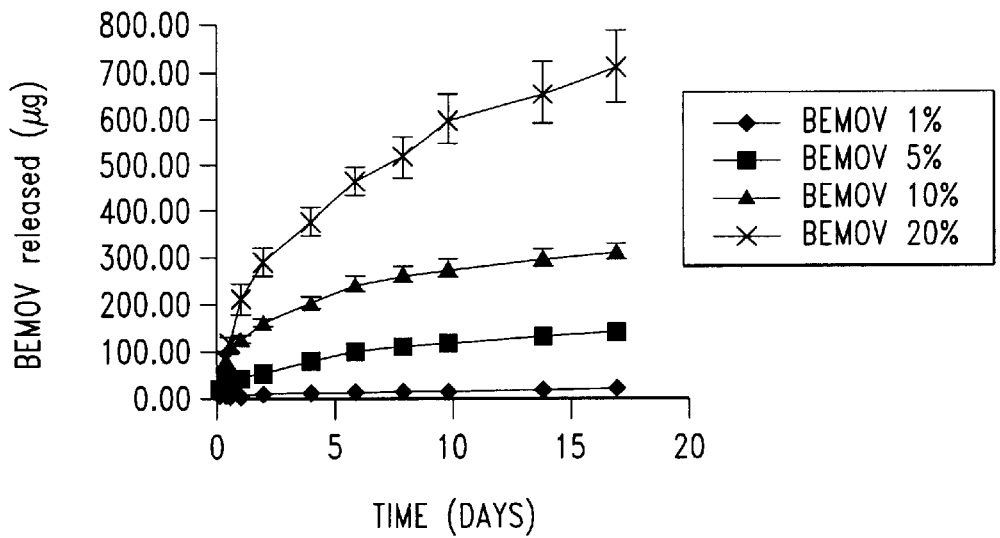
FIGS. 73A and 73B are two graphs.
Figure 73B:
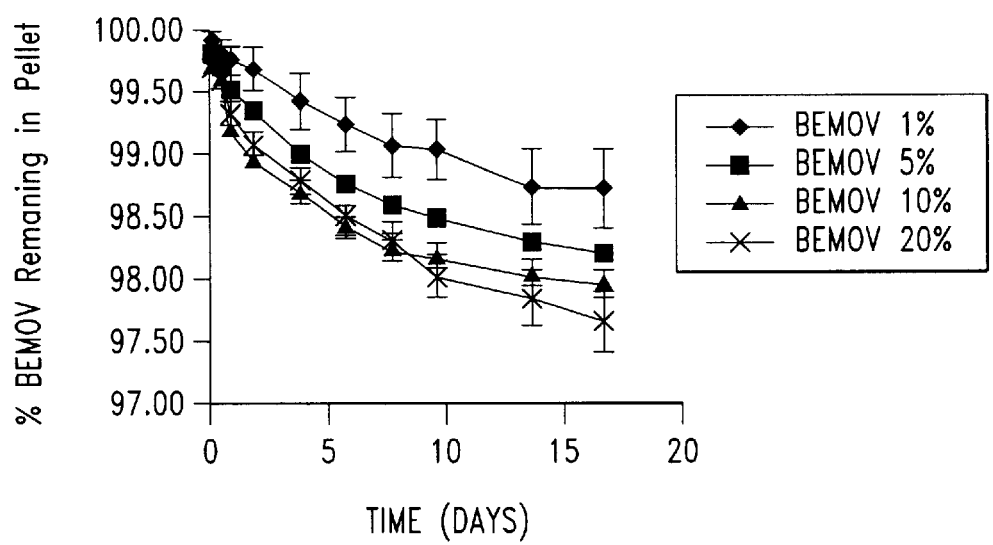
Figure 74A:
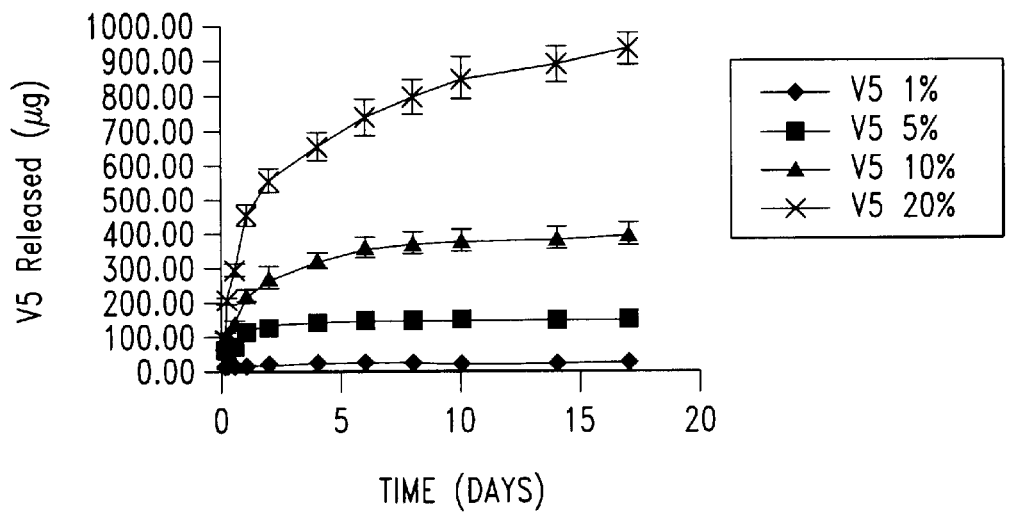
FIGS. 74A and 74B are two graphs.
Figure 74B:
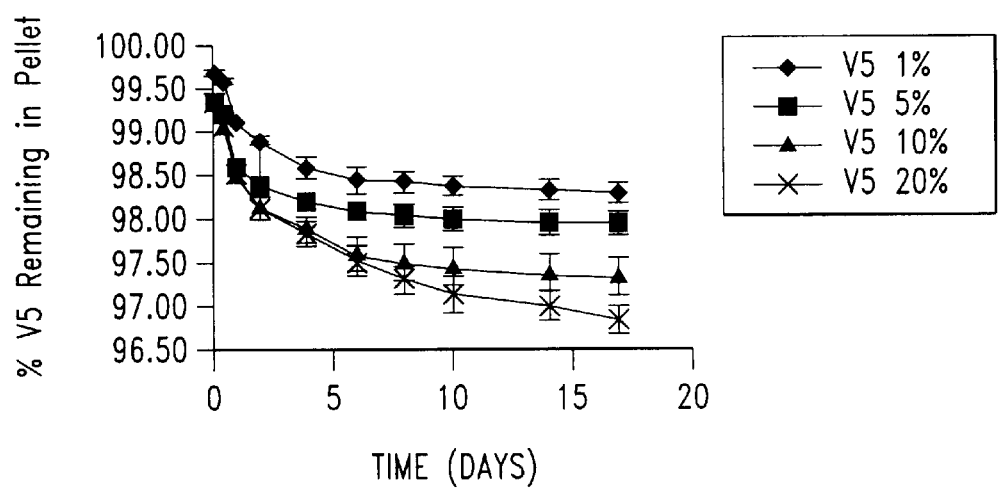
Figure 75A:
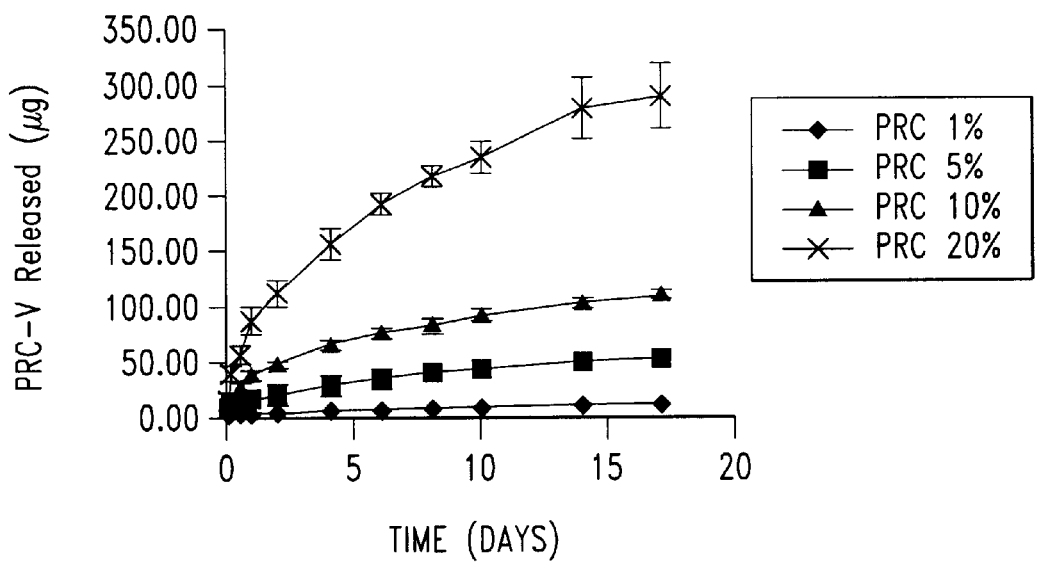
FIGS. 75A and 75B are two graphs.
Figure 75B:
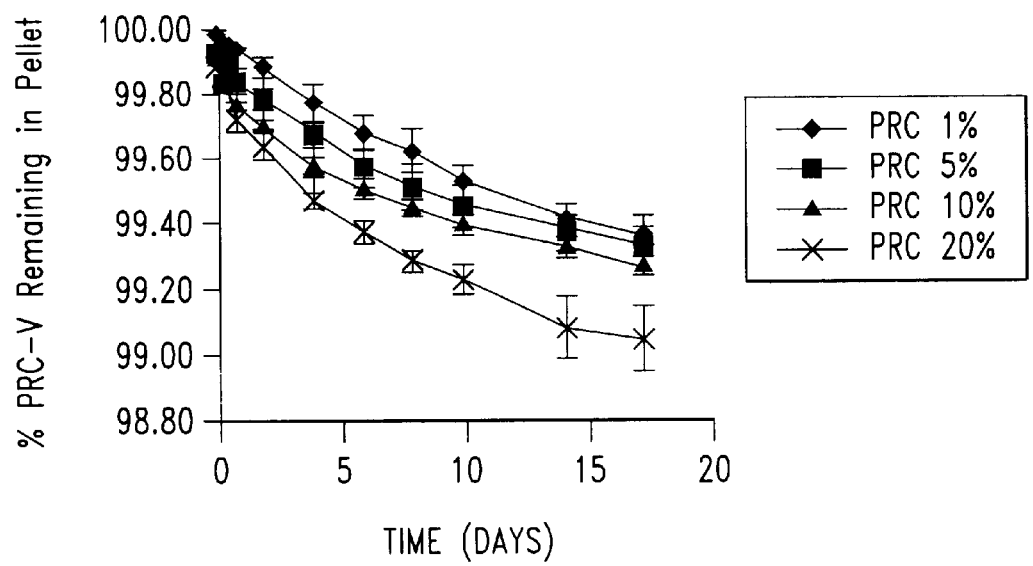
Figure 76A:
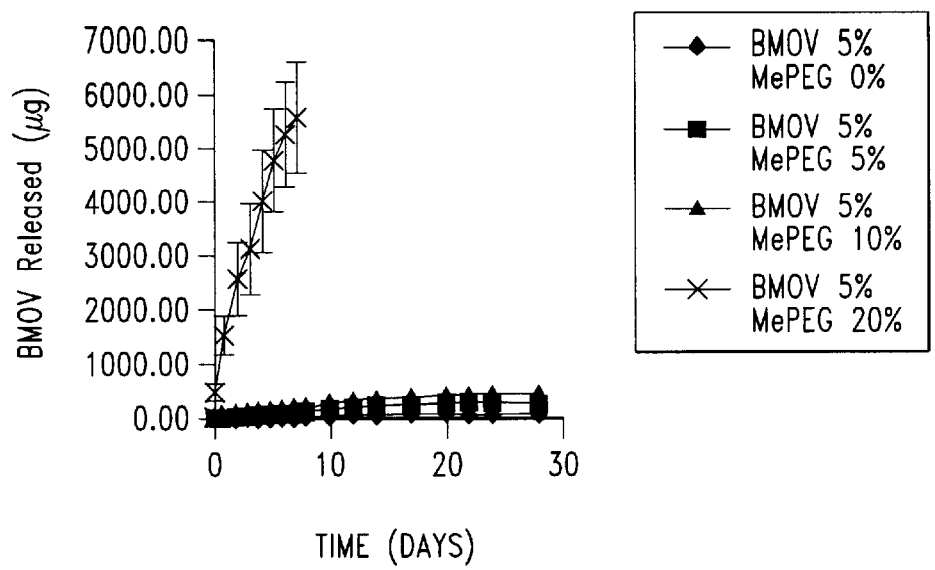
FIGS. 76A, 76B, 76C and 76D are a series of graphs which show the effect of loading different concentrations of MePEG in PCL thermopaste (150 mg pellet) with 5% BMOV (76A), 10% BMOV (76B), 15% BMOV (76C), and 20% BMOV (76D) on the time course of BMOV released into 15 mL PBS/ALB.
Figure 76B:
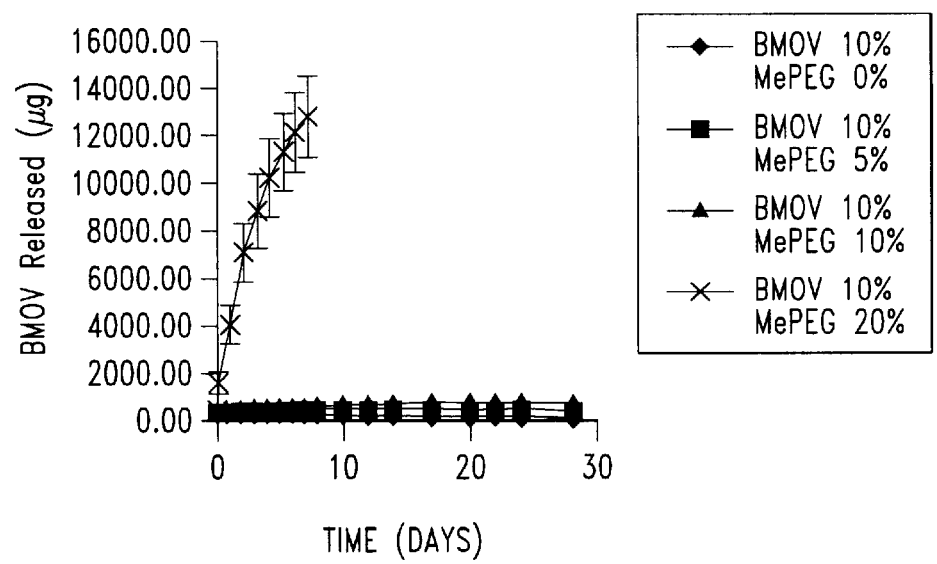
Figure 76C:
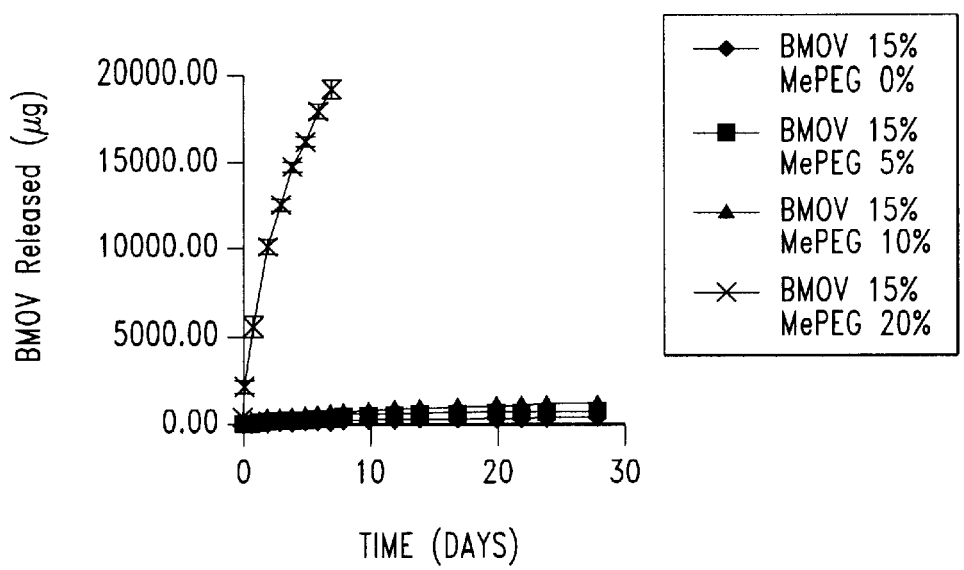
Figure 76D:
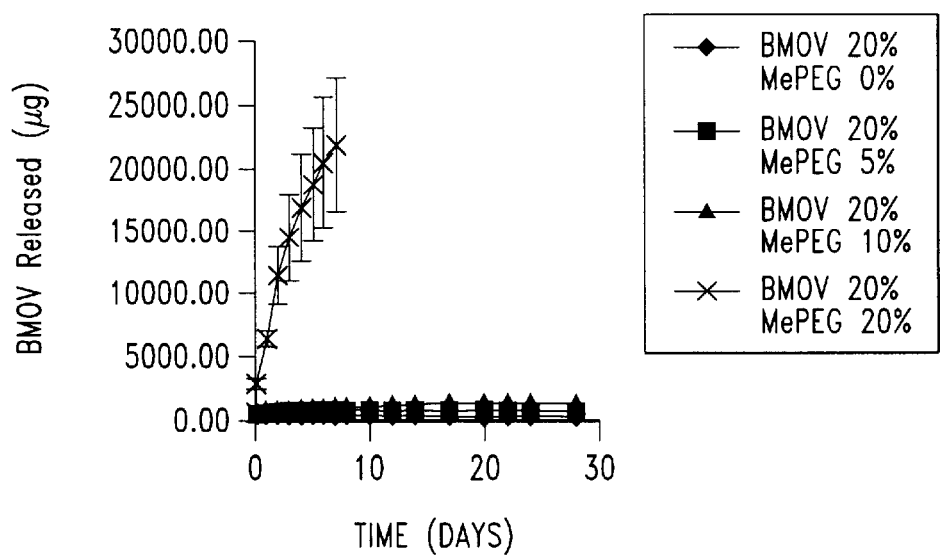
Figure 77A:
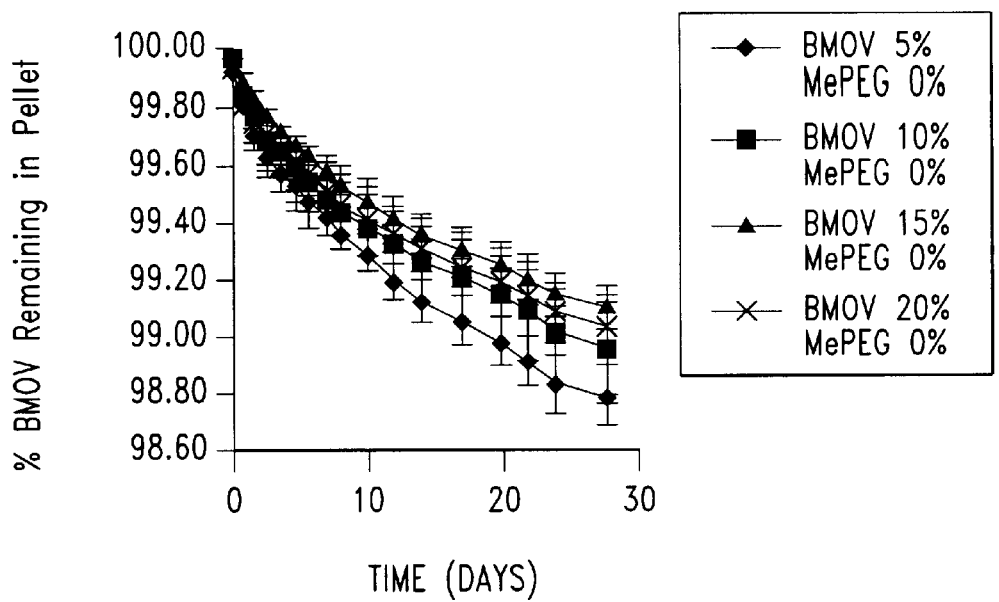
FIGS. 77A, 77B, 77C and 77D are a series of graphs which show the effect of loading different concentrations of MePEG in PCL thermopaste (150 mg pellet) with 0% MePEG (77A), 5% MePEG (77B), 10% MePEG (77C), and 15% MePEG (77D) on the time course of BMOV released into 15 mL PBS/ALB. Drug release is expressed as the % of BMOV remaining in the pellet.
Figure 77B:
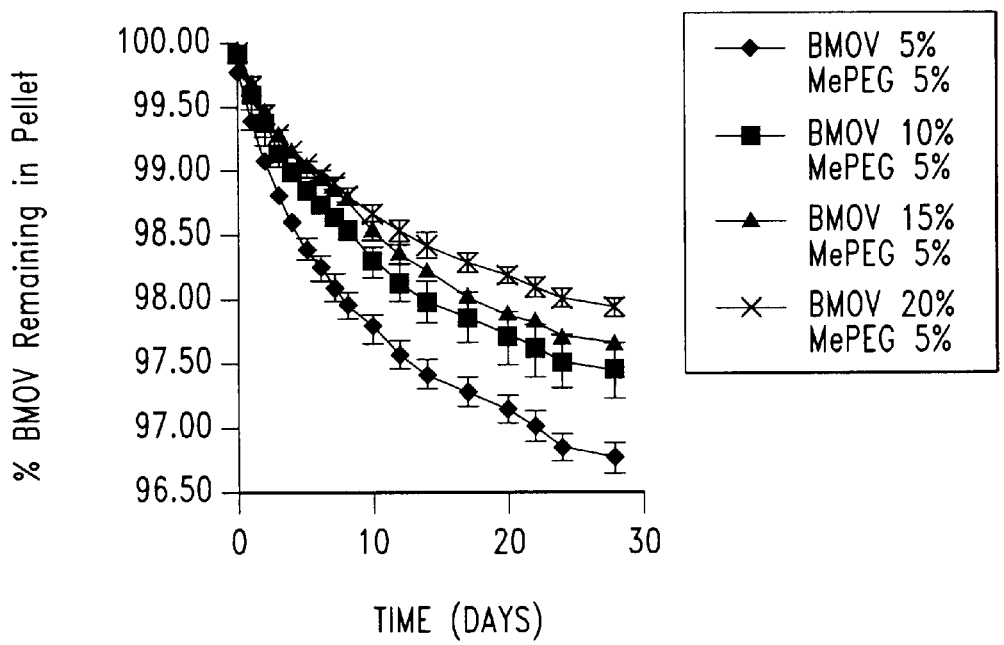
Figure 77C:
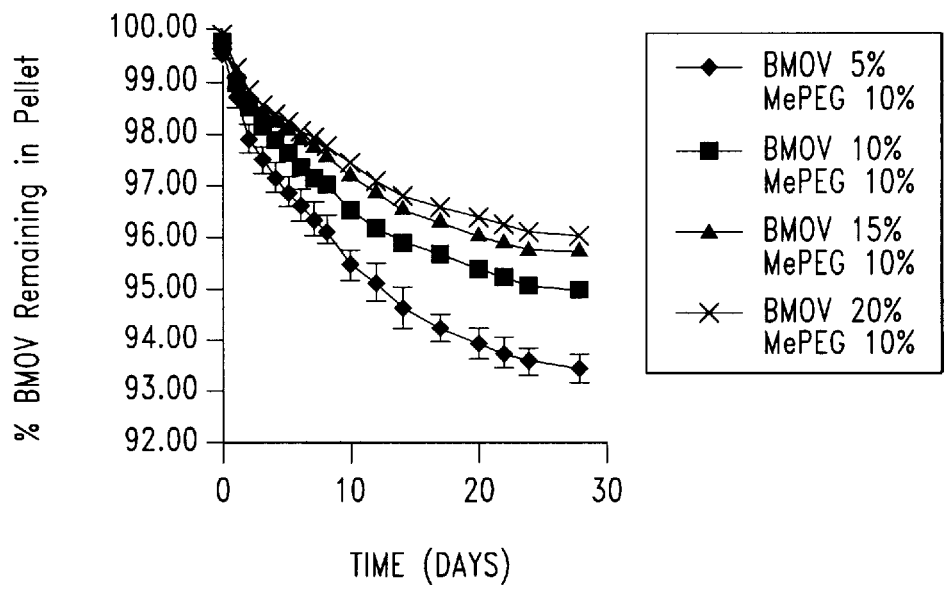
Figure 77D:
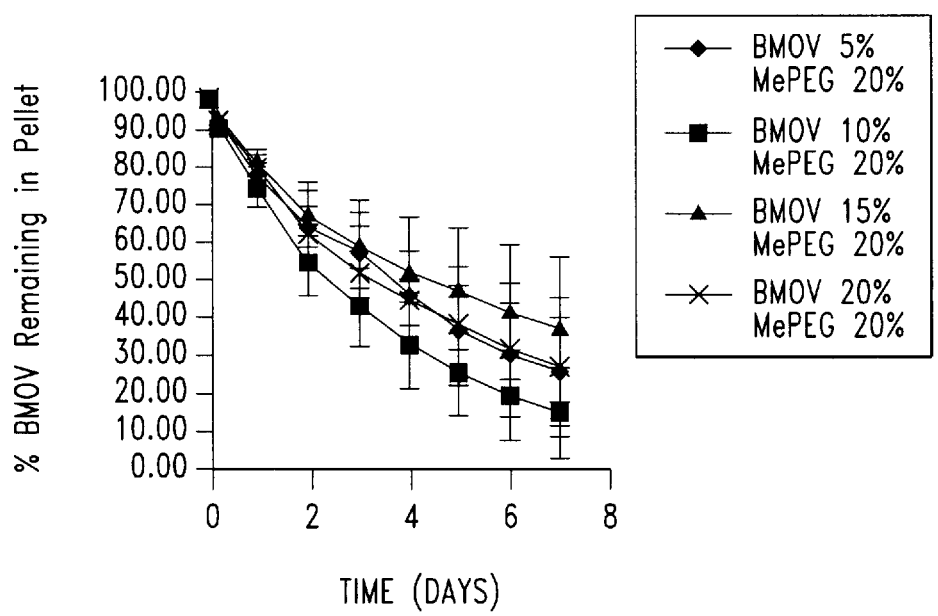

FIG. 69A shows the morphology of the BMOV crystals under high magnification. FIG. 69B and 69C show the morphology of the polymer-drug matrices both before and after the two month drug release study in aqueous buffer. The PCL-BMOV matrices for 15%, 20% and 30% BMOV loadings were typically smooth on their external faces before the release study and a representative SEM is shown in FIG. 69B. Following incubation in the aqueous buffer for two months the external surfaces were rough and pitted.

E. Discussion

This compound was found to release very slowly from the PCL matrix with almost ideal release characteristics for the maintenance of sustained concentrations of vanadium. These characteristics included only a small burst effect of drug release in the first few days followed by almost zero order release kinetics at most drug loadings (FIG. 67). BMOV is less water soluble than vanadyl sulphate or sodium orthovanadate and the hydrophobicity of the molecule probably increases the affinity of the BMOV molecules for the hydrophobic PCL matrix and decreases the rate of drug release into an aqueous incubation medium.

The addition of 20% MEPEG to PCL has been shown to improve the thermal flow properties of the paste by reducing the viscosity of the matrix and the temperature at which the polymer solidifies. These properties are important in applying the paste to a peritubular tumor site as better coverage of the site is obtained under these conditions. The addition of MEPEG to the BMOV-PCL paste matrix has been shown to enhance the release rates of BMOV in vitro (FIG. 68) at all BMOV loading concentrations (5% to 20%) relative to the release rates from BMOV-PCL (no MEPEG) (FIG. 67). The 5% BMOV loaded PCL-MEPEG paste was shown to release between 500 an 1000 ug of BMOV per day (which was similar to the release rate from 35% BMOV loaded PCL).

Example 28

In Vitro and In Vivo Efficacy of Bis(Maltolato) oxoVanadium Loaded Thermopaste

BMOV loaded polymeric PCL thermopaste was prepared as described previously and was tested for its efficacy against tumor cell lines both in vitro and in vivo.

A. Human Tumor Cell Lines The HT-29 colon, MCF-7 breast and SKMES1 non-small cell lung human tumor cell lines were obtained from the American Type Culture Collection. The HT-29 colon cell line was cultured in RPMI 1640 with 10% heat inactivated fetal bovine serum (HIFBS), the MCF-7 breast cell line in Iscove's modified Eagles medium with 5% HIFBS plus 10–9 M insulin, and the SKMES1 lung cell line in Eagle's minimal essential medium with 10% non-heat inactivated FBS.

B. Normal Human Marrow Cells

Normal human bone marrow (histologically negative for tumor cells) was obtained from patients who were to have bone marrow transplants for their solid tumors but died before the marrow was used. After centrifugation, the buffy coat was removed and cells were treated with lysis buffer and washed twice with and then resuspended in RPMI 1640 with 20% HIFBS. The cells were drawn through a 25 g needle and counted.

C. Radiometric (Bactec) System

The Bactec system (Johnston Laboratories, Towson, Md.) is based on a clinical instrument which was developed to detect bacteria in blood cultures and has been used to screen for new antineoplastic agents. This radiometric system is a rapid, semiautomated system which utilizes the inhibition of the conversion of $^{14}C$ glucose to $^{14}C^4CO_2$ as an index of cytotoxicity. The Bactec machine automatically flushes out the $^{14}CO_2$ into an ion chamber where the signal of the radiolabelled $CO_2$ is changed into a proportional electrical signal or growth index value on a scale of 1 to 1000. For the continuous exposure, the tumor cells or normal marrow cells were added to 2 ml of the appropriate growth medium containing 2 uC of $^{14}C$ glucose plus BMOV at final concentrations of 0.01,0.1,1,10,25 and 50 uM and injected into 20 ml rubber stoppered serum vials which contained a mixture of 5% $CO_2$ and air, and incubated at 37° C. for 24 days. For one more hour exposure, cells and BMOV at the same final concentrations were incubated in 15 ml polypropylene conicals in a 37° C. water bath for one hour. The cells were then centrifuged and washed in medium, then resuspended in 2 ml of the appropriate growth medium containing 2 uCi of $^{14}C$ glucose and injected into 20 ml rubber stoppered serum vials which contained a mixture of 5% $CO_2$ and air, and incubated at 37° C. for 24 days at days 6, 9 and 12 for tumor cell lines and days 6, 15 and 24 for marrow cells the vials were removed and inserted into the Bactec instrument for determination of the amount of $^{14}CO_2$ produced by the cells upon metabolizing the $^{14}C$ glucose. The growth index values of BMOV treated cells were compared to the growth index values of non-treated cells and the % survival compared to untreated controls was calculated.

D. Resected Tumor Studies

Seven week old, male C3H/HeJ mice were used in these studies. RIF-1 (murine radiation induced fibrosarcoma) cells were cultured in alpha-MEM media containing 10% FBS (Gibco Canada). Cells were suspended in 1% Hanks buffered salt solution (HBSS pH 7.4) (Gibco Canada) at a concentration of $1 \times 10^7$ cells/ml. One hundred microliters of these cells ($1 \times 10^6$ cells) was injected into the right flank of each mouse. The tumors were allowed to grow for 5 days (at which time the tumors ranged from 6 to 8 mm in diameter). At day 5 the mice were anesthetized with a Ketamine:Rompom (70 mg/kg:10 mg/kg) combination (0.02 ml/g). An incision was made 5 mm from the tumor edge and approximately 90% of each tumor was removed and 150 mg of molten (50° C.) PCL-BMOV or PCL alone (control) was extruded from a 500 ul syringe onto the entire surface of the resected tumor site. The PCL solidified within 30 seconds and the area was closed with 5-0 prolene sutures. The mice were examined on days 4,5,6 and 7. On each day tumors were measured (long and short diameters) and images taken. When the tumors reached a maximum diameter of 9 mm the mice were sacrificed and the tumor area was excised for future histological studies.

Results are shown in FIG. 72.

E. Tumor Inhibition Studies

The MDAY-D2 haematopoetic cell line (obtained from Dr. J Dennis, Mount Sinai Hospital, Toronto) was plated or grown in suspension in DMEM containing 5% FBS (Gibco Canada). Each mouse was injected subcutaneously on the posterior lateral side with $4 \times 10^5$ cells in 100 ul of PBS. After 5 days tumor growth, 150 mg of the PCL or PCL-BMOV molten paste was implanted in an area adjacent to the tumor site of each mouse. After 15 days the mice were sacrificed, weighed and the tumors dissected and weighed. Results are shown in FIG. 71.

F. Results and Discussion

Against the normal human bone marrow cells, the one hour exposure BMOV also had very little effect, even at a concentration of 50 $\mu M$. Using a continuous exposure, the effect of BMOV on the marrow cells was still not very pronounced, with sensitivity (49% survival) observed at the 50 $\mu M$ concentration only. Thus the BMOV compound did not appear to be very myleosuppressive at the concentrations and exposures tested.

In this study, the antineoplastic effect of BMOV have been shown in vitro against three human cancer cell lines under conditions that ensure continuous exposure to the drug. However, in vivo, the efficacy may depend on the continuous exposure of the tumor cells to BMOV. The main objective of this study was to design and test (in vivo) a biodegradable polymeric delivery system that might provide a continuous supply of vanadium (BMOV form) at low concentrations.

In vivo experiments showed that single administration of PCL-BMOV paste subcutaneously inhibited MDAY D2 tumor growth. FIG. 71 shows the data for tumor weights from control mice (PCL-no BMOV) and mice treated with 25%, 30% and 35% BMOV loaded PCL. There was a 54% inhibition of tumor growth for 25% BMOV loaded PCL (significant at p<0.05). The 30% and 35% BMOV loadings produced 76% and 80% inhibition of tumor growth respectively and one of the six mice in the 35% BMOV group showed complete eradication of the tumor.

Interestingly, the in vivo drug release profiles showed that paste consisting of 25% and 30% BMOV released approximately 500 ug of BMOV per day which has previously shown efficacy. However, 35% BMOV loaded PCL paste which was the most effective in reducing tumor growth, released approximately twice this amount of drug in vitro. These data demonstrate that sustained release of low quantities of vanadium compounds will be an equally or more effective antineoplastic regime compared to a daily vanadate administration regime.

Although, PCL-BMOV paste was equally effective in inhibiting tumor growth, the mice showed no signs of stress and weight loss. Increased stress and weight loss commonly observed with daily injections of high doses of vanadate is most likely related to toxicity induced by the high vanadate levels in the plasma immediately following administration. Using PCL-BMOV paste to provide sustained release of vanadate for long periods may reduce large fluctuations in plasma vanadate concentrations and prevent vanadate induced toxicity. These data are consistent with our hypothesis that a slow sustained release of BMOV is equally or more effective in reducing tumor growth and prevents vanadate induced toxicity.

Example 29

Effect of BMOV Microspheres on Tumor Growth in Mice

The objective of this study was to test the ability of BMOV-loaded PLLA microspheres (20%) to regress tumor growth in mice.

Twenty of twenty-four mice were injected subcutaneously with 100 ml of MDAY-D2 cells with density of $10 \times 10^6$/ml. On day 6 the mice were divided into 6 groups. Group 1, empty control, group 2, tumor control, group 3, were injected subcutaneously with 0.25 mg/100 ul BMOV, twice a day. Group 4 was injected IP with 20 mg PLLA microspheres containing 5 mg of BMOV. Group 5 was injected IP with 10 mg of BMOV microspheres on day 6 and day 9 respectively. Group 6 was injected intramuscularly with 10 mg of BMOV microspheres on day 6 and day 9. On day 16, the mice were sacrificed and tumors were dissected.

The results of these experiments are shown in Tables VI and VII below.

TABLE VI

Body weights of mice in control and treated groups

| | Control | Tumor Control | BMOV Solution 0.25 mg × 1 | BMOV beads, IP 5 mg/once | BMOV beads, IP 2 mg × 2 | BMOV beads, IM 2 mg × 2 |
|---|---|---|---|---|---|---|
| 1 | 19 | 23.9 | 18 | 18.8 | 19.2 | 18.2 |
| 2 | 20.2 | 21 | 17.8 | 19.3 | 18.9 | 22.6 |
| 3 | 18.4 | 20 | 18.4 | 21.6 | 17.2 | 20.1 |
| 4 | 22.2 | 24.1 | 17.3 | | 19.1 | 22.2 |
| Average | 19.95 | 22.25 | 17.87 | 19.9 | 18.6 | 20.78 |

TABLE VII

Tumor weight of control and treated groups

| | Tumor control | BMOV solution s.c. | BMOV beads, IP 5 mg/once | BMOV beads, IP 2 mg × 2 | BMOV beads, Im 2 mg × 2 |
|---|---|---|---|---|---|
| 1 | 3.8 | 0.4 | 0.2 | 0.12 | 2.0 |
| 2 | 1.2 | 0.12 | 0.9 | 0.4 | 3.3 |
| 3 | 1.3 | 0.07 | 0.26 | 0.3 | 1.1 |
| 4 | 1.5 | 0.04 | died | 1.2 | 1.6 |
| Average | 1.95 | 0.15 | 0.45 | 0.50 | 1.6 |

Example 30

Controlled-release Polymeric Drug Delivery System: Comparative Study of the In Vitro Drug Release Profiles of Organic Vanadium Complexes From Poly (ε-caprolactone) (PCL) Thermopastes and PCL-methoxypolyethylene Glycol (PCL-MePEG) Thermopastes This study was conducted to investigate the encapsulation and in vitro release kinetics of the four organic complex forms of vanadium (BMOV, BEMOV, V5, PRC-V) in poly (ε-caprolactone) (PCL) thermopastes and/or PCL-methoxypolyethylene glycol (PCL-MePEG) thermopastes.

A. Method

Quantitative analysis (UV/VIS spectrophometric analysis) was done with different concentrations of vanadium solutions to obtain the wavelengths of peak absorbance and the calibration equations. Solubility of vanadium was studies in 10 mM phosphate buffered saline with albumin (PBS/ALB) (pH 7.4). 1%, 5%, 10%, and 20% (% vanadium complex in PCL) of each organic complex form of vanadium were encapsulated in a biodegradable polymer PCL and/or in blends of PLC with MePEG (MW 350) to produce a polymeric drug delivery product called a "thermopaste". In vitro release studies of the various forms of vanadium from thermopastes were carried out at 37° C. in PBS/ALB with vanadium release measured by UV/VIS absorbance spectroscopy.

B. Results

Results are shown in FIGS. 73 to 77. Briefly, the peak absorbance of BMOV, BEMOV, and V5 occurred at 276 nm and that of PRC-V was at 266 nm. The rate and extent of solubility of each form of vanadium was in the order of V5>BMOV & BEMOV>PRC-V. In vitro release studies showed that the rate of drug released from the thermopastes increased with (1) increasing drug solubility, (2) increasing drug concentration, and (3) increasing amount of MePEG incorporated into the thermopastes.

C. Conclusion

A controlled dose of vanadium may be released from PCL thermopastes by using a different form of vanadium (as the drug), by changing the % loading of the particular form of vanadium in the PCL, or by including MePEG into the PCL. Whereas changing the % loading of a particular form of vanadium may control the release rate in the short term, the delivery of a controlled dose may involve the implantation of a huge (and potentially toxic) depot of the drug (in PCL) into the animal. Therefore, the use of an alternative form of vanadium or the inclusion of MePEG into the PCL may offer an alternative method delivering a controlled dose of vanadium.

Example 31

Encapsulation of Camptothecin Into PCL Thermopaste and Anti-angiogenesis Analysis A. Incorporation of Camptothecin into PCL Camptothecin was ground with a pestle and mortar to reduce the particle size to below 5 microns. It was then mixed as a dry powder with polycaprolactone (molecular wt. 18,000 Birmingham Polymers, AL USA). The mixture is heated to 65° C. for 5 minutes and the molten polymer/agent mixture is stirred into a smooth paste for 5 minutes. The molten paste is then taken into a 1 ml syringe and extruded to form 3 mg pellets. These pellets were then placed onto the CAM to assess their anti-angiogenic properties.

B. Results

Camptothecin-loaded thermopaste was effective at inhibiting angiogenesis when compared to control PCL pellets. At 5% drug loading, 4/5 of the CAMs tested showed potent angiogenesis inhibition. In addition, at 1% and 0.25% loading, ⅔ and ¾ of the CAMs showed angiogenesis inhibition respectively. Therefore, it is evident from these results that camptothecin was sufficiently released from the PCL thermopaste and it has therapeutic anti-angiogenic efficacy.

Example 32

Manufacture of S-phosphonate-loaded Thermopaste

In this study, we demonstrated that s-phosphonate, an ether lipid with antineoplastic activity, was successfully incorporated into PCL thermopaste and showed efficacy in the CAM assay.

A. Manufacture of S-phosphonate Loaded Paste

Polycaprolactone (Birmingham Polymers, Birmingham, Ala.) and s-phosphonate were levigated in the appropriate proportions at 55° C. for 2 minutes. The molten mixture was then pipetted into 3 mg semi-spherical pellets and allowed to set at 4° C.

B. CAM Bioassay

Fertilized, domestic chick embryos (Fitzsimmons Consulting & Research Services Ltd., B.C.) were incubated for 4 days and then windowed. Briefly, a small bole (measuring approximately 2 cm in diameter) was formed by removing the shell and inner shell membrane from the blunt end of the egg (air space site) and then the exposed area was sealed with sterilized Parafilm wax. The egg was then placed into an incubator at 37° C. for an additional 2 days with the window upright. On day 6 of incubation, 3 mg pellets of s-phosphonate-loaded polymer or control (no drug) polymer was placed on the surface of the growing CAM vessels. After a 2 day exposure (day 8 of incubation), the vasculature was examined using a stereomicroscope fitted with a Contax camera system. To increase the contrast of the vessels and to mask any background information, the CAM was injected with 1 ml of intralipid solution (Abbott Laboratories) prior to imaging.

C. Results

PCL pellets loaded with s-phosphonate at 0%, 1%, 2%, 4% and 8% induced a dose-dependent anti-angiogenic reaction in the CAM. The anti-angiogenic reaction is characterized by the absence of blood vessels in the region directly below the s-phosphonate loaded pellet. The normal growth of the dense capillary network seen in the control CAM has clearly been inhibited in the s-phosphonate treated CAM's. At higher concentrations (4% and 8%), the treated CAMs were structurally altered in the vicinity of the drug/polymer pellet. This alteration included a pronounced thickening of the CAM immediately adjacent to the s-phosphonate/polymer pellet and membrane thinning subjacent to the pellet. In all of the CAMs treated with s-phosphonate, an avascular zone was apparent after a two day exposure; this was defined as an area devoid of a capillary network measuring approximately 3 mm in area.

Example 33

Encapsulation of Tyrosine Kinase Inhibitors into PCL Thermopaste and Analysis Using the CAM Assay Tyrosine kinase inhibitors were ground with a pestle and mortar to reduce the particle size to below 5 microns. They were then mixed as a dry powder with polycaprolactone (molecular wt. 18000 Birmingham Polymers, AL USA). The mixture is heated to 65° C. for 5 minutes and the molten polymer/agent mixture is stirred into a smooth paste for 5 minutes. The molten paste is then taken into a 1 ml syringe, and extruded to form 3 mg pellets. These pellets were then tested in the CAM assay. The tyrosine kinase inhibitors that were tested in the CAM assay include, lavendustine-c, erbstatin, herbimysin, and genistein. When comparing the anti-angiogenic inhibition effects of these agents, herbimysin (2% in PCL) was the most potent inducing an avascular zone in 4/4 of the CAMs tested.

Example 34

Encapsulation of Vinca Alkaloids into PCL Thermopaste and Analysis Using the CAM Assay A. Incorporation of Inhibitors into PCL Thermopaste Vinca alkaloids (vinblastine and vincristine) were ground with a pestle and mortar to reduce the particle size to below 5 microns. They were then mixed as a dry powder with polycaprolactone (molecular wt. 18000 Birmingham Polymers, AL USA). The mixture is heated to 65° C. for 5 minutes and the molten polymer/agent mixture is stirred into a smooth paste for 5 minutes. The molten paste is then taken into a 1 ml syringe and extruded to form 3 mg pellets. These pellets were then tested in the CAM assay.

B. Results

When testing the formulations on the CAM, it was evident that the agents were being released from the PCL pellet in sufficient amounts to induce a biological effect. Both vinblastine and vincristine induced anti-angiogenic effects in the CAM assay when compared to control PCL thermopaste pellets.

At concentrations of 0.5% and 0.1% drug loading, vincristine induced angiogenesiss inhibition in all of the CAMs tested. When concentrations exceeding 2% were tested, toxic drug levels were achieved and unexpected embryonic death occurred.

Vinblastine was also effective in inhibiting angiogenesis on the CAM at concentrations of 0.25%, 0.5% and 1%. However, at concentrations exceeding 2%, vinblastine was also toxic to the embryo.

Example 35

Bioadhesive Microspheres

A. Preparation of Bioadhesive Microspheres

Microspheres were made from 100 kg/mol PLLA with a particle diameter range of 10–60 μm. The microspheres were incubated in a sodium hydroxide solution to produce carboxylic acid groups on the surface by hydrolysis of the polyester. The reaction was characterized with respect to sodium hydroxide concentration and incubation time by measuring surface charge. The reaction reached completion after 45 minutes of incubation in 0.1 M sodium hydroxide. Following base treatment, the microspheres were coated with dimethylaminoproylcarbodiimide (DEC), a cross-linking agent by suspending the microspheres in an alcoholic solution of DEC and allowing the mixture to dry into a dispersible powder. The weight ratio of microspheres to DEC was 9:1. After the microspheres ere dried, they were dispersed with stirring into a 2% w/v solution of poly (acrylic acid) and the DEC allowed to react with PAA to produce a water insoluble network of cross-linked PAA on the microspheres surface. Scanning electron microscopy was used to confirm the presence of PAA on the surface of the microspheres.

Differential scanning calorimetry of the microspheres before and after treatment with base revealed that no changes in bulk thermal properties (Tg, melting, and degree of crystallinity) were observed by scanning electron microscopy.

B. In Vitro Paclitaxel Release Rates

Paclitaxel loaded microspheres, (10% and 30% w/w loadings) with the same particle diameter size range were manufactured and in vitro release profiles for 10 days release in phosphate buffered saline. Release was proportional to drug loading, with 400 μg of Paclitaxel released from 5 mg of 30% loaded microspheres in 10 days and 150 μg released from 10% loaded microspheres in the same period. The efficiency of encapsulation was about 80%. The Paclitaxel loaded microspheres were incubated in 0.1M sodium hydroxide for 45 minutes and the zeta potential measured before and after incubation in sodium hydroxide. The surface charge of Paclitaxel loaded microspheres was lower than microspheres with no Paclitaxel both before and after treatment with base.

C. Preparation and In Vitro Evaluation of PLLA Coated with Either Poly-lysine or Fibronectin.

Figure 78A:
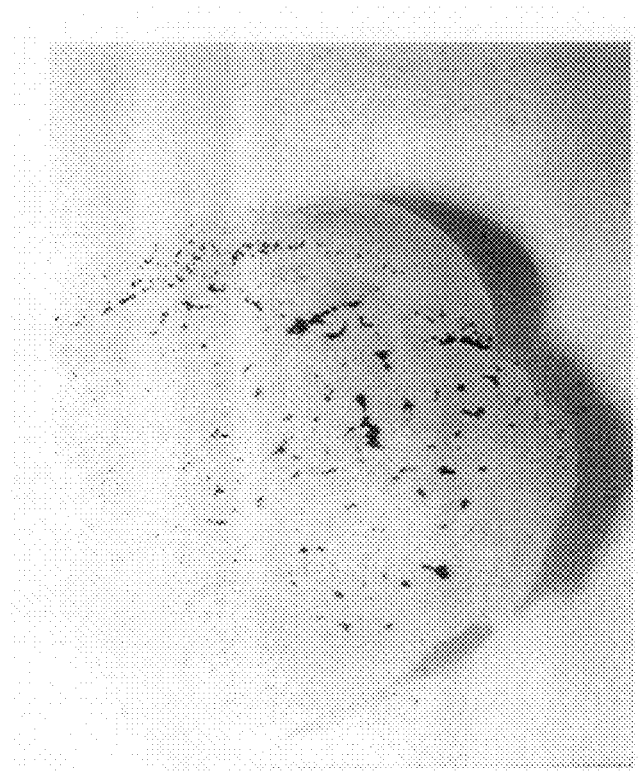
FIGS. 78A and 78B are photographs of fibronectin coated PLLA microspheres on bladder tissue (78A), and poly (L-lysine) microspheres on bladder tissue.
Figure 78B:

PLLA microspheres were prepared containing 1% sudan black (to color the microspheres). These spheres were suspended in a 2% (w/volume) solution of either poly-lysine (Sigma chemicals—Hydrobromell form) or Fibronectin (Sigma) for 10 minutes. The microspheres were wasted in buffer once and placed on the inner surface of freshly prepared bladders from rats. The bladder were left for 10 minutes then washed three times in buffer. Residual (bound) microspheres were present on the bladder wall after the process therefore showing bioadhesion had occurred (FIGS. 78A and 78B) for both Fibronectin and poly-1-lysine coated microspheres.

Example 36

Synthesis of Poly(N-isopropylacrylamide)

Polyacrylamide and its derivatives may be readily synthesized through free radical polymerization and irradiation induced polymerization. The following is an example of synthesizing poly(N-isopropylacrylamide), wherein the monomer N-isopropylacrylamide is purified by recrystallization from an organic solvent such as hexane and toluene.

Briefly, N-isopropylacrylamide is dissolved in toluene at a temperature such as 60° C. This solution is cooled down to a lower temperature (e.g. 4° C.) to allow the recrystallization of the monomer. The monomer is then collected by filtration and dried under vacuum. For synthesis, the purified monomer (20 g) is dissolved in distilled water (180 ml) in a round bottomed glass flask. The solution is purged with nitrogen for 30 minutes to replace dissolved oxygen. The temperature is then raised to 65° C. and a small amount (0.1 g) of initiator such as ammonium persulfate and 2,2'-azobis-isobutyronitrile is added to start the polymerization. The polymerization is completed within 10 hours and is under the protection of nitrogen and stirring. Finally, poly(N-isopropylacrylamide) is precipitated by adding ethanol. The polymer is dried and stored.

Example 37

Synthesis of Poly(Acrylic Acid) Derivatives

Poly(acrylic acid) and its derivatives can be synthesized through free radical polymerization and irradiation induced polymerization. The following is an example of synthesizing poly(acrylic acid), wherein monomer acrylic acid is purified by distillation (e.g., 40° C.) under a reduced pressure (e.g., 10 mmHg).

Briefly, the purified monomer (20 g) is dissolved in dioxane (180 ml) in a round bottomed glass flask. The solution is purged with nitrogen for 30 minutes to replace the dissolved oxygen. The temperature is then raised to 65° C. and a small amount (0.1 g) of initiator 2,2'-azobis-isobutyronitrile is added to start the polymerization. The polymerization is completed within 24 hours and is under the protection of nitrogen and stirring. Finally, poly(acrylic acid) is precipitated by adding n-hexane. The polymer is dried and stored.

Example 38

Preparation of Micellular Paclitaxel

A. Synthesis of Diblock Copolymer of PDLLA-MePEG

Monomers of methoxy polyethylene glycol (e.g., M.W. 2000, 150 g) and DL-lactide (100 g) are added to a round bottomed flask and the temperature is raised to 130–150° C. After the melting of the monomers, 0.6 g catalyst stannous octoate is added. The polymerization is finished within 0 hours. The reaction is under protection of $N_2$ and with stirring.

B. Preparation of Micellar Paclitaxel

The PDLLA-MePEG copolymer is dissolved in acetonitrile or 50:50 ethanol:acetone (polymer conc.<40%). The polymer solution is centrifuged (14000 rpm) for 5 min. The supernatant (insoluble polymer discarded) is transferred to a glass test tube. Paclitaxel is dissolved in acetonitrile or 50:50 ethanol:acetone and is added to the purified polymer solution. After vortex mixing, the solvent is evaporated at 60° C. under a stream of nitrogen (normally takes 2 hours for a typical 40 mg paclitaxel batch). The residual solvent can be removed by applying vacuum and heat. The matrix is heated at about 60° C. until it becomes a transparent gel. Then a certain volume of water (>4 times of matrix weight) is added to the matrix. This is followed immediately by vortex mixing until the solubilization of the paclitaxel/polymer matrix.

C. Preparation of Delivery Systems of Micellar Paclitaxel/Thermogelling Polymers A thermogelling polymer such as poly(N-isopropylacrylamide), is dissolved in distilled water. Separately, water is added to a micellar paclitaxel/polymer matrix, e.g., 10% paclitaxel loaded PDLLA-MePEG 2000-40/60, to form a micellar paclitaxel solution. Both solutions are cooled (e.g., 4° C.) and mixed to form the thermogelling delivery system.

DDM c:\angio\405ins.doc

Example 39

Perivascular Administration of Paclitaxel

WISTAR rats weighing 250–300 g are anesthetized by the intramuscular injection of Innovar (0.33 ml/kg). Once sedated they are then placed under Halothane anesthesia. After general anesthesia is established, fur over the neck region is shaved, the skin clamped and swabbed with betadine. A vertical incision is made over the left carotid artery and the external carotid artery exposed. Two ligatures are placed around the external carotid artery and a transverse arteriotomy is made. A number 2 FRENCH FOGART balloon catheter is then introduced into the carotid artery and passed into the left common carotid artery and the balloon is inflated with saline. The catheter is passed up and down the carotid artery three times. The catheter is then removed and the ligature is tied off on the left external carotid artery.

Paclitaxel (33%) in ethelyne vinyl acetate (EVA) is then injected in a circumferential fashion around the common carotid artery in ten rats. EVA alone is injected around the common carotid artery in ten additional rats. Five rats from each group are sacrificed at 14 days and the final five at 28 days. The rats are observed for weight loss or other signs of systemic illness. After 14 or 28 days the animals are anesthetized and the left carotid artery is exposed in the manner of the initial experiment. The carotid artery is isolated, fixed at 10% buffered formaldehyde and examined for histology.

Example 40

Treatment of Artherosclerosis

A. Atherosclerosis

Atherosclerotic lesions are created in New Zealand white rabbits by diet only. Briefly, New Zealand white rabbits weighing approximately 1.6 kg are placed on a powdered chow supplemented by 0.25% cholesterol by weight. Total plasma cholesterol is measured on a weekly basis by taking samples from a marginal ear vein after an injection of Innovar (0.1 ml/kg) to dilate blood vessels. Samples are mixed with EDTA to achieve a 0.15% concentration in the sample and placed on ice until separation of plasma by low speed centrifugation.

One week after initiation of the full cholesterol diet, the animals are randomized into 3 groups of 10. After anaesthetic induction with Ketamine 35 mg/kg and Xylazine 7 mg/kg, and then general anesthesia via intubation, the fur is shaved and the skin sterilized over the abdomen. A laparotomy is performed and the abdominal aorta isolated. Using a 22 g needle, ethylene vinyl acetate paste, ethylene vinyl acetate paste containing 5% paclitaxel, or ethylene vinyl acetate paste containing 33% paclitaxel is placed in a circumferential manner around the proximal half of the infrarenal abdominal aorta. The distal half of the aorta extending to the aortic bifurcation is not treated. In 10 control rabbits, the infrarenal abdominal aorta is isolated, but nothing is injected around it.

The atherogenic chow is continued for 24 weeks. At that time, the animals are anesthetized with an injection of Ketamine (350 mg/kg) and xylazine (7 mg/kg) intramuscularly and then sacrificed with an intravenous overdose of Euthanol (240 mg/ml; 2 ml/4.5 kg). The animals are then perfusion fixed at 100 mm mercury via the left ventricle by perfusing Hanks' balanced salt solution with 0.15 mmol/liter N-2-hydroxyethylpaparazine-N'-2-ethanesulfonic acid (ph 7.4) containing Heparin (1 IU/ml) for ten minutes followed by dilute Karnovsky's fixative for 15 minutes. The thoracic and abdominal aorta and iliac arteries are removed en bloc and are placed in a similar solution for a further 30 minutes.

Serial thin sections are then performed through the thoracic aorta and particularly through the infrarenal abdominal aorta. Movat, H&E, and Masson stains are performed and histologic analysis made to examined the degree of luminal compromise, the degree of atherosclerotic lesion development, and any perilumenl reaction to the circumferential arterial medications.

Example 41

Treatment of Restenosis

WISTAR rats weighing 250–300 g are anesthetized by the intramuscular injection of innovar (0.33 ml/kg). Once they are sedated they are placed under Halothane anesthesia. After general anesthesia is established, the fur over the neck region is shaved and the skin cleansed with betadine. A vertical incision is made over the left carotid artery and the external carotid artery exposed. Two ligatures are placed around the external carotid artery and a transverse arteriotomy is made between them. A 2 Fr Fogarty balloon catheter is introduced into the external carotid artery and passed into the left common carotid artery and the balloon is inflated with saline. The catheter is passed up and down the carotid artery three times to denude the endothelium. The catheter is removed and the ligatures tied off on the left external carotid artery.

The animals are randomized into groups of 5. Subgroups of 5 rats are control, carrier polymer alone, carrier polymer plus 1, 5, 10, 20, and 33% paclitaxel is delivered. There are two carrier polymers to be investigated; EVA and EVA/PLA blend. The polymer mixture is placed in a circumferential manner around the carotid artery. The wound is then closed. Rats in each group are sacrificed at 14 and 28 days. In the interim, the rats are observed for weight loss or other signs of systemic. After 14 or 28 days, the animals are sacrificed by initial sedation with intramuscular Innovar (0.33 ml/kg). The arteries are then examined for histology.

Example 42

Intimal Hyperplasia Causing Graft Stenosis
A. Animal Studies

General anaesthesia is induced into domestic swine. The neck region is shaved and the skin sterilized with cleansing solution. Vertical incisions are made on each side of the neck and the carotid artery is exposed and 8mm PTFE graft is inserted by 2 end to side anastomoses, the proximal anastomosis on the common carotid artery and the distal anastomosis on the internal carotid artery bilaterally. The intervening bypassed artery is ligated. The animals are randomized into groups of 10 pigs receiving carrier polymer alone, 10 pigs receiving carrier polymer plus 5% paclitaxel, and 10 pigs receiving carrier polymer plus 33% paclitaxel adjacent to each surgical created anastamosis on the left side only. The right sided grafts will serve as a control in each pig. The wounds are closed and the pigs recovered.

A second group of pigs are studied. The grafts are created in a similar manner. No vasoactive agent is placed next to the anastamotic sites at the time of operation. The animals are recovered. Two weeks after the graft has been performed, a second general anaesthetic is administered and the left carotid artery is reexplored. Adjacent to the proximal and distal anastamoses, 10 pigs each receive carrier alone, carrier polymer plus 5% paclitaxel and carrier polymer plus 33% paclitaxel in a circumferential manner adjacent to both proximal and distal anastamoses. The wounds are closed and the pigs recovered. Opposite the right sided graft serves as a control.

At 3 months, all pigs undergo general anesthetic. A cutdown is made on the femoral artery and a pigtail catheter is inserted in the ascending thoracic aorta under fluoroscopic guidance. Arch injection with imaging of the carotid vasculature is performed. Specifically, the degree of stenoses of the proximal and distal grafts and the artery immediately distal to the distal anastamosis of the graft is measured and the % stenosis calculated. If necessary, selective injections of the common carotid arteries are performed.

Five pigs in each group are sacrificed. The animals are then perfusion fixed at 100 mm mercury via the left ventricle by perfusing Hanks' balanced salt solution with 0.1 5 mmol/liter N-2-hydroxyethylpaparazine-N'-2-ethanesulfonic acid (ph 7.4) containing Heparin (1 IU/ml) for ten minutes followed be dilute Karnovsky's fixative for 15 minutes. The thoracic and abdominal aorta and carotid arteries are removed en bloc and are placed in a similar solution for a further 30 minutes.

Histological sections through the carotid artery immediately proximal to the proximal anastamosis, at the proximal anastamosis, at the distal anastamosis and the carotid artery immediately distal to the distal anastamosis are made. The sections are stained with Movat and H&E and Masson stains. Histologic analysis of intimal and advantitial reaction as well as perivascular reaction are noted. Morphometric analysis with degree of luminal narrowing is calculated.

The remaining pigs are studied at 6 months and a similar angiography sacrifice procedures is performed.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for treating or preventing vascular diseases associated with body passageways, comprising delivering to an external portion of the body passageway paclitaxel, or an analogue or derivative thereof.

2. A method for treating or preventing vascular diseases associated with body passageways, comprising delivering to smooth muscle cells via the adventia of the body passageway a composition comprising paclitaxel, or an analogue or derivative thereof.

3. The method according to claim 1 or 2 wherein the paclitaxel, or analogue or derivative thereof further comprises a polymer.

4. The method according to claim 3 wherein the polymer comprises microspheres having an average size ranging from about 0.5 mm to 200 mm.

5. The method according to claim 3 wherein the polymer is a copolymer of lactic acid and glycolic acid.

6. The method according to claim 3 wherein the polymer is poly (caprolactone).

7. The method according to claim 3 wherein the polymer is poly (lactic acid).

8. The method according to claim 3 wherein the polymer is a copolymer of poly (lactic acid) and poly (caprolactone).

9. The method according to claim 3 wherein the polymer is poly(ethylene-vinyl acetate).

10. The method according to claim 3 wherein the polymer is gelatin.

11. The method according to claim 1 or 2 wherein the body passageway is an artery.

12. The method according to claim 1 or 2 wherein the paclitaxel, or analogue or derivative thereof is delivered to an artery via an outer wall of the artery into an adventia.

13. The method according to claim 1 or 2 wherein the vascular disease is stenosis.

14. The method according to claim 1 or 2 wherein the vascular disease is restenosis.

15. The method according to claim 1 or 2 wherein the vascular disease is atherosclerosis.

16. The method according to claim 1 or 2 wherein the body passageway is a vein.

17. The method according to claim 1 or 2 wherein the body passageway is a capillary.

18. The method according to claim 1 wherein the body passageway is an artery.

19. The method according to claim 11 wherein the artery is a coronary artery.

20. The method according to claim 11 wherein the artery is a carotid artery or an aorta.

21. A method for treating or preventing disease associated with graft anastomosis, comprising delivering to an external portion of the site of graft anastomosis paclitaxel, or an analogue or derivative thereof.

22. The method according to claim 21 wherein said paclitaxel, or analogue or derivative thereof further comprises a polymer.

23. The method according to claim 22 wherein the polymer is a copolymer of lactic acid and glycolic acid.

24. The method according to claim 22 wherein the polymer is poly (caprolactone).

25. The method according to claim 22 wherein the polymer is poly (lactic acid).

26. The method according to claim 22 wherein the polymer is a copolymer of poly (lactic acid) and poly (caprolactone).

27. The method according to claim 22 wherein the polymer is poly(ethylene-vinyl acetate).

28. The method according to claim 22 wherein the polymer comprises microspheres having an average size ranging from about 0.5 mm to 200 mm.

29. The method according to claim 22 wherein the polymer is in the form of a paste, film, or spray.

30. The method according to claim 21 or 22 wherein the graft is a PTFE graft.

31. The method according to claims 1, 2, or 21 wherein the paclitaxel, or an analogue or derivative thereof is paclitaxel.

* * * * *

UNITED STATES PATENT AND TRADEMARK OFFICE
CERTIFICATE OF CORRECTION

PATENT NO. : 6,759,431 B2 Page 1 of 1
APPLICATION NO. : 09/933652
DATED : July 6, 2004
INVENTOR(S) : William L. Hunter et al.

It is certified that error appears in the above-identified patent and that said Letters Patent is hereby corrected as shown below:

Column 80
Line 59, "0.5 mm to 200 mm" should read as --0.5 µm to 200 µm--

Column 82
Line 18, "0.5 mm to 200 mm" should read as --0.5 µm to 200 µm--

Signed and Sealed this

Fifteenth Day of August, 2006

JON W. DUDAS
*Director of the United States Patent and Trademark Office*